(12) United States Patent
Fishkin et al.

(10) Patent No.: US 10,364,294 B2
(45) Date of Patent: *Jul. 30, 2019

(54) METHODS OF PREPARATION OF CONJUGATES

(71) Applicant: IMMUNOGEN, INC., Waltham, MA (US)

(72) Inventors: Nathan Elliott Fishkin, Weymouth, MA (US); Michael Louis Miller, Framingham, MA (US); Wei Li, Acton, MA (US); Rajeeva Singh, Framingham, MA (US)

(73) Assignee: IMMUNOGEN, INC., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/677,846

(22) Filed: Aug. 15, 2017

(65) Prior Publication Data

US 2018/0037659 A1 Feb. 8, 2018

Related U.S. Application Data

(63) Continuation of application No. 15/097,979, filed on Apr. 13, 2016, now Pat. No. 9,868,791, which is a continuation of application No. 13/397,205, filed on Feb. 15, 2012, now Pat. No. 9,353,127.

(60) Provisional application No. 61/443,092, filed on Feb. 15, 2011, provisional application No. 61/443,062, filed on Feb. 15, 2011, provisional application No. 61/483,499, filed on May 6, 2011.

(51) Int. Cl.
| | | |
|---|---|---|
| *A61K 39/00* | (2006.01) |
| *A61K 45/06* | (2006.01) |
| *A61K 47/54* | (2017.01) |
| *A61K 47/68* | (2017.01) |
| *C07K 16/30* | (2006.01) |
| *C07D 487/04* | (2006.01) |
| *C07D 519/00* | (2006.01) |
| *A61K 31/5517* | (2006.01) |

(52) U.S. Cl.
CPC .......... *C07K 16/30* (2013.01); *A61K 31/5517* (2013.01); *A61K 45/06* (2013.01); *A61K 47/545* (2017.08); *A61K 47/6803* (2017.08); *A61K 47/6849* (2017.08); *A61K 47/6851* (2017.08); *A61K 47/6867* (2017.08); *C07D 487/04* (2013.01); *C07D 519/00* (2013.01); *A61K 2039/505* (2013.01); *C07K 2317/24* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 3,763,183 A | 10/1973 | Carabateas | |
| 3,860,600 A | 1/1975 | Carabateas | |
| 8,426,402 B2 | 4/2013 | Li et al. | |
| 8,765,740 B2 | 7/2014 | Li et al. | |
| 8,802,667 B2 | 8/2014 | Li et al. | |
| 8,809,320 B2 | 8/2014 | Li et al. | |
| 8,889,669 B2 | 11/2014 | Li et al. | |
| 9,353,127 B2 | 5/2016 | Fishkin et al. | |
| 9,434,748 B2 | 9/2016 | Li et al. | |
| 9,534,000 B2 | 1/2017 | Chari | |
| 9,840,564 B2 * | 12/2017 | Li | C07D 487/04 |
| 9,868,791 B2 * | 1/2018 | Fishkin | C07D 487/04 |
| 2009/0036431 A1 | 2/2009 | Gauzy et al. | |
| 2010/0316656 A1 | 12/2010 | Bouchard et al. | |
| 2011/0256157 A1 | 10/2011 | Howard et al. | |
| 2012/0238731 A1 | 9/2012 | Fishkin et al. | |
| 2013/0302359 A1 | 11/2013 | Li et al. | |

FOREIGN PATENT DOCUMENTS

| | | |
|---|---|---|
| EP | 0219292 A2 | 4/1987 |
| EP | 2019104 A1 | 1/2009 |
| JP | 57131791 | 8/1982 |
| JP | 5977522 B2 | 8/2016 |
| JP | 6204294 B2 | 9/2017 |
| RU | 2005133443 A | 4/2006 |
| RU | 2005133442 A | 5/2006 |
| WO | WO-1993/018045 A1 | 9/1993 |
| WO | WO-2000/012507 A2 | 3/2000 |
| WO | WO-2000/012508 A2 | 3/2000 |
| WO | WO-2004/087716 A1 | 10/2004 |
| WO | WO-2004/087717 A1 | 10/2004 |
| WO | WO-2005/040170 A2 | 5/2005 |
| WO | WO-2005/085250 A1 | 9/2005 |

(Continued)

OTHER PUBLICATIONS

Guo et al., "Synthesis and evaluation of a cyclic imine derivative conjugated to a fluorescent molecule for labeling of proteins," Bioorg Med Chem Lett., vol. 19, No. 4, pp. 1210-1213, 2009.
International Preliminary Report on Patentability on International Application PCT/US2010/023150, dated Aug. 9, 2011.
International Preliminary Report on Patentability on International Application PCT/US2012/025252 dated Jun. 14, 2013.
International Preliminary Report on Patentability on International Application PCT/US2012/025257, dated Aug. 21, 2013.
International Preliminary Report on Patentability on the Application PCT/US2012/025292, dated Aug. 21, 2013.

(Continued)

*Primary Examiner* — Marcela M Cordero Garcia
(74) *Attorney, Agent, or Firm* — McCarter & English, LLP; Yu Lu; Xin Zhang

(57) ABSTRACT

The present invention is directed to methods of preparing a conjugate of a cell-binding agent and a drug (such as a cytotoxic compound). The methods comprise the use of an imine reactive compound to enable efficient conjugations of cytotoxic compounds with cell binding agents.

3 Claims, 30 Drawing Sheets

Specification includes a Sequence Listing.

(56) References Cited

FOREIGN PATENT DOCUMENTS

| WO | WO-2005/110423 A2 | 11/2005 |
| WO | WO-2007/039752 A1 | 4/2007 |
| WO | 2007/085930 A1 | 8/2007 |
| WO | WO-2009/016647 A1 | 2/2009 |
| WO | WO-2010/043880 A1 | 4/2010 |
| WO | WO-2010/091150 A1 | 8/2010 |
| WO | WO-2011/106528 A1 | 9/2011 |
| WO | WO-2011/130613 A1 | 10/2011 |
| WO | WO-2011/130616 A1 | 10/2011 |
| WO | WO-2012/112687 A1 | 8/2012 |
| WO | WO-2014/031566 A1 | 2/2014 |

OTHER PUBLICATIONS

International Search Report and Written Opinion dated Mar. 31, 2010, issued in International Application No. PCT/US2010/23150.

International Search Report and Written Opinion issued in International Application PCT/US2012/025252, dated Jun. 26, 2012.

International Search Report and Written Opinion issued in International Application PCT/US2012/025257, dated Jun. 29, 2012.

Kamal et al., "Design, synthesis, and evaluation of mixed imine-amine pyrrolobenzodiazepine dimers with efficient DNA binding affinity and potent cytotoxicity," Bioorg. Med. Chem. (2004) 12:5427-5436.

Kamal et al., "Development of Pyrrolo[2,1-c][1,4]benzodiazepine ß-Galactoside Prodrugs for Selective Therapy of Cancer by ADEPT and PMT," ChemMedChem (2008) 3:794-802.

Li et al.; "Design, Synthesis and Evaluation of a Novel DNA-Interactive Agent: A Promising New Class of Cytotoxic Molecules for Use in Antibody-Drug Conjugates," 239th ACS National Meeting, SanFrancisco, CA 2010 [MEDI 251](2010).

Masterson et al., "Synthesis and biolgoical evaluation of novel pyrrolo[2,1-c][1,4]benzodiazepine prodrugs for use in antibody-directed enzyme prodrug therapy," Bioorg. Med. Chem. Lett. (2006) 16:252-256.

Miller et al., "Abstract B126: Potent antigen-specific anti-tumor activity observed with antibody-drug conjugates (ADCs) made using a new class of DNA-crosslinking agents," Mol. Cancer Ther., 8(12) Suppl 1 (2009).

Miller et al.; "Potent antigen-specific anti-tumor activity observed with antibody-drug conjugates (ADCs) made using a new class of DNA-crosslinking agents," Mol. Cancer Ther.—Poster Presentation AACR-NCI-EORTC; 8(12):Supplement 1 [Abstract B126] (Nov. 2009).

Thurston et al.; "Synthesis and reactivity of a novel oxazolo[2,3-c][1,4]benziodiazepine ring system with DNA recognition potential: a new class of anthramycins," J. Chem. Soc.; 12:874-876 (1990).

Tozuka et al.; "Studies on tomaymycin. III. Syntheses and antitumor activity of tomaymycin analogs," J. Antibiot., 36(12):1699-1708 (1983).

* cited by examiner

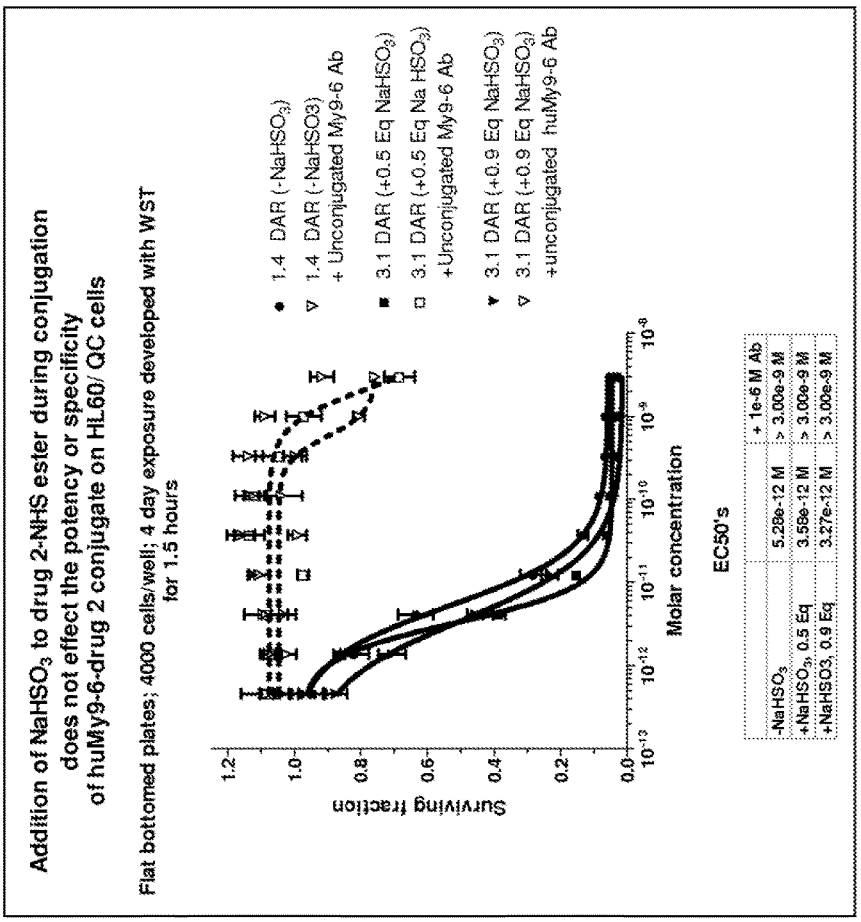

Anti-CD22 Ab-2 conjugates prepared without and with sodium bisulfite show similar *in vitro* cytotoxicity toward CD22-antigen expressing BJAB cells.

Reverse phase HPLC analysis of 2-NHS and sodium bisulfite-treated 2-NHS

Addition of sodium bisulfite in 1-SPDB-NHS conjugation reaction did not result in fragmentation of antibody (non-reducing SDS-PAGE: gel chip analysis)

FIG. 15

| Reactant | Drug/Ab (UV) | % monomer (SEC) | % drug on monomer |
|---|---|---|---|
| Sodium Hydrosulfite | 2.6 | 88 | 82 |
| Sodium Bisulfite | 2.6 | 88 | 83 |
| Sodium Metabisulfite | 2.7 | 88 | 82 |
| No additive | 0.1 | 98 | 94 |

Two-step Conjugation Scheme

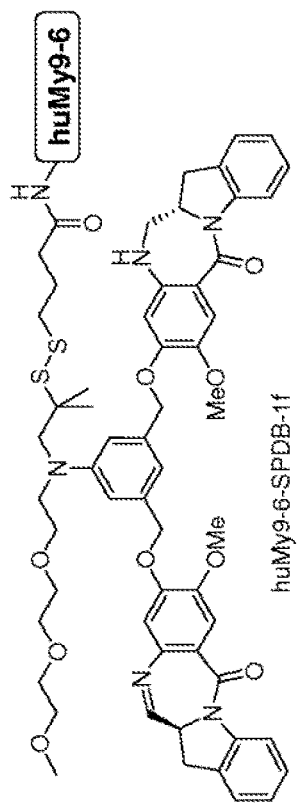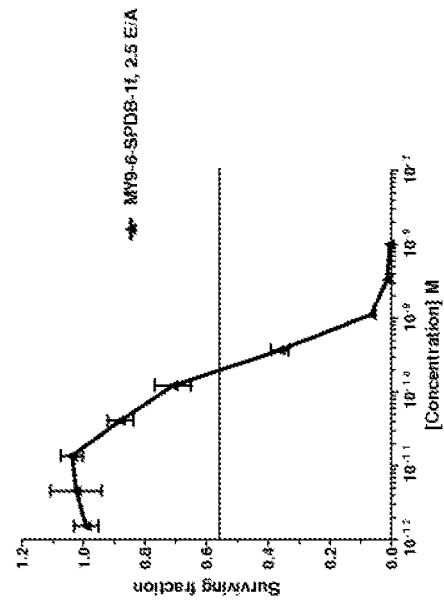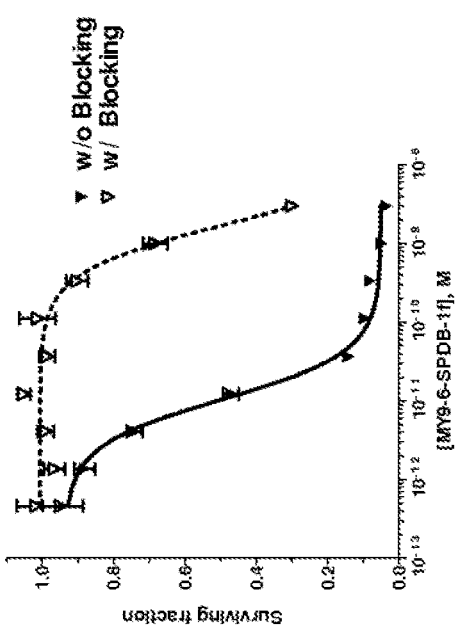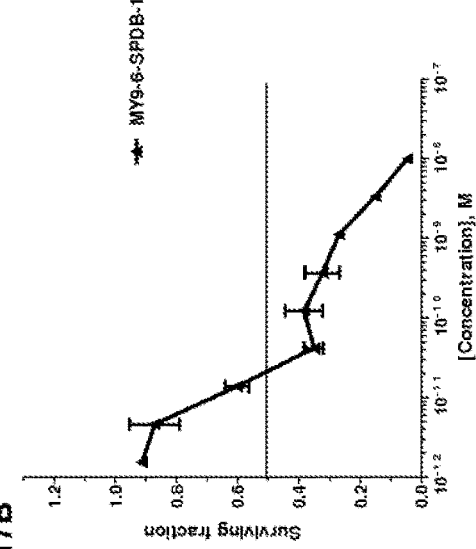
FIG. 17A  FIG. 17B  FIG. 17C

FIG. 18
Binding Affinity of huMY9-6-SPDB-1f (FACS analysis)
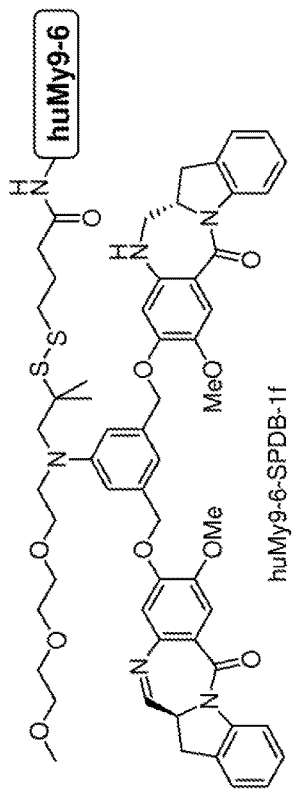
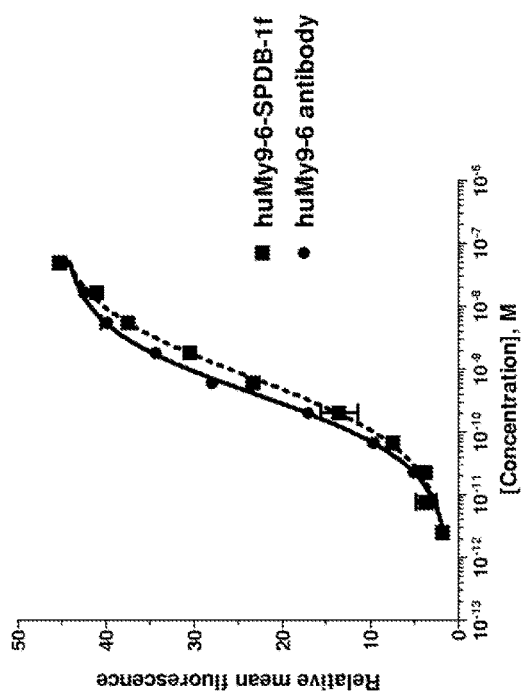

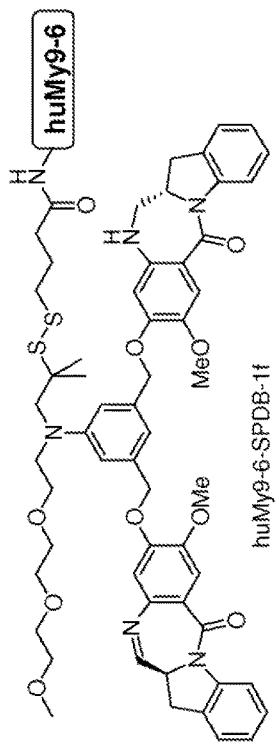
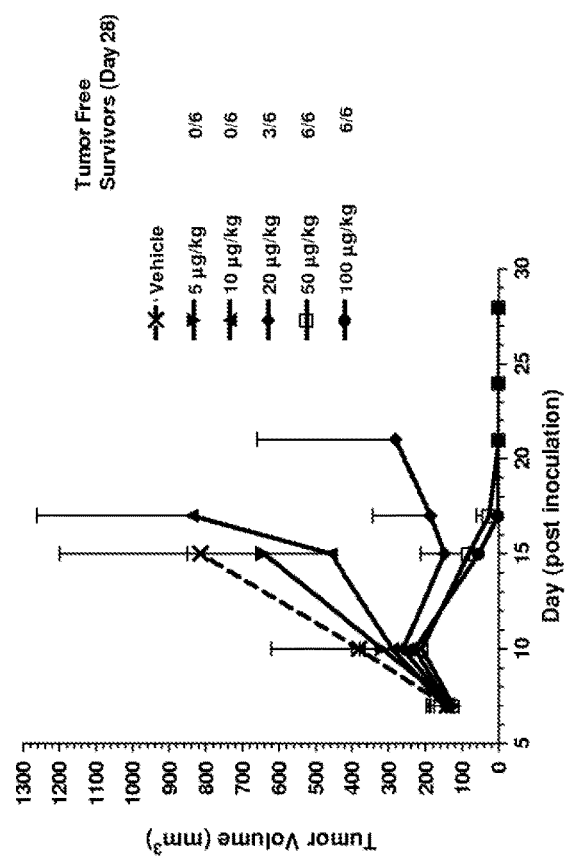
FIG. 19
*In vivo* Efficacy of huMy9-6-SPDB-1f in HL60/QC Tumor Bearing Nude Mice

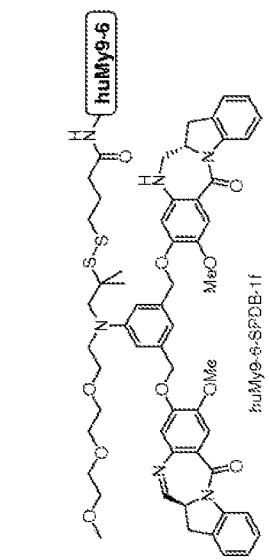
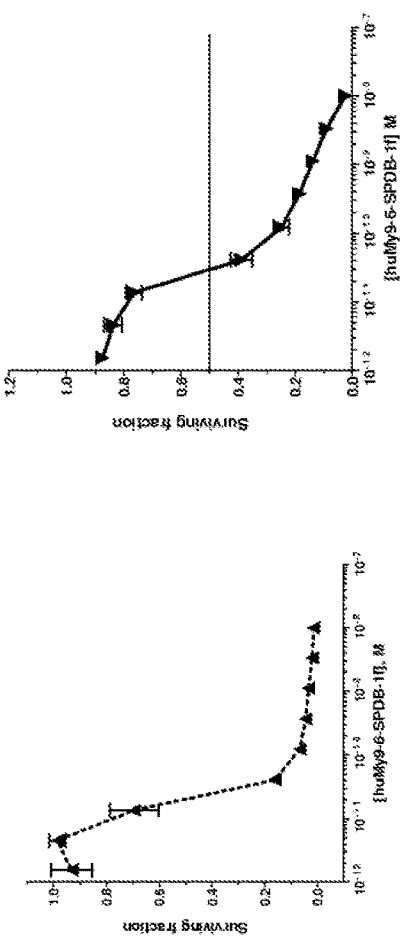
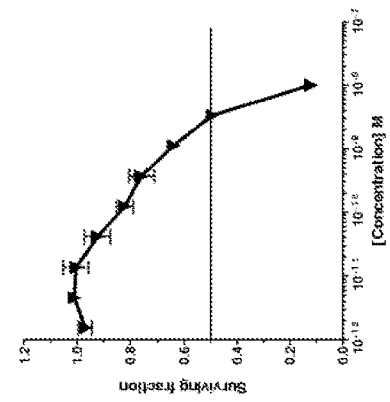
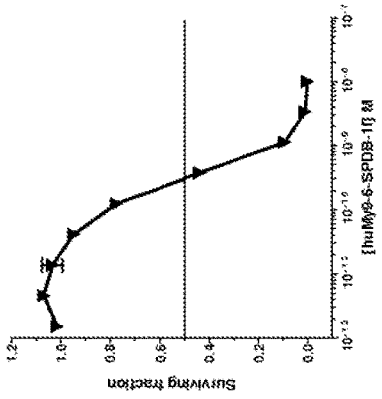
FIG. 20A
FIG. 20B
FIG. 20C
FIG. 20D

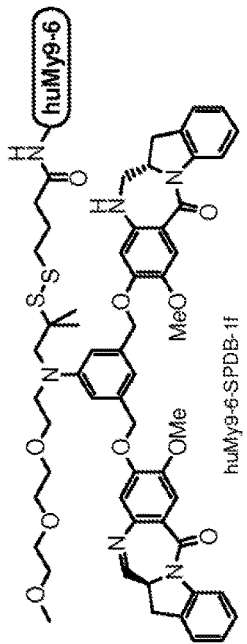
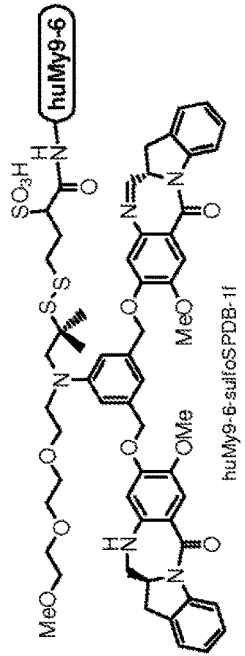
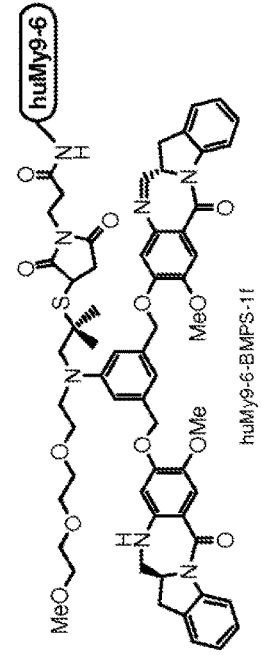
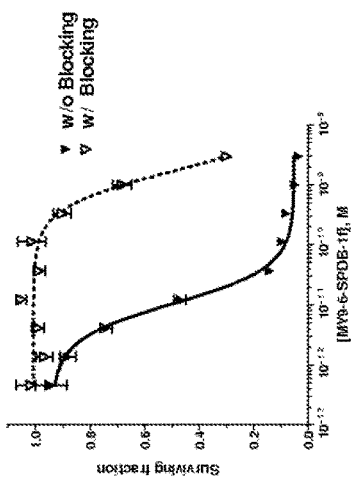
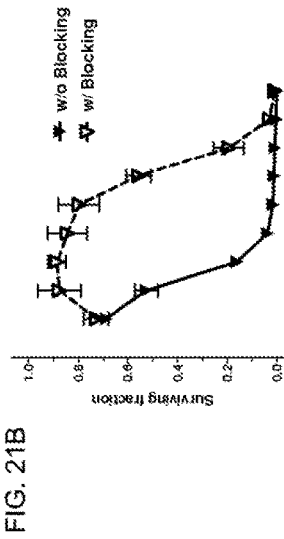
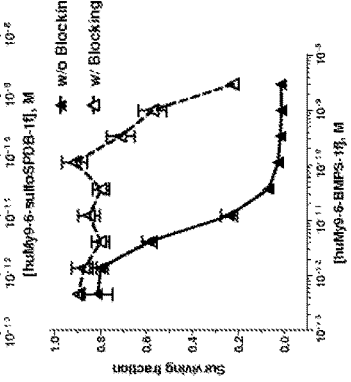
FIG. 21A
FIG. 21B
FIG. 21C

*In vivo* Efficacy of huMy9-6-SPDB-1f in HL60/QC Tumor Bearing Mice

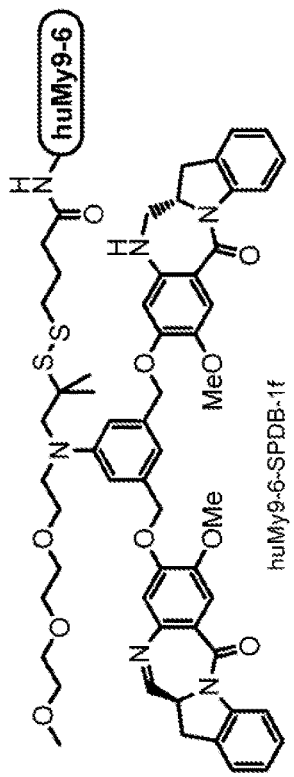
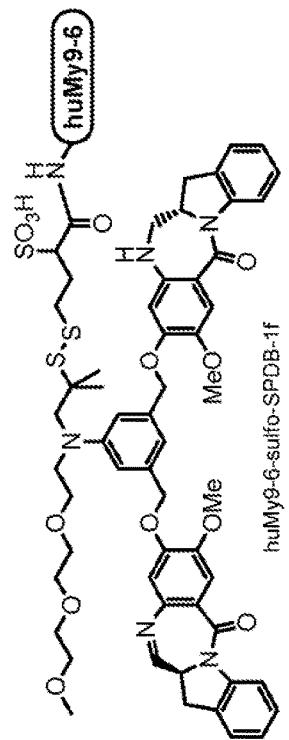
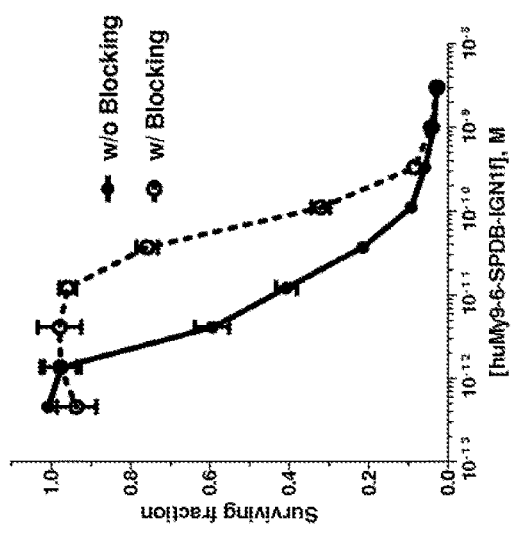
FIG. 24A
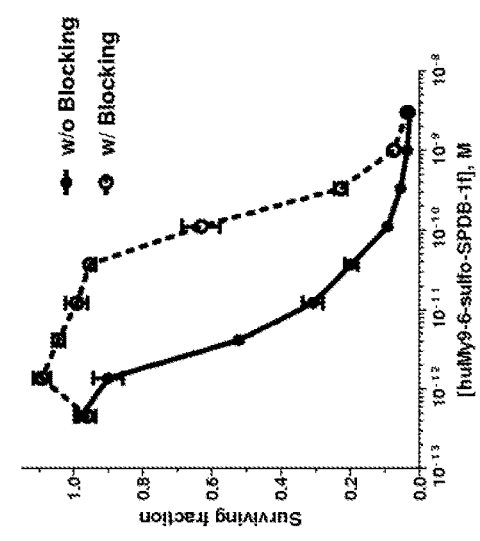
FIG. 24B

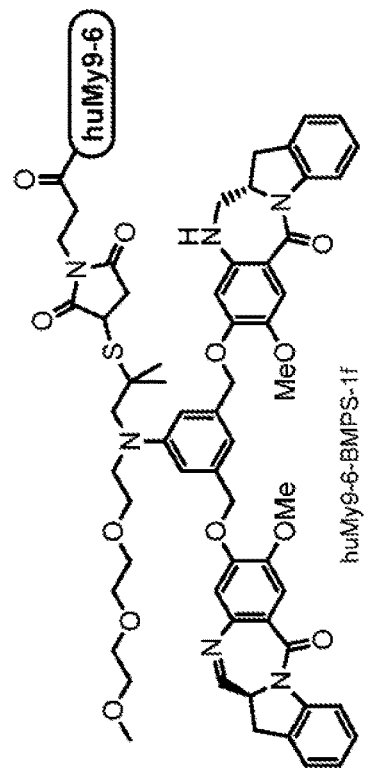
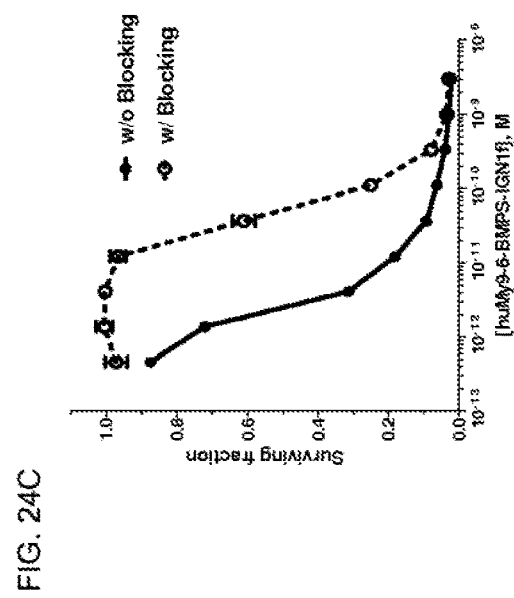
FIG. 24C

*In vivo* Efficacy of huMy9-6-BMPS-1f in MOLM-13 Tumor Bearing Mice

Representative Synthesis Scheme for a Sulfonated Folate / Cytotoxic Compound Conjugate

METHODS OF PREPARATION OF CONJUGATES

REFERENCE TO RELATED APPLICATIONS

This application is a continuation application of U.S. Utility application Ser. No. 15/097,979, filed on Apr. 13, 2016, which is a continuation application of U.S. Utility application Ser. No. 13/397,205, filed on Feb. 15, 2012, now U.S. Pat. No. 9,353,127, issued on May 31, 2016, which claims the benefit of the filing date under 35 U.S.C. § 119(e), of U.S. Provisional Application No. 61/443,062, filed on Feb. 15, 2011, U.S. Provisional Application No. 61/483,499, filed on May 6, 2011, and U.S. Provisional Application No. 61/443,092, filed on Feb. 15, 2011. The entire contents of each of the above-referenced applications, including all drawings, formulae, specifications, and claims, are incorporated herein by reference.

FIELD OF THE INVENTION

This invention describes the use of imine reactive reagents for the preparation of conjugates of cell-binding agents with DNA-binding cytotoxic drugs containing one or more imine functional groups.

BACKGROUND OF THE INVENTION

Monoclonal antibodies are increasingly being explored as therapeutic agents against cancer. Several monoclonal antibodies against cancer cell-surface antigens have already been approved for cancer treatment, such as rituximab for non-Hodgkin's lymphoma, trastuzumab for breast cancer, cetuximab for head and neck and colorectal cancer, cetuximab, panitimumab, and bevacizumab for colorectal cancer, and alemtuzumab for chronic lymphocytic leukemia (Strome, S. E., Sausville, E. A., and Mann, D., 2007, *The Oncologist*, 12, 1084-1095). However, the cytotoxic activity of a "naked" antibody can be limited to the mechanisms of receptor function inhibition, complement-dependent cytotoxicity (CDC), and antibody-dependent cell-mediated cytotoxicity (ADCC).

An approach to enhance the cytotoxic activity of antibody toward target cancer cells is by linking antibody with cytotoxic effectors (A. D. Ricart, and A. W. Tolcher, 2007, *Nat. Clin. Pract. Oncol.* 4, 245-255; Lambert, J., 2010, *Drugs of the Future* 35, 471-480). The antibody-cytotoxic drug conjugate (ADC) binds specifically to cancer cells, followed by conjugate internalization and degradation, which results in the intracellular release of the toxic drug and ultimately to the death of the cancer cells. The cytotoxic drugs that have been employed in linkage with antibodies include antitubulin drugs such as maytansinoids and auristatins, DNA-binding drugs such as calicheamicin that causes sequence-specific double-stranded DNA cleavage. Another class of DNA-binding cytotoxic drugs includes imine-containing pyrrolobenzodiazepines (PBD) such as N-2-imidazolyl alkyl substituted 1,2,5-benzothiadiazepine-1,1-dioxide, U.S. Pat. No. 6,156,746), benzo-pyrido or dipyrido thiadiazepine (WO 2004/069843), pyrrolo [1,2-b][1,2,5] benzothiadiazepines and pyrrole [1,2-b][1,2,5] benzodiazepine derivatives (WO2007/015280), tomaymycin derivatives (e.g., pyrrolo[1,4]benzodiazepines), such as those described in WO 00/12508, WO2005/085260, WO2007/085930, EP 2019104, and U.S. Pat. No. 6,156,746). Other DNA-binding benzodiazepine drugs are described in US Patent Publication No. 2010/0203007A1. These benzodiazepine drugs containing imine bonds bind to the minor groove of DNA and interfere with DNA function, resulting in cell death.

There is a need for new methods for preparing conjugates of cell-binding agent and cytotoxic drugs bearing an imine group.

BRIEF SUMMARY OF THE INVENTION

The present invention describes the use of imine-reactive reagents for treating an imine-containing drug, which resulted in an unexpected improvement in its conjugation reaction with cell binding agents (CBA) such as antibodies. The reagents are such that the cell killing properties of the drug are not diminished and the integrity of the CBA (antibody) is fully maintained.

In one embodiment, the present invention is directed to a method for preparing a conjugate comprising a cell-binding agent (CBA) conjugated to a cytotoxic compound with a linking group, the method comprising reacting a cytotoxic compound with a modified CBA at a pH of about 4 to about 9, wherein:
  a) the modified CBA comprises a residue of a bifunctional crosslinking agent bonded to the CBA, and the residue comprises the linking group and a thiol-reactive group; and
  b) the cytotoxic compound comprises a thiol group, and a group represented by:

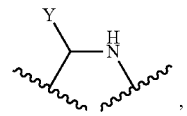

wherein:
  Y is a leaving group, and is a sulfite ($HSO_3$, $HSO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono-, di-, tri-, and tetra-thiophosphate ($PO_3SH_3$, $PO_2S_2H_2$, $POS_3H_2$, $PS_4H_2$ or a salt of $PO_3S^{3-}$, $PO_2S_2^{3-}$, $POS_3^{3-}$ or $PS_4^{3-}$ formed with a cation), thio phosphate ester ($R^iO)_2PS$ ($OR^i$), $R^iS$—, $R^iSO$, $R^iSO_2$, $R^iSO_3$, thiosulfate ($HS_2O_3$ or a salt of $S_2O_3^{2-}$ formed with a cation), dithionite ($HS_2O_4$ or a salt of $S_2O_4^{2-}$ formed with a cation), phosphorodithioate ($P(=S)(OR^{k'})(S)(OH)$ or a salt thereof formed with a cation), hydroxamic acid ($R^{k'}C(=O)NOH$ or a salt formed with a cation), formaldehyde sulfoxylate ($HOCH_2SO_2^-$ or a salt of $HOCH_2SO_2^-$ formed with a cation, such as $HOCH_2SO_2^-Na^+$) or a mixture thereof, wherein $R^i$ is a linear or branched alkyl having 1 to 10 carbon atoms and is substituted with at least one substituent selected from —$N(R^j)_2$, —$CO_2H$, —$SO_3H$, and —$PO_3H$; $R^i$ can be further optionally substituted with a substituent for an alkyl described herein; $R^j$ is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl.

In certain embodiments, the cytotoxic compound is produced by reacting an imine-containing cytotoxic compound bearing the thiol group with an imine reactive reagent.

In another embodiment, the present invention is directed to a method for preparing a conjugate comprising a cell-binding agent (CBA) conjugated to a cytotoxic compound with a linking group, the method comprising reacting the CBA with an imine-containing cytotoxic compound, an imine reactive reagent, and a bifunctional crosslinking agent comprising the linking group to form the conjugate.

In another embodiment, the present invention is directed to a method for preparing a conjugate comprising a cell-binding agent (CBA) conjugated to a cytotoxic compound with a linking group, the method comprising:

a) reacting a cytotoxic compound with a bifunctional crosslinking agent comprising the linking group, a group reactive with the CBA (such as a thiol group, a maleimide group, a haloacetamide group, or an amine group), and a group reactive with the cytotoxic compound, to form a modified cytotoxic compound covalently bonded to a residue of the bifunctional crosslinking agent, wherein the residue comprises the linking group and the group reactive with the CBA;

wherein the cytotoxic compound is represented by one of the following formulas, or a pharmaceutically acceptable salt thereof:

X' is selected from —H, an amine-protecting group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3 to 18-membered heterocyclic ring having 1 to 6 heteroatoms;

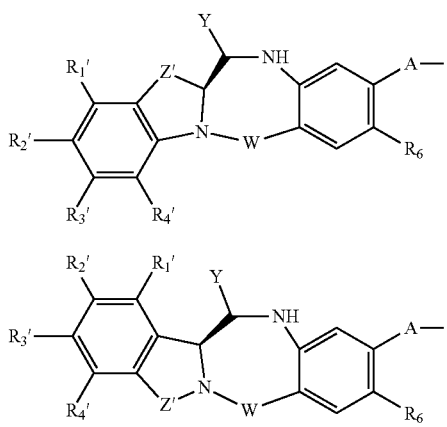

(I')

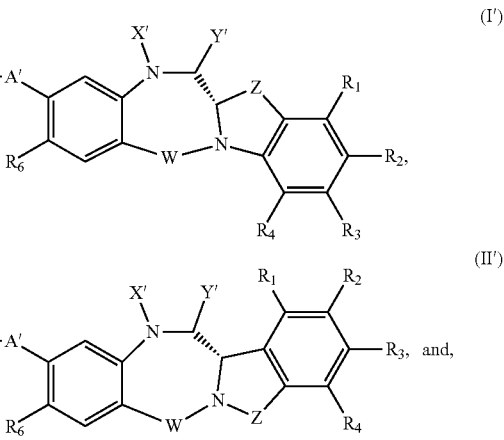

(II')

wherein:

Y is a leaving group, and is a sulfite (HSO$_3$, HSO$_2$ or a salt of HSO$_3^-$, SO$_3^{2-}$ or HSO$_2^-$ formed with a cation), metabisulfite (H$_2$S$_2$O$_5$ or a salt of S$_2$O$_5^{2-}$ formed with a cation), mono-, di-, tri-, and tetra-thiophosphate (PO$_3$SH$_3$, PO$_2$S$_2$H$_2$, POS$_3$H$_2$, PS$_4$H$_2$ or a salt of PO$_3$S$^{3-}$, PO$_2$S$_2^{3-}$, POS$_3^{3-}$ or PS$_4^{3-}$ formed with a cation), thio phosphate ester (R$^i$O)$_2$PS(OR$^i$), R$^i$S—, R$^i$SO, R$^i$SO$_2$, R$^i$SO$_3$, thiosulfate (HS$_2$O$_3$ or a salt of S$_2$O$_3^{2-}$ formed with a cation), dithionite (HS$_2$O$_4$ or a salt of S$_2$O$_4^{2-}$ formed with a cation), phosphorodithioate (P(=S)(OR$^{k'}$)(S)(OH) or a salt thereof formed with a cation), hydroxamic acid (R$^{k'}$C(=O)NOH or a salt formed with a cation), formaldehyde sulfoxylate (HOCH$_2$SO$_2^-$ or a salt of HOCH$_2$SO$_2^-$ formed with a cation, such as HOCH$_2$SO$_2^-$Na$^+$) or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl;

R$^c$ is —H or a substituted or unsubstituted linear or branched alkyl having 1 to 4 carbon atoms;

R$_1$, R$_2$, R$_3$, R$_4$, R$_1$', R$_2$', R$_3$' and R$_4$' are each independently selected from the group consisting of —H, an optionally substituted linear, branched or cyclic alkyl, alkenyl or alkynyl having from 1 to 10 carbon atoms, a polyethylene glycol unit —(OCH$_2$CH$_2$)$_n$—R$^c$, halogen, guanidinium [—NH(C=NH)NH$_2$], —OR, —NR'R'', —NO$_2$, —NCO, —NR'COR'', —SR, a sulfoxide represented by —SOR', a sulfone represented by —SO$_2$R', a sulfonate —SO$_3^-$M$^+$, a sulfate —OSO$_3^-$M$^+$, a sulfonamide represented by —SO$_2$NR'R'', cyano, an azido, —COR', —OCOR', —OCONR'R'';

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3-18-membered heterocyclic ring having 1 to 6 heteroatoms independently selected from O, S, N and P;

n is an integer from 1 to 24;

W is selected from C=O, C=S, CH$_2$, BH, SO and SO$_2$;

R$_6$ is —H, —R, —OR, —SR, —NR'R", —NO$_2$, or, halogen;

Z and Z' are independently selected from —(CH$_2$)$_{n'}$—, —(CH$_2$)$_{n'}$—CR$_7$R$_8$—(CH$_2$)$_{na'}$—, —(CH$_2$)$_{n'}$—NR$_9$—(CH$_2$)$_{na'}$—, —(CH$_2$)$_{n'}$—O—(CH$_2$)$_{na'}$— and —(CH$_2$)$_{n'}$—S—(CH$_2$)$_{na'}$—;

L is absent, or when present, comprises the thiol group, or is a polyethylene glycol unit (—OCH$_2$CH$_2$)$_n$—, a linear, branched or cyclic alkyl or alkenyl having 1 to 10 carbon atoms, a phenyl group, a 3- to 18-membered heterocyclic ring or a 5- to 18-membered heteroaryl ring having 1 to 6 heteroatoms independently selected from O, S, N and P, wherein the alkyl, alkenyl, phenyl, or heterocyclic or heteroaryl ring is optionally substituted; and, b) reacting the modified cytotoxic compound with the CBA through the group reactive with the CBA, at a pH of about 4 to about 9, to form the conjugate.

In any of the above embodiments, the imine-containing cytotoxic compound may be represented by any one of the following formulas, or a pharmaceutically acceptable salt thereof:

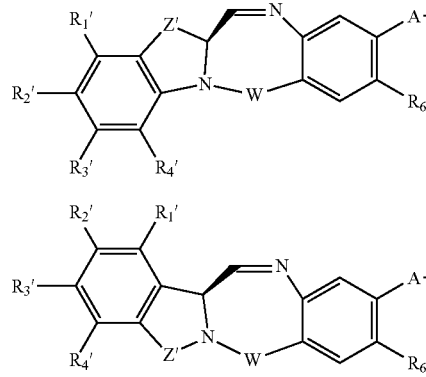
(I)

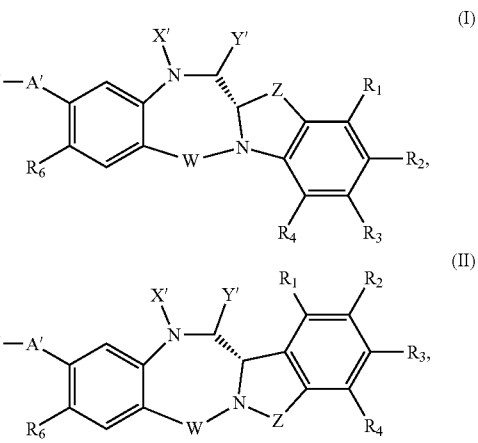
(II)

n' and na' are the same or different, and are selected from 0, 1, 2 and 3;

R$_7$ and R$_8$ are the same or different, and are each independently selected from —H, —OH, —SH, —COOH, —NHR', a polyethylene glycol unit —(OCH$_2$CH$_2$)$_n$—, an amino acid, a peptide unit bearing 2 to 6 amino acids, an optionally substituted linear, branched or cyclic alkyl having from 1 to 10 carbon atoms;

R$_9$ is independently selected from —H, an optionally substituted linear, branched or cyclic alkyl having from 1 to 10 carbon atoms, a polyethylene glycol unit —(OCH$_2$CH$_2$)$_n$—;

A and A' are the same or different, and are independently selected from —O—, oxo (—C(=O)—), —CRR'O—, —CRR'—, —S—, —CRR'S—, —N(R$_5$)— and —CRR'N(R$_5$)—, R$_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;

wherein:

X' is selected from —H, an amine-protecting group, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3 to 18-membered heterocyclic ring having 1 to 6 heteroatoms;

R$^c$ is —H or a substituted or unsubstituted linear or branched alkyl having 1 to 4 carbon atoms;

R$_1$, R$_2$, R$_3$, R$_4$, R$_1$', R$_2$', R$_3$' and R$_4$' are each independently selected from the group consisting of —H, an optionally substituted linear, branched or cyclic alkyl, alkenyl or alkynyl having from 1 to 10 carbon atoms, a polyethylene glycol unit —(OCH$_2$CH$_2$)$_n$—R$^c$, halogen, guanidinium [—NH(C=NH)NH$_2$], —OR, —NR'R", —NO$_2$, —NCO, —NR'COR", —SR, a sulfoxide represented by —SOR', a sulfone represented by —SO$_2$R', a sulfonate —SO$_3^-$M$^+$, a sulfate —OSO$_3^-$M$^+$, a sulfonamide represented by —SO$_2$NR'R", cyano, an azido, —COR', —OCOR', —OCONR'R" and the linking group;

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3-18-membered heterocyclic ring having 1 to 6 heteroatoms independently selected from O, S, N and P;

n is an integer from 1 to 24;

W is selected from C=O, C=S, CH$_2$, BH, SO and SO$_2$;

R$_6$ is —H, —R, —OR, —SR, —NR'R", —NO$_2$, or halogen;

Z and Z' are independently selected from —(CH$_2$)$_{n'}$—, —(CH$_2$)$_{n'}$—CR$_7$R$_8$—(CH$_2$)$_{na'}$—, —(CH$_2$)$_{n'}$—NR$_9$—(CH$_2$)$_{na'}$—, —(CH$_2$)$_{n'}$—O—(CH$_2$)$_{na'}$— and —(CH$_2$)$_{n'}$—S—(CH$_2$)$_{na'}$—;

n' and na' are the same or different, and are selected from 0, 1, 2 and 3;

R$_7$ and R$_8$ are the same or different, and are each independently selected from —H, —OH, —SH, —COOH, —NHR', a polyethylene glycol unit —(OCH$_2$CH$_2$)$_n$—, an amino acid, a peptide unit bearing 2 to 6 amino acids, an optionally substituted linear, branched or cyclic alkyl having from 1 to 10 carbon atoms;

R$_9$ is independently selected from —H, an optionally substituted linear, branched or cyclic alkyl having from 1 to 10 carbon atoms, a polyethylene glycol unit —(OCH$_2$CH$_2$)$_n$—;

A and A' are the same or different, and are independently selected from —O—, oxo (—C(=O)—), —CRR'O—, —CRR'—, —S—, —CRR'S—, —N(R$_5$)— and —CRR'N(R$_5$)—, R$_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;

L is absent, or when present, comprises the thiol group, and is a polyethylene glycol unit (—OCH$_2$CH$_2$)$_n$—, a linear, branched or cyclic alkyl or alkenyl having 1 to 10 carbon atoms, a phenyl group, a 3- to 18-membered heterocyclic ring or a 5- to 18-membered heteroaryl ring having 1 to 6 heteroatoms independently selected from O, S, N and P, wherein the alkyl, alkenyl, phenyl, or heterocyclic or heteroaryl ring is optionally substituted.

In yet another embodiment, the present invention is directed to a method for preparing a conjugate comprising a cell-binding agent (CBA) conjugated to a cytotoxic compound with a linking group, the method comprising reacting a modified cytotoxic compound with the CBA at a pH of about 4 to about 9, wherein the modified cytotoxic compound comprises:

a) a residue of a bifunctional crosslinking agent bonded to the cytotoxic compound, and the residue comprises the linking group and a reactive group selected from a reactive ester and a thiol-reactive group, and, b) a group represented by:

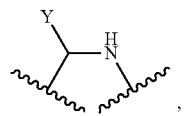

wherein:

Y is a leaving group, and is a sulfite (HSO$_3$, HSO$_2$ or a salt of HSO$_3^-$, SO$_3^{2-}$ or HSO$_2^-$ formed with a cation), metabisulfite (H$_2$S$_2$O$_5$ or a salt of S$_2$O$_5^{2-}$ formed with a cation), mono-, di-, tri-, and tetra-thiophosphate (PO$_3$SH$_3$, PO$_2$S$_2$H$_2$, POS$_3$H$_2$, PS$_4$H$_2$ or a salt of PO$_3$S$^{3-}$, PO$_2$S$_2^{3-}$, POS$_3^{3-}$ or PS$_4^{3-}$ formed with a cation), thio phosphate ester (R$^i$O)$_2$PS(OR$^i$), R$^i$S—, R$^i$SO, R$^i$SO$_2$, R$^i$SO$_3$, thiosulfate (HS$_2$O$_3$ or a salt of S$_2$O$_3^{2-}$ formed with a cation), dithionite (HS$_2$O$_4$ or a salt of S$_2$O$_4^{2-}$ formed with a cation), phosphorodithioate (P(=S)(OR$^{k'}$)(S)(OH) or a salt thereof formed with a cation), hydroxamic acid (R$^{k'}$C(=O)NOH or a salt formed with a cation), formaldehyde sulfoxylate (HOCH$_2$SO$_2^-$ or a salt of HOCH$_2$SO$_2^-$ formed with a cation, such as HOCH$_2$SO$_2^-$Na$^+$) or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl.

In certain embodiments, the modified cytotoxic compound is produced by reacting an imine reactive reagent with an imine-containing cytotoxic compound bearing the linking group and the reactive group.

In any of the above embodiments, the modified cytotoxic compound is represented by any one of the following formulas:

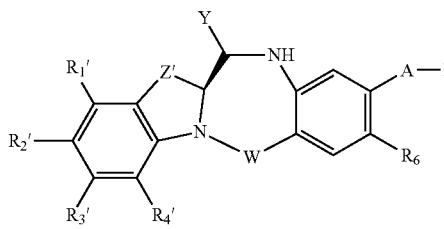
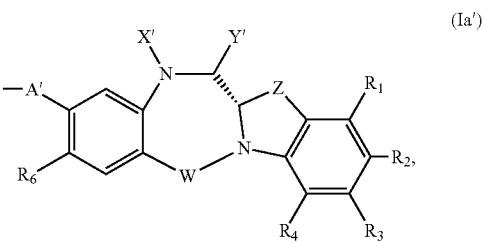

(Ia')

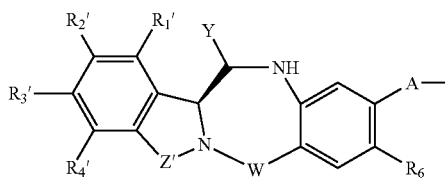
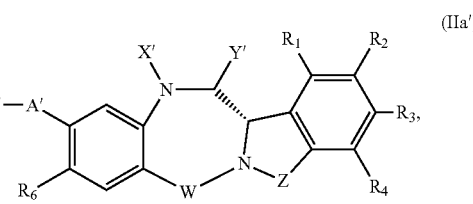

(IIa')

or a pharmaceutically acceptable salt thereof, wherein:

Y is a sulfite ($HSO_3$, $HSO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono-, di-, tri-, and tetra-thiophosphate ($PO_3SH_3$, $PO_2S_2H_2$, $POS_3H_2$, $PS_4H_2$ or a salt of $PO_3S^{3-}$, $PO_2S_2^{3-}$, $POS_3^{3-}$ or $PS_4^{3-}$ formed with a cation), thio phosphate ester $(R^iO)_2PS(OR^i)$, $R^iS-$, $R^iSO$, $R^iSO_2$, $R^iSO_3$, thiosulfate ($HS_2O_3$ or a salt of $S_2O_3^{2-}$ formed with a cation), dithionite ($HS_2O_4$ or a salt of $S_2O_4^{2-}$ formed with a cation), phosphorodithioate ($P(=S)(OR^{k'})(S)(OH)$ or a salt thereof formed with a cation), hydroxamic acid ($R^{k'}C(=O)NOH$ or a salt formed with a cation), formaldehyde sulfoxylate ($HOCH_2SO_2^-$ or a salt of $HOCH_2SO_2^-$ formed with a cation, such as $HOCH_2SO_2^-Na^+$) or a mixture thereof, wherein $R^i$ is a linear or branched alkyl having 1 to 10 carbon atoms and is substituted with at least one substituent selected from $-N(R^j)_2$, $-CO_2H$, $-SO_3H$, and $-PO_3H$; $R^i$ can be further optionally substituted with a substituent for an alkyl described herein; $R^j$ is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl;

X' is selected from —H, an amine-protecting group, the linking group with the reactive group bonded thereto, an optionally substituted linear, branched or cyclic alkyl, alkenyl or alkynyl having from 1 to 10 carbon atoms, a polyethylene glycol unit $-(CH_2CH_2O)_n-R^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, the linking group with the reactive group bonded thereto, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

$R^c$ is —H or a substituted or unsubstituted linear or branched alkyl having 1 to 4 carbon atoms, or the linking group with the reactive group bonded thereto;

$R_1$, $R_2$, $R_3$, $R_4$, $R_1'$, $R_2'$, $R_3'$ and $R_4'$ are each independently selected from the group consisting of —H, an optionally substituted linear, branched or cyclic alkyl, alkenyl or alkynyl having from 1 to 10 carbon atoms, a polyethylene glycol unit $-(OCH_2CH_2)_n-R^c$, halogen, guanidinium $[-NH(C=NH)NH_2]$, —OR, —NR'R'', —NO₂, —NCO, —NR'COR'', —SR, a sulfoxide represented by —SOR', a sulfone represented by —SO₂R', a sulfonate —SO₃⁻M⁺, a sulfate —OSO₃⁻M⁺, a sulfonamide represented by —SO₂NR'R'', cyano, an azido, —COR', —OCOR', —OCONR'R'', and the linking group with the reactive group bonded thereto;

R, for each occurrence, is independently selected from the group consisting of —H, an optionally substituted linear, branched or cyclic alkyl, alkenyl or alkynyl having from 1 to 10 carbon atoms, a polyethylene glycol unit $-(CH_2CH_2O)_n-R^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R'' are each independently selected from —H, —OH, —OR, —NHR, —NR₂, —COR, an optionally substituted linear, branched or cyclic alkyl, alkenyl or alkynyl having from 1 to 10 carbon atoms, a polyethylene glycol unit $-(CH_2CH_2O)_n-R^c$, and an optionally substituted 3- to 18-membered heterocyclic ring having 1 to 6 heteroatoms independently selected from O, S, N and P;

n is an integer from 1 to 24;

W is selected from C=O, C=S, CH₂, BH, SO and SO₂;

$R_6$ is —H, —R, —OR, —SR, —NR'R'', —NO₂, halogen or the linking group with the reactive group bonded thereto;

Z and Z' are independently selected from —$(CH_2)_{n'}$—, —$(CH_2)_{n'}$—$CR_7R_8$—$(CH_2)_{na'}$—, —$(CH_2)_{n'}$—$NR_9$—$(CH_2)_{na'}$—, —$(CH_2)_{n'}$—O—$(CH_2)_{na'}$— and —$(CH_2)_{n'}$—S—$(CH_2)_{na'}$—;

n' and na' are the same or different, and are selected from 0, 1, 2 and 3;

$R_7$ and $R_8$ are the same or different, and are each independently selected from —H, —OH, —SH, —COOH, —NHR', a polyethylene glycol unit —$(OCH_2CH_2)_n$—, an amino acid, a peptide unit bearing 2 to 6 amino acids, an optionally substituted linear, branched or cyclic alkyl having from 1 to 10 carbon atoms;

$R_9$ is independently selected from —H, an optionally substituted linear, branched or cyclic alkyl having from 1 to 10 carbon atoms, a polyethylene glycol unit —$(OCH_2CH_2)_n$—;

A and A' are the same or different, and are independently selected from —O—, oxo (—C(=O)—), —CRR'O—, —CRR'—, —S—, —CRR'S—, —$NR_5$— and —CRR'N($R_5$)—;

$R_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—$OCH_2CH_2)_n$—;

L is absent, the linking group with the reactive group bonded thereto, a polyethylene glycol unit (—$OCH_2CH_2)_n$—, a linear, branched or cyclic alkyl or alkenyl having 1 to 10 carbon atoms, a phenyl group, a 3 to 18-membered heterocyclic ring or a 5- to 18-membered heteroaryl ring having 1 to 6 heteroatoms independently selected from O, S, N and P, wherein the alkyl or alkenyl is optionally substituted with the linking group with the reactive group bonded thereto; phenyl or heterocyclic or heteroaryl ring can be optionally substituted, wherein the substituent can be the linking group with the reactive group bonded thereto.

In any of the above embodiments, the cytotoxic compound and the linking group of the conjugate is represented by any one of the following formulas:

or a pharmaceutically acceptable salt thereof, wherein:

Y is a leaving group, and is a sulfite ($HSO_3$, $HSO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono-, di-, tri-, and tetra-thiophosphate ($PO_3SH_3$, $PO_2S_2H_2$, $POS_3H_2$, $PS_4H_2$ or a salt of $PO_3S^{3-}$, $PO_2S_2^{3-}$, $POS_3^{3-}$ or $PS_4^{3-}$ formed with a cation), thio phosphate ester ($R^iO)_2PS(OR^i$), $R^iS$—, $R^iSO$, $R^iSO_2$, $R^iSO_3$, thiosulfate ($HS_2O_3$ or a salt of $S_2O_3^{2-}$ formed with a cation), dithionite ($HS_2O_4$ or a salt of $S_2O_4^{2-}$ formed with a cation), phosphorodithioate (P(=S)($OR^{k'}$)(S)(OH) or a salt thereof formed with a cation), hydroxamic acid ($R^{k'}$C(=O)NOH or a salt formed with a cation), formaldehyde sulfoxylate ($HOCH_2SO_2^-$ or a salt of $HOCH_2SO_2^-$ formed with a cation, such as $HOCH_2SO_2^-Na^+$) or a mixture thereof, wherein $R^i$ is a linear or branched alkyl having 1 to 10 carbon atoms and is substituted with at least one substituent selected from —$N(R^j)_2$, —$CO_2H$, —$SO_3H$, and —$PO_3H$; $R^i$ can be further optionally substituted with a substituent for an alkyl described herein; $R^j$ is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl;

X' is selected from —H, an amine-protecting group, the linking group, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, the linking group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen,

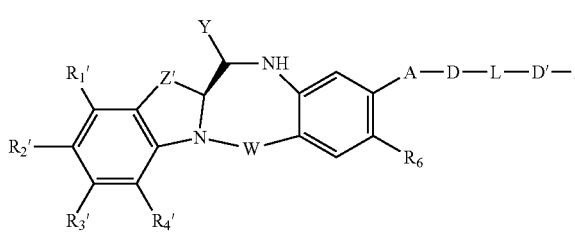

(Ib')

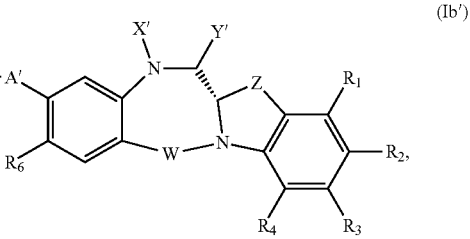

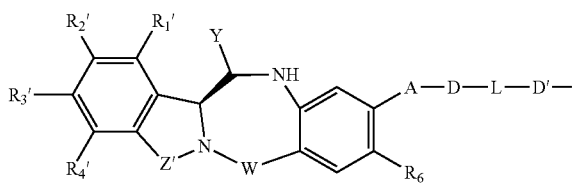

(IIb')

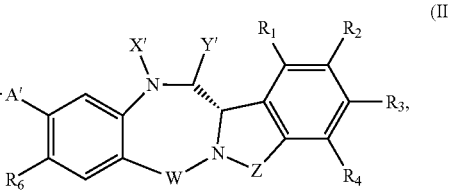

oxygen, and sulfur, an optionally substituted 3- to 18-membered heterocyclic ring having 1 to 6 heteroatoms;

$R^c$ is —H or a substituted or unsubstituted linear or branched alkyl having 1 to 4 carbon atoms, or the linking group;

$R_1$, $R_2$, $R_3$, $R_4$, $R_1'$, $R_2'$, $R_3'$ and $R_4'$ are each independently selected from the group consisting of —H, an optionally substituted linear, branched or cyclic alkyl, alkenyl or alkynyl having from 1 to 10 carbon atoms, a polyethylene glycol unit —$(OCH_2CH_2)_n$—$R^c$, halogen, guanidinium [—NH(C=NH)NH$_2$], —OR, —NR'R", —NO$_2$, —NCO, —NR'COR", —SR, a sulfoxide represented by —SOR', a sulfone represented by —SO$_2$R', a sulfonate —SO$_3^-$M$^+$, a sulfate —OSO$_3^-$M$^+$, a sulfonamide represented by —SO$_2$NR'R", cyano, an azido, —COR', —OCOR', —OCONR'R" and the linking group;

M is —H or a pharmaceutically acceptable cation, such as Na$^+$;

R, for each occurrence, is independently selected from the group consisting of —H, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —$(CH_2CH_2O)_n$—$R^c$, and an optionally substituted 3-18-membered heterocyclic ring having 1 to 6 heteroatoms independently selected from O, S, N and P;

n is an integer from 1 to 24;

W is selected from C=O, C=S, CH$_2$, BH, SO and SO$_2$;

$R_6$ is —H, —R, —OR, —SR, —NR'R", —NO$_2$, halogen or the linking group;

Z and Z' are independently selected from —$(CH_2)_{n'}$—, —$(CH_2)_{n'}$—CR$_7$R$_8$—$(CH_2)_{na'}$—, —$(CH_2)_{n'}$—NR$_9$—$(CH_2)_{na'}$—, —$(CH_2)_{n'}$—O—$(CH_2)_{na'}$— and —$(CH_2)_{n'}$—S—$(CH_2)_{na'}$—;

n' and na' are the same or different, and are selected from 0, 1, 2 and 3;

$R_7$ and $R_8$ are the same or different, and are each independently selected from —H, —OH, —SH, —COOH, —NHR', a polyethylene glycol unit —$(OCH_2CH_2)_n$—, an amino acid, a peptide unit bearing 2 to 6 amino acids, an optionally substituted linear, branched or cyclic alkyl having from 1 to 10 carbon atoms;

$R_9$ is independently selected from —H, an optionally substituted linear, branched or cyclic alkyl having from 1 to 10 carbon atoms, a polyethylene glycol unit —$(OCH_2CH_2)_n$—;

A and A' are the same or different, and are independently selected from —O—, oxo (—C(=O)—), —CRR'O—, —CRR'—, —S—, —CRR'S—, —N(R$_5$)— and —CRR'N(R$_5$)—, $R_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;

L is absent, the linking group, a polyethylene glycol unit (—OCH$_2$CH$_2$)$_n$—, an optionally substituted linear, branched or cyclic alkyl or alkenyl having 1 to 10 carbon atoms, a phenyl group, a 3- to 18-membered heterocyclic ring or a 5- to 18-membered heteroaryl ring having 1 to 6 heteroatoms independently selected from O, S, N and P, wherein the alkyl or alkenyl is optionally substituted with the linking group; phenyl or heterocyclic or heteroaryl ring can be optionally substituted, wherein the substituent can comprise the linking group.

Several preferred conjugates that may be produced according to any of the methods of the invention include:

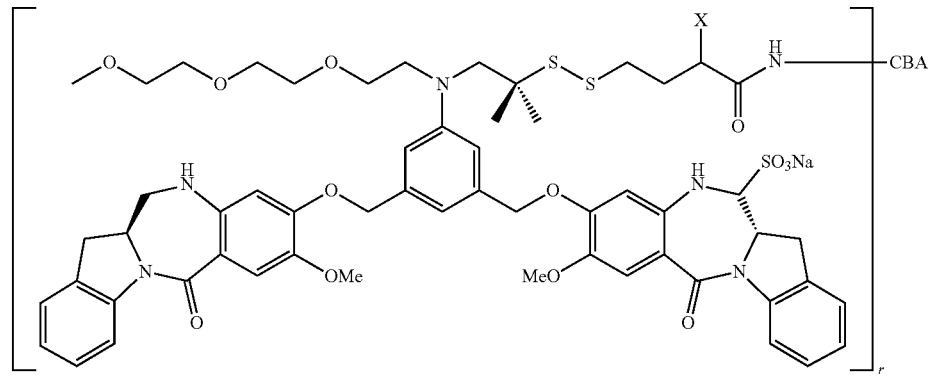

CBA = Cell Binding Agent
X = H or SO$_3$Na

CBA = Cell Binding Agent wherein CBA is a cell binding agent, such as an antibody, and r is an integer between 1-20, preferably between 1-10 or 1-5.

As used herein, when referring to a group (e.g., $R^c$, L, X' etc.) "is/be" (or "is not") the linking group or the linking group with the reactive group bounded thereto, it is meant that the group "comprises" (or "does not comprise") the linking group or the linking group with the reactive group bounded thereto.

BRIEF DESCRIPTION OF THE FIGURES

FIG. 2 shows similar in vitro cytotoxicity of HuMy9-6-Drug 2 conjugates prepared without and with sodium bisulfite against CD33-antigen expressing HL60 cells.

FIG. 5A shows conjugate prepared without sodium bisulfite with average 1.4 drug 1/Ab and antibody species with up to three linked drug 1 molecules. FIG. 5B shows conjugate prepared with sodium bisulfite with average of 2.5 1/Ab and antibody species with up to seven linked drug 1 molecules.

FIG. 15 shows the use of covalent imine reactants to improve Ab-drug conjugate specifications (% monomer and drug load).

FIGS. 17A, 17B and 17C show the in vitro cytotoxicity and specificity of the huMy9-6-SPDB-1f conjugates against various cell lines. Note that sodium bisulfite was added to the conjugation reaction for making the conjugate.

FIG. 18 shows conjugation of dimer does not reduce binding affinity of antibody. Note that sodium bisulfite was added to the conjugation reaction for making the conjugate.

FIG. 19 shows the in vivo antitumor activity of huMy9-6 conjugate. Note that sodium bisulfite was added to the conjugation reaction for making the conjugate.

FIGS. 20A, 20B, 20C and 20D show in vitro cytotoxicity of huMy9-6-SPDB-1f conjugate against antigen positive cells. Note that sodium bisulfite was added to the conjugation reaction for making the conjugate.

FIGS. 21A, 21B and 21C show in vitro cytotoxicity for huMy9-6-SPDB-1f (FIG. 21A), huMy9-6-sulfoSPDB-1f (FIG. 21B) and huMy9-6-BMPS-1f (FIG. 21C) against HL60/QC ($Ag^+$) cells with and without blocking of antigen binding sites. Note that in all three experiments sodium bisulfite were added to the conjugation reaction for making the conjugate.

FIGS. 24A, 24B and 24C show antiproliferative activity by comparing (FIG. 24A) huMy9-6-SPDB-1f, (FIG. 24B) huMy9-6-sulfoSPDB-1f, and (FIG. 24C) huMy9-6-BMPS-1f, against OCI-AML3 ($Ag^+$) cells with and without blocking of antigen binding sites. Note that in all three experiments, sodium bisulfite was added to the conjugation reaction for making the conjugate.

DETAILED DESCRIPTION OF THE INVENTION

Figure 1A:
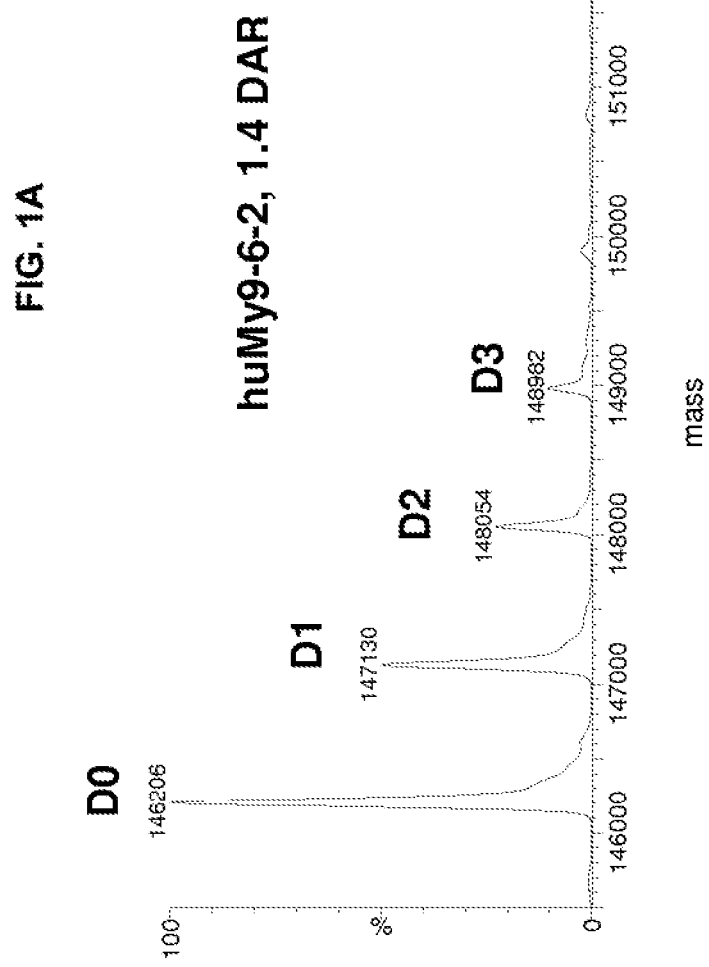
FIGS. 1A and 1B show mass spectra of deglycosylated huMy9-6-2 conjugates prepared without and with bisulfite, containing 1.4 DAR (FIG. 1A) and 3.1 DAR (FIG. 1B), respectively. DAR: drug antibody ratio.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention.

It should be understood that any of the embodiments described herein, including those described under different aspects of the invention (e.g., compounds, compound-linker molecules, conjugates, compositions, methods of making and using) and different parts of the specification (including embodiments described only in the Examples) can be combined with one or more other embodiments of the invention, unless explicitly disclaimed or improper. Combination of embodiments are not limited to those specific combinations claimed via the multiple dependent claims.

Definitions

"Linear or branched alkyl" as used herein refers to a saturated linear or branched-chain monovalent hydrocarbon radical of one to twenty carbon atoms. Examples of alkyl include, but are not limited to, methyl, ethyl, 1-propyl, 2-propyl, 1-butyl, 2-methyl-1-propyl, —CH$_2$CH(CH$_3$)$_2$), 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl), 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Preferably, the alkyl has one to ten carbon atoms. More preferably, the alkyl has one to four carbon atoms.

"Linear or branched alkenyl" refers to linear or branched-chain monovalent hydrocarbon radical of two to twenty carbon atoms with at least one site of unsaturation, i.e., a carbon-carbon, double bond, wherein the alkenyl radical includes radicals having "cis" and "trans" orientations, or alternatively, "E" and "Z" orientations. Examples include, but are not limited to, ethylenyl or vinyl (—CH═CH$_2$), allyl (—CH$_2$CH═CH$_2$), and the like. Preferably, the alkenyl has two to ten carbon atoms. More preferably, the alkyl has two to four carbon atoms.

"Linear or branched alkynyl" refers to a linear or branched monovalent hydrocarbon radical of two to twenty carbon atoms with at least one site of unsaturation, i.e., a carbon-carbon, triple bond. Examples include, but are not limited to, ethynyl, propynyl, 1-butynyl, 2-butynyl, 1-pentynyl, 2-pentynyl, 3-pentynyl, hexynyl, and the like. Preferably, the alkynyl has two to ten carbon atoms. More preferably, the alkynyl has two to four carbon atoms.

The term "carbocycle," "carbocyclyl" and "carbocyclic ring" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo [4,5], [5,5], [5,6], or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The terms "cyclic alkyl" and "cycloalkyl" can be used interchangeably. They refer to a monovalent saturated carbocyclic ring radical. Preferably, the cyclic alkyl is 3 to 7 membered monocyclic ring radical. More preferably, the cyclic alkyl is cyclohexyl.

The term "cyclic alkenyl" refers to a carbocyclic ring radical having at least one double bond in the ring structure.

The term "cyclic alkynyl" refers to a carbocyclic ring radical having at least one triple bond in the ring structure.

"Aryl" means a monovalent aromatic hydrocarbon radical of 6-18 carbon atoms derived by the removal of one hydrogen atom from a single carbon atom of a parent aromatic ring system. Some aryl groups are represented in the exemplary structures as "Ar." Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronapthalene, 1,2,3,4-tetrahydronapthyl, and the like. Preferably, aryl is phenyl group.

The terms "heterocycle," "heterocyclyl," and "heterocyclic ring" are used interchangeably herein and refer to a saturated or a partially unsaturated (i.e., having one or more double and/or triple bonds within the ring) carbocyclic radical of 3 to 18 ring atoms in which at least one ring atom is a heteroatom selected from nitrogen, oxygen, phosphorus, and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (═O) moieties are pyrimidinonyl and 1,1-dioxo-thiomorpholinyl.

The term "heteroaryl" refers to a monovalent aromatic radical of 5- or 6-membered rings, and includes fused ring systems (at least one of which is aromatic) of 5-18 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or O-carboline.

The heteroatoms present in heteroaryl or heterocyclyl include the oxidized forms such as NO, SO, and $SO_2$.

The term "halo" or "halogen" refers to F, Cl, Br or I.

The alkyl, alkenyl, alkynyl, cyclic alkyl, cyclic alkenyl, cyclic alkynyl, carbocyclyl, aryl, heterocyclyl and heteroaryl described above can be optionally substituted with one more (e.g., 2, 3, 4, 5, 6 or more) substituents.

If a substituent is described as being "substituted," a non-hydrogen substituent is in the place of a hydrogen substituent on a carbon, oxygen, sulfur or nitrogen of the substituent. Thus, for example, a substituted alkyl substituent is an alkyl substituent wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent may be identical or different (unless otherwise stated).

If a substituent is described as being "optionally substituted," the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent. One exemplary substituent may be depicted as —NR'R'', wherein R' and R'' together with the nitrogen atom to which they are attached, may form a heterocyclic ring. The heterocyclic ring formed from R' and R'' together with the nitrogen atom to which they are attached may be partially or fully saturated. In one embodiment, the heterocyclic ring consists of 3 to 7 atoms. In another embodiment, the heterocyclic ring is selected from the group consisting of pyrrolyl, imidazolyl, pyrazolyl, triazolyl, tetrazolyl, isoxazolyl, pyridyl and thiazolyl.

This specification uses the terms "substituent," "radical," and "group" interchangeably.

If a group of substituents are collectively described as being optionally substituted by one or more of a list of substituents, the group may include: (1) unsubstitutable substituents, (2) substitutable substituents that are not substituted by the optional substituents, and/or (3) substitutable substituents that are substituted by one or more of the optional substituents.

If a substituent is described as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. Such substituents, in non-limiting examples, can be selected from a linear, branched or cyclic alkyl, alkenyl or alkynyl having from 1 to 10 carbon atoms, aryl, heteroaryl, heterocycyclyl, halogen, guanidinium [—NH(C=NH)NH$_2$], —OR$^{100}$, NR$^{101}$R$^{102}$, —NO$_2$, —NR$^{101}$COR$^{102}$, —SR$^{100}$, a sulfoxide represented by —SOR$^{101}$, a sulfone represented by —SO$_2$R$^{101}$, a sulfonate —SO$_3$M, a sulfate —OSO$_3$M, a sulfonamide represented by —SO$_2$NR$^{101}$R$^{102}$, cyano, an azido, —COR$^{101}$, —OCOR$^{101}$, —OCONR$^{101}$R$^{102}$ and a polyethylene glycol unit (—OCH$_2$CH$_2$)$_n$R$^{101}$, wherein M is H or a pharmaceutically acceptable cation (such as Na$^+$ or K$^+$); R$^{101}$, R$^{102}$ and R$^{103}$ are each independently selected from H, linear, branched or cyclic alkyl, alkenyl or alkynyl having from 1 to 10 carbon atoms, a polyethylene glycol unit (—OCH$_2$CH$_2$)$_n$—R$^{104}$, wherein n is an integer from 1 to 24, an aryl having from 6 to 10 carbon atoms, a heterocyclic ring having from 3 to 10 carbon atoms and a heteroaryl having 5 to 10 carbon atoms; and R$^{104}$ is H or a linear or branched alkyl having 1 to 4 carbon atoms, wherein the alkyl, alkenyl, alkynyl, aryl, heteroaryl and heterocyclyl in the groups represented by R$^{100}$, R$^{101}$, R$^{102}$, R$^{103}$ and R$^{104}$ are optionally substituted with one or more (e.g., 2, 3, 4, 5, 6 or more) substituents independently selected from halogen, —OH, —CN, —NO$_2$ and unsubstituted linear or branched alkyl having 1 to 4 carbon atoms. Preferably, the substituents for the optionally substituted alkyl, alkenyl, alkynyl, cyclic alkyl, cyclic alkenyl, cyclic alkynyl, carbocyclyl, aryl, heterocyclyl and heteroaryl described above include halogen, —CN, —NR$^{102}$R$^{103}$, —CF$_3$, —OR$^{101}$, aryl, heteroaryl, heterocycl, —SR$^{101}$, —SOR$^{101}$, —SO$_2$R$^{101}$ and —SO$_3$M.

The term "compound" or "cytotoxic compound," "cytotoxic dimer" and "cytotoxic dimer compound" are used interchangeably. They are intended to include compounds for which a structure or formula or any biologically active derivative thereof has been disclosed in the present invention or a structure or formula or any derivative thereof that has been incorporated by reference. The term also includes, stereoisomers, geometric isomers, tautomers, solvates, metabolites, salts (e.g., pharmaceutically acceptable salts) and prodrugs, and prodrug salts of a compound of all the formulae disclosed in the present invention. The term also includes any solvates, hydrates, and polymorphs of any of the foregoing. The specific recitation of "stereoisomers," "geometric isomers," "tautomers," "solvates," "metabolites," "salt" "prodrug," "prodrug salt," "conjugates," "conjugates salt," "solvate," "hydrate," or "polymorph" in certain aspects of the invention described in this application shall not be interpreted as an intended omission of these forms in other aspects of the invention where the term "compound" is used without recitation of these other forms. In one embodiment, cytotoxic compound comprises a linking group or a linking group with a reactive group bonded thereto. Alternatively, cytotoxic compound does not comprise a linking group or a linking group with a reactive group bonded thereto.

The term "conjugate" as used herein refers to a compound described herein or a derivative thereof that is linked to a cell binding agent.

The term "linkable to a cell binding agent" as used herein refers to the compounds described herein or derivates thereof comprising at least one linking group or a precursor thereof suitable to bond these compounds or derivatives thereof to a cell binding agent.

The term "precursor" of a given group refers to any group which may lead to that group by any deprotection, a chemical modification, or a coupling reaction.

The term "linked to a cell binding agent" refers to a conjugate molecule comprising at least one of the compounds described herein (e.g., compounds and drug-linker compounds describe herein), or derivative thereof bound to a cell binding agent via a suitable linking group or a precursor thereof.

The term "chiral" refers to molecules which have the property of non-superimposability of the mirror image partner, while the term "achiral" refers to molecules which are superimposable on their mirror image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., "Stereochemistry of Organic Compounds," John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereo selection or stereo specificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "prodrug" as used in this application refers to a precursor or derivative form of a compound of the invention that is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, ester-containing prodrugs, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

The term "prodrug" is also meant to include a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO$_2$, —ONO, or —ONO$_2$ moieties. Prodrugs can typically be prepared using well-known methods, such as those described by Burger's Medicinal Chemistry and Drug Discovery (1995) 172-178, 949-982 (Manfred E. Wolff ed., 5th ed); see also Goodman and Gilman's, The Pharmacological basis of Therapeutics, 8th ed., McGraw-Hill, Int. Ed. 1992, "Biotransformation of Drugs."

One preferred form of prodrug of the invention includes compounds (with or without any linker groups) and conjugates of the invention comprising an adduct formed between an imine bond of the compounds/conjugates and an imine reactive reagent.

The term "imine reactive reagent" refers to a reagent that is capable of reacting with an imine group. Examples of imine reactive reagent includes, but is not limited to, sulfites (H$_2$SO$_3$, H$_2$SO$_2$ or a salt of HSO$_3^-$, SO$_3^{2-}$ or HSO$_2^-$ formed with a cation), metabisulfite (H$_2$S$_2$O$_5$ or a salt of S$_2$O$_5^{2-}$ formed with a cation), mono, di, tri, and tetra-thiophosphates ($PO_3SH_3$, $PO_2S_2H_3$, $POS_3H_3$, $PS_4H_3$ or a salt of $PO_3S^{3-}$, $PO_2S_2^{3-}$, $POS_3^{3-}$ or $PS_4^{3-}$ formed with a cation), thio phosphate esters (($R^iO)_2PS(OR^i$), $R^iSH$, $R^iSOH$, $R^iSO_2H$, $R^iSO_3H$), various amines (hydroxyl amine (e.g., $NH_2OH$), hydrazine (e.g., $NH_2NH_2$), $NH_2O$—$R^i$, $R^{i\prime\prime}NH$—$R^i$, $NH_2$—$R^i$), $NH_2$—CO—$NH_2$, $NH_2$—C(=S)—$NH_2'$ thiosulfate ($H_2S_2O_3$ or a salt of $S_2O_3^{2-}$ formed with a cation), dithionite ($H_2S_2O_4$ or a salt of $S_2O_4^{2-}$ formed with a cation), phosphorodithioate (P(=S)($OR^k$)(SH)(OH) or a salt thereof formed with a cation), hydroxamic acid ($R^kC$(=O)NHOH or a salt formed with a cation), hydrazide ($R^kCONHNH_2$), formaldehyde sulfoxylate ($HOCH_2SO_2H$ or a salt of $HOCH_2SO_2^-$ formed with a cation, such as $HOCH_2SO_2^-$ $Na^+$), glycated nucleotide (such as GDP-mannose), fludarabine or a mixture thereof, wherein $R^i$ and $R^{i\prime}$ are each independently a linear or branched alkyl having 1 to 10 carbon atoms and are substituted with at least one substituent selected from —N($R^j)_2$, —$CO_2H$, —$SO_3H$, and —$PO_3H$; $R^i$ and $R^{i\prime}$ can be further optionally substituted with a substituent for an alkyl described herein; $R^j$ is a linear or branched alkyl having 1 to 6 carbon atoms; and $R^k$ is a linear, branched or cyclic alkyl, alkenyl or alkynyl having 1 to 10 carbon atoms, aryl, heterocyclyl or heteroaryl (preferably, $R^k$ is a linear or branched alkyl having 1 to 4 carbon atoms; more preferably, $R^k$ is methyl, ethyl or propyl). Preferably, the cation is a monovalent cation, such as $Na^+$ or $K^+$. Preferably, the imine reactive reagent is selected from sulfites, hydroxyl amine, urea and hydrazine. More preferably, the imine reactive reagent is $NaHSO_3$ or $KHSO_3$.

As used herein and unless otherwise indicated, the terms "biohydrolyzable amide," "biohydrolyzable ester," "biohydrolyzable carbamate," "biohydrolyzable carbonate," "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, amino acids, hydroxyalkylamines, heterocyclic and heteroaromatic amines, and polyether amines. Particularly favored prodrugs and prodrug salts are those that increase the bioavailability of the compounds of this invention when such compounds are administered to a mammal.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

As used herein, the term "solvate" means a compound which further includes a stoichiometric or non-stoichiometric amount of solvent such as water, isopropanol, acetone, ethanol, methanol, DMSO, ethyl acetate, acetic acid, and ethanolamine dichloromethane, 2-propanol, or the like, bound by non-covalent intermolecular forces. Solvates or hydrates of the compounds are readily prepared by addition of at least one molar equivalent of a hydroxylic solvent such as methanol, ethanol, 1-propanol, 2-propanol or water to the compound to result in solvation or hydration of the imine moiety.

A "metabolite" is a product produced through metabolism in the body of a specified compound, a derivative thereof, or a conjugate thereof, or salt thereof. Metabolites of a compound, a derivative thereof, or a conjugate thereof, may be identified using routine techniques known in the art and their activities determined using tests such as those described herein. Such products may result for example from the oxidation, hydroxylation, reduction, hydrolysis, amidation, deamidation, esterification, deesterification, enzymatic cleavage, and the like, of the administered compound. Accordingly, the invention includes metabolites of compounds, a derivative thereof, or a conjugate thereof, of the invention, including compounds, a derivative thereof, or a conjugate thereof, produced by a process comprising contacting a compound, a derivative thereof, or a conjugate thereof, of this invention with a mammal for a period of time sufficient to yield a metabolic product thereof.

The phrase "pharmaceutically acceptable" indicates that the substance or composition must be compatible chemically and/or toxicologically, with the other ingredients comprising a formulation, and/or the mammal being treated therewith.

The term "protecting group" or "protecting moiety" refers to a substituent that is commonly employed to block or protect a particular functionality while reacting other functional groups on the compound, a derivative thereof, or a conjugate thereof. For example, an "amine-protecting group" or an "amino-protecting moiety" is a substituent attached to an amino group that blocks or protects the amino functionality in the compound. Such groups are well known in the art (see for example P. Wuts and T. Greene, 2007, Protective Groups in Organic Synthesis, Chapter 7, J. Wiley & Sons, NJ) and exemplified by carbamates such as methyl and ethyl carbamate, FMOC, substituted ethyl carbamates, carbamates cleaved by 1,6-β-elimination (also termed "self immolative"), ureas, amides, peptides, alkyl and aryl derivatives. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see P. G. M. Wuts & T. W. Greene, Protective Groups in Organic Synthesis, John Wiley & Sons, New York, 2007.

The term "leaving group" refers to an group of charged or uncharged moiety that departs during a substitution or displacement. Such leaving groups are well known in the art and include, but not limited to, halogens, esters, alkoxy, hydroxyl, tosylates, triflates, mesylates, nitriles, azide, carbamate, disulfides, thioesters, thioethers and diazonium compounds.

The term "bifunctional crosslinking agent," "bifunctional linker" or "crosslinking agents" refers to modifying agents that possess two reactive groups connected to a "linking group"; one of which is capable of reacting with a cell binding agent while the other one reacts with the cytotoxic compound to link the two moieties together. Such bifunctional crosslinkers are well known in the art (see, for example, Isalm and Dent in *Bioconjugation* chapter 5, p 218-363, Groves Dictionaries Inc. New York, 1999). For example, bifunctional crosslinking agents that enable linkage via a thioether bond include N-succinimidyl-4-(N-maleimidomethyl)-cyclohexane-1-carboxylate (SMCC) to introduce maleimido groups, or with N-succinimidyl-4-(iodoacetyl)-aminobenzoate (SIAB) to introduce iodoacetyl groups. Other bifunctional crosslinking agents that introduce maleimido groups or haloacetyl groups on to a cell binding agent are well known in the art (see US Patent Applications 2008/0050310, 20050169933, available from Pierce Biotechnology Inc., P.O. Box 117, Rockland, Ill. 61105, USA) and include, but not limited to, bis-maleimidopolyethyleneglycol (BMPEO), BM(PEO)$_2$, BM(PEO)$_3$, N-(β-maleimidopropyloxy)succinimide ester (BMPS), γ-maleimidobutyric acid N-succinimidyl ester (GMBS), ε-maleimidocaproic acid N-hydroxysuccinimide ester (EMCS), 5-maleimidovaleric acid NHS, HBVS, N-succinimidyl-4-(N-maleimidomethyl)-cyclohexane-1-carboxy-(6-amidocaproate), which is a "long chain" analog of SMCC (LC-SMCC), m-maleimidobenzoyl-N-hydroxysuccinimide ester (MBS), 4-(4-N-maleimidophenyl)-butyric acid hydrazide or HCl salt (MPBH), N-succinimidyl 3-(bromoacetamido)propionate (SBAP), N-succinimidyl iodoacetate (SIA), K-maleimidoundecanoic acid N-succinimidyl ester (KMUA), N-succinimidyl 4-(p-maleimidophenyl)-butyrate (SMPB), succinimidyl-6-(β-maleimidopropionamido) hexanoate (SMPH), succinimidyl-(4-vinylsulfonyl)benzoate (SVSB), dithiobis-maleimidoethane (DTME), 1,4-bis-maleimidobutane (BMB), 1,4 bismaleimidyl-2,3-dihydroxybutane (BMDB), bis-maleimidohexane (BMH), bis-maleimidoethane (BMOE), sulfosuccinimidyl 4-(N-maleimidomethyl)cyclohexane-1-carboxylate (sulfo-SMCC), sulfosuccinimidyl(4-iodo-acetyl)aminobenzoate (sulfo-SIAB), m-maleimidobenzoyl-N-hydroxysulfosuccinimide ester (sulfo-MBS), N-(γ-maleimidobutryloxy)sulfosuccinimde ester (sulfo-GMBS), N-(ε-maleimidocaproyloxy)sulfosuccimido ester (sulfo-EMCS), N-(κ-maleimidoundecanoyloxy)sulfosuccinimide ester (sulfo-KMUS), and sulfosuccinimidyl 4-(p-maleimidophenyl)butyrate (sulfo-SMPB).

Heterobifunctional crosslinking agents are bifunctional crosslinking agents having two different reactive groups. Heterobifunctional crosslinking agents containing both an amine-reactive N-hydroxysuccinimide group (NHS group) and a carbonyl-reactive hydrazine group can also be used to link the cytotoxic compounds described herein with a cell-binding agent (e.g., antibody). Examples of such commercially available heterobifunctional crosslinking agents include succinimidyl 6-hydrazinonicotinamide acetone hydrazone (SANH), succinimidyl 4-hydrazidoterephthalate hydrochloride (SHTH) and succinimidyl hydrazinium nicotinate hydrochloride (SHNH). Conjugates bearing an acid-labile linkage can also be prepared using a hydrazine-bearing benzodiazepine derivative of the present invention. Examples of bifunctional crosslinking agents that can be used include succinimidyl-p-formyl benzoate (SFB) and succinimidyl-p-formylphenoxyacetate (SFPA).

Bifunctional crosslinking agents that enable the linkage of cell binding agent with cytotoxic compounds via disulfide bonds include N-succinimidyl-4-(4-nitropyridyl-2-dithio)butanoate, and other agents known in the art that include N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB), N-succinimidyl-4-(2-pyridyldithio)2-sulfo butanoate (sulfo-SPDB) to introduce dithiopyridyl groups. Other bifunctional crosslinking agents that can be used to introduce disulfide groups are known in the art and are disclosed in U.S. Pat. Nos. 6,913,748, 6,716,821 and US Patent Publications 20090274713 and 20100129314, all of which are incorporated herein by reference. Alternatively, crosslinking agents such as 2-iminothiolane, homocysteine thiolactone or S-acetylsuccinic anhydride that introduce thiol groups can also be used.

A "linker," "linker moiety," or "linking group" as defined herein refers to a moiety that connects two moieties, such as a cell binding agent and a cytotoxic compound, together. A bifunctional crosslinking agent may comprise two reactive groups, one at each ends of a linker moiety, such that one reactive group can be first reacted with the cytotoxic compound to provide a compound bearing the linker moiety and a second reactive group, which can then react with a cell binding agent. Alternatively, one end of the bifunctional crosslinking agent can be first reacted with the cell binding agent to provide a cell binding agent bearing a the linker moiety and a second reactive group, which can then react with a cytotoxic compound. The linking moiety may contain a chemical bond that allows for the release of the cytotoxic moiety at a particular site. Suitable chemical bonds are well known in the art and include disulfide bonds, thioether bonds, acid labile bonds, photolabile bonds, peptidase labile bonds and esterase labile bonds (see for example U.S. Pat. Nos. 5,208,020; 5,475,092; 6,441,163; 6,716,821; 6,913, 748; 7,276,497; 7,276,499; 7,368,565; 7,388,026 and 7,414, 073). Preferred are disulfide bonds, thioether and peptidase labile bonds. Other linkers that can be used in the present invention include non-cleavable linkers, such as those described in are described in detail in U.S. publication number 20050169933, or charged linkers or hydrophilic linkers and are described in US 2009/0274713, US 2010/01293140 and WO 2009/134976, each of which is expressly incorporated herein by reference, each of which is expressly incorporated herein by reference.

In one embodiment, the linking group with a reactive group attached at one end, such as a reactive ester, is selected from the following "List 1":

—O(CR$_{20}$R$_{21}$)$_m$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',

—O(CR$_{20}$R$_{21}$)$_m$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'',

—O(CR$_{20}$R$_{21}$)$_m$(alkynyl)$_{n'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —O(CR$_{20}$R$_{21}$)$_m$(piperazino)$_{t'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —O(CR$_{20}$R$_{21}$)$_m$(pyrrolo)$_{t'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —O(CR$_{20}$R$_{21}$)$_m$A''$_{m''}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —S(CR$_{20}$R$_{21}$)$_m$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —S(CR$_{20}$R$_{21}$)$_m$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —S(CR$_{20}$R$_{21}$)$_m$(alkynyl)$_{n'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —S(CR$_{20}$R$_{21}$)$_m$(piperazino)$_{t'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —S(CR$_{20}$R$_{21}$)$_m$(pyrrolo)$_{t'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —S(CR$_{20}$R$_{21}$)$_m$A''$_{m''}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —NR$_{33}$(C=O)$_{p''}$(CR$_{20}$R$_{21}$)$_m$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —NR$_{33}$(C=O)$_{p''}$(CR$_{20}$R$_{21}$)$_m$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —NR$_{33}$(C=O)$_{p''}$(CR$_{20}$R$_{21}$)$_m$(alkynyl)$_{n'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$—(CO)$_t$X'', —NR$_{33}$(C=O)$_{p''}$(CR$_{20}$R$_{21}$)$_m$(piperazino)$_{t'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —NR$_{33}$(C=O)$_{p''}$(CR$_{20}$R$_{21}$)$_m$(pyrrolo)$_{t'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —NR$_{33}$(C=O)$_{p''}$(CR$_{20}$R$_{21}$)$_m$A''$_{m''}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —(CR$_{20}$R$_{21}$)$_m$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —(CR$_{20}$R$_{21}$)$_m$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —(CR$_{20}$R$_{21}$)$_m$(alkynyl)$_{n'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —(CR$_{20}$R$_{21}$)$_m$(piperazino)$_{t'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —(CR$_{20}$R$_{21}$)$_m$A''$_{m''}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —(CR$_{20}$R$_{21}$)$_m$(CR$_{29}$=N—NR$_{30}$)$_{n''}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —(CR$_{20}$R$_{21}$)$_m$(CR$_{29}$=N—NR$_{30}$)$_{n''}$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —(CR$_{20}$R$_{21}$)$_m$(CR$_{29}$=N—NR$_{30}$)$_{n''}$(alkynyl)$_{n'}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', —(CR$_{20}$R$_{21}$)$_m$(CR$_{29}$=N—NR$_{30}$)$_{n''}$A''$_{m''}$(CR$_{22}$R$_{23}$)$_n$(OCH$_2$CH$_2$)$_p$(CR$_{40}$R$_{41}$)$_{p''}$Y''(CR$_{24}$R$_{25}$)$_q$(CO)$_t$X'', wherein:

m, n, p, q, m', n', t' are integer from 1 to 10, or are optionally 0;

t, m'', n'' and p'' are 0 or 1;

X'' is selected from OR$_{36}$, SR$_{37}$, NR$_{38}$R$_{39}$, wherein R$_{36}$, R$_{37}$, R$_{38}$, R$_{39}$ are H, or linear, branched or cyclic alkyl, alkenyl or alkynyl having from 1 to 20 carbon atoms and, or, a polyethylene glycol unit —(OCH$_2$CH$_2$)$_n$, R$_{37}$, optionally, is a thiol protecting group when t=1, COX'' forms a reactive ester selected from N-hydroxysuccinimide esters, N-hydroxyphthalimide esters, N-hydroxy sulfo-succinimide esters, para-nitrophenyl esters, dinitrophenyl esters, pentafluorophenyl esters and their derivatives, wherein said derivatives facilitate amide bond formation;

Y'' is absent or is selected from O, S, S—S or NR$_{32}$, wherein R$_{32}$ has the same definition as given above for R, or when Y'' is not S—S and t=0, X'' is selected from a maleimido group, a haloacetyl group or SR$_{37}$, wherein R$_{37}$ has the same definition as above;

A'' is an amino acid selected from glycine, alanine, leucine, valine, lysine, citrulline and glutamate or a polypeptide containing between 2 to 20 amino acid units;

R$_{20}$, R$_{21}$, R$_{22}$, R$_{23}$, R$_{24}$, R$_{25}$, R$_{26}$, and R$_{27}$ are the same or different and are H or a linear or branched alkyl having from 1 to 5 carbon atoms;

R$_{29}$ and R$_{30}$ are the same or different and are H or alkyl from 1 to 5 carbon atoms;

R$_{33}$ is H or linear, branched or cyclic alkyl, alkenyl or alkynyl having from 1 to 12 carbon atoms, a polyethylene glycol unit —(OCH$_2$CH$_2$)$_n$, or R$_{33}$ is —COR$_{34}$, —CSR$_{34}$, —SOR$_{34}$, or —SO$_2$R$_{34}$, wherein R$_{34}$ is H or linear, branched or cyclic alkyl, alkenyl or alkynyl having from 1 to 20 carbon atoms or, a polyethylene glycol unit —(OCH$_2$CH$_2$)$_n$; and one of R$_{40}$ and R$_{41}$ is optionally a negatively or positively charged functional group and the other is H or alkyl, alkenyl, alkynyl having 1 to 4 carbon atoms.

The term "amino acid" refers to naturally occurring amino acids or non-naturally occurring amino acid represented by NH$_2$—C(R$^{aa'}$R$^{aa}$)—C(=O)OH, wherein R$^{aa}$ and R$^{aa'}$ are each independently H, an optionally substituted linear, branched or cyclic alkyl, alkenyl or alkynyl having 1 to 10 carbon atoms, aryl, heteroaryl or heterocyclyl. The term "amino acid" also refers to the corresponding residue when one hydrogen atom is removed from the amine and/or carboxy end of the amino acid, such as —NH—C(R$^{aa'}$R$^{aa}$)—C(=O)O—.

The term "cation" refers to an ion with positive charge. The cation can be monovalent (e.g., Na$^+$, K$^+$, etc.), bi-valent (e.g., Ca$^{2+}$, Mg$^{2+}$, etc.) or multi-valent (e.g., Al$^{3+}$ etc.). Preferably, the cation is monovalent.

The term "therapeutically effective amount" means that amount of active compound or conjugate that elicits the desired biological response in a subject. Such response includes alleviation of the symptoms of the disease or disorder being treated, prevention, inhibition or a delay in the recurrence of symptom of the disease or of the disease itself, an increase in the longevity of the subject compared with the absence of the treatment, or prevention, inhibition or delay in the progression of symptom of the disease or of the disease itself. Determination of the effective amount is well within the capability of those skilled in the art, especially in light of the detailed disclosure provided herein. Toxicity and therapeutic efficacy of compound I can be determined by standard pharmaceutical procedures in cell cultures and in experimental animals. The effective amount of compound or conjugate of the present invention or other therapeutic agent to be administered to a subject will depend on the stage, category and status of the multiple myeloma and characteristics of the subject, such as general health, age, sex, body weight and drug tolerance. The effective amount of compound or conjugate of the present invention or other therapeutic agent to be administered will also depend on administration route and dosage form. Dosage amount and interval can be adjusted individually to provide plasma levels of the active compound that are sufficient to maintain desired therapeutic effects.

The term "thiol reactive group" refers to a functional group that will react with a thiol moiety. Examples of thiol reactive group includes, but is not limited to, maleimido, vinylpyridine, vinyl sulfone, vinyl sulfonamide, a haloacetyl-based group (e.g., haloacetamido) or a disulfide (e.g., —SSR$^d$, wherein R$^d$ is a linear or branched alkyl having 1 to 4 carbon atoms, phenyl, nitrophenyl, dinitrophenyl, carboxynitrophenyl, pyridyl, 2-nitropyridyl, 4-nitropyridyl, or 3-carboxy-4-nitropyridyl).

The term "reactive ester" refers to an ester contains a leaving group that is readily displaced by an amine group or a hydroxyl group. Examples of reactive ester includes, but is not limited to, N-hydroxysuccinimide ester, N-hydroxy sulfosuccinimide ester, nitrophenyl ester, dinitrophenyl ester, tetrafluorophenyl ester, sulfo-tetraflurophenyl ester, and pentafluorophenyl ester. Preferably, the reactive ester is N-hydroxysuccinimide (NHS) ester.

The term "an imine-containing drug" or "an imine-containing cytotoxic compound" refers to a compound described herein (without a linker group) that has at least one imine functional group. Preferably, the imine-containing drug contains one imine functional group.

Methods of the Present Invention

In a first aspect, the present invention is directed to a method for preparing a conjugate comprising a cell-binding agent (CBA) conjugated to a cytotoxic compound with a linking group, the method comprising reacting a cytotoxic compound with a modified CBA at a pH of about 4 to about 9, wherein:
a) the modified CBA comprises a residue of a bifunctional crosslinking agent bonded to the CBA, and the residue comprises the linking group and a thiol-reactive group; and
b) the cytotoxic compound comprises a thiol group, and a group represented by:

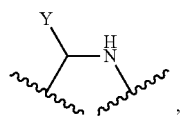

wherein:
Y is a leaving group, and is a sulfite (HSO$_3$, HSO$_2$ or a salt of HSO$_3^-$, SO$_3^{2-}$ or HSO$_2^-$ formed with a cation), metabisulfite (H$_2$S$_2$O$_5$ or a salt of S$_2$O$_5^{2-}$ formed with a cation), mono-, di-, tri-, and tetra-thiophosphate (PO$_3$SH$_3$, PO$_2$S$_2$H$_2$, POS$_3$H$_2$, PS$_4$H$_2$ or a salt of PO$_3$S$^{3-}$, PO$_2$S$_2^{3-}$, POS$_3^{3-}$ or PS$_4^{3-}$ formed with a cation), thio phosphate ester (R$^i$O)$_2$PS (OR$^i$), R$^i$S—, R$^i$SO, R$^i$SO$_2$, R$^i$SO$_3$, thiosulfate (HS$_2$O$_3$ or a salt of S$_2$O$_3^{2-}$ formed with a cation), dithionite (HS$_2$O$_4$ or a salt of S$_2$O$_4^{2-}$ formed with a cation), phosphorodithioate (P(=S)(OR$^{k'}$)(S)(OH) or a salt thereof formed with a cation), hydroxamic acid (R$^{k'}$C(=O)NOH or a salt formed with a cation), formaldehyde sulfoxylate (HOCH$_2$SO$_2^-$ or a salt of HOCH$_2$SO$_2^-$ formed with a cation, such as HOCH$_2$SO$_2^-$Na$^+$) or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl.

In certain embodiments, the cytotoxic compound is produced by reacting an imine-containing cytotoxic compound bearing the thiol group with an imine reactive reagent.

In certain embodiments, the method may further comprises purifying the cytotoxic compound prior to reacting with the modified CBA.

In certain embodiments,
(1) the imine-containing cytotoxic compound is represented by one of the following formulae, or a pharmaceutically acceptable salt thereof:

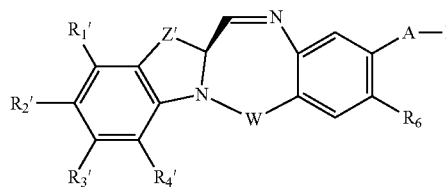

(I)

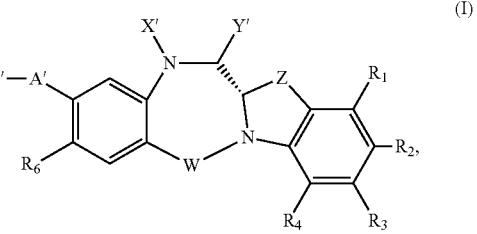

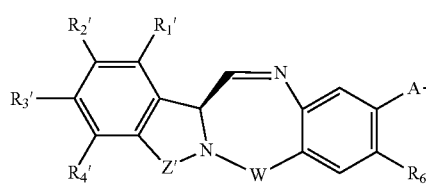

(II)

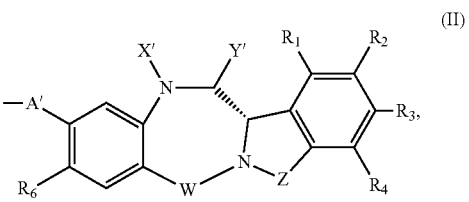

(2) the cytotoxic compound is represented by one of the following formulae, or a pharmaceutically acceptable salt thereof:

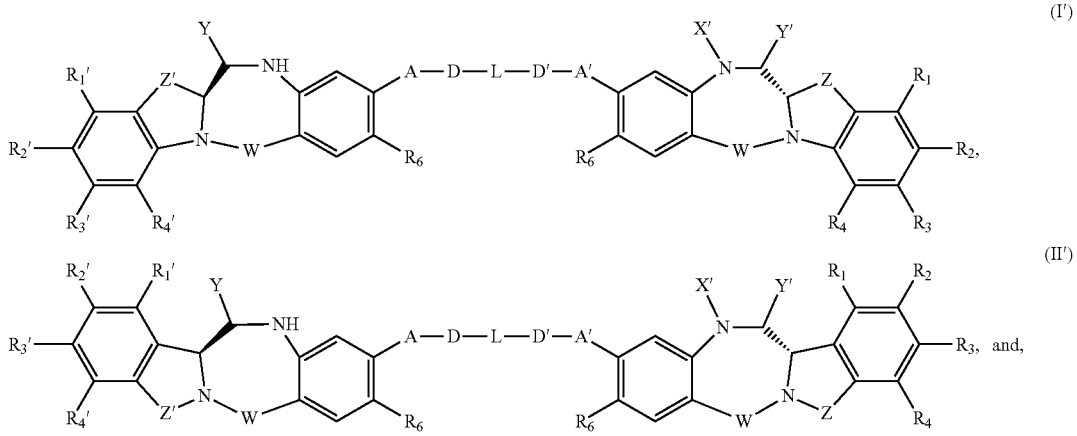

(3) the cytotoxic compound and the linking group portion of the conjugate is represented by one of the following formulae:

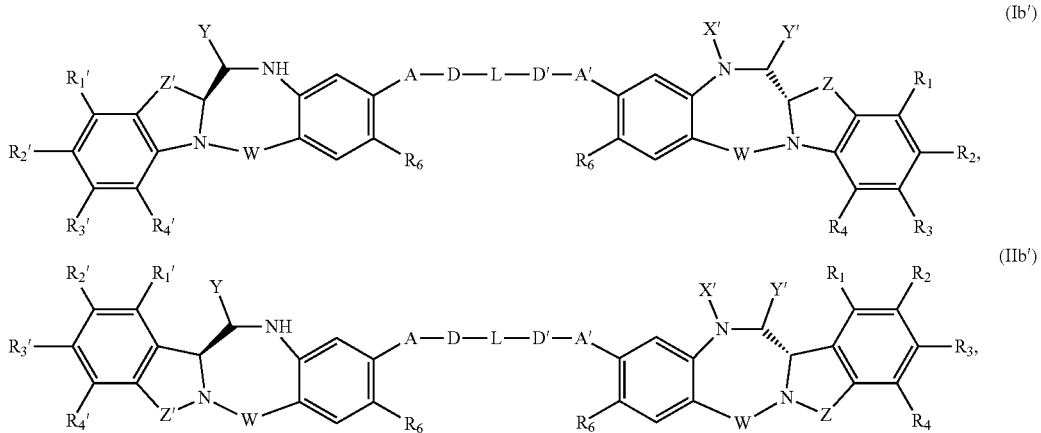

wherein:
X' is selected from —H, an amine-protecting group, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms indepen dently selected from nitrogen, oxygen, and sulfur, an optionally substituted 3 to 18-membered heterocyclic ring having 1 to 6 heteroatoms;

$R^c$ is —H or a substituted or unsubstituted linear or branched alkyl having 1 to 4 carbon atoms;

$R_1$, $R_2$, $R_3$, $R_4$, $R_1'$, $R_2'$, $R_3'$ and $R_4'$ are each independently selected from the group consisting of —H, an optionally substituted linear, branched or cyclic alkyl, alkenyl or alkynyl having from 1 to 10 carbon atoms, a polyethylene glycol unit —$(OCH_2CH_2)_n$—$R^c$, halogen, guanidinium [—NH(C=NH)$NH_2$], —OR, —NR'R'', —$NO_2$, —NCO, —NR'COR'', —SR, a sulfoxide represented by —SOR', a sulfone represented by —$SO_2R'$, a sulfonate —$SO_3^-M^+$, a sulfate —$OSO_3^-M^+$, a sulfonamide represented by —$SO_2NR'R''$, cyano, an azido, —COR', —OCOR', —OCONR'R'';

R, for each occurrence, is independently selected from the group consisting of —H, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3-18-membered heterocyclic ring having 1 to 6 heteroatoms independently selected from O, S, N and P;

n is an integer from 1 to 24;

W is selected from C=O, C=S, CH$_2$, BH, SO and SO$_2$;

R$_6$ is —H, —R, —OR, —SR, —NR'R", —NO$_2$, or halogen;

Z and Z' are independently selected from —(CH$_2$)$_{n'}$—, —(CH$_2$)$_{n'}$—CR$_7$R$_8$—(CH$_2$)$_{na'}$—, —(CH$_2$)$_{n'}$—NR$_9$—(CH$_2$)$_{na'}$—, —(CH$_2$)$_{n'}$—O—(CH$_2$)$_{na'}$— and —(CH$_2$)$_{n'}$—S—(CH$_2$)$_{na'}$—;

n' and na' are the same or different, and are selected from 0, 1, 2 and 3;

R$_7$ and R$_8$ are the same or different, and are each independently selected from —H, —OH, —SH, —COOH, —NHR', a polyethylene glycol unit —(OCH$_2$CH$_2$)$_n$—, an amino acid, a peptide unit bearing 2 to 6 amino acids, an optionally substituted linear, branched or cyclic alkyl having from 1 to 10 carbon atoms;

R$_9$ is independently selected from —H, an optionally substituted linear, branched or cyclic alkyl having from 1 to 10 carbon atoms, a polyethylene glycol unit —(OCH$_2$CH$_2$)$_n$—;

A and A' are the same or different, and are independently selected from —O—, oxo (—C(=O)—), —CRR'O—, —CRR'—, —S—, —CRR'S—, —N(R$_5$)— and —CRR'N(R$_5$)—, R$_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;

L is absent, or when present, comprises the thiol group, or is a polyethylene glycol unit (—OCH$_2$CH$_2$)$_n$—, a linear, branched or cyclic alkyl or alkenyl having 1 to 10 carbon atoms, a phenyl group, a 3- to 18-membered heterocyclic ring or a 5- to 18-membered heteroaryl ring having 1 to 6 heteroatoms independently selected from O, S, N and P, wherein the alkyl, alkenyl, phenyl, or heterocyclic or heteroaryl ring is optionally substituted;

wherein at least one of X', Y', R$_6$, R$^c$, R$_1$, R$_2$, R$_3$, R$_4$, R$_1$', R$_2$', R$_3$', R$_4$', L (e.g., through an optionally substituted group), is bonded to the linking group in formulas (Ib') or (IIb').

In certain embodiments, the modified CBA is prepared by reacting the CBA with the bifunctional crosslinking agent, said bifunctional crosslinking agent comprising the thiol-reactive group and a group reactive with the CBA, both bonded to the linking group.

In certain embodiments, the group reactive with the CBA reacts with an amino group of the CBA (such as the amino group of a Lys sidechain), or with a thiol group of the CBA (such as the thiol group of a Cys sidechain).

In certain embodiments, the thiol-reactive group is selected from the group consisting of maleimido, vinylpyridine, vinyl sulfone, vinyl sulfonamide, a haloacetyl-based group and a disulfide group.

alternatively, the thiol-reactive group may be maleimido, haloacetamido or —SSR$^d$, wherein R$^d$ is a linear or branched alkyl having 1 to 4 carbon atoms, phenyl, nitrophenyl, dinitrophenyl, carboxynitrophenyl, pyridyl, 2-nitropyridyl, 4-nitropyridyl, or 3-carboxy-4-nitropyridyl.

In certain embodiments, the modified CBA is:

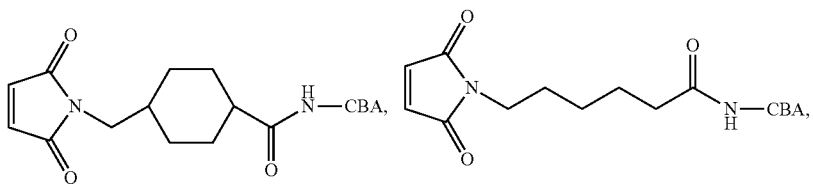

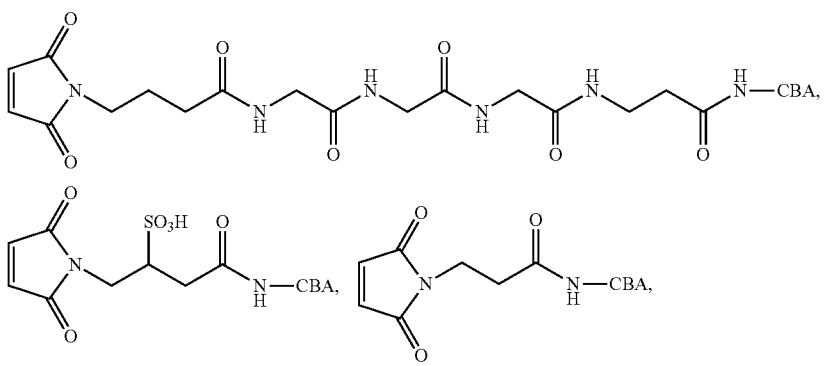

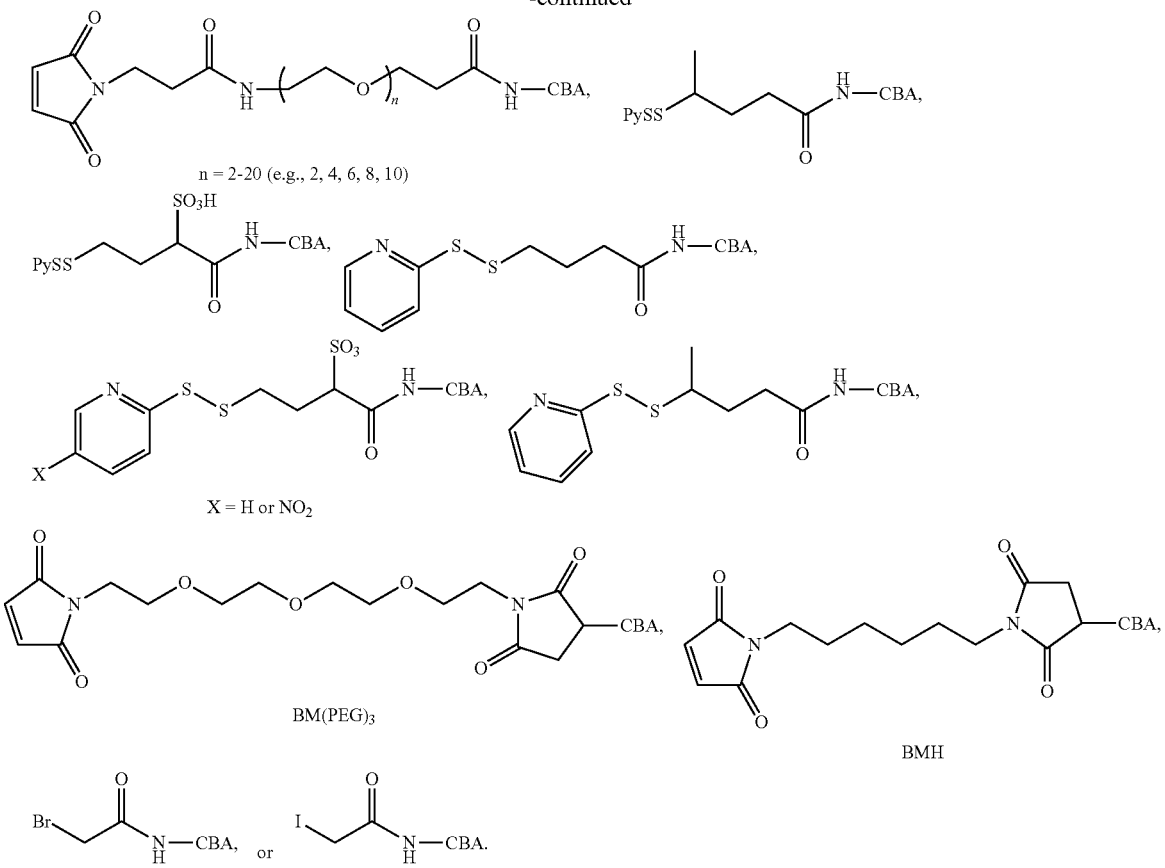

n = 2-20 (e.g., 2, 4, 6, 8, 10)

X = H or NO₂

BM(PEG)₃

BMH

Figure 8:
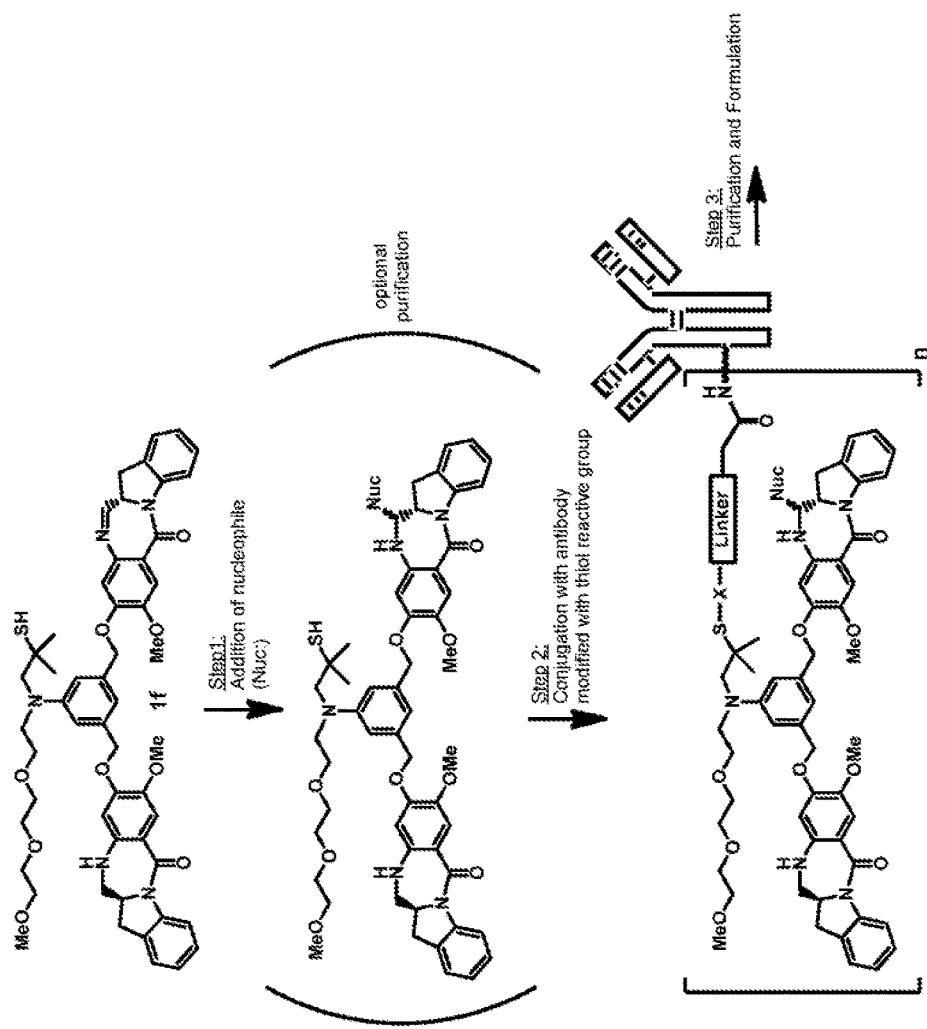

An exemplary reaction scheme is shown in FIG. 8, in which in "step one," an imine reactive reagent (shown in the reaction scheme as a nucleophile (Nuc:)) is added to the drug containing a thiol and allowed to react and form a modified drug bearing the thiol group. The modified drug is optionally purified to remove excess imine reactive reagent. In "step two," the antibody is modified with a linker containing a thiol reactive group X (maleimide, SSPy, vinyl sulfone, etc), and reacted with the modified drug bearing the thiol group at pH 6-9 to generate a stable disulfide or thioether bond between the drug and the antibody. In "step three," the side products (such as excess imine reactive reagent, the modified drug that does not react with the antibody, etc.) are removed and the conjugate is formulated. The number of the drug molecules conjugated to the antibody is equal to n, which can be from, for example, 1-10.

Figure 16:
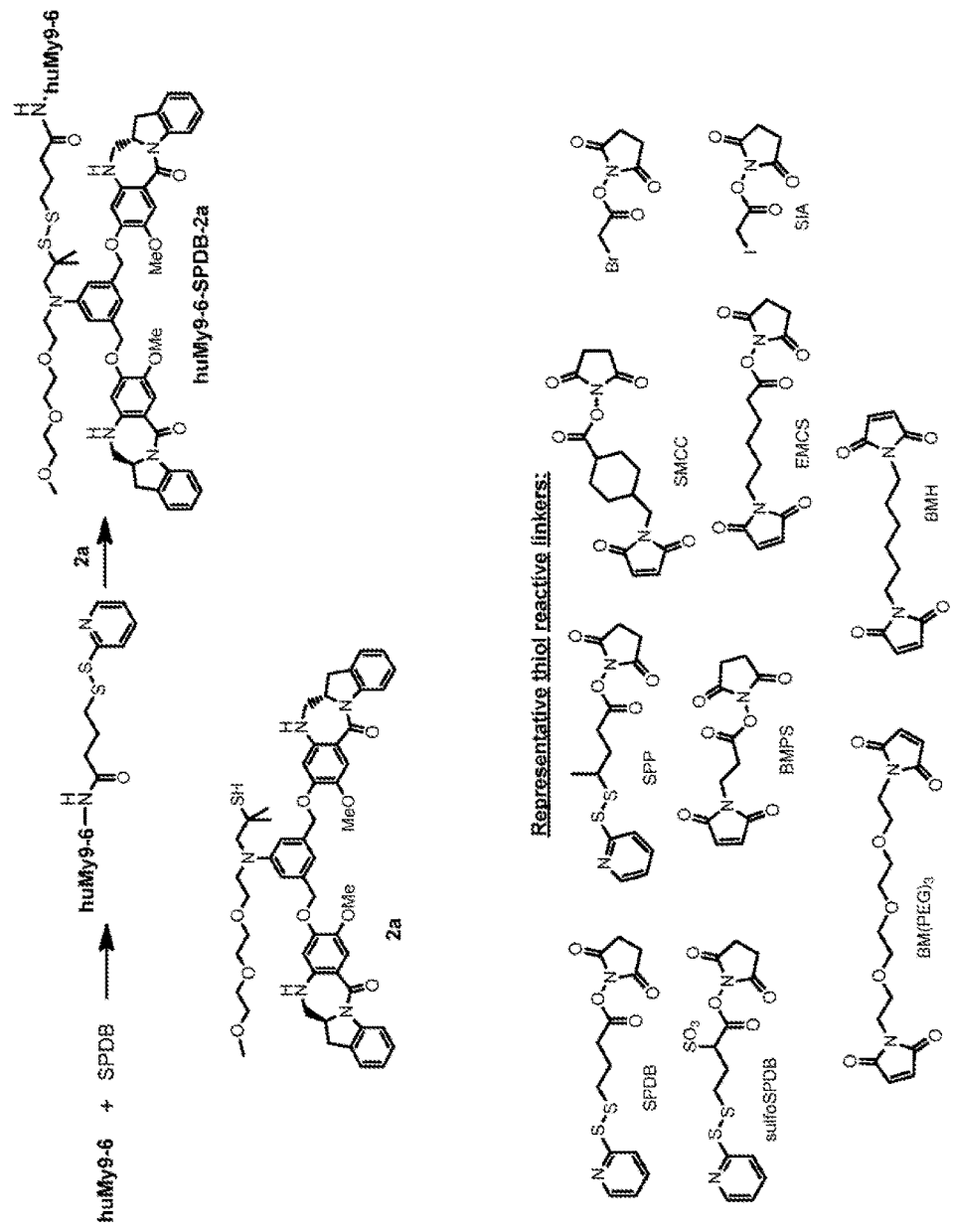
FIG. 16 shows the scheme for the two-step synthesis of the representative antibody-drug conjugates.
Figure 22B:
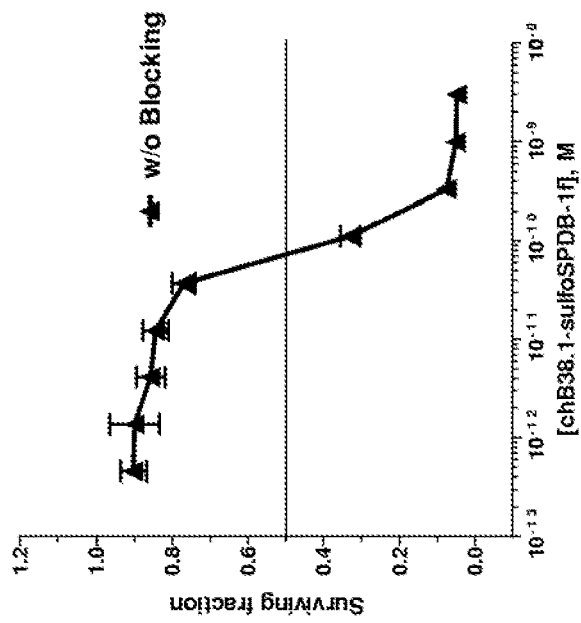
FIGS. 22A and 22B show in vitro cytotoxicity for chB38.1-SPDB-1f (FIG. 22A), and chB38.1-sulfoSPDB-1f (FIG. 22B) against COL0205 ($Ag^+$) cells. Note that in both experiments, sodium bisulfite was added to the conjugation reaction for making the conjugate.
Figure 22A:
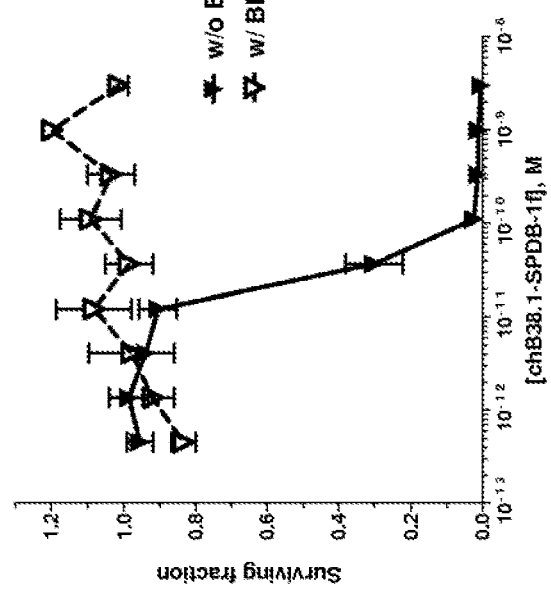
Figure 23:
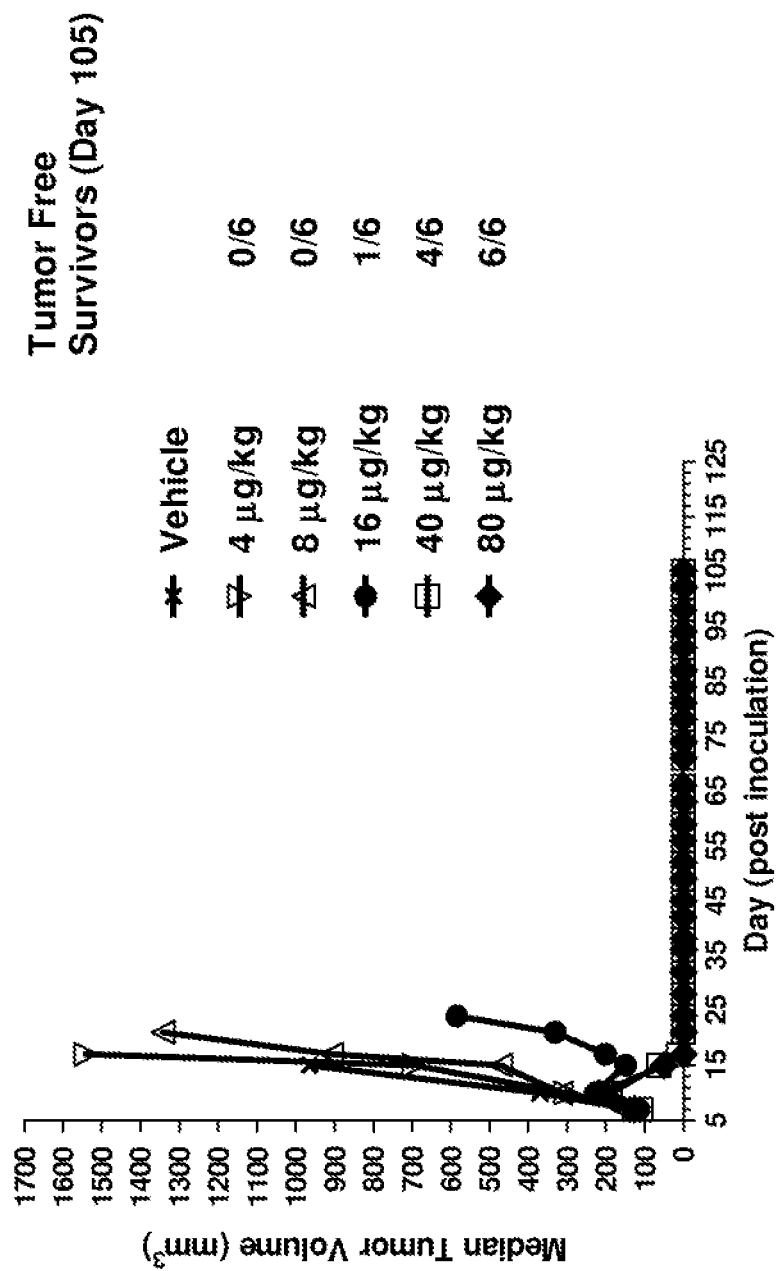
FIG. 23 shows in vivo efficacy of huMy9-6-SPDB-1f in HL60/QC bearing mice. Note that sodium bisulfite was added to the conjugation reaction.
Figure 25:
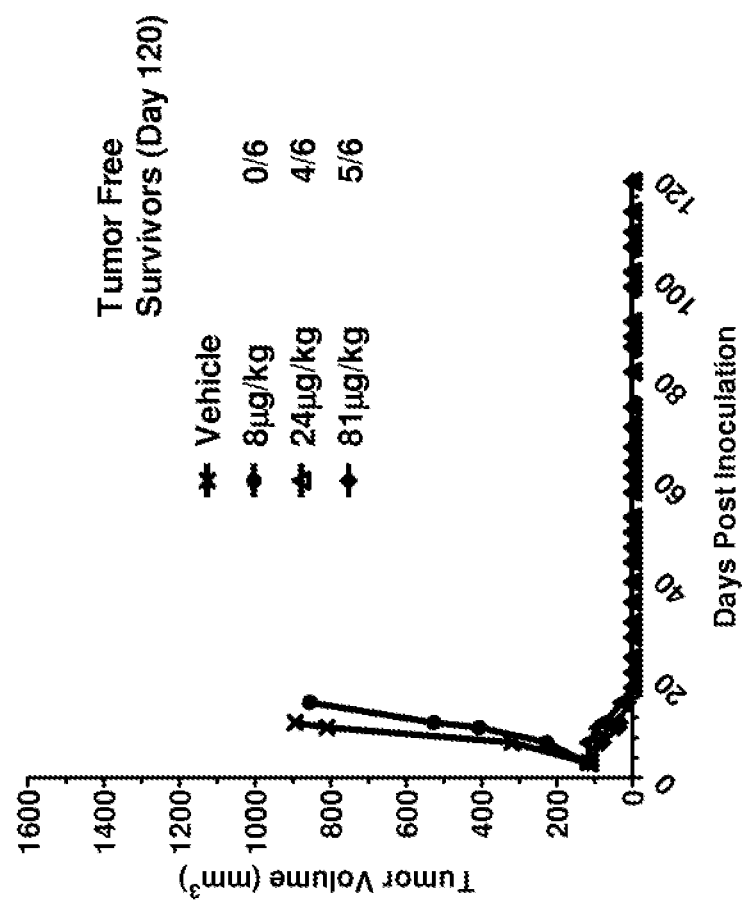
FIG. 25 shows in vivo efficacy of huMy9-6-BMPS-1f in MOLM-13 tumor bearing mice. Note that sodium bisulfite was added to the conjugation reaction for making the conjugate.

A representative example of a two-step conjugation method is described in FIG. 16, wherein an antibody is first modified with a bifunctional crosslinking agent resulting in an antibody that possesses a desired number of linkers suitable for reaction with a dimer compound having a free thiol moiety. In this example the antibody huMy9-6 was first modified with SPDB to give an antibody with linkers containing the dithiopyridyl moiety. The modified antibody was then exposed to a free thiol, such as 2a, generating the desired conjugate huMy9-6-SPDB-2a. Additional suitable thiol reactive linkers that may be used in similar reactions are included in FIG. 16.

The imine reactive reagent can be mixed with the drug bearing a thiol group in organic solvent (e.g., dimethylacetamide, dimethylformamide, dimethylsulfoxide, acetonitrile, ethanol, methanol, methylene chloride, chloroform, dioxane, or a mixture thereof) or a mixture of water (e.g., deionized water) and one or more organic solvents. When only organic solvent is used, the imine reactive reagent can be mixed with the drug at room temperature for 30 min or longer (for example, about 1 hour, about 2 hours, about 3 hours, about 4 hours, about 5 hours, about 10 hours, about 24 hours or until the reaction is complete). Preferably, the incubation/reaction time is about 0-4 hrs, or 1-3 hrs. The resulting mixture can be used immediately to react with the cell-binding agent (e.g., antibody) modified with a thiol-reactive group buffered at pH about 4 to about 9, preferably about 6 to about 9. Alternatively, the mixture can be frozen and stored, for example, at −20° C. or −80° C., and used later while maintaining its reactivity with the cell-binding agent (e.g., antibody). If a mixture of water and organic solvent(s) is used as a miscible co-solvent system (e.g., water and dimethylacetamide), the reaction mixture of drug and imine reactive reagent is used immediately or kept frozen until use after mixing to react with the cell-binding agent bearing a thiol-reactive group. If a mixture of water and organic solvent(s) is used as a non-miscible co-solvent system (e.g., water and methylene chloride), the drug and the imine reactive reagent are mixed for 10 min or longer (for example, about 30 mins, about 1 hour, about 2 hours, about 5 hours, about 10 hours, about 24 hours or until the reaction is complete), and the aqueous layer is collected, quantified for the drug and reactive thiol (e.g., by UV spectroscopy and Ellman's assay with DTNB (5,5'-dithiobis-(2-nitrobenzoic acid)) reagent) and added to the cell-binding agent (e.g., antibody) bearing a thiol-reactive group buffered at pH of about 4 to about 9, preferably about 6 to about 9.

In a second aspect, the present invention provides a method for preparing a conjugate comprising a cell-binding agent (CBA) conjugated to a cytotoxic compound with a linking group, the method comprising reacting the CBA with an imine-containing cytotoxic compound, an imine reactive reagent, and a bifunctional crosslinking agent comprising the linking group to form the conjugate.

In certain embodiments, the cell-binding agent (e.g., antibody) is contacted with a drug (e.g., the imine-containing cytotoxic compound) and an imine reactive reagent to form a first mixture; and the first mixture is then contacted with a bifunctional crosslinking agent to form the cell-binding agent-drug conjugate. Preferably, the bifunctional crosslinking agent is contacted with the first mixture immediately after the formation of the first mixture. Alternatively, the first mixture was held for a time interval (e.g., about 1-10 mins, about 10-30 mins, about 30 mins to 1 hr, about 1 to 5 hrs, about 5 to 24 hrs, or about 1 to 2 days) before it is contacted with a bifunctional crosslinking agent.

In certain embodiments, the method may further comprises purifying the conjugate.

Figure 10:
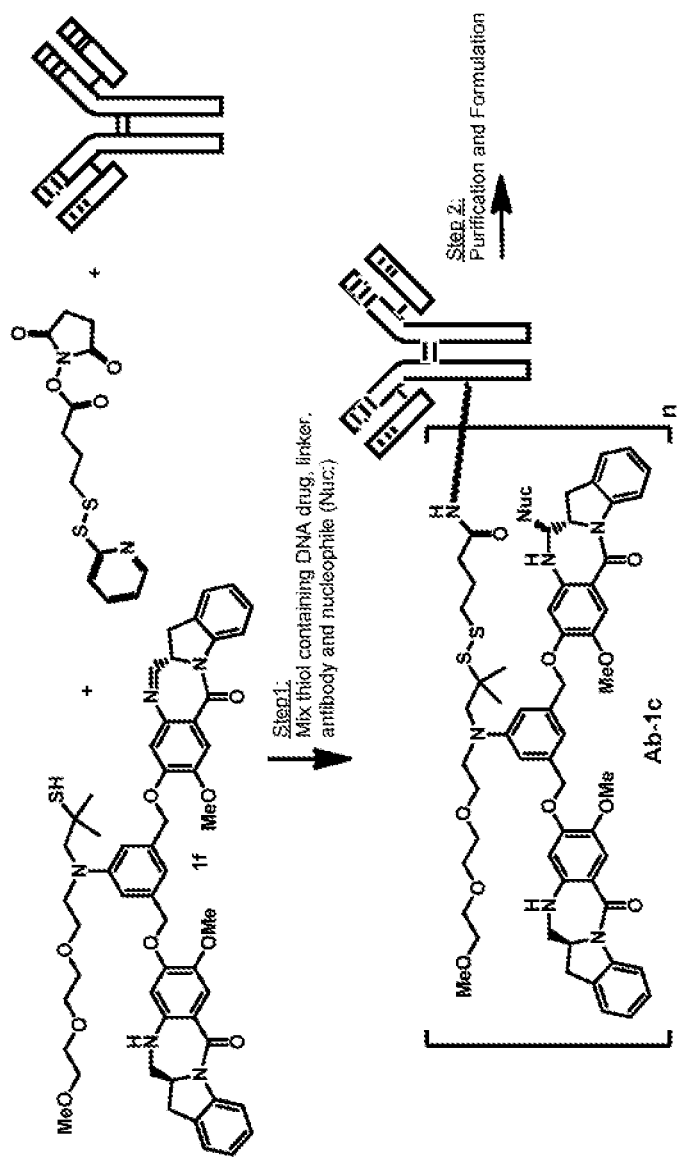

An exemplary reaction scheme is shown in FIG. 10, in which in "step 1," an imine reactive reagent (shown in the reaction scheme as a nucleophile (Nuc:)) is added to the CBA (e.g., an antibody), a drug containing a thiol, a bifunctional crosslinking agent containing both a thiol reactive group X (maleimide, SSPy, vinyl sulfone, etc) and a reactive ester group, and allow the reaction to proceed at pH 6-9 to generate a stable drug-antibody conjugate. In "step two," the side products (such as excess imine reactive reagent, the modified drug that does not react with the antibody, etc.) are removed and the conjugate is formulated. The number of the drug molecules conjugated to the antibody is equal to n, which can be from, for example, 1-10.

In a third aspect, the present invention provides a method for preparing a conjugate comprising a cell-binding agent (CBA) conjugated to a cytotoxic compound with a linking group, the method comprising:

a) reacting a cytotoxic compound with a bifunctional crosslinking agent comprising the linking group, a group reactive with the CBA (such as a thiol group, a maleimide group, a haloacetamide group, or an amine group), and a group reactive with the cytotoxic compound, to form a modified cytotoxic compound covalently bonded to a residue of the bifunctional crosslinking agent, wherein the residue comprises the linking group and the group reactive with the CBA;

wherein the cytotoxic compound is represented by one of the following formulas, or a pharmaceutically acceptable salt thereof:

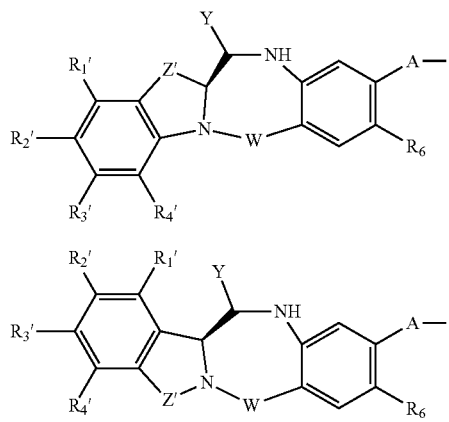

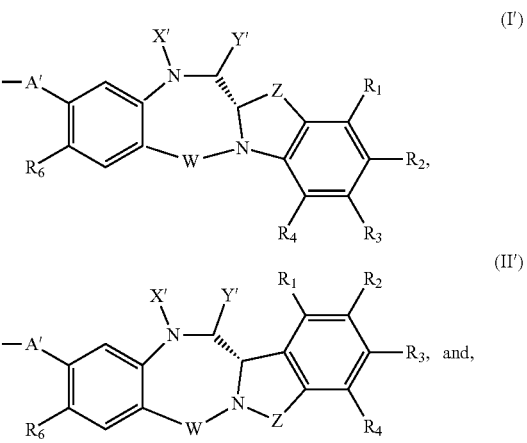

wherein:
Y is a leaving group, and is a sulfite ($HSO_3$, $HSO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono-, di-, tri-, and tetra-thiophosphate ($PO_3SH_3$, $PO_2S_2H_2$, $POS_3H_2$, $PS_4H_2$ or a salt of $PO_3S^{3-}$, $PO_2S_2^{3-}$, $POS_3^{3-}$ or $PS_4^{3-}$ formed with a cation), thio phosphate ester $(R^iO)_2PS(OR^i)$, $R^iS$—, $R^iSO$, $R^iSO_2$, $R^iSO_3$, thiosulfate ($HS_2O_3$ or a salt of $S_2O_3^{2-}$ formed with a cation), dithionite ($HS_2O_4$ or a salt of $S_2O_4^{2-}$ formed with a cation), phosphorodithioate ($P(=S)(OR^{k'})(S)(OH)$ or a salt thereof formed with a cation), hydroxamic acid ($R^{k'}C(=O)NOH$ or a salt formed with a cation), formaldehyde sulfoxylate ($HOCH_2SO_2^-$ or a salt of $HOCH_2SO_2^-$ formed with a cation, such as $HOCH_2SO_2^-Na^+$) or a mixture thereof, wherein $R^i$ is a linear or branched alkyl having 1 to 10 carbon atoms and is substituted with at least one substituent selected from —$N(R^j)_2$, —$CO_2H$, —$SO_3H$, and —$PO_3H$; $R^i$ can be further optionally substituted with a substituent for an alkyl described herein; $R^j$ is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl;

X' is selected from —H, an amine-protecting group, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3 to 18-membered heterocyclic ring having 1 to 6 heteroatoms;

$R^c$ is —H or a substituted or unsubstituted linear or branched alkyl having 1 to 4 carbon atoms;

$R_1$, $R_2$, $R_3$, $R_4$, $R_1'$, $R_2'$, $R_3'$ and $R_4'$ are each independently selected from the group consisting of —H, an optionally substituted linear, branched or cyclic alkyl, alkenyl or alkynyl having from 1 to 10 carbon atoms, a polyethylene glycol unit —$(OCH_2CH_2)_n$—$R^c$, halogen, guanidinium [—NH(C=NH)NH$_2$], —OR, —NR'R", —NO$_2$, —NCO, —NR'COR", —SR, a sulfoxide represented by —SOR', a sulfone represented by —SO$_2$R', a sulfonate —SO$_3^-$M$^+$, a sulfate —OSO$_3^-$M$^+$, a sulfonamide represented by —SO$_2$NR'R", cyano, an azido, —COR', —OCOR', —OCONR'R";

R, for each occurrence, is independently selected from the group consisting of —H, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —$(CH_2CH_2O)_n$—$R^c$, and an optionally substituted 3-18-membered heterocyclic ring having 1 to 6 heteroatoms independently selected from O, S, N and P;

n is an integer from 1 to 24;

W is selected from C=O, C=S, CH$_2$, BH, SO and SO$_2$;

$R_6$ is —H, —R, —OR, —SR, —NR'R", —NO$_2$, or, halogen;

Z and Z' are independently selected from —$(CH_2)_{n'}$—, —$(CH_2)_{n'}$—$CR_7R_8$—$(CH_2)_{na'}$—, —$(CH_2)_{n'}$—NR$_9$—$(CH_2)_{na'}$—, —$(CH_2)_{n'}$—O—$(CH_2)_{na'}$— and —$(CH_2)_{n'}$—S—$(CH_2)_{na'}$—;

n' and na' are the same or different, and are selected from 0, 1, 2 and 3;

$R_7$ and $R_8$ are the same or different, and are each independently selected from —H, —OH, —SH, —COOH, —NHR', a polyethylene glycol unit —$(OCH_2CH_2)_n$—, an amino acid, a peptide unit bearing 2 to 6 amino acids, an optionally substituted linear, branched or cyclic alkyl having from 1 to 10 carbon atoms;

$R_9$ is independently selected from —H, an optionally substituted linear, branched or cyclic alkyl having from 1 to 10 carbon atoms, a polyethylene glycol unit —$(OCH_2CH_2)_n$—;

A and A' are the same or different, and are independently selected from —O—, oxo (—C(=O)—), —CRR'O—, —CRR'—, —S—, —CRR'S—, —N(R$_5$)— and —CRR'N(R$_5$)—, $R_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;

L is absent, or when present, comprises the thiol group, or is a polyethylene glycol unit (—OCH$_2$CH$_2$)$_n$—, a linear, branched or cyclic alkyl or alkenyl having 1 to 10 carbon atoms, a phenyl group, a 3- to 18-membered heterocyclic ring or a 5- to 18-membered heteroaryl ring having 1 to 6 heteroatoms independently selected from O, S, N and P, wherein the alkyl, alkenyl, phenyl, or heterocyclic or heteroaryl ring is optionally substituted; and, b) reacting the modified cytotoxic compound with the CBA through the group reactive with the CBA, at a pH of about 4 to about 9, to form the conjugate.

In certain embodiments, the cytotoxic compound is produced by reacting an imine-containing cytotoxic compound bearing the thiol group of the following formulas with an imine reactive reagent in a reaction mixture

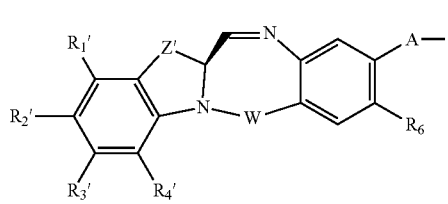
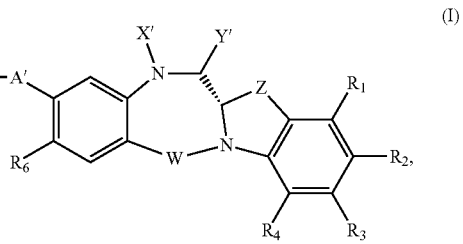

(I)

-continued

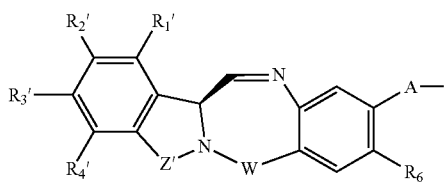 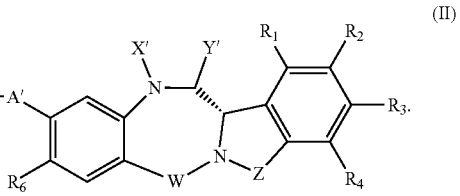

(II)

In certain embodiments, the method may further comprises purifying the cytotoxic compound prior to step a).

In certain embodiments, the method may further comprises purifying the modified cytotoxic compound prior to step b).

In certain embodiments, the reaction mixture is stored frozen before the frozen mixture is thawed and step a) is carried out.

In certain embodiments, the method may further comprises storing the reaction mixture of step a) frozen before thawing and before step b) is carried out.

In certain embodiments, the bifunctional crosslinking agent is bis-maleimidohexane or BMPEO.

Figure 11:
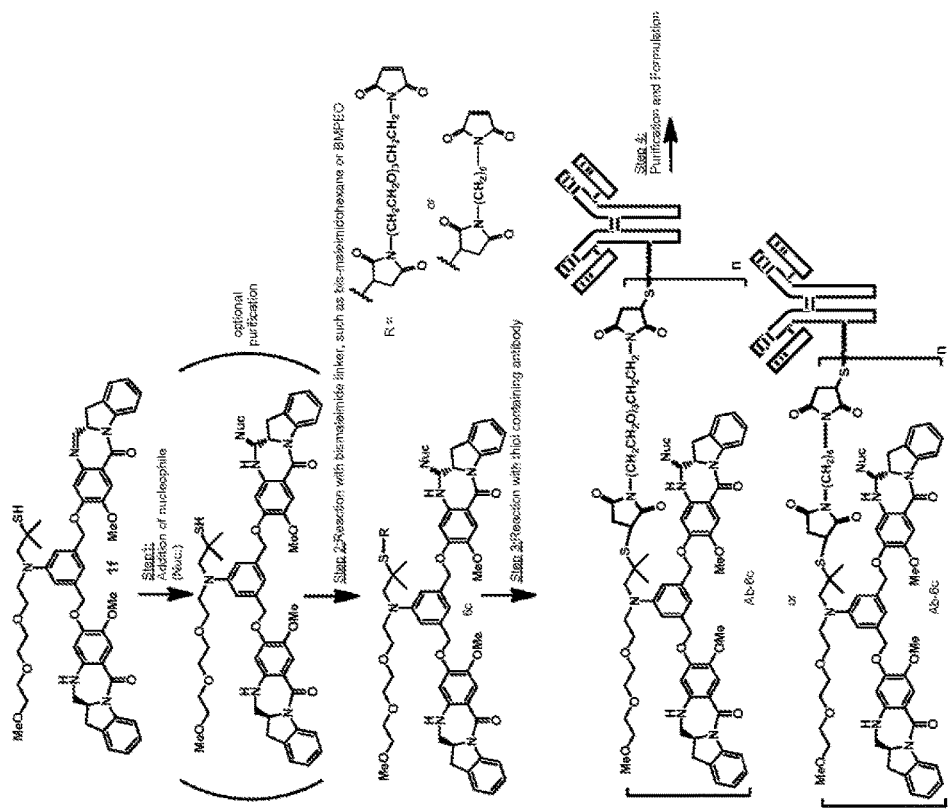

An exemplary reaction scheme is shown in FIG. 11, in which in "step 1," an imine reactive reagent (shown in the reaction scheme as a nucleophile (Nuc:)) is added to a cytotoxic compound containing a thiol. The resulting cytotoxic compound is optionally purified, before the cytotoxic compound is reacted in "step two" with a bifunctional crosslinking agent (such as a bismaleimidohexane or BMPEO) to produce a second modified drug bearing a thiol-reacting group. Then in "step three," a thiol-containing CBA (such as antibody) is added, and the reaction is allowed to proceed (at pH 6-9) to generate a stable drug-antibody conjugate. In "step four," the side products (such as excess imine reactive reagent, the modified drug that does not react with the antibody, etc.) are removed and the conjugate is formulated. The number of the drug molecules conjugated to the antibody is equal to n, which can be from, for example, 1-10.

The imine reactive reagent can be mixed with the drug bearing a thiol-reactive group in organic solvent (e.g., dimethylacetamide, dimethylformamide, dimethylsulfoxide, acetonitrile, ethanol, methanol, methylene chloride, chloroform, dioxane, or a mixture thereof) or a mixture of water (e.g., deionized water) and one or more organic solvents. When only organic solvent is used, the imine reactive reagent can be mixed with the drug at room temperature for 30 min or longer (for example, about 1 hour, about 2 hours, about 3 hours, about 4 hours, about 5 hours, about 10 hours, about 24 hours or until the reaction is complete). Preferably, the incubation/reaction time is about 0-4 hrs, or 1-3 hrs. The resulting mixture can be used immediately to react with the cell-binding agent (e.g., antibody) modified with a thiol-reactive group buffered at pH about 4 to about 9, preferably about 6 to about 9. Alternatively, the mixture can be frozen and stored, for example, at −20° C. or −80° C., and used later while maintaining its reactivity with the cell-binding agent (e.g., antibody). If a mixture of water and organic solvent(s) is used as a miscible co-solvent system (e.g., water and dimethylacetamide), the reaction mixture of the drug and the imine reactive reagent is used immediately after mixing or kept frozen until use to react with the cell-binding agent bearing a thiol-reactive group. If a mixture of water and organic solvent(s) is used as a non-miscible co-solvent system (e.g., water and methylene chloride), the drug and the imine reactive reagent are mixed for 10 min or longer (for example, about 30 mins, about 1 hour, about 2 hours, about 5 hours, about 10 hours, about 24 hours or until the reaction is complete), and the aqueous layer is collected, quantified for the drug (e.g., by UV spectroscopy) and added to the cell-binding agent (e.g., antibody) bearing a thiol group buffered at pH of about 4 to about 9, preferably about 6 to about 9.

In a fourth aspect, the present invention is directed to a method for preparing a conjugate comprising a cell-binding agent (CBA) conjugated to a cytotoxic compound with a linking group, the method comprising reacting a modified cytotoxic compound with the CBA at a pH of about 4 to about 9, wherein the modified cytotoxic compound comprises:

a) a residue of a bifunctional crosslinking agent bonded to the cytotoxic compound, and the residue comprises the linking group and a reactive group selected from a reactive ester and a thiol-reactive group, and, b) a group represented by:

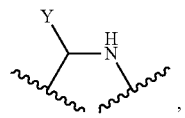

, wherein:

Y is a leaving group, and is a sulfite ($HSO_3$, $HSO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono-, di-, tri-, and tetra-thiophosphate ($PO_3SH_3$, $PO_2S_2H_2$, $POS_3H_2$, $PS_4H_2$ or a salt of $PO_3S^{3-}$, $PO_2S_2^{3-}$, $POS_3^{3-}$ or $PS_4^{3-}$ formed with a cation), thio phosphate ester $(R^iO)_2PS(OR^i)$, $R^iS-$, $R^iSO$, $R^iSO_2$, $R^iSO_3$, thiosulfate ($HS_2O_3$ or a salt of $S_2O_3^{2-}$ formed with a cation), dithionite ($HS_2O_4$ or a salt of $S_2O_4^{2-}$ formed with a cation), phosphorodithioate ($P(=S)(OR^{k'})(S)(OH)$ or a salt thereof formed with a cation), hydroxamic acid ($R^{k'}C(=O)NOH$ or a salt formed with a cation), formaldehyde sulfoxylate ($HOCH_2SO_2^-$ or a salt of $HOCH_2SO_2^-$ formed with a cation, such as $HOCH_2SO_2^-Na^+$) or a mixture thereof, wherein $R^i$ is a linear or branched alkyl having 1 to 10 carbon atoms and is substituted with at least one substituent selected from $-N(R^j)_2$, $-CO_2H$, $-SO_3H$, and $-PO_3H$; $R^i$ can be further optionally substituted with a substituent for an alkyl described herein; $R^j$ is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl.

In certain embodiments, the modified cytotoxic compound is produced by reacting an imine reactive reagent with an imine-containing cytotoxic compound bearing the linking group and the reactive group.

In certain embodiments, the method may further comprises purifying the modified cytotoxic compound prior to reacting with the CBA.

In certain embodiments, the reactive ester may be selected from the group consisting of N-hydroxysuccinimide ester, N-hydroxy sulfosuccinimide ester, nitrophenyl ester, dinitrophenyl ester, tetrafluorophenyl ester, sulfo-tetraflurophenyl ester, and pentafluorophenyl ester. Preferably, the reactive ester is N-hydroxysuccinimide ester.

In certain embodiments, the thiol-reactive group may be selected from the group consisting of maleimido, vinylpyridine, vinyl sulfone, vinyl sulfonamide, a haloacetyl-based group and a disulfide group.

In certain embodiments, the thiol-reactive group may be maleimido, haloacetamido or —SSR$^d$, wherein R$^d$ is a linear or branched alkyl having 1 to 4 carbon atoms, phenyl, nitrophenyl, dinitrophenyl, carboxynitrophenyl, pyridyl, 2-nitropyridyl, 4-nitropyridyl, or 3-carboxy-4-nitropyridyl.

Figure 7:
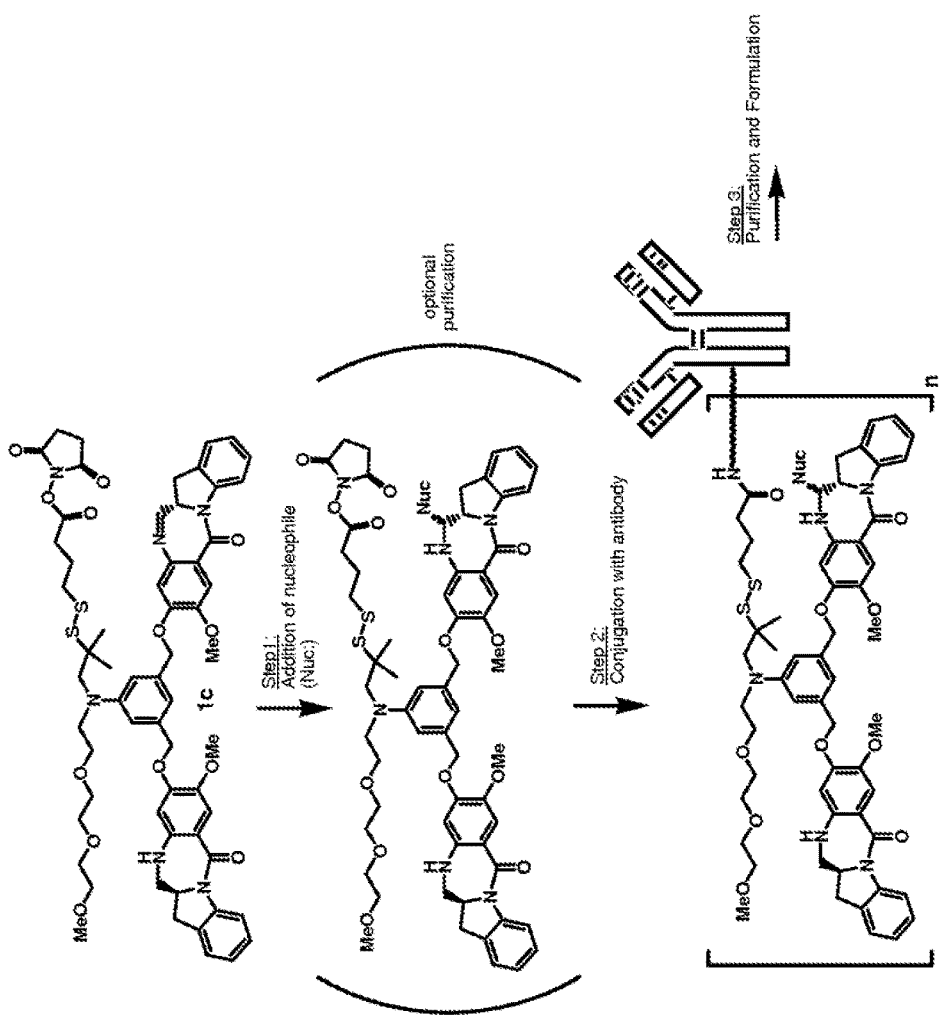
FIGS. 7, 8, 9, 10 and 11 show exemplary methods of the present invention for preparing a cell-binding agent-drug conjugate.

An exemplary reaction scheme is shown in FIG. 7, in which in "step one," an imine reactive reagent (shown in the reaction scheme as a nucleophile (Nuc:)) is added to the drug containing an reactive ester (1c) and allowed to react to form a modified drug. The modified drug can be optionally purified to remove excess imine reactive reagent. In "step two," the modified drug with a reactive ester is reacted with an antibody buffered at pH 6-9. In "step three," the side products (such as excess imine reactive reagent, modified drug that does not react with the antibody, etc.) are removed, and the conjugate is formulated. The number of the drug molecules conjugated to the antibody is equal to n, which can be from, for example, 1 to 10.

Figure 9:
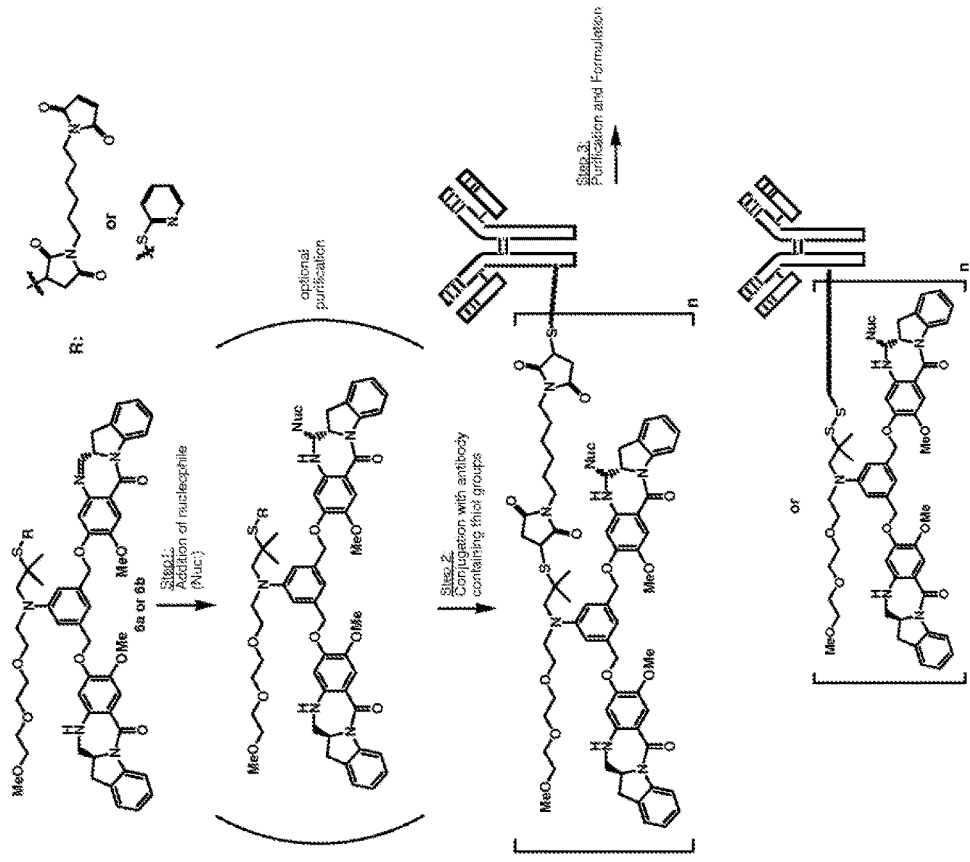

Another reaction scheme depicting an exemplary method of the present invention is shown in FIG. 9. In "step one," an imine reactive regent is added to the drug containing a thiol-reactive group (where R is maleimide group, SSPy, etc.) and allowed to react and form a modified drug. The modified drug is optionally purified to remove excess imine reactive reagent. In "step two," the modified drug is reacted with an antibody containing a reactive thiol to form an antibody-drug conjugate having antibody covalently linked to the drug through a stable disulfide or thioether bond. Antibodies with reactive thiol group can be generated by methods described herein, for example, by reducing interchain disulfides, genetically encoding cysteine, or modifying antibody with linkers containing thiols or chemically masked thiols. In "step three," the drug which does not react with the antibody is removed and the conjugate is formulated. The number of the drug molecules conjugated to the antibody is equal to n, which can be from, for example, 1-10.

The imine reactive reagent can be mixed with the drug bearing an activated ester (e.g., N-hydroxysuccinimidyl ester, pentafluorophenol ester, sulfo N-hydroxysuccinimidyl ester) in an organic solvent (e.g., dimethyl acetamide, ethanol, methylene chloride, chloroform, dioxane, or a mixture thereof) or a mixture of water (e.g., deionized water) and one or more organic solvents. When only organic solvent is used, the imine reactive reagent can be mixed with the drug at a temperature of 0 to 100° C., preferably at a temperature of 0 to 30° C., more preferably at room temperature for 5 min or longer (for example, about 30 min, 1 hour, about 2 hours, about 3 hours, about 4 hours, about 5 hours, about 10 hours, about 24 hours or until the reaction is complete). Preferably, the incubation/reaction time is about 0-4 hrs, or 1-3 hrs. The resulting reaction mixture can be used immediately to react with the cell-binding agent (e.g., antibody) buffered in pH of about 4 to about 9, preferably about 6 to about 9. Alternatively, the reaction mixture can be frozen and stored, for example, at about −20° C. or −80° C. and used later while maintaining its reactivity with the antibody. Preferably, no purification of intermediate products is required. When a mixture of water and organic solvent is used as a miscible co-solvent system (e.g., water and dimethylacetamide), the drug and imine reaction mixture is used immediately after mixing, or kept frozen until use, to react with the cell-binding agent (e.g., antibody). When a mixture of water and organic solvent is used as a non-miscible co-solvent system (e.g., water and methylene chloride), the drug and the imine reactive reagent are mixed for 10 min or longer, and the aqueous layer is collected, quantified for the drug and added to the cell-binding agent (e.g., antibody) buffered at pH about 4 to about 9, preferably about 6 to about 9.

In any of the above aspects, a suitable amount of the imine reactive reagent can be used. For example, about 0.1 to about 30 molar equivalents of the imine reactive reagent to the drug can be used. Preferably, about 1 to about 10 molar equivalents, more preferably, about 1 to about 5 molar equivalents, and even more preferably about 3 to about 5 molar equivalents of the imine reactive reagent can be used.

Using this general procedure, in any of the above aspects, any of the following imine reactive reagent can be used: sulfites ($H_2SO_3$, $H_2SO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono, di, tri, and tetra-thiophosphates ($PO_3SH_3$, $PO_2S_2H_3$, $POS_3H_3$, $PS_4H_3$ or a salt of $PO_3S^{3-}$, $PO_2S_2^{3-}$, $POS_3^{3-}$ or $PS_4^{3-}$ formed with a cation), thio phosphate esters (($R^iO)_2PS(OR^i$), $R^i$SH, $R^i$SOH, $R^i$SO$_2$H, $R^i$SO$_3$H), various amines (hydroxyl amine (e.g., $NH_2OH$), hydrazine (e.g., $NH_2NH_2$), $NH_2O$—$R^i$, $R^{ii}$NH—$R^i$, $NH_2$—$R^i$), $NH_2$—CO—$NH_2$, $NH_2$—C(=S)—$NH_2$, thiosulfate ($H_2S_2O_3$ or a salt of $S_2O_3^{2-}$ formed with a cation), dithionite ($H_2S_2O_4$ or a salt of $S_2O_4^{2-}$ formed with a cation), phosphorodithioate (P(=S)(OR$^k$)(SH)(OH) or a salt thereof formed with a cation), hydroxamic acid (R$^k$C(=O)NHOH or a salt formed with a cation), hydrazide (R$^k$CONHNH$_2$), formaldehyde sulfoxylate (HOCH$_2$SO$_2$H or a salt of HOCH$_2$SO$_2^-$ formed with a cation, such as HOCH$_2$SO$_2^-$Na$^+$), glycated nucleotide (such as GDP-mannose), fludarabine or a mixture thereof, wherein $R^i$ and $R^{i'}$ are each independently a linear or branched alkyl having 1 to 10 carbon atoms and are substituted with at least one substituent selected from —N(R$^j$)$_2$, —CO$_2$H, —SO$_3$H, and —PO$_3$H; $R^i$ and $R^{i'}$ can be further optionally substituted with a substituent for an alkyl described herein; $R^j$ is a linear or branched alkyl having 1 to 6 carbon atoms; and $R^k$ is a linear, branched or cyclic alkyl, alkenyl or alkynyl having 1 to 10 carbon atoms, aryl, heterocyclyl or heteroaryl (preferably, $R^k$ is a linear or branched alkyl having 1 to 4 carbon atoms; more preferably, $R^k$ is methyl, ethyl or propyl). Preferably, the cation is a monovalent cation, such as Na$^+$ or K$^+$.

Preferably, the imine reactive reagent is selected from sulfites (e.g., NaHSO$_3$ or KHSO$_3$), hydroxylamine, hydrazine and urea. More preferably, the imine reactive reagent is NaHSO$_3$ or KHSO$_3$.

In one embodiment, the modified drugs described in any of the above aspects are purified before reacting with a cell-binding agent. Any suitable methods known in the art can be used for purifying the modified drug. For example, the modified drug can be purified by column chromatography (e.g., silica gel chromatography) or HPLC.

In another embodiment, the cell-binding agent-drug conjugate prepared according to any of the aspects above is purified by tangential flow filtration, adsorptive chromatography, adsorptive filtration, selective precipitation, non-absorptive filtration or combination thereof. Preferably, tangential flow filtration (TFF, also known as cross flow filtration, ultrafiltration and diafiltration) and/or adsorptive chromatography resins are used for the purification of the conjugates.

Any suitable TFF systems may be utilized, including a Pellicon type system (Millipore, Billerica, Mass.), a Sartocon Cassette system (Sartorius AG, Edgewood, N.Y.), and a Centrasette type system (Pall Corp., East Hills, N.Y.).

Any suitable adsorptive chromatography resin may be utilized. Preferred adsorptive chromatography resins include resins for hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof. Examples of suitable hydroxyapatite resins include ceramic hydroxyapatite (CHT Type I and Type II, Bio-Rad Laboratories, Hercules, Calif.), HA Ultrogel hydroxyapatite (Pall Corp., East Hills, N.Y.), and ceramic fluoroapatite (CFT Type I and Type II, Bio-Rad Laboratories, Hercules, Calif.). An example of a suitable HCIC resin is MEP Hypercel resin (Pall Corp., East Hills, N.Y.). Examples of suitable HIC resins include Butyl-Sepharose, Hexyl-Sepaharose, Phenyl-Sepharose, and Octyl Sepharose resins (all from GE Healthcare, Piscataway, N.J.), as well as Macro-prep Methyl and Macro-Prep t-Butyl resins (Biorad Laboratories, Hercules, Calif.). Examples of suitable ion exchange resins include SP-Sepharose, CM-Sepharose, and Q-Sepharose resins (all from GE Healthcare, Piscataway, N.J.), and Unosphere S resin (Bio-Rad Laboratories, Hercules, Calif.). Examples of suitable mixed mode ion exchangers include Bakerbond ABx resin (JT Baker, Phillipsburg N.J.). Examples of suitable IMAC resins include Chelating Sepharose resin (GE Healthcare, Piscataway, N.J.) and Profinity IMAC resin (Bio-Rad Laboratories, Hercules, Calif.). Examples of suitable dye ligand resins include Blue Sepharose resin (GE Healthcare, Piscataway, N.J.) and Affi-gel Blue resin (Bio-Rad Laboratories, Hercules, Calif.). Examples of suitable affinity resins include Protein A Sepharose resin (e.g., Mab-Select, GE Healthcare, Piscataway, N.J.), where the cell binding agent is an antibody, and lectin affinity resins, e.g. Lentil Lectin Sepharose resin (GE Healthcare, Piscataway, N.J.), where the cell binding agent bears appropriate lectin binding sites. Alternatively an antibody specific to the cell binding agent may be used. Such an antibody can be immobilized to, for instance, Sepharose 4 Fast Flow resin (GE Healthcare, Piscataway, N.J.). Examples of suitable reversed phase resins include C4, C8, and C18 resins (Grace Vydac, Hesperia, Calif.).

Any suitable non-absorptive chromatography resins can be used in the methods of the present invention. Examples of suitable chromatography resins include, but are not limited to, SEPHADEX™ G-25, G-50, G-100, SEPHACRYL™ resins (e.g., S-200 and S-300), SUPERDEX™ resins (e.g., SUPERDEX™ 75 and SUPERDEX™ 200), BIO-GEL® resins (e.g., P-6, P-10, P-30, P-60, and P-100), and others known to those of ordinary skill in the art.

Drugs Bearing a Linking Moiety

Drugs that can be used in the present methods include compounds described in US2010/0316656, US 2010/003641, US2010/0203007, all of which are incorporated herein by reference.

In certain other embodiments, cytotoxic compounds that can be conjugated with cell-binding agents via a linking group do not comprise the linking group. Instead, a bifunctional cross-linking reagent (comprising the linking group) may be required to conjugate the linkerless cytotoxic compound with the CBA through the linker group.

Thus in the first specific embodiment, a drug covalently connected to a linking group with a reactive group bonded thereto, which can be used in the methods of the present invention (such as in the 1-step reagent method as described in the fourth aspect of the invention above), or which may be an intermediate product of the methods of the invention (such as the method described in the third aspect of the invention), is a cytotoxic compound bearing a reactive group, such as a reactive ester or a thiol-reactive group (collectively "the reactive group"), comprising a linking group with the reactive group bonded thereto, capable of covalently linking the cytotoxic compound to the CBA, wherein the cytotoxic compound is represented by any one of the following formulas:

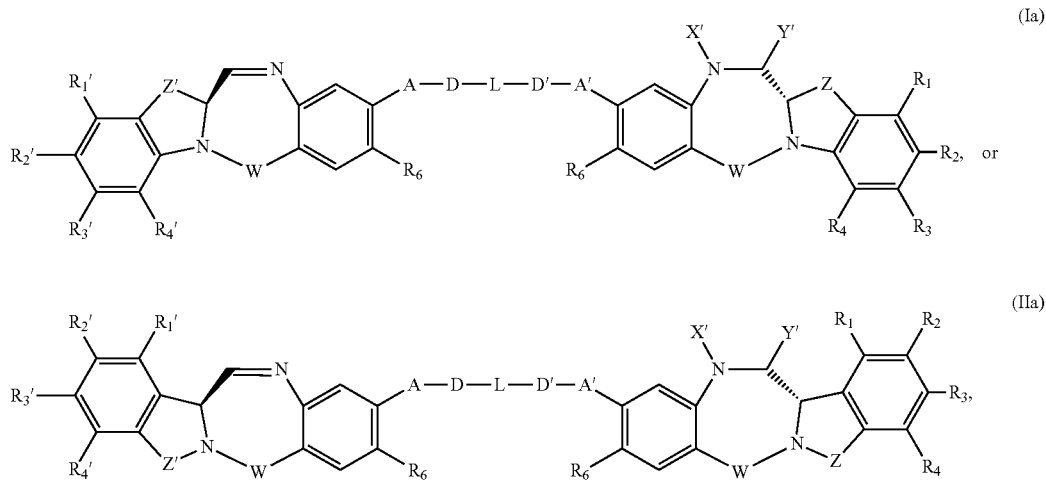

or a pharmaceutically acceptable salt thereof. Upon reacting with the imine reactive reagent, the cytotoxic compounds may be represented by any one of the following formulas:

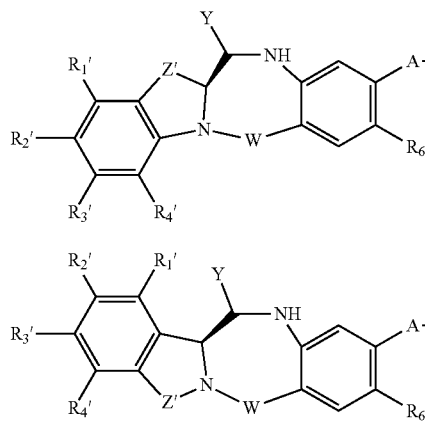

(Ia')

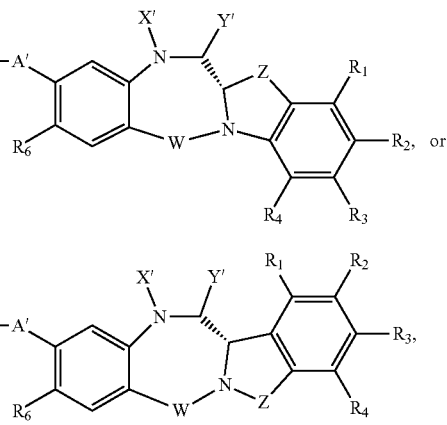

(IIa')

wherein:
- Y is a sulfite (HSO$_3$, HSO$_2$ or a salt of HSO$_3^-$, SO$_3^{2-}$ or HSO$_2^-$ formed with a cation), metabisulfite (H$_2$S$_2$O$_5$ or a salt of S$_2$O$_5^{2-}$ formed with a cation), mono-, di-, tri-, and tetra-thiophosphate (PO$_3$SH$_3$, PO$_2$S$_2$H$_2$, POS$_3$H$_2$, PS$_4$H$_2$ or a salt of PO$_3$S$^{3-}$, PO$_2$S$_2^{3-}$, POS$_3^{3-}$ or PS$_4^{3-}$ formed with a cation), thio phosphate ester (R$^i$O)$_2$PS(OR$^i$), R$^i$S—, R$^i$SO, R$^i$SO$_2$, R$^i$SO$_3$, thiosulfate (HS$_2$O$_3$ or a salt of S$_2$O$_3^{2-}$ formed with a cation), dithionite (HS$_2$O$_4$ or a salt of S$_2$O$_4^{2-}$ formed with a cation), phosphorodithioate (P(=S)(OR$^{k'}$)(S)(OH) or a salt thereof formed with a cation), hydroxamic acid (R$^k$C(=O)NOH or a salt formed with a cation), formaldehyde sulfoxylate (HOCH$_2$SO$_2^-$ or a salt of HOCH$_2$SO$_2^-$ formed with a cation, such as HOCH$_2$SO$_2^-$Na$^+$) or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl;
- X' is selected from —H, —OH, an amine-protecting group, the linking group with the reactive group bonded thereto, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;
- Y' is selected from —H, an oxo group, the linking group with the reactive group bonded thereto, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;
- R$^c$ is —H or a substituted or unsubstituted linear or branched alkyl having 1 to 4 carbon atoms, or the linking group with the reactive group bonded thereto;
- R$_1$, R$_2$, R$_3$, R$_4$, R$_1$', R$_2$', R$_3$' and R$_4$' are each independently selected from the group consisting of —H, an optionally substituted linear, branched or cyclic alkyl, alkenyl or alkynyl having from 1 to 10 carbon atoms, a polyethylene glycol unit —(OCH$_2$CH$_2$)$_n$—R$^c$, halogen, guanidinium [—NH(C=NH)NH$_2$], —OR, —NR'R'', —NO$_2$, —NCO, —NR'COR'', —SR, a sulfoxide represented by —SOR', a sulfone represented by —SO$_2$R', a sulfonate —SO$_3^-$M$^+$, a sulfate —OSO$_3^-$M$^+$, a sulfonamide represented by —SO$_2$NR'R'', cyano, an azido, —COR', —OCOR', —OCONR'R'', and the linking group with the reactive group bonded thereto;
- R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;
- R' and R'' are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3- to 18-membered heterocyclic ring having 1 to 6 heteroatoms independently selected from O, S, N and P;
- n is an integer from 1 to 24;
- W is selected from C=O, C=S, CH$_2$, BH, SO and SO$_2$;
- R$_6$ is —H, —R, —OR, —SR, —NR'R'', —NO$_2$, halogen or the linking group with the reactive group bonded thereto;

Z and Z' are independently selected from —(CH$_2$)$_{n'}$—, —(CH$_2$)$_{n'}$—CR$_7$R$_8$—(CH$_2$)$_{na'}$—, —(CH$_2$)$_{n'}$—NR$_9$—(CH$_2$)$_{na'}$—, —(CH$_2$)$_{n'}$—O—(CH$_2$)$_{na'}$— and —(CH$_2$)$_{n'}$—S—(CH$_2$)$_{na'}$—;

n' and na' are the same or different, and are selected from 0, 1, 2 and 3;

R$_7$ and R$_8$ are the same or different, and are each independently selected from —H, —OH, —SH, —COOH, —NHR', a polyethylene glycol unit —(OCH$_2$CH$_2$)$_n$—, an amino acid, a peptide unit bearing 2 to 6 amino acids, an optionally substituted linear, branched or cyclic alkyl having from 1 to 10 carbon atoms;

R$_9$ is independently selected from —H, an optionally substituted linear, branched or cyclic alkyl having from 1 to 10 carbon atoms, a polyethylene glycol unit —(OCH$_2$CH$_2$)$_n$—;

A and A' are the same or different, and are independently selected from —O—, oxo (—C(=O)—), —CRR'O—, —CRR'—, —S—, —CRR'S—, —NR$_5$ and —CRR'N(R$_5$)—;

R$_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;

L is absent, the linking group with the reactive group bonded thereto, a polyethylene glycol unit (—OCH$_2$CH$_2$)$_n$—, a linear, branched or cyclic alkyl or alkenyl having 1 to 10 carbon atoms, a phenyl group, a 3 to 18-membered heterocyclic ring or a 5- to 18-membered heteroaryl ring having 1 to 6 heteroatoms independently selected from O, S, N and P, wherein the alkyl or alkenyl is optionally substituted with the linking group with the reactive group bonded thereto; phenyl or heterocyclic or heteroaryl ring can be optionally substituted, wherein the substituent can be the linking group with the reactive group bonded thereto.

Preferably, L is absent, or is selected from an optionally substituted phenyl group and an optionally substituted pyridyl group, wherein the phenyl and the pyridyl group bears the linking group with the reactive group bonded thereto, or L is an amine group bearing the linking group with the reactive group bonded thereto (i.e., —N(linking group)-), or L is a linear, branched or cyclic alkyl or alkenyl having from 1 to 6 carbon atoms and bearing the linking group with the reactive group bonded thereto.

Several representative compounds of formulas (Ia') and (IIa') are listed below:

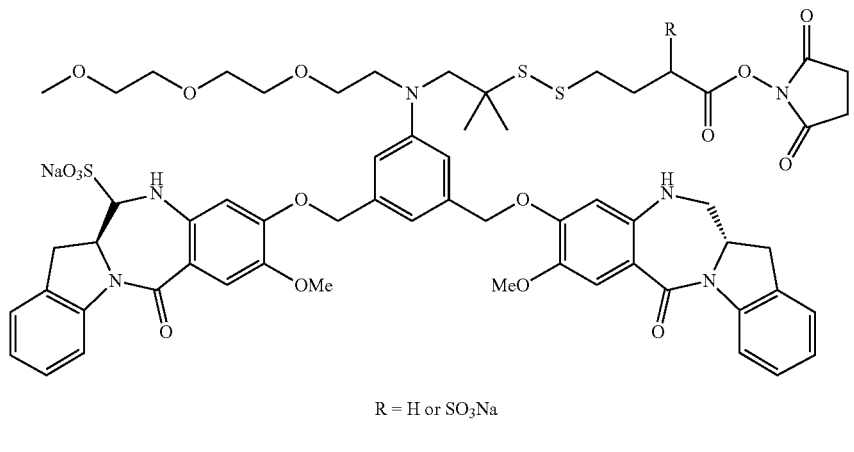

R = H or SO$_3$Na

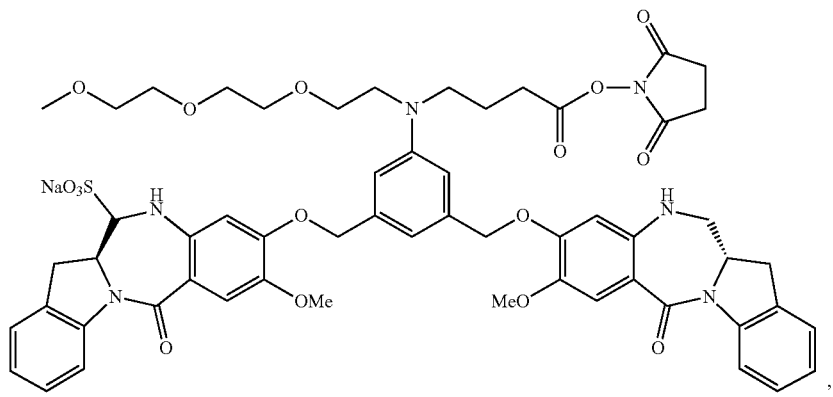

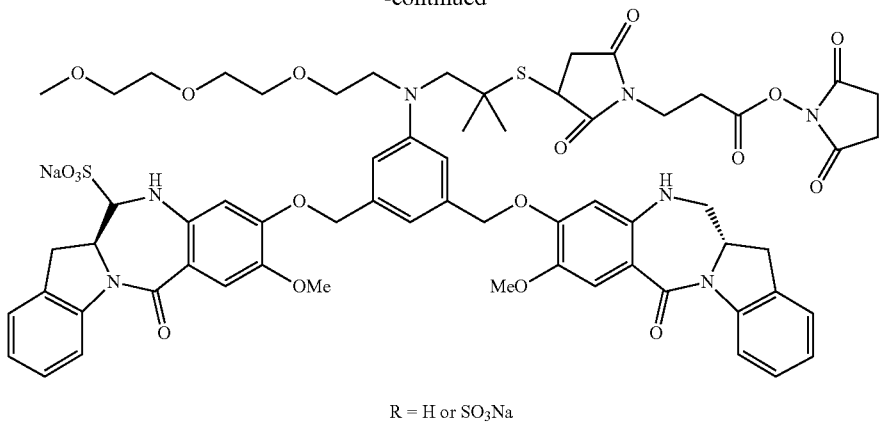

R = H or SO₃Na

In certain embodiments,

X' is selected from the group consisting of —H, —OH, an optionally substituted linear, branched or cyclic alkyl, alkenyl or alkynyl having from 1 to 10 carbon atoms, phenyl, the linking group with the reactive group bonded thereto, and an amine-protecting group. Preferably, X' is —H, —OH, -Me or the linking group with the reactive group bonded thereto. More preferably, X' is —H;

Y' is selected from the group consisting of —H, an oxo group, a substituted or unsubstituted linear, branched or cyclic alkyl, alkenyl or alkynyl having from 1 to 10 carbon atoms. Preferably, Y' is selected from —H or oxo. More preferably, Y' is —H;

W is C=O;

$R_1$, $R_2$, $R_3$, $R_4$, $R_1'$, $R_2'$, $R_3'$, and $R_4'$ are each independently selected from —H, —NR'R", —NR'(C=O)R, —OR, —SR, —NO₂ and the linking group with the reactive group bonded thereto. Preferably, one of $R_2$, $R_3$, $R_2'$, and $R_3'$ is the linking group with the reactive group bonded thereto and the rest are —H;

R, for each occurrence, is independently selected from the group consisting of —H, an optionally substituted linear, branched or cyclic alkyl, alkenyl or alkynyl having from 1 to 10 carbon atoms or phenyl;

R' and R" are the same or different, and are independently selected from —H, —OH, —OR, an optionally substituted linear, branched or cyclic alkyl, alkenyl or alkynyl having from 1 to 10 carbon atoms or phenyl;

$R_6$ is —OR$^c$ or —SR$^c$, wherein R$^c$ is —H, a linear or branched alkyl having 1 to 4 carbon atoms. Preferably, $R_6$ is —OMe or —SMe. Even more preferably, $R_6$ is —OMe;

Z and Z' are —CH₂—;

A and A' are the same or different, and are selected from —O—, —S—, —NR₅ and oxo (C=O). Preferably, A and A' are the same or different, and are selected from —O— and —S—. More preferably, A and A' are —O—;

D and D' are the same or different, and are independently selected from a polyethylene glycol unit (—OCH₂CH₂)$_n$, wherein n is an integer from 1 to 24, an amino acid, a peptide bearing 2 to 6 amino acids, or a linear, branched or cyclic alkyl, alkenyl or alkynyl having 1 to 10 carbon atoms, wherein the alkyl, alkenyl and alkynyl are optionally substituted with one or more (e.g., 2, 3, 4, 5, 6 or more) substituents independently selected from the group consisting of halogen, —OR, —NR'COR", —SR, and —COR';

Preferably, D and D' are the same or different, and are independently selected from linear, branched or cyclic alkyl, alkenyl or alkynyl having from 1 to 10 carbon atoms. More preferably, D and D' are linear or branched alkyl bearing 1 to 4 carbon atoms. Still more preferably, D and D' are the same or different, and are selected from a linear alkyl having 1 to 4 carbon atoms;

L is absent, or is selected from an optionally substituted phenyl group and an optionally substituted pyridyl group, wherein the phenyl and the pyridyl group bears the linking group with the reactive group bonded thereto, or L is an amine group bearing the linking group with the reactive group bonded thereto (i.e., —N(linking group)-), or L is a linear, branched or cyclic alkyl or alkenyl having from 1 to 6 carbon atoms and bearing the linking group with the reactive group bonded thereto.

In a second specific embodiment, for cytotoxic dimers (Ia) or (IIa), the variables are as described below:

W is C=O;

$R_1$, $R_2$, $R_1'$, $R_2'$, $R_4$, and $R_4'$ are —H;

one of $R_3$ or $R_3'$ is optionally the linking group with the reactive group bonded thereto and the other is —H;

$R_6$ is —OMe;

Z and Z' are —CH₂—;

X' is —H;

Y' is —H;

A and A' are —O—; and the remainder of the variables are as described in the first specific embodiment.

In a third specific embodiment, the cytotoxic dimers (bonded to the linking group with the reactive group attached thereto) of formula (Ia') and (IIa') are represented by the following formulas:

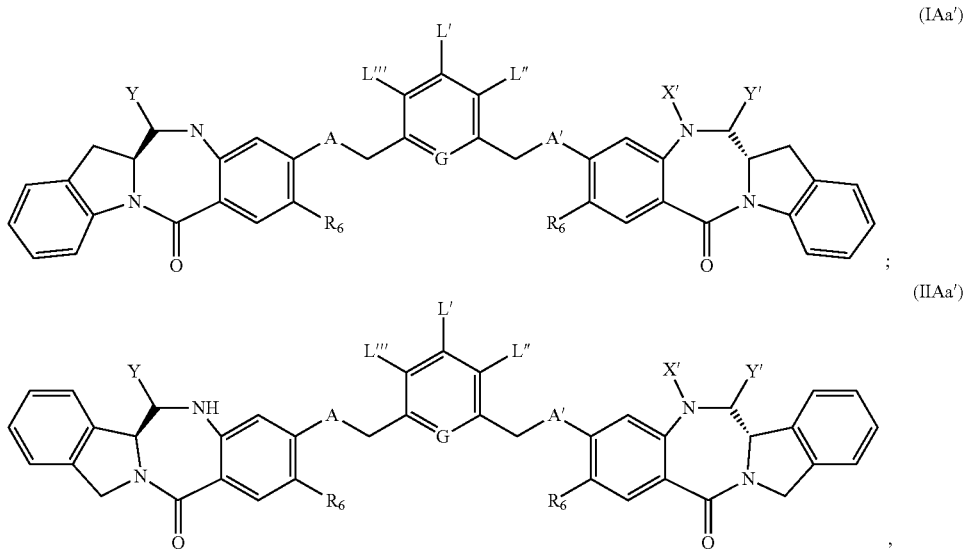

wherein:
- X' is selected from the group consisting of —H, —OH, a substituted or unsubstituted linear, branched or cyclic alkyl, alkenyl or alkynyl having from 1 to 10 carbon atoms, phenyl, and an amine-protecting group. Preferably, X' is —H, —OH or -Me. More preferably, X' is —H;
- Y' is selected from the group consisting of —H, an oxo group, a substituted or unsubstituted linear, branched or cyclic alkyl, alkenyl or alkynyl having from 1 to 10 carbon atoms. Preferably, Y' is selected from —H or -Me. More preferably Y' is —H;
- L', L", and L'" are same or different and are independently selected from —H, an optionally substituted linear, branched or cyclic alkyl, alkenyl or alkynyl having from 1 to 10 carbon atoms, a polyethylene glycol unit —(OCH$_2$CH$_2$)$_n$—R$^c$, halogen, guanidinium [—NH(C=NH)NH$_2$], —OR, —NR'R", —NO$_2$, —NR'COR", —SR, a sulfoxide represented by —SOR', a sulfone represented by —SO$_2$R', a sulfonate —SO$_3^-$M$^+$, a sulfate —OSO$_3^+$M$^-$, a sulfonamide represented by —SO$_2$NR'R", cyano, an azido, —COR', —OCOR', —OCONR'R" and the linking group with the reactive group bonded thereto, provided only one of L', L" and L'" is the linking group with the reactive group bonded thereto. Preferably, L' is the linking group with the reactive group bonded thereto. Alternatively, one of L', L", or L'" is the linking group with the reactive group bonded thereto, while the others are —H. More preferably, L' is the linking group with the reactive group bonded thereto, and L" and L'" are —H;
- R$_6$ is —OR$^c$ or —SR$^c$, wherein R$^c$ is a linear or branched alkyl having 1 to 4 carbon atoms. Preferably, R$_6$ is —OMe or —SMe. Even more preferably, R$_6$ is —OMe;
- A and A' are selected from —O— and —S—. Preferably, A and A' are —O—;
- R is —H, an optionally substituted linear, branched or cyclic alkyl, alkenyl or alkynyl having from 1 to 10 carbon atoms or a PEG group (CH$_2$CH$_2$O)n-R$^c$;
- n is an integer from 1 to 24; and,
- R$^c$ is a linear or branched alkyl having 1 to 4 carbon atoms;
- R' and R" are the same or different, and are selected from —H, —OH, —OR, —NRR$^{g'}$, —COR, an optionally substituted linear, branched or cyclic alkyl, alkenyl or alkynyl having from 1 to 10 carbon atoms, an optionally substituted aryl having from 6 to 18 carbon atoms, an optionally substituted 3- to 18-membered heterocyclic ring having 1 to 6 heteroatoms selected from O, S, N and P, a PEG group —(CH$_2$CH$_2$O)$_n$—R$^c$, wherein n is an integer from 1 to 24, preferably n is 2, 4 or 8; and R$^{g'}$ is —H, an optionally substituted linear, branched or cyclic alkyl, alkenyl or alkynyl having from 1 to 10 carbon atoms or a PEG group (CH$_2$CH$_2$O)n-R$^c$;
- G is selected from —CH— or —N—; and the remainder of the variables are as described in the first specific embodiment.

In a fourth specific embodiment, for the cytotoxic dimers of formula (IAa') or (IIAa'), L' is represented by the formula:

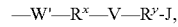

—W'—R$^x$—V—R$^y$-J, wherein:
- W' and V are the same or different, and are each independently absent, or selected from —CR$^e$R$^{e'}$—, —O—, —O—C(=O)—, —C(=O)—O—, —S—, —SO—, —SO$_2$—, —CH$_2$—S—, —CH$_2$O—, —CH$_2$NR$^e$—, —O—(C=O)O—, —O—(C=O)N(R$^e$)—, —N(R$^e$)—, —N(R$^e$)—C(=O)—, —C(=O)—N(R$^e$)—, —N(R$^e$)—C(=O)O—, —N(C(=O)R$^e$)C(=O)—, —N(C(=O)R$^e$)—, —(O—CH$_2$—CH$_2$)$_n$—, —SS—, or —C(=O)—, or an amino acid, or a peptide having 2 to 8 amino acids;
- R$^x$ and R$^y$ are the same or different, and are each independently absent or an optionally substituted linear, branched or cyclic alkyl, alkenyl or alkynyl having 1 to 10 carbon atoms, an aryl bearing 6 to 10 carbon atoms or a 3- to 8-membered heterocyclic ring bearing 1 to 3 heteroatoms selected from O, N or S;

R$^e$ and R$^{e'}$ are the same or different, and are selected from —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5- or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms; preferably, R$^{101}$ and R$^{102}$ are each independently a linear or branched alkyl having 1 to 6 carbon atoms;

n is an integer from 1 to 24; and

J comprises the reactive group bonded thereto, and is selected from a maleimide, a haloacetamido, —SH, —SSR$^d$, —CH$_2$SH, —CH(Me)SH, —C(Me)$_2$SH, and —COE, wherein —COE represents a reactive ester selected from, but not limited to, N-hydroxysuccinimde ester, N-hydroxy sulfosuccinimide ester, nitrophenyl (e.g., 2 or 4-nitrophenyl) ester, dinitrophenyl (e.g., 2,4-dinitrophenyl) ester, sulfo-tetraflurophenyl (e.g., 4-sulfo-2,3,5,6-tetrafluorophenyl) ester, and pentafluorophenyl ester, and wherein R$^{c1}$ is —H or a substituted or unsubstituted linear or branched alkyl having 1 to 4 carbon atoms, and, R$^d$ is selected from phenyl, nitrophenyl (e.g., 2 or 4-nitrophenyl), dinitrophenyl (e.g., 2 or 4-nitrophenyl), carboxynitrophenyl (e.g., 3-carboxy-4-nitrophenyl), pyridyl or nitropyridyl (e.g., 4-nitropyridyl).

Preferably, J is —SH, —SSR$^d$, a maleimide, or a N-hydroxysuccinimide ester.

Preferably, R$^{e'}$ is —H or -Me; R$^e$ is a linear or branched alkyl having 1 to 6 carbon atoms or —(CH$_2$—CH$_2$—O)$_n$—R$^k$; n is an integer from 2 to 8; preferably R$^k$ is —H, -Me or —CH$_2$CH$_2$—NMe$_2$, and the remainder of the variables are as described above in the third specific embodiment.

In another preferred embodiment, V is an amino acid or a peptide having 2 to 8 amino acids. More preferably, V is valine-citrulline, gly-gly-gly or ala-leu-ala-leu.

In another preferred embodiment, W' is —O—, —N(R$^e$)— or —N(R$^e$)—C(=O)—; R$^e$ is —H, a linear or branched alkyl having 1 to 4 carbon atoms, or —(CH$_2$—CH$_2$—O)$_n$—R$^k$; R$^x$ is a linear or branched alkyl having 1 to 6 carbon atoms; V is absent, —(O—CH$_2$—CH$_2$)$_n$—, —C(=O)—NH—, —S—, —NH—C(=O)—; R$^y$ is absent or a linear or branched alkyl having 1 to 4 carbon atoms; and J is —SH, —SSR$^d$ or —COE (preferably, N-hydroxysuccinimide ester). The remainder of the variables is as described in the fourth specific embodiment.

In another preferred embodiment, W' is —O—, —N(R$^e$)— or —N(R$^e$)—C(=O)—; R$^e$ is H, -Me, or —(CH$_2$—CH$_2$—O)$_n$-Me; n is an integer from 2 to 6; R$^x$ is linear or branched alkyl bearing 1 to 6 carbon atoms; V and R$^y$ are absent; and J is —COE, preferably N-hydroxysuccinimide ester.

In a fifth specific embodiment, L' is represented by the following formula:

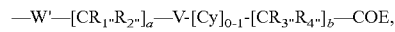

wherein:

R$_{1''}$, R$_{2''}$, and R$_{3''}$ are each independently —H or -Me;
R$_{4''}$ is —H, -Me, —SO$_3$H, or —SO$_3^-$M$^+$, wherein M$^+$ is a pharmaceutically acceptable cation;
a is an integers from 0-2, b is an integer from 0-3; and,
Cy is an optionally substituted 5-membered heterocyclic ring bearing an N heteroatom, preferably Cy is

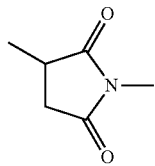

In certain embodiments, such as in the fourth or the fifth specific embodiments, W' is —N(R$^e$)—.

In certain embodiments, such as in the fourth or the fifth specific embodiments, R$^e$ is —(CH$_2$—CH$_2$—O)$_{2-6}$—R$^k$, wherein R$^k$ is a —H, a linear, branched cyclic alkyl having 1 to 6 carbon atoms.

In certain embodiments, such as in the fourth or the fifth specific embodiments, V is —S— or —SS—.

In a sixth specific embodiment, L', such as in the fourth or the fifth specific embodiment, is represented by the following formula:

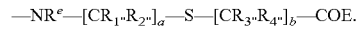

In certain embodiments, the cytotoxic compound bonded to the linking group with the reactive group attached thereto, as in the 4th, 5th, and 6th specific embodiments, is:

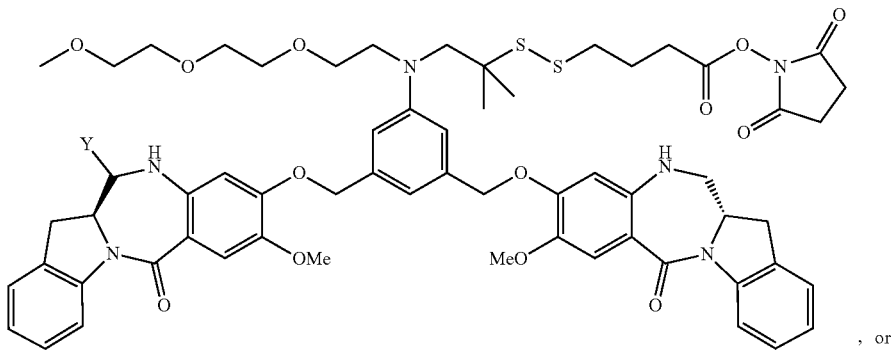

, or

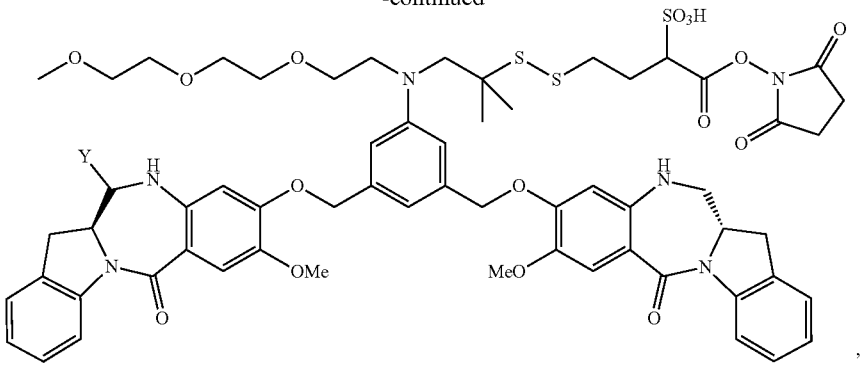

wherein Y is —SO$_3$M, and M is —H or a pharmaceutically acceptable cation.

In a seventh specific embodiment, L', such as in the fourth, fifth, or sixth specific embodiment, is represented by the following formula:

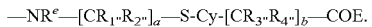

In certain embodiments, the cytotoxic compound bonded to the linking group with the reactive group attached thereto, as in the 4th, 5th, and 7th specific embodiment, is:

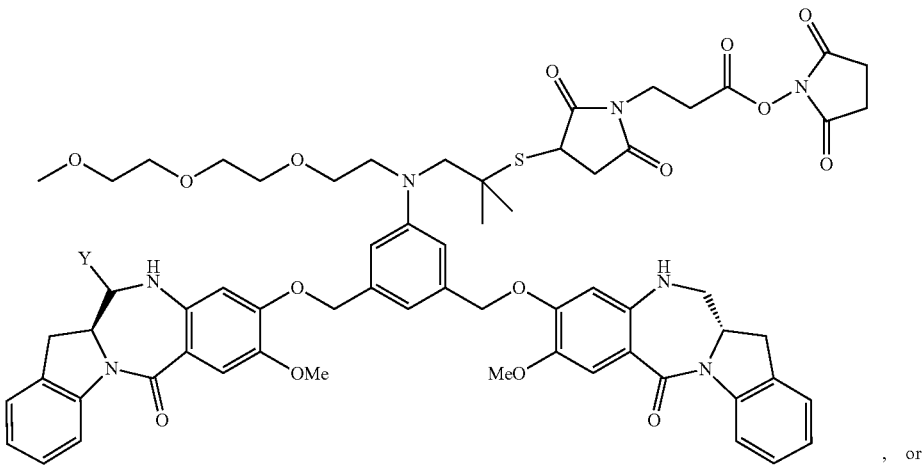

, or

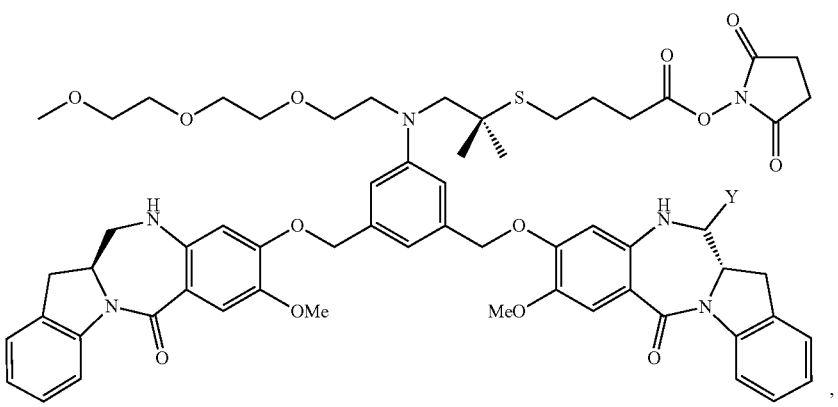

, wherein Y is —SO₃M, and M is —H or a pharmaceutically acceptable cation.

In an eighth specific embodiment, the cytotoxic compounds of formula (Ia) and (IIa) are represented by the following formulas:

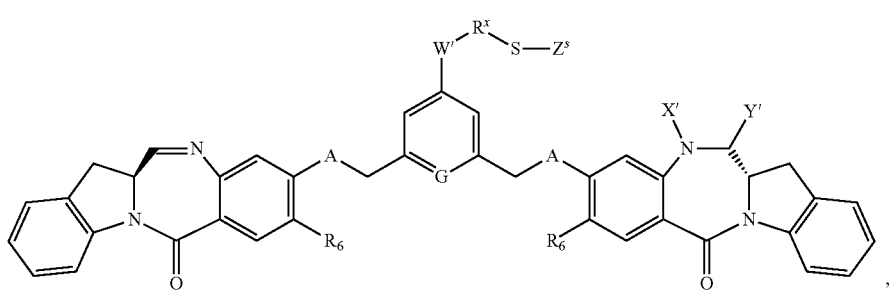
(IBa)

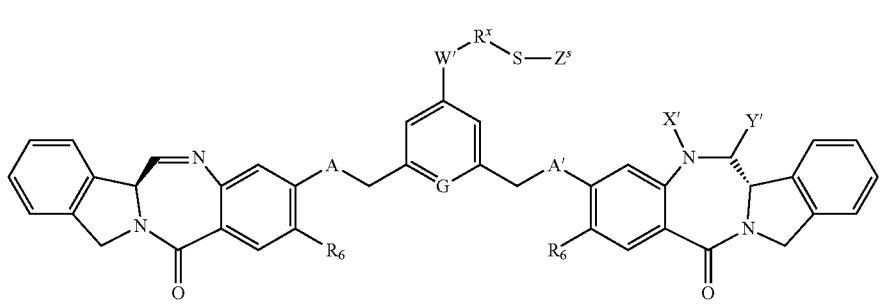
(IIBa)

wherein:
W' is absent, or selected from —O—, —N(R^e)—, —N(R^e)—C(=O)—, —N(C(=O)R^e)—, —S— or —CH₂—S—, —CH₂NR^e—;

R^x is absent or selected from a linear, branched or cyclic alkyl having 1 to 10 carbon atoms;

R^e is —H, a linear, branched or cyclic alkyl, alkenyl or alkynyl having 1 to 10 carbon atoms or —(CH₂—CH₂—O)_N—R^k, wherein R^k is a —H, a linear, branched cyclic alkyl having 1 to 6 carbon atoms, optionally bearing a secondary amino (e.g., —NHR¹⁰¹) or tertiary amino (—NR¹⁰¹R¹⁰²) group or a 5 or 6-membered nitrogen containing heterocycle, such as piperidine or morpholine, wherein R¹⁰¹ and R¹⁰² are each independently a linear, branched, or cyclic alkyl, alkenyl or alkynyl having 1 to 10 carbon atoms. Preferably, R¹⁰¹ and R¹⁰² are each independently a linear or branched alkyl having 1 to 6 carbon atoms;

Z^s is —H, —SR^m;

R^m is R^d or a substituted or unsubstituted linear or branched alkyl having 1 to 4 carbon atoms bearing a reactive ester, selected from N-hydroxysuccinimide esters, N-hydroxyphtalimide esters, N-hydroxy sulfo-succinimide esters, para-nitrophenyl esters, dinitrophenyl esters, pentafluorophenyl esters;

R^d is selected from phenyl, nitrophenyl, dinitrophenyl, carboxynitrophenyl, pyridyl or nitropyridyl;

n is an integer from 1 to 24; and the remainder of the variables are as described above in the fourth specific embodiment.

Preferably, R^k is —H or -Me and n is an integer from 2 to 8. Preferably, R^x is a linear or branched alkyl having 1 to 6 carbon atoms; and the remainder of the variables is as described above in the fifth specific embodiment.

In certain embodiments, for compounds of formula (IBa) and (IIBa) described in the eighth specific embodiment, the variables are as described below:

X' and Y' are both —H;
A and A' are both —O—;
R₆ is —OMe;
R^x is a linear or branched alkyl having 1 to 6 carbon atoms; and the remainder of the variables is as described above in the eighth specific embodiment.

Preferably, R^x is —(CH₂)_p—(CR^fR^g)—, wherein R^f and R^g are each independently selected from H or a linear or branched alkyl having 1 to 4 carbon atoms; p is 0, 1, 2 or 3. More preferably, R^f and R^g are the same or different and are selected from —H and -Me; and p is 1.

In a ninth specific embodiment, the cytotoxic compound bonded to the linking group with the reactive group attached thereto is represented by any one of the following formulas:

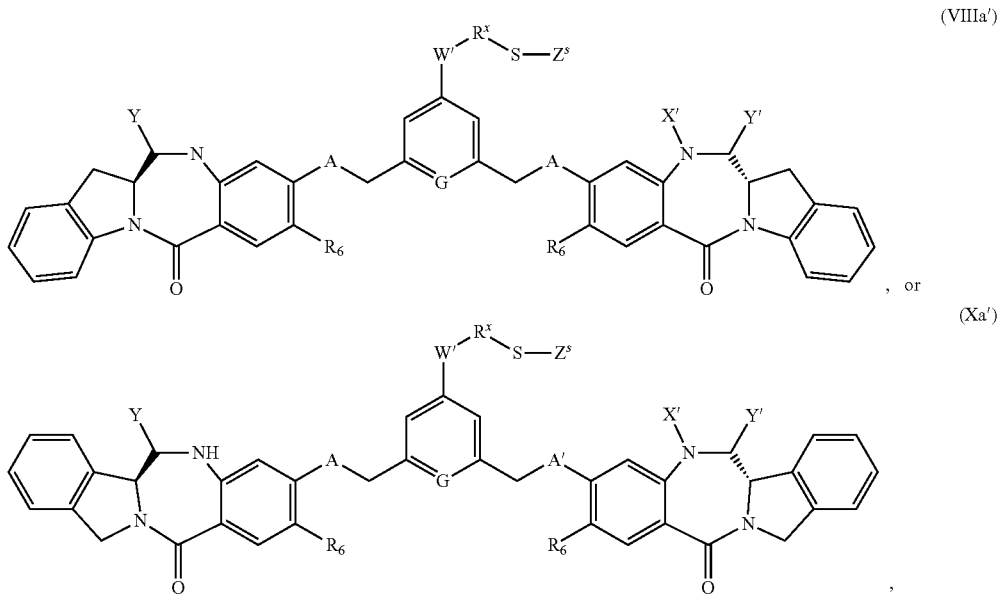

wherein:
  Y is selected from —SO₃M, —SO₂M or —OSO₃M;
  M is —H or a pharmaceutically acceptable cation such as Na⁺ or K⁺;
  X' is selected from the group consisting of —H, —OH, a substituted or unsubstituted linear, branched or cyclic alkyl, alkenyl or alkynyl having from 1 to 10 carbon atoms, phenyl, and an amine-protecting group;
  Y' is selected from the group consisting of —H, an oxo group, a substituted or unsubstituted linear, branched or cyclic alkyl, alkenyl or alkynyl having from 1 to 10 carbon atoms;
  A and A' are selected from —O— and —S—;
  W' is absent, or selected from —O—, —N(Rᵉ)—, —N(Rᵉ)—C(=O)—, —N(C(=O)Rᵉ)—, —S— or —CH₂—S—, —CH₂NRᵉ—;

Rˣ is absent or selected from a linear, branched or cyclic alkyl having 1 to 10 carbon atoms;
  Rᵉ is —H, a linear, branched or cyclic alkyl, alkenyl or alkynyl having 1 to 10 carbon atoms or —(CH₂—CH₂—O)$_n$—Rᵏ, wherein Rᵏ is a —H, a linear, branched cyclic alkyl having 1 to 6 carbon atoms, optionally bearing a secondary amino (e.g., —NHR¹⁰¹) or tertiary amino (—NR¹⁰¹R¹⁰²) group or a 5- or 6-membered nitrogen containing heterocycle, such as piperidine or morpholine, wherein R¹⁰¹ and R¹⁰² are each independently a linear, branched, or cyclic alkyl, alkenyl or alkynyl having 1 to 10 carbon atoms;
  G is selected from —CH— or —N—;
  Zˢ is —H, or is selected from any one of the following formulas:

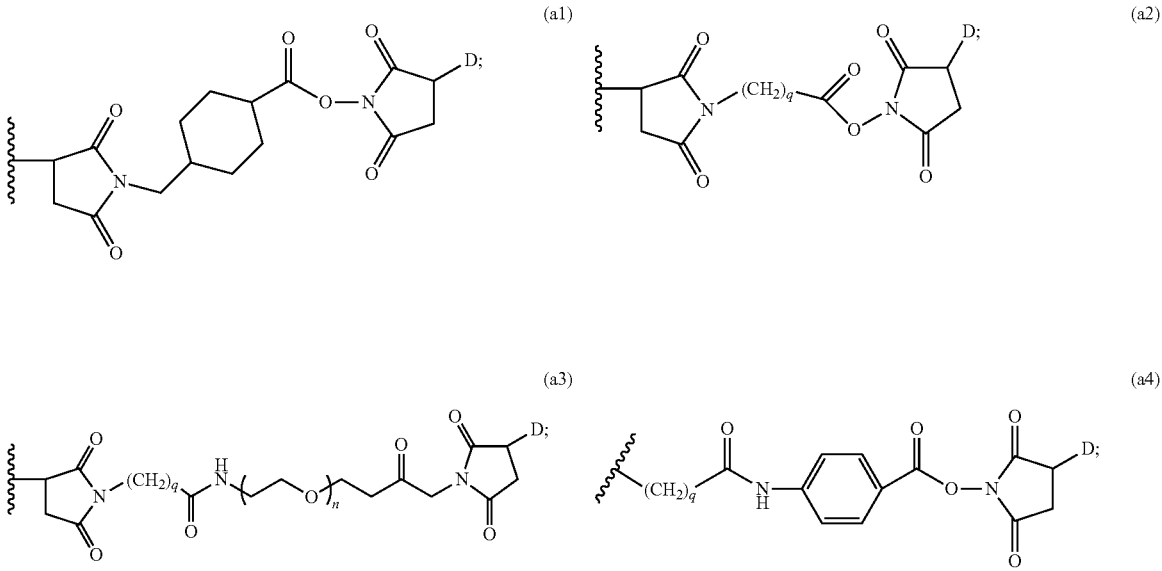

(a-5), (a-6), (a-7), (A-8), (a-9), (a-10) [structures]

wherein:
q is an integer from 1 to 5; preferably q is 2;
n is an integer from 2 to 6; preferably n is 4;
D is —H or —SO$_3$M;
M is —H or a pharmaceutically acceptable cation, such as Na$^+$ or K$^+$.

In certain embodiments, Z$^s$ is represented by any one of the following formulas:

(a1), (a4'), (a5'), (a12), (a13) [structures]

In certain embodiments, such as the ninth specific embodiment, W' is —N(R$^e$)—.

In certain embodiments, R$^e$ is —(CH$_2$—CH$_2$—O)$_n$—R$^k$, wherein R$^k$ is a —H, a linear, branched cyclic alkyl having 1 to 6 carbon atoms.

In certain embodiments, R$^k$ is —H or -Me, n is 4, and q is 2.

In certain embodiments, R$^x$ is a linear or branched alkyl having 1 to 6 carbon atoms.

In certain embodiments, R$^x$ is —(CH$_2$)$_p$—(CR$^f$R$^g$)—, wherein R$^f$ and R$^g$ are each independently selected from —H or a linear or branched alkyl having 1 to 4 carbon atoms; and p is 0, 1, 2 or 3.

In certain embodiments, R$^f$ and R$^g$ are the same or different, and are selected from —H and -Me; and p is 1.

In a tenth specific embodiment, the variables of the ninth specific embodiment are represented below: Y is —SO$_3$M;

M is —H or a pharmaceutically acceptable cation (e.g., Na$^+$); X' and Y' are both —H; A and A' are both —O—; R$_6$ is —OMe; and R$^x$ is a linear or branched alkyl having 1 to 6 carbon atoms.

In any of the embodiments above, such as the 1$^{st}$ through the 9$^{th}$ specific embodiments, Y is selected from —SO$_3$M, —SO$_2$M and a sulfate —OSO$_3$M. Preferably, Y is —SO$_3$M, wherein M is preferably —H, Na$^+$ or K$^+$.

In any of the embodiments above, such as the 1$^{st}$ through the 10$^{th}$ specific embodiments, W, when present, is C=O.

In any of the embodiments above, such as the 1$^{st}$ through the 10$^{th}$ specific embodiments, Z and Z', when present, are —CH$_2$—.

In any of the embodiments above, such as the 1$^{st}$ through the 10$^{th}$ specific embodiments, X' is selected from the group consisting of —H, —OH, an optionally substituted linear, branched or cyclic alkyl, alkenyl or alkynyl having from 1 to 10 carbon atoms, phenyl, the linking group with the reactive group bonded thereto, and an amine-protecting group. Preferably, X' is —H, —OH, -Me or the linking group with the reactive group bonded thereto. More preferably, X' is —H.

In any of the embodiments above, such as the 1$^{st}$ through the 10$^{th}$ specific embodiments, Y' is selected from the group consisting of —H, an oxo group, a substituted or unsubstituted linear, branched or cyclic alkyl, alkenyl or alkynyl having from 1 to 10 carbon atoms. Preferably, Y' is —H or oxo. More preferably, Y' is —H.

In any of the embodiments above, such as the 1$^{st}$ through the 10$^{th}$ specific embodiments, A and A' are the same or different, and are selected from —O—, —S—, —NR$_5$—, and oxo —(C=O)—. Preferably, A and A' are the same or different, and are selected from —O— and —S—. More preferably, A and A' are —O—.

In any of the embodiments above, such as the 1$^{st}$ through the 10$^{th}$ specific embodiments, D and D', when present, are the same or different, and are independently selected from a polyethylene glycol unit (—OCH$_2$CH$_2$)$_n$, wherein n is an integer from 1 to 24, an amino acid, a peptide bearing 2 to 6 amino acids, or a linear, branched or cyclic alkyl, alkenyl or alkynyl having 1 to 10 carbon atoms, wherein the alkyl, alkenyl and alkynyl are optionally substituted with one or more substituents independently selected from the group consisting of halogen, —OR, —NR'COR'', —SR and —COR'. Preferably, D and D' are linear or branched alkyl bearing 1 to 4 carbon atoms.

In a eleventh specific embodiment, the various groups of the cytotoxic compounds of the first, third, and ninth specific embodiment, are represented below: W is C=O; R$_1$, R$_2$, R$_1$', R$_2$', R$_4$ and R$_4$' are —H; one of R$_3$, or R$_3$' is optionally the linking group with the reactive group bonded thereto and the other is —H; R$_6$ is —OMe; Z and Z' are —CH$_2$—; X' is —H; Y' is —H; and A and A' are —O—.

in another embodiment, the linking group with the reactive group attached thereto as in any of the specific embodiment above is any one of those listed in List 1.

In another embodiment, cytoxic dimers without a linker moieties (such as the linker moieties described above) attached thereto may further react with a bifunctional cross-linking reagent to form a drug bearing a linking moiety with a reactive group attached thereto, in order to be used in the methods of the present invention (e.g., to further react with a cell-binding agent to form the drug-CBA conjugate). Alternatively, cytoxic dimers without a linker moieties (such as the linker moieties described above) attached thereto may further react with a bifunctional crosslinking reagent and a cell-binding reagent in a one-step reaction to directly form the drug-CBA conjugate. In either case, an imine-reactive reagent may be added to the reaction mixture to form a drug-imine reactive reagent adduct (such as a bisulfite adduct) prior to the reaction to create the drug-CBA conjugate. Preferably, the cytoxic dimers without a linker moieties (such as the linker moieties described above) attached thereto may be first pre-incubated with the imine reactive reagent to form the adduct, before the reaction mixture is used in the subsequent reactions to form the drug-CBA conjugate.

Thus in a twelfth specific embodiment, the imine-containing cytotoxic compound is represented by any one of the following formulas, or a pharmaceutically acceptable salt thereof:

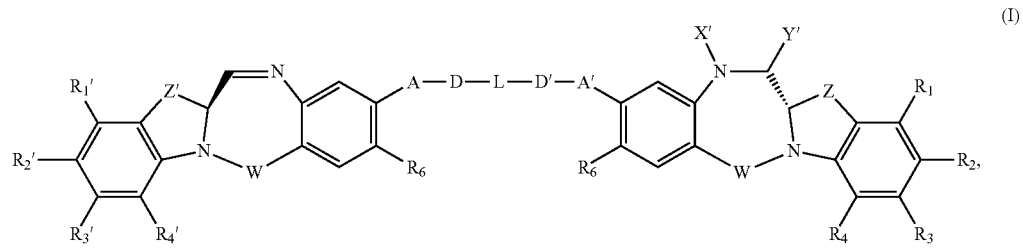

(I)

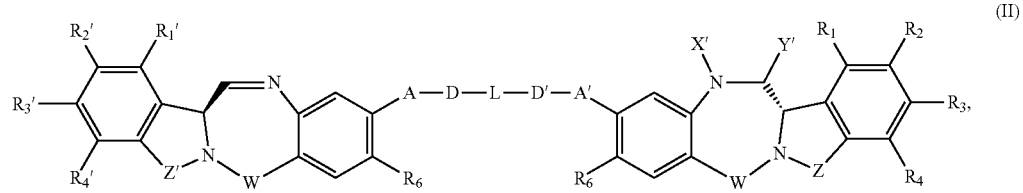

(II)

and, after reacting with the imine reactive reagent, the cytotoxic compound is represented by the following formula, or a pharmaceutically acceptable salt thereof:

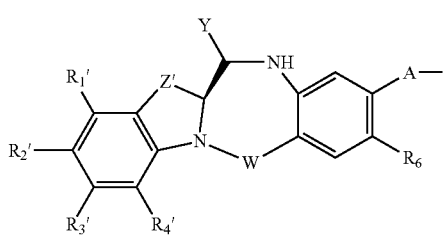 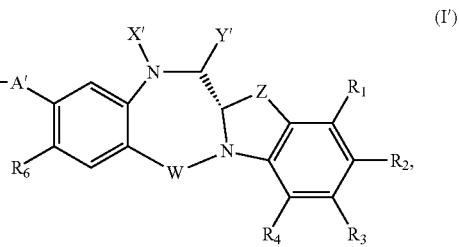 (I')

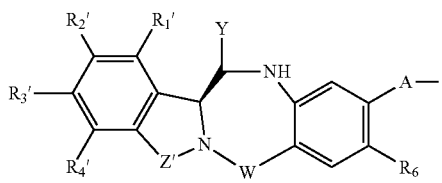 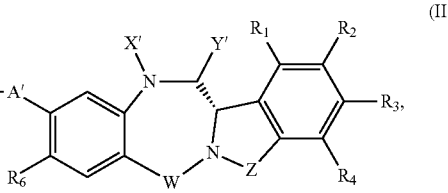 (II')

wherein:

Y is a sulfite ($HSO_3$, $HSO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono-, di-, tri-, and tetra-thiophosphate ($PO_3SH_3$, $PO_2S_2H_2$, $POS_3H_2$, $PS_4H_2$ or a salt of $PO_3S^{3-}$, $PO_2S_2^{3-}$, $POS_3^{3-}$ or $PS_4^{3-}$ formed with a cation), thio phosphate ester $(R^iO)_2PS(OR^i)$, $R^iS$—, $R^iSO$, $R^iSO_2$, $R^iSO_3$, thiosulfate ($HS_2O_3$ or a salt of $S_2O_3^{2-}$ formed with a cation), dithionite ($HS_2O_4$ or a salt of $S_2O_4^{2-}$ formed with a cation), phosphorodithioate ($P(\!=\!S)(OR^{k'})(S)(OH)$ or a salt thereof formed with a cation), hydroxamic acid ($R^{k'}C(\!=\!O)NOH$ or a salt formed with a cation), formaldehyde sulfoxylate ($HOCH_2SO_2^-$ or a salt of $HOCH_2SO_2^-$ formed with a cation, such as $HOCH_2SO_2^-Na^+$) or a mixture thereof, wherein $R^i$ is a linear or branched alkyl having 1 to 10 carbon atoms and is substituted with at least one substituent selected from —$N(R^j)_2$, —$CO_2H$, —$SO_3H$, and —$PO_3H$; $R^i$ can be further optionally substituted with a substituent for an alkyl described herein; $R^j$ is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl; preferably, Y is an adduct of a bisulfite, a hydro sulfite, or a metabisulfite, or salts thereof (such as sodium salt);

X' is selected from the group consisting of —H, —OH, an amine-protecting group, an optionally substituted linear, branched or cyclic alkyl, alkenyl or alkynyl having from 1 to 10 carbon atoms, a polyethylene glycol unit —$(CH_2CH_2O)_n R^c$, an optionally substituted aryl having 6 to 18 carbon atoms (e.g., phenyl), an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P. Preferably, X' is —H, —OH, or -Me. More preferably, X' is —H;

Y' is selected from the group consisting of —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms. Preferably, Y' is selected from —H or oxo. More preferably, Y' is —H;

$R^c$ is —H or a substituted or unsubstituted linear or branched alkyl having 1 to 4 carbon atoms;

$R_1$, $R_2$, $R_3$, $R_4$, $R_1'$, $R_2'$, $R_3'$, and $R_4'$ are each independently selected from the group consisting of —H, an optionally substituted linear, branched or cyclic alkyl, alkenyl or alkynyl having from 1 to 10 carbon atoms, a polyethylene glycol unit —$(OCH_2CH_2)_n$—$R^c$, halogen, guanidinium [—$NH(C\!=\!NH)NH_2$], —OR, —NR'R", —$NO_2$, —NCO, —NR'COR", —SR, a sulfoxide represented by —SOR', a sulfone represented by —$SO_2R'$, a sulfonate —$SO_3^-M^+$, a sulfate —$OSO_3^-M^+$, a sulfonamide represented by —$SO_2NR'R"$, cyano, an azido, —COR', —OCOR', and —OCONR'R". Preferably, 1, 2, 3, or all of $R_2$, $R_3$, $R_2'$ and $R_3'$ is —H;

M is —H or a pharmaceutically acceptable cation;

R, for each occurrence, is independently selected from the group consisting of —H, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are the same or different, and are independently selected from —H, —OH, —OR, —NHR, —$NR_2$, —COR, an optionally substituted linear, branched or cyclic alkyl, alkenyl or alkynyl having from 1 to 10 carbon atoms, a polyethylene glycol unit —$(CH_2CH_2O)_n$—$R^c$, and an optionally substituted 3- to 18-membered heterocyclic ring having 1 to 6 heteroatoms independently selected from O, S, N and P;

n is an integer from 1 to 24;

W is selected from C=O, C=S, $CH_2$, BH, SO, and $SO_2$;

$R_6$ is —H, —R, —OR, —SR, —NR'R", —$NO_2$, halogen, —$OR^c$ or —$SR^c$; preferably, $R_6$ is —OMe or —SMe. Even more preferably, $R_6$ is —OMe;

Z and Z' are independently selected from —$(CH_2)_{n'}$—, —$(CH_2)_{n'}$—$CR_7R_8$—$(CH_2)_{na'}$—, —$(CH_2)_{n'}$—$NR_9$—$(CH_2)_{na'}$—, —$(CH_2)_{n'}$—O—$(CH_2)_{na'}$— and —$(CH_2)_{n'}$—S—$(CH_2)_{na'}$—;

n' and na' are the same or different, and are selected from 0, 1, 2 and 3;

$R_7$ and $R_8$ are the same or different, and are each independently selected from —H, —OH, —SH, —COOH, —NHR', a polyethylene glycol unit —$(OCH_2CH_2)_n$—, an amino acid, a peptide unit bearing 2 to 6 amino acids, an optionally substituted linear, branched or cyclic alkyl having from 1 to 10 carbon atoms;

$R_9$ is independently selected from —H, an optionally substituted linear, branched or cyclic alkyl having from 1 to 10 carbon atoms, a polyethylene glycol unit —$(OCH_2CH_2)_n$—;

A and A' are the same or different, and are independently selected from —O—, oxo (—C(=O)—), —CRR'O—, —CRR'—, —S—, —CRR'S—, —N($R_5$)— and —CRR'N($R_5$)—. Preferably, A and A' are the same or different, and are selected from —O— and —S—. More preferably, A and A' are —O—;

$R_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—$OCH_2CH_2)_n$—;

L is absent, or when present, comprises the thiol group, and is a polyethylene glycol unit (—$OCH_2CH_2)_n$—, a linear, branched or cyclic alkyl or alkenyl having 1 to 10 carbon atoms, a phenyl group, a 3- to 18-membered heterocyclic ring or a 5- to 18-membered heteroaryl ring having 1 to 6 heteroatoms independently selected from O, S, N and P, wherein the alkyl, alkenyl, phenyl, or heterocyclic or heteroaryl ring is optionally substituted.

Representative structures of such imine-containing cytotoxic compounds are shown in Table 15. See compounds 1, 3, 4, 5, and 1d.

In certain embodiments,

W is C=O;

$R_1$, $R_2$, $R_3$, $R_4$, $R_{1'}$, $R_{2'}$, $R_{3'}$, and $R_{4'}$ are —H;

Z and Z' are —$CH_2$—;

A and A' are both —O—;

W is —(C=O)—;

G is —CH—;

$R_6$ is —H, or optionally substituted C1-C10 linear, C1-C10 branched, or C3-C7 cyclic alkyl, —O-alkyl, or —O-halo-alkyl, such as —OMe;

X' is selected from the group consisting of —H, —OH, a substituted or unsubstituted linear, branched or cyclic alkyl, alkenyl or alkynyl having from 1 to 10 carbon atoms, phenyl, and an amine-protecting group; and Y' is selected from the group consisting of —H, an oxo group, a substituted or unsubstituted linear, branched or cyclic alkyl, alkenyl or alkynyl having from 1 to 10 carbon atoms.

Preferably, Y is selected from —$SO_3M$, —$SO_2M$, or —$OSO_3M$, and wherein M is —H or a pharmaceutically acceptable cation such as $Na^+$ or $K^+$.

Preferably, Y is —$SO_3M$; M is —H or $Na^+$.

In certain embodiments, the imine-containing cytotoxic compound is represented by any one of the following formulas:

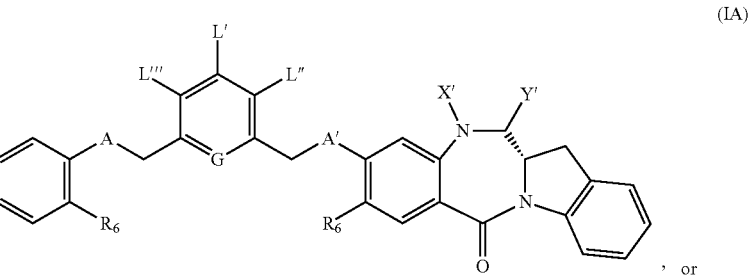
(IA)
, or

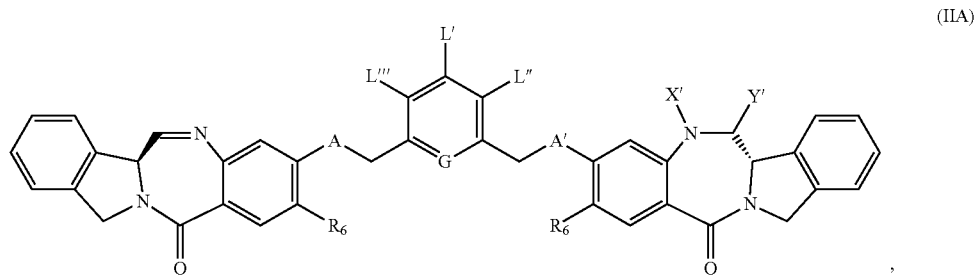
(IIA)
, wherein:
L', L", and L'" are the same or different, and are independently selected from —H, an optionally substituted linear, branched or cyclic alkyl, alkenyl or alkynyl having from 1 to 10 carbon atoms, a polyethylene glycol unit —(OCH$_2$CH$_2$)$_n$—R$^c$, halogen, guanidinium [—NH(C=NH)NH$_2$], —OR, —NR'R", —NO$_2$, —NR'COR", —SR, a sulfoxide represented by —SOR', a sulfone represented by —SO$_2$R', a sulfonate —SO$_3$M, a sulfate —OSO$_3$M, a sulfonamide represented by —SO$_2$NR'R", cyano, an azido, —COR', —OCOR', —OCONR'R";
M is —H or a pharmaceutically acceptable cation; and,
G is selected from —CH— or —N—.
In certain embodiments, the cytotoxic compound, when present, is represented by one of the following formulas, or a pharmaceutically acceptable salt thereof:

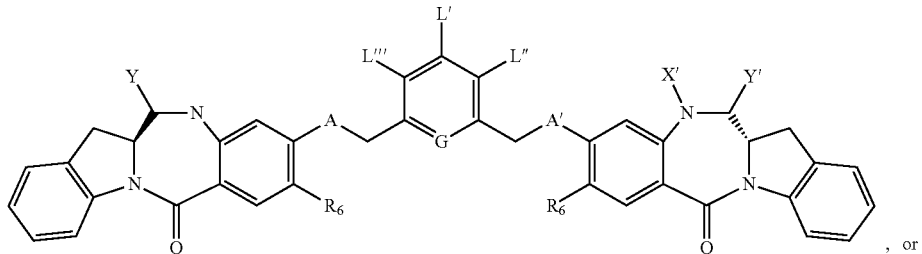

(IA')

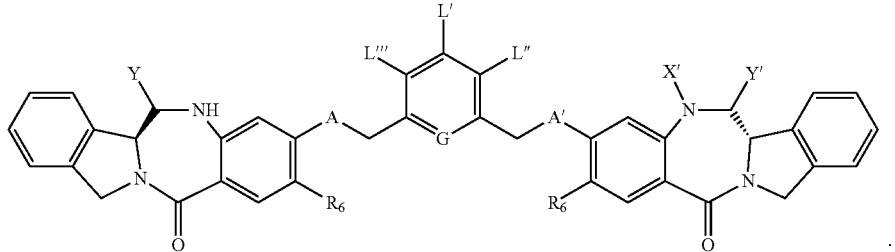

(IIA')

In certain embodiments, one of L', L", or L'" bears the thiol group, while the others are —H. Preferably, L' bears the thiol group, and L" and L'" are —H.

In certain embodiments, A and A' are both —O—; R$_6$ is —OMe; and G is —CH—.

In certain embodiments, the imine-containing cytotoxic compound may be represented by any one of the following formulas:

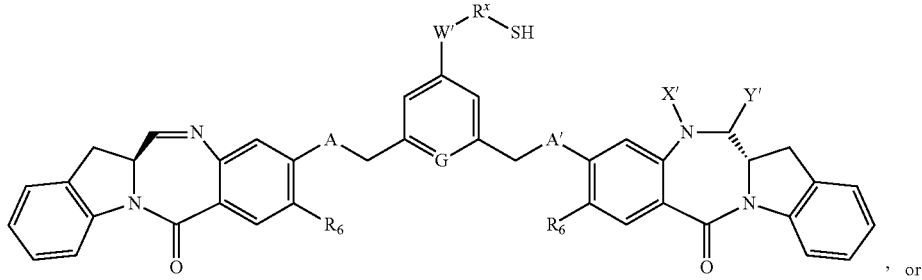

(IC)

, or

-continued

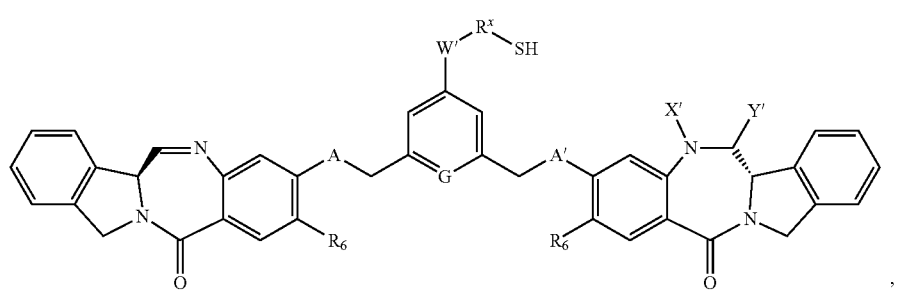
(IIC)

wherein:
W' is absent, or when present, is selected from —CR$^e$R$^{e'}$—, —O—, —O—C(=O)—, —C(=O)—O—, —S—, —SO—, —SO$_2$—, —CH$_2$—S—, —CH$_2$O—, —CH$_2$NR$^e$—, —O—(C=O)O—, —O—(C=O)N(R$^e$)—, —N(R$^e$)—, —N(R$^e$)—C(=O)—, —C(=O)—N(R$^e$)—, —N(R$^e$)—C(=O)O—, —N(C(=O)R$^e$)C(=O)—, —N(C(=O)R$^e$)—, —(O—CH$_2$—CH$_2$)$_n$—, —SS—, or —C(=O)—, or an amino acid, or a peptide having 2 to 8 amino acids;

R$^x$ is absent, or when present, is an optionally substituted linear, branched or cyclic alkyl, alkenyl or alkynyl having 1 to 10 carbon atoms, an aryl bearing 6 to 10 carbon atoms or a 3- to 8-membered heterocyclic ring bearing 1 to 3 heteroatoms selected from O, N or S;

R$^e$ and R$^{e'}$ are the same or different, and are selected from —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5- or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms; preferably, R$^{101}$ and R$^{102}$ are each independently a linear or branched alkyl having 1 to 6 carbon atoms;

n is an integer from 1 to 24.

In certain embodiments, the cytotoxic compound, when present, may be represented by one of the following formulas, or a pharmaceutically acceptable salt thereof:

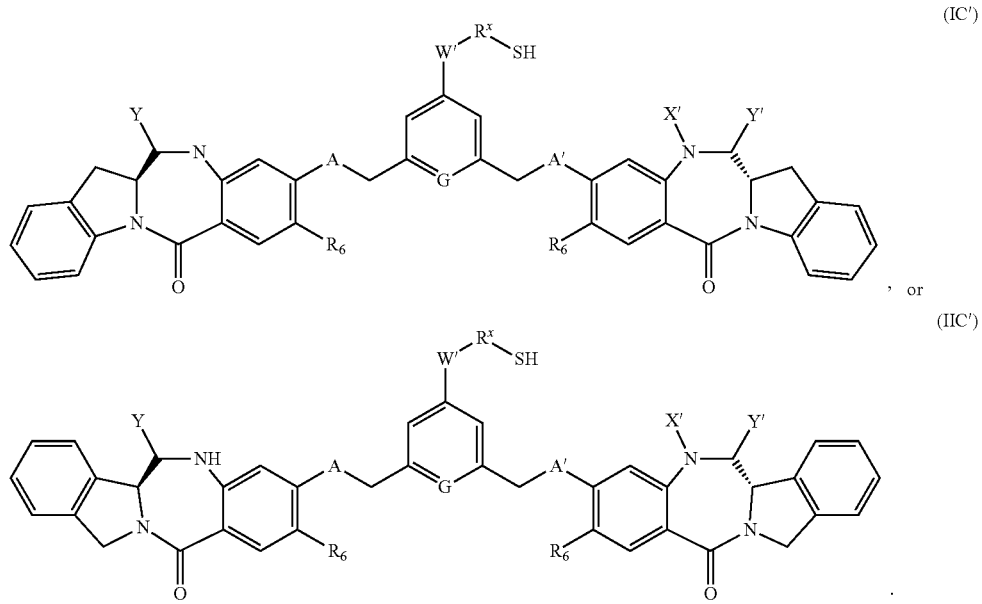
(IC')

, or (IIC')

In certain embodiments,
Y is selected from —SO$_3$M, —SO$_2$M or —OSO$_3$M;
M is —H or a pharmaceutically acceptable cation such as Na$^+$ or K$^+$;
X' is selected from the group consisting of —H, —OH, a substituted or unsubstituted linear, branched or cyclic alkyl, alkenyl or alkynyl having from 1 to 10 carbon atoms, phenyl, and an amine-protecting group;
Y' is selected from the group consisting of —H, an oxo group, a substituted or unsubstituted linear, branched or cyclic alkyl, alkenyl or alkynyl having from 1 to 10 carbon atoms;
A and A' are selected from —O— and —S—;

W' is absent, or selected from —O—, —N(R$^e$)—, —N(R$^e$)—C(=O)—, —N(C(=O)R$^e$)—, —S— or —CH$_2$—S—, —CH$_2$NR$^e$—;

R$^x$ is absent or selected from a linear, branched or cyclic alkyl having 1 to 10 carbon atoms;

R$^e$ is —H, a linear, branched or cyclic alkyl, alkenyl or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino group (—NR$^{101}$R$^{102}$) or a 5- or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms;

G is selected from —CH— or —N—.

In certain embodiments, W' is —N(R$^e$)—.

In certain embodiments, R$^e$ is —(CH$_2$—CH$_2$—O)$_n$—R$^k$, wherein R$^k$ is a —H, a linear, branched cyclic alkyl having 1 to 6 carbon atoms.

In certain embodiments, R$^k$ is —H or -Me, n is 4, and q is 2.

In certain embodiments, R$^x$ is a linear or branched alkyl having 1 to 6 carbon atoms.

In certain embodiments, R$^x$ is —(CH$_2$)$_p$—(CR$^f$R$^g$)—, wherein R$^f$ and R$^g$ are each independently selected from —H or a linear or branched alkyl having 1 to 4 carbon atoms; and p is 0, 1, 2 or 3.

In certain embodiments, R$^f$ and R$^g$ are the same or different, and are selected from —H and -Me; and p is 1.

In certain embodiments,
Y is —SO$_3$M, —SO$_2$M, or a sulfate —OSO$_3$M; preferably —SO$_3$M;
M is —H or a pharmaceutically acceptable cation (e.g., Na$^+$);
X' and Y' are both —H;
A and A' are both —O—;
R$_6$ is —OMe; and
R$^x$ is a linear or branched alkyl having 1 to 6 carbon atoms.

In certain embodiments, the bifunctional crosslinking agent is: a maleimido-based moiety selected from: N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), N-succinimidyl 4-(p-maleimidophenyl)-butyrate (SMPB), N-(p-maleimidophenyl)isocyanate (PMPI), N-succinimidyl-4-(4-nitropyridyl-2-dithio)butanoate; or, a haloacetyl-based moiety selected from: N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP), bis-maleimidopolyethyleneglycol (BMPEO), BM(PEO)$_2$, BM(PEO)$_3$, N-(β-maleimidopropyloxy)succinimide ester (BMPS), 5-maleimidovaleric acid NHS, HBVS, 4-(4-N-maleimidophenyl)-butyric acid hydrazide.HCl (MPBH), Succinimidyl-(4-vinylsulfonyl)benzoate (SVSB), dithiobis-maleimidoethane (DTME), 1,4-bis-maleimidobutane (BMB), 1,4-bismaleimidyl-2,3-dihydroxybutane (BMDB), bis-maleimidohexane (BMH), bis-maleimidoethane (BMOE), sulfosuccinimidyl 4-(N-maleimido-methyl)cyclohexane-1-carboxylate (sulfo-SMCC), sulfosuccinimidyl(4-iodo-acetyl)aminobenzoate (sulfo-SIAB), m-maleimidobenzoyl-N-hydroxysulfo succinimide ester (sulfo-MBS), N-(γ-maleimidobutryloxy)sulfosuccinimde ester (sulfo-GMBS), N-(ε-maleimidocaproyloxy)sulfosuccimido ester (sulfo-EMCS), N-(κ-maleimidoundecanoyloxy)sulfosuccinimide ester (sulfo-KMUS), sulfosuccinimidyl 4-(p-maleimidophenyl)butyrate (sulfo-SMPB), CX1-1, sulfo-Mal and PEG$_n$-Mal.

In certain embodiments, the bifunctional crosslinking agent is selected from the group consisting of SMCC, Sulfo-SMCC, BMPS, GMBS, SIA, SIAB, N-succinimidyl-4-(4-nitropyridyl-2-dithio)butanoate, bis-maleimidohexane or BMPEO.

In certain embodiments, the modified CBA, when present, is:

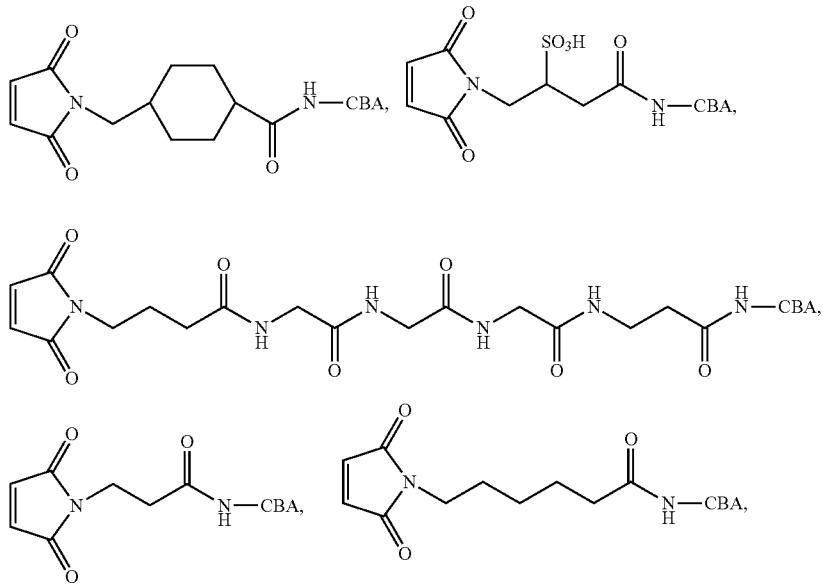

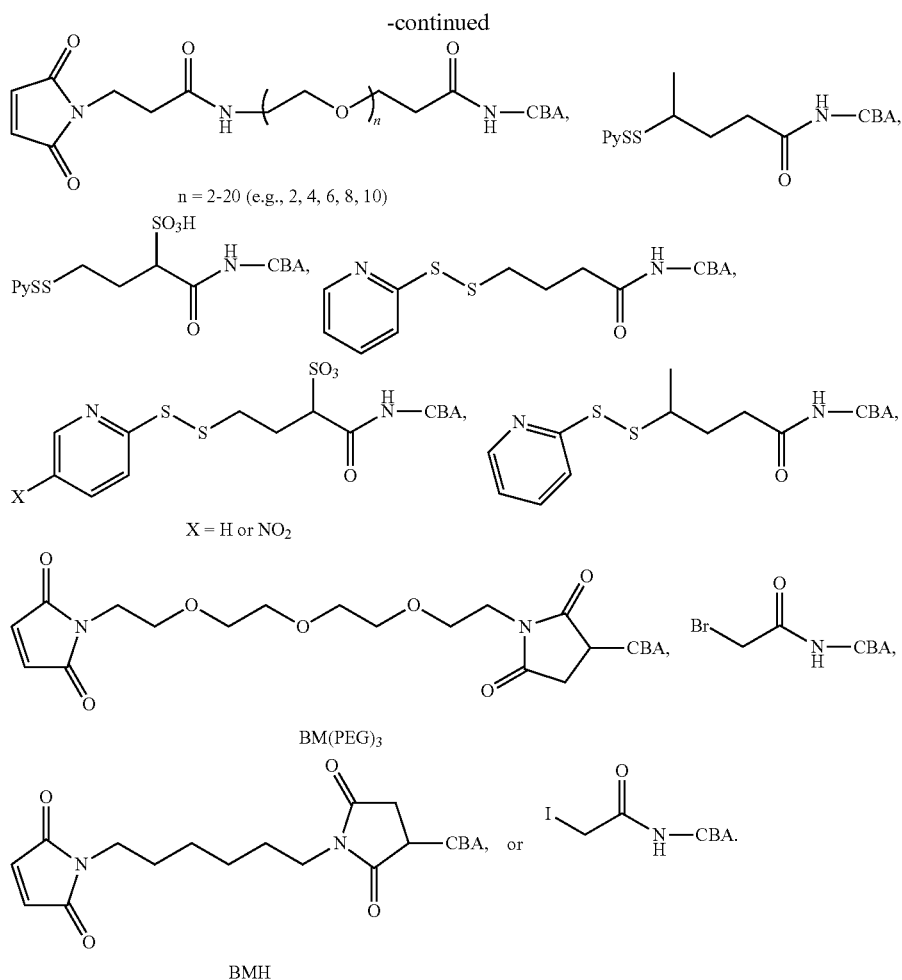

In a thirteens specific embodiment, the imine-containing cytotoxic compound is:

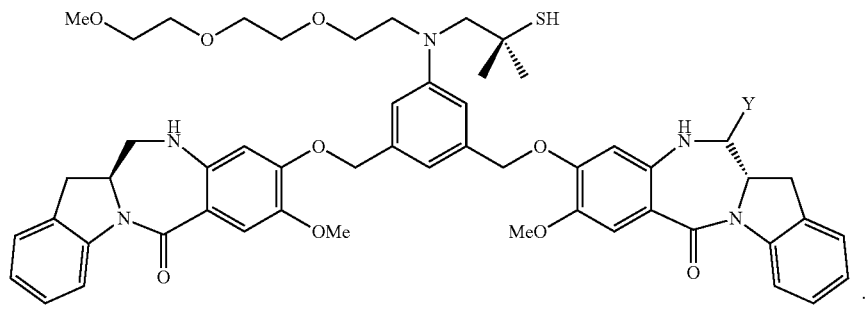

The bifunctional crosslinking agents can be any bifunctional linker known in the art. For example, the bifunctional linkers can be used for making the drug-linker compounds are those that form disulfide bonds, thioether bonds, acid labile bonds, photolabile bonds, peptidase labile bonds and esterase labile bonds with the cytotoxic compounds (see for example, U.S. Pat. Nos. 5,208,020; 5,475,092; 6,441,163; 6,716,821; 6,913,748; 7,276,497; 7,276,499; 7,368,565; 7,388,026 and 7,414,073, all of which are incorporated herein by reference). Preferably, the bifunctional crosslinking agents are those that form disulfide bonds, thioether and peptidase labile bonds with the cytotoxic compounds. Other bifunctional crosslinking agents that can be used in the present invention include non-cleavable linkers, such as those described in U.S. publication number US 2005/0169933, or charged linkers or hydrophilic linkers and are described in US 2009/0274713, US 2010/01293140 and WO 2009/134976, each of which is expressly incorporated herein by reference. The bifunctional crosslinking agents that can be used for making the drug-linker compounds of the present invention also include those described in Thermo Scientific Pierce Crosslinking Technical Handbook, the entire teaching of which is incorporated herein by reference.

In another preferred embodiment, the drug (with or without a linker group with a reactive group attached thereto) that can be used in the present invention is any one of the compounds shown in Tables 1-7. In another preferred embodiment, the cell-binding agent-drug conjugate that can be made by the present invention is any one of the conjugates shown in Table 8.

TABLE 1

Structures of representative compounds in the present invention.

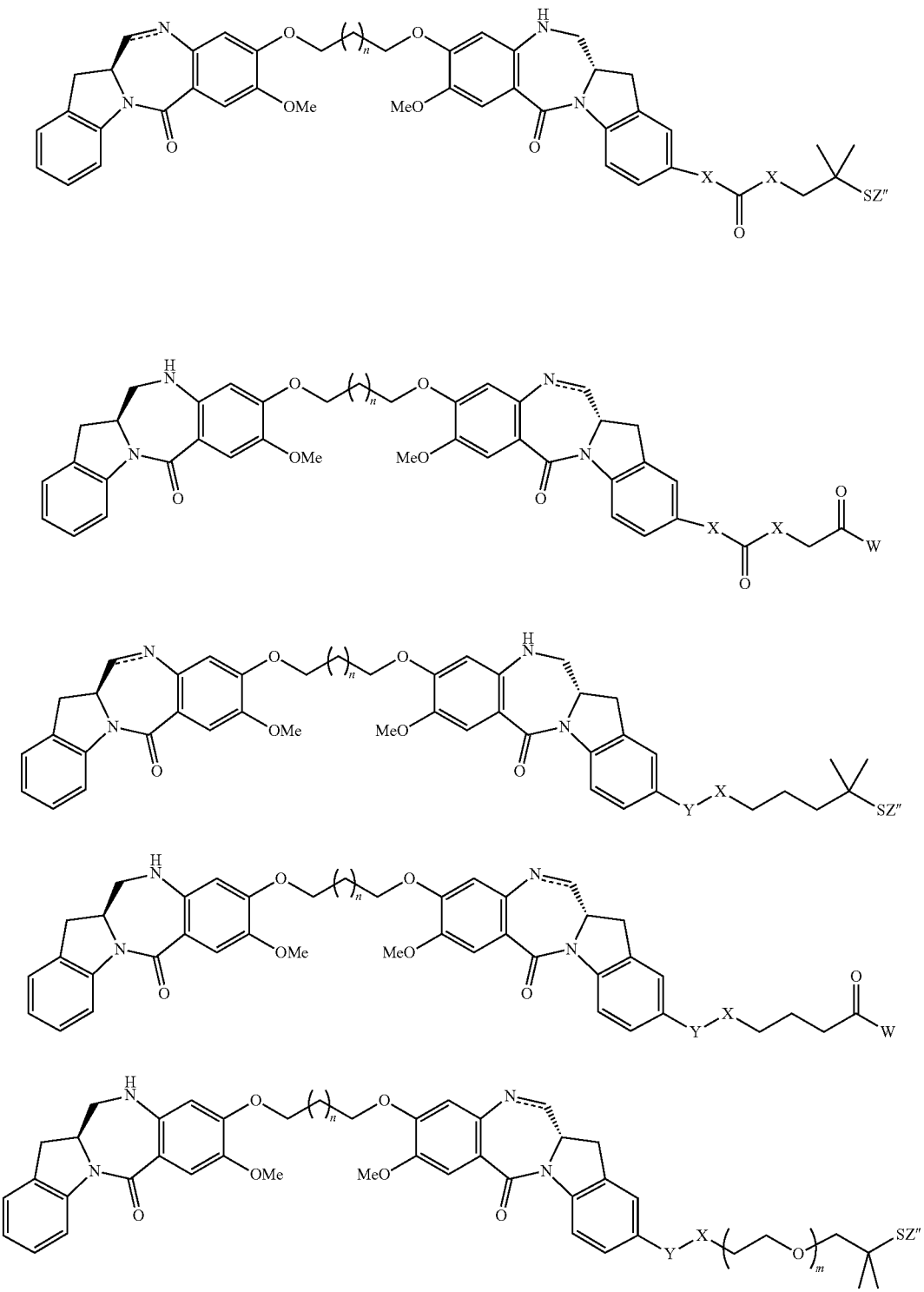

TABLE 1-continued
Structures of representative compounds in the present invention.
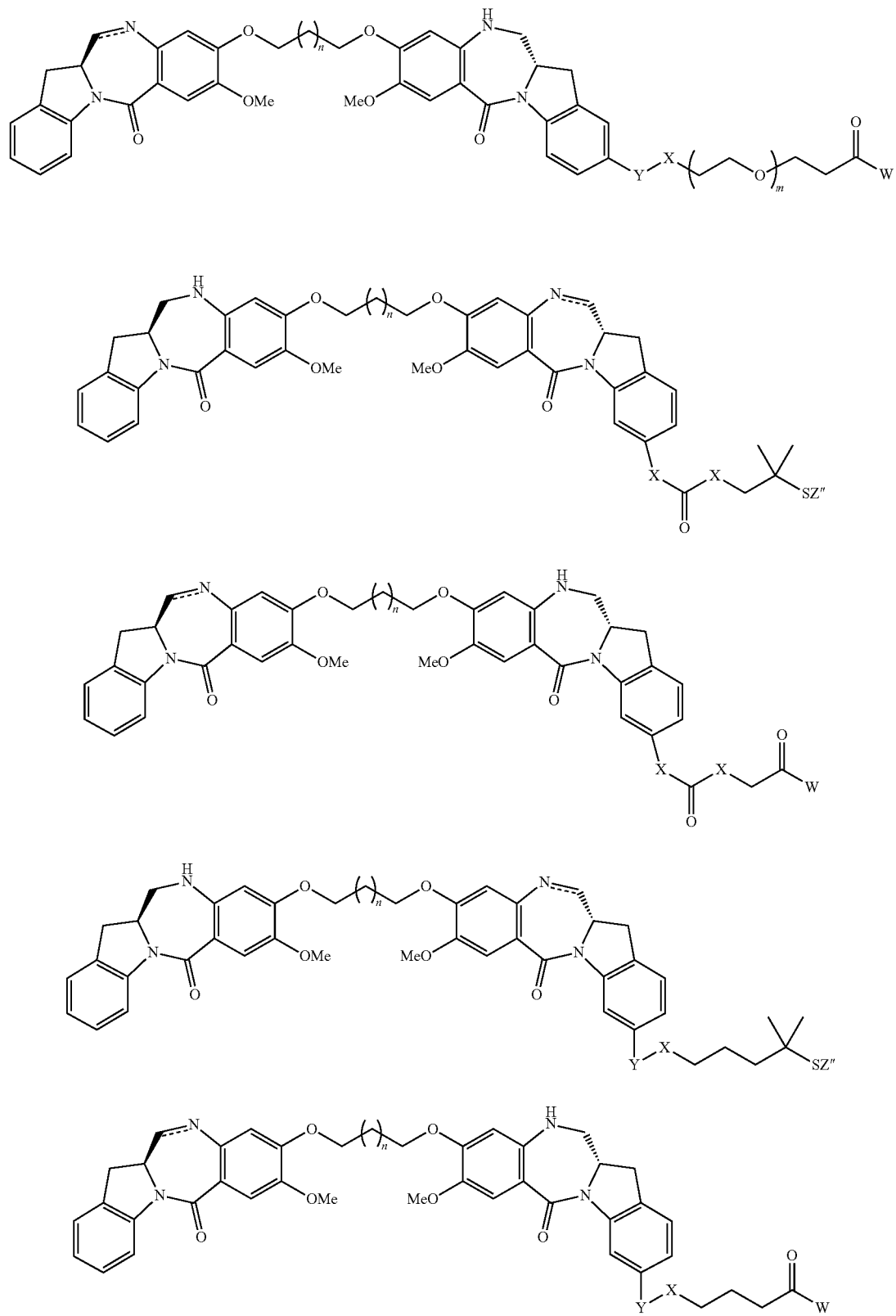

TABLE 1-continued
Structures of representative compounds in the present invention.
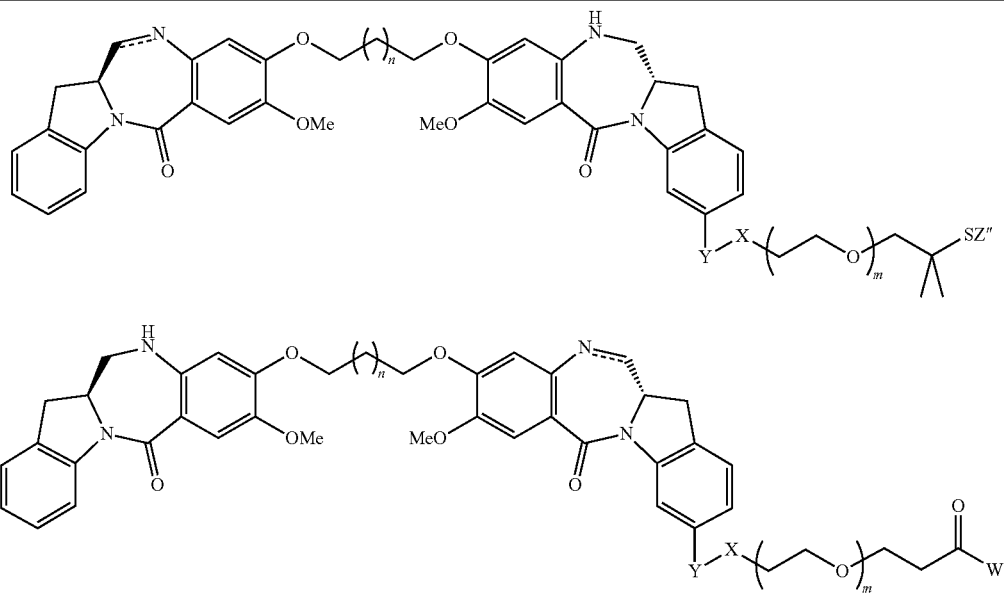
Notes:
n = 1 or 3
m = 3 or 4
W = OH, OMe, ONHS, NHNH$_2$, H, Me, Ph, Peptide
X = CH$_2$, O, S, NH or NMe
Y = CH$_2$ or absent
Z" = H, Me, SMe, S(CH$_2$)$_3$C(O)NHS or CH$_2$C(O)NHS or BMPS or SMCC or SPy or SPy-NO$_2$
TABLE 2
Structures of representative compounds in the present invention (Continued).
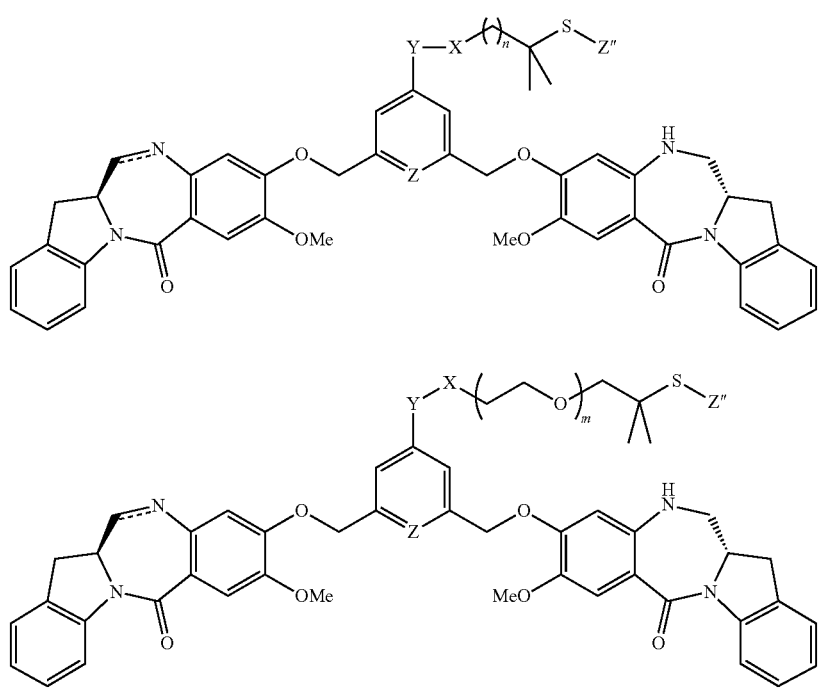

TABLE 2-continued
Structures of representative compounds in the present invention (Continued).
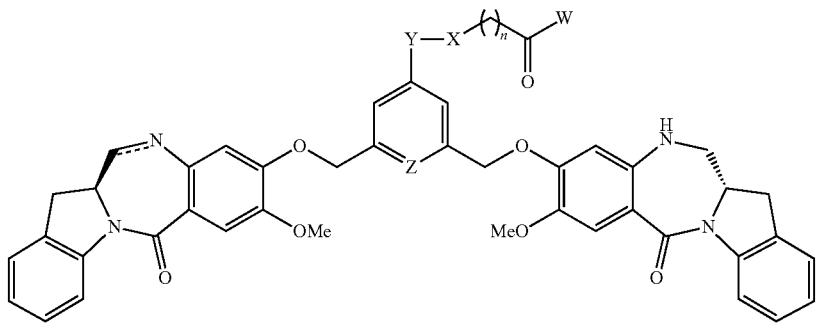
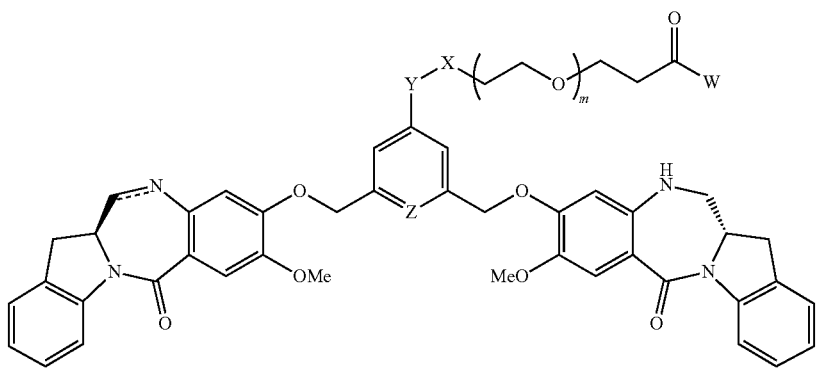
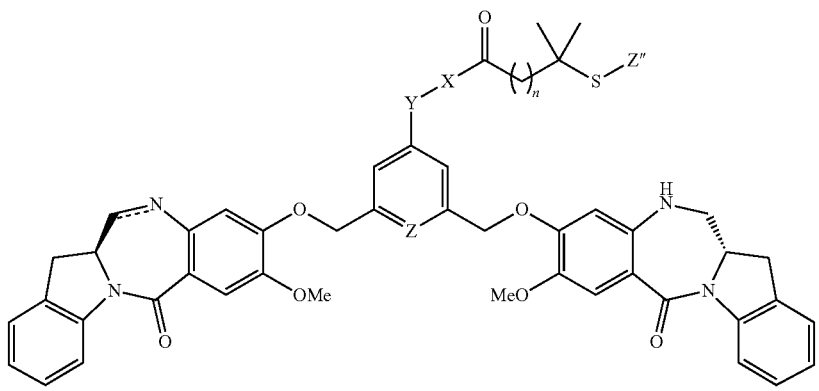
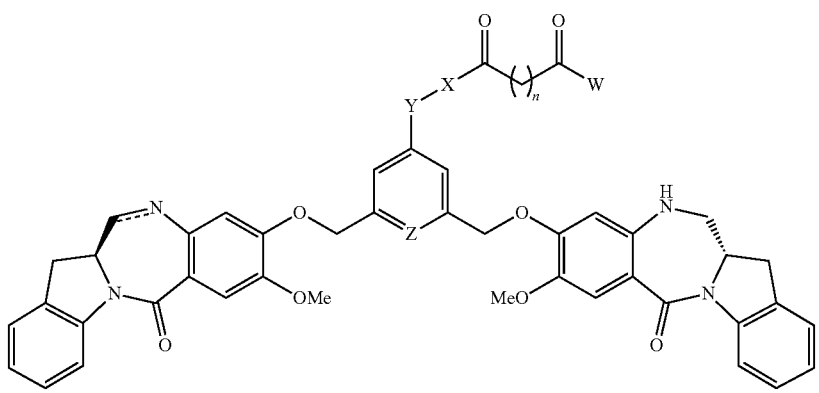

TABLE 2-continued
Structures of representative compounds in the present invention (Continued).
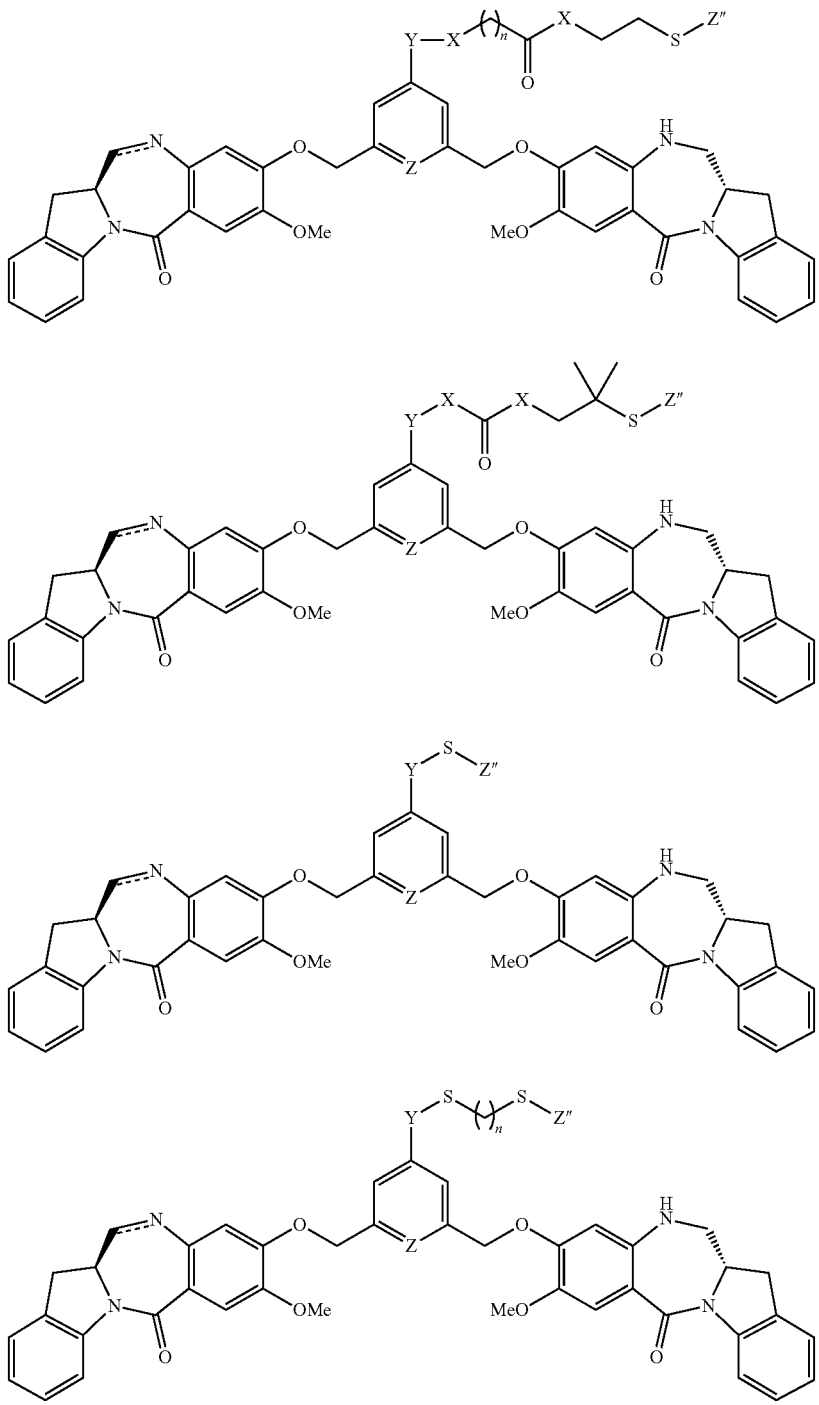
Note:
n = 1, 2 or 3
m = 3 or 4
W = OH, OMe, ONHS, NHNH$_2$, H, Me, Ph, Peptide
X = CH$_2$, O, S, NH, NMe
Y = absent or CH$_2$
Z = CH or N
Z" = H, Me, SMe, S(CH$_2$)$_3$C(O)NHS or CH$_2$C(O)NHS or BMPS or SMCC or SPy or SPy-NO$_2$ TABLE 3
Structures of representative compounds in the present invention (Continued).
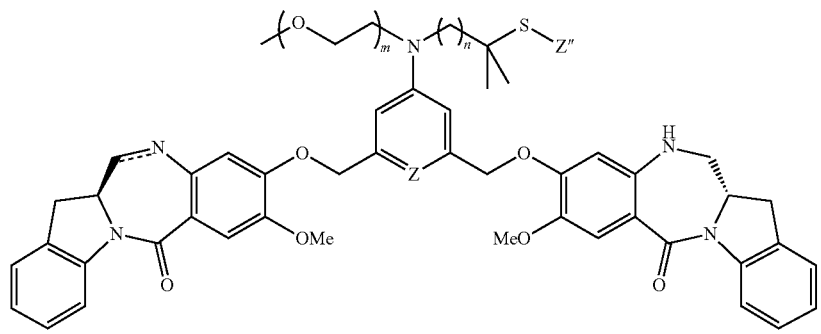
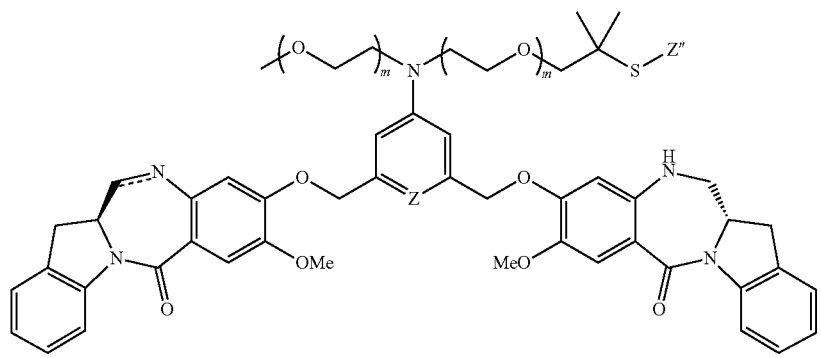
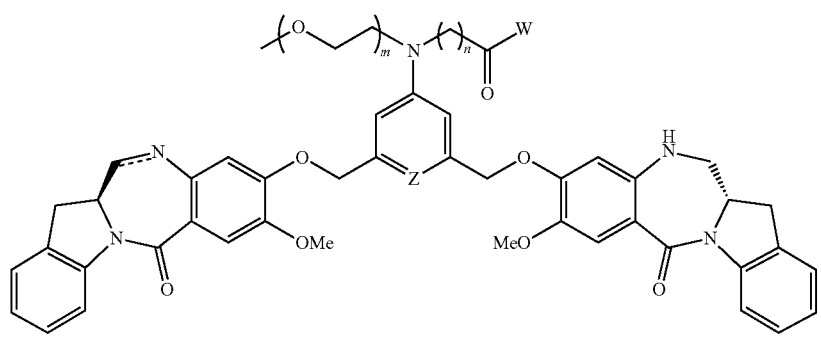
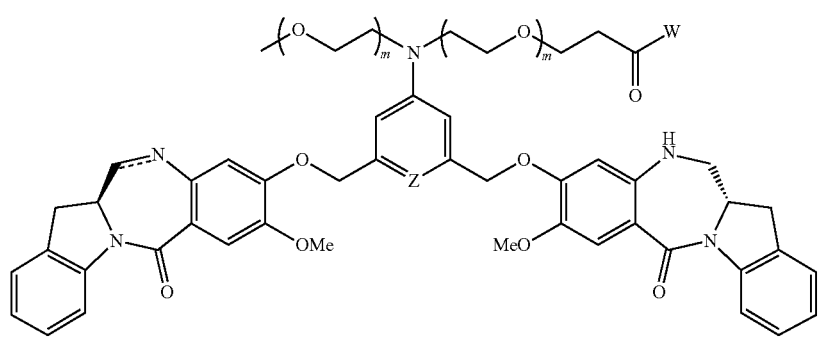

TABLE 3-continued
Structures of representative compounds in the present invention (Continued).
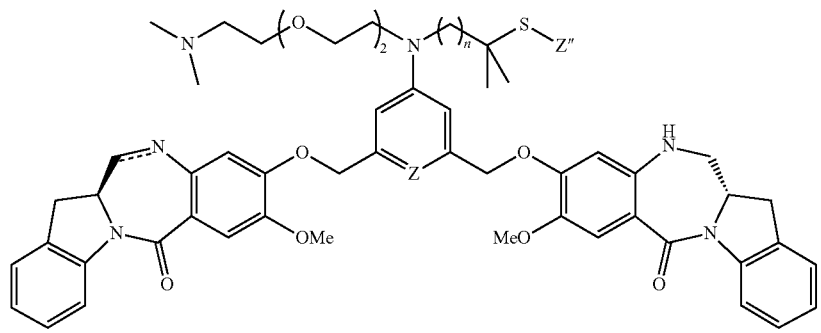
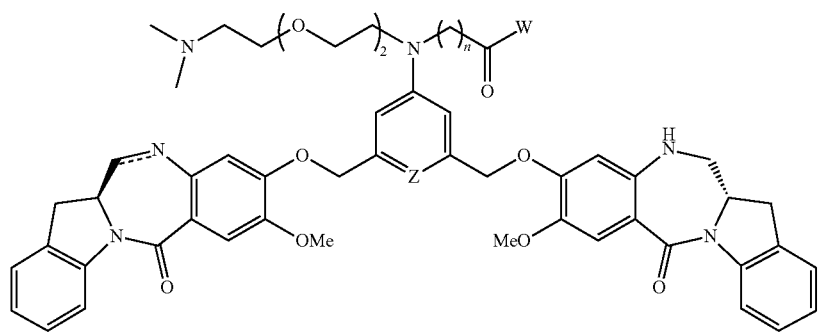
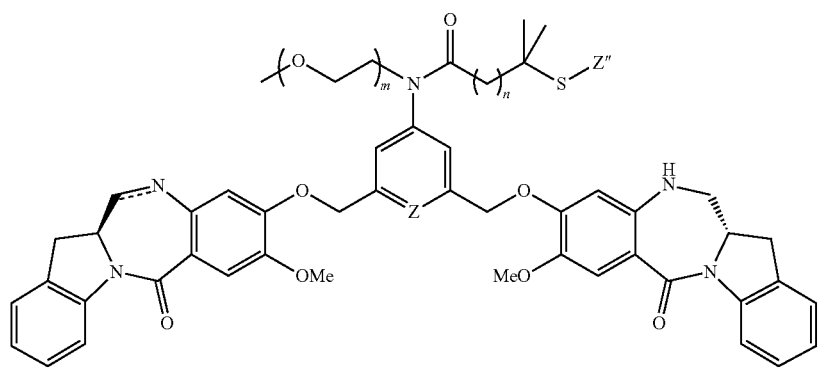
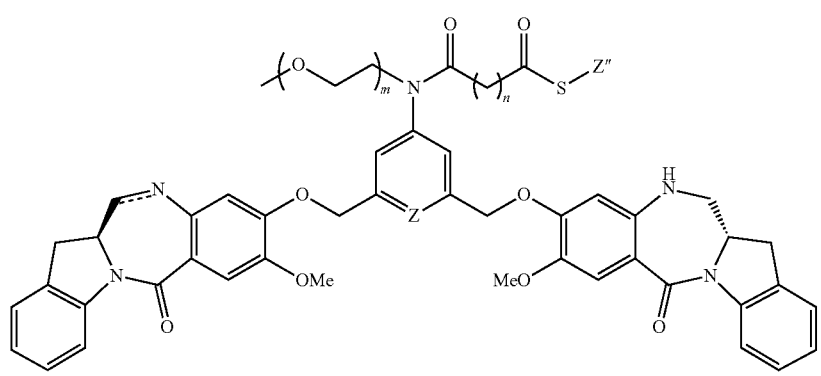

TABLE 3-continued
Structures of representative compounds in the present invention (Continued).
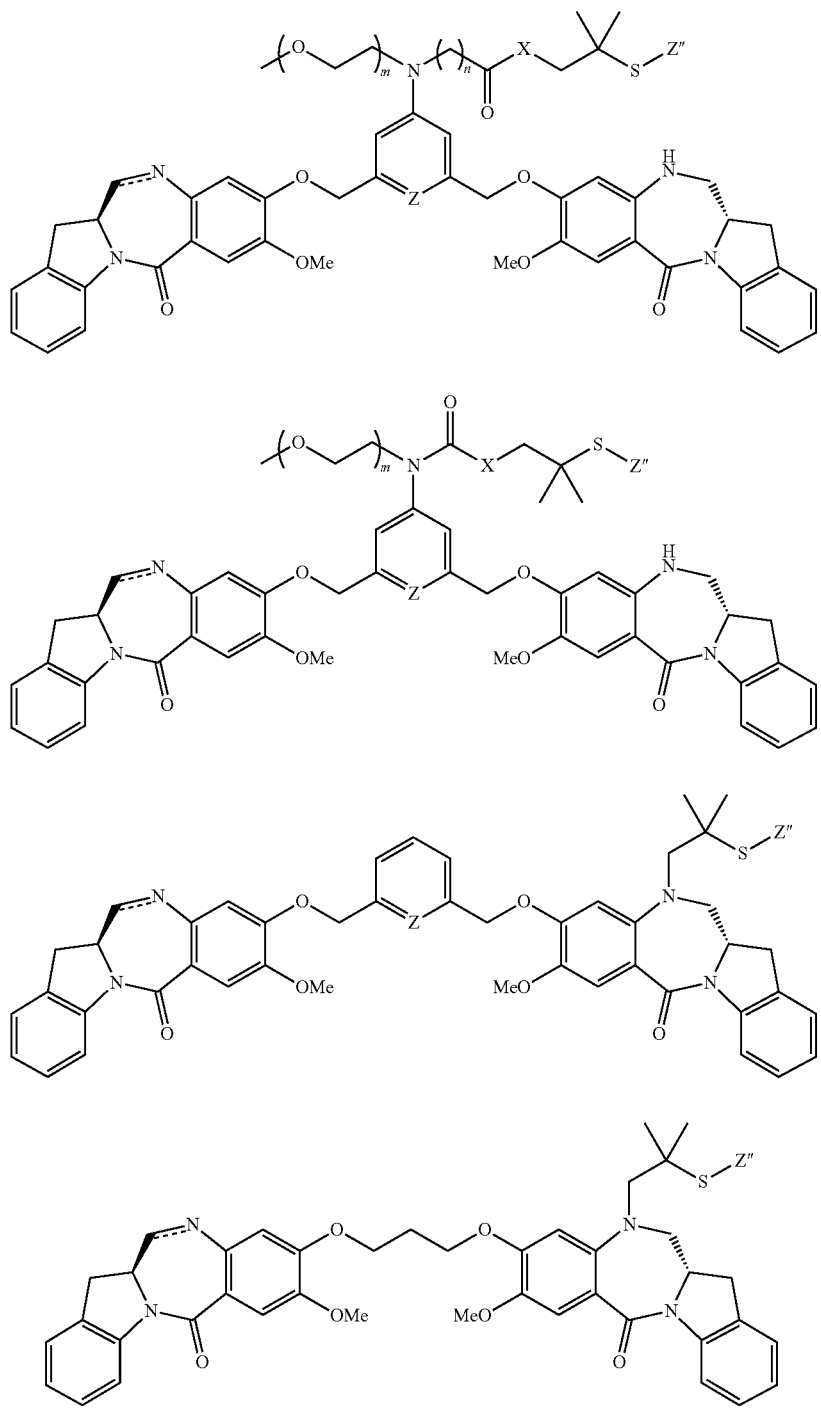
Note:
n = 1, 2 or 3
m = 3 or 4
W = OH, OMe, ONHS, NHNH$_2$, H, Me, Ph, Peptide
X = CH$_2$, O, S, NH, NMe
Z = CH or N
Z" = H, Me, SMe, S(CH$_2$)$_3$C(O)NHS or CH$_2$C(O)NHS or BMPS or SMCC or SPy or SPy-NO$_2$ TABLE 4
Structures of representative compounds in the present invention (Continued).
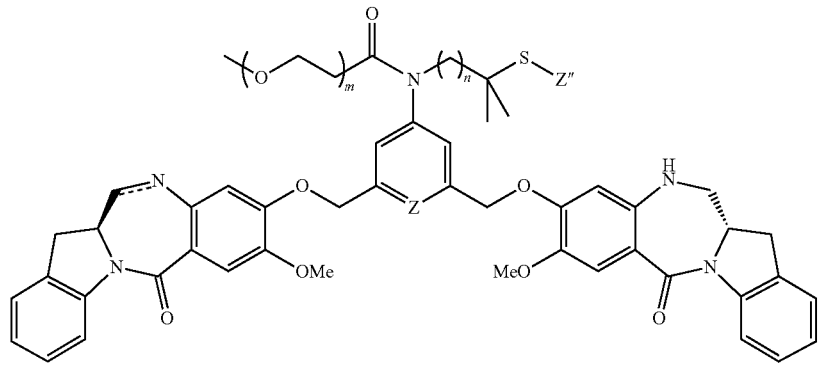
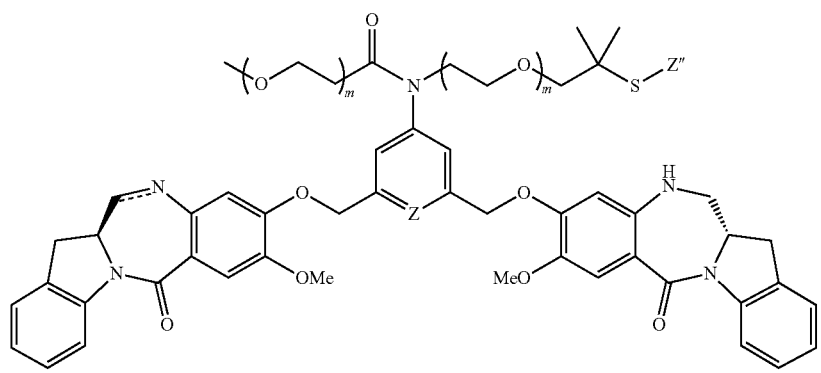
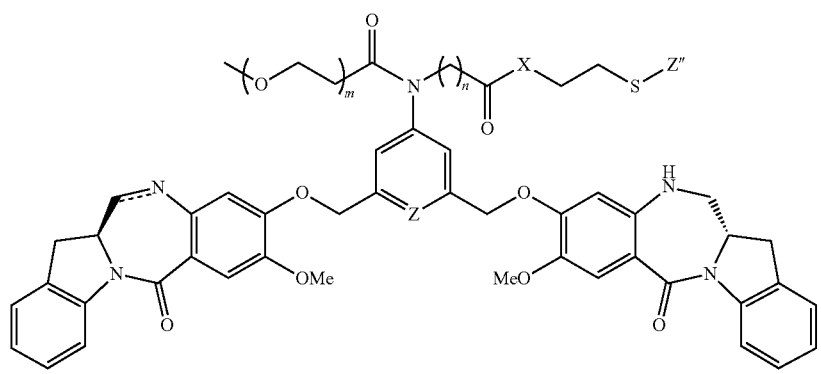
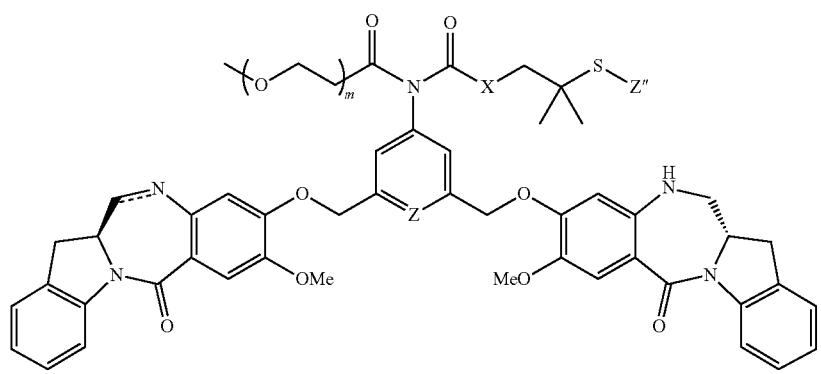

TABLE 4-continued
Structures of representative compounds in the present invention (Continued).
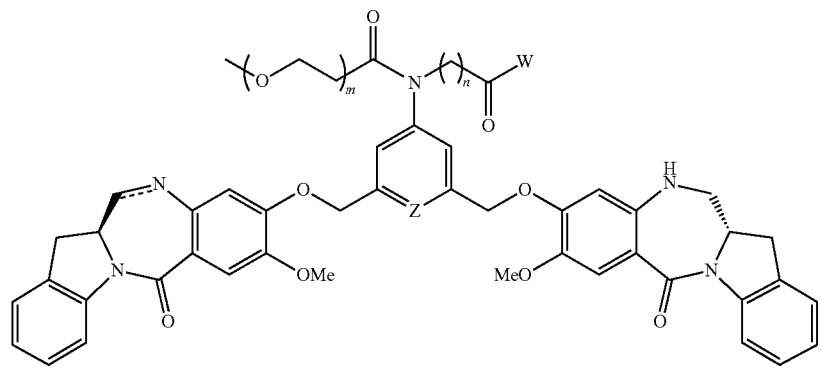
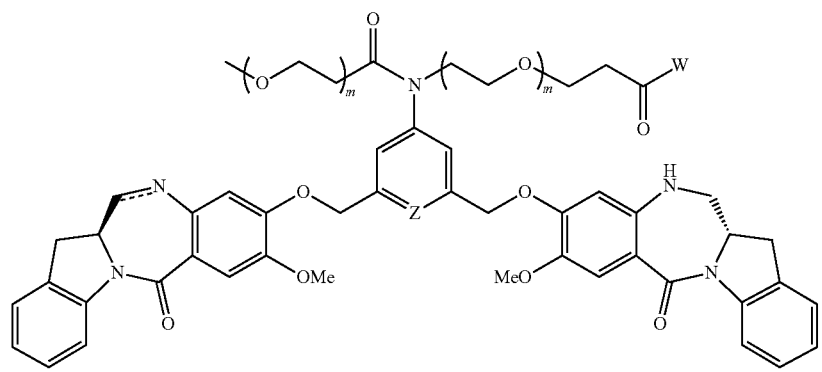
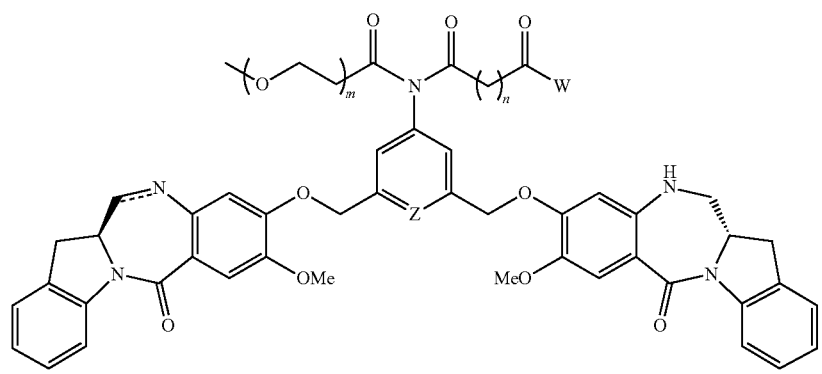
Note:
n = 1, 2 or 3
m = 3 or 4
W = OH, OMe, ONHS, NHNH$_2$, H, Me, Ph, Peptide
X = CH$_2$, O, S, NH, NMe
Z = CH or N
Z" = H, Me, SMe, S(CH$_2$)$_3$C(O)NHS or CH$_2$C(O)NHS or BMPS or SMCC or SPy or SPy-NO$_2$ TABLE 5
Structures of representative compounds in the present invention.
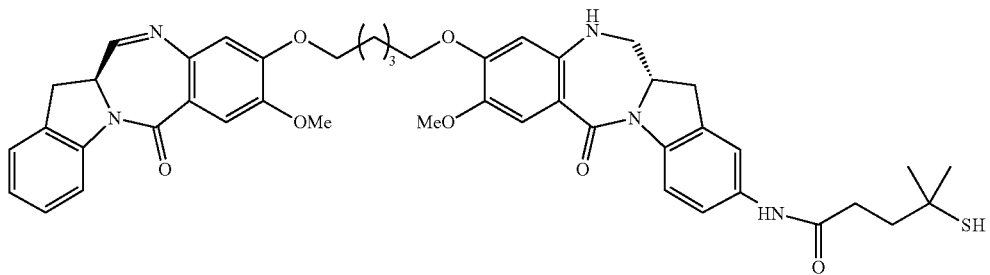
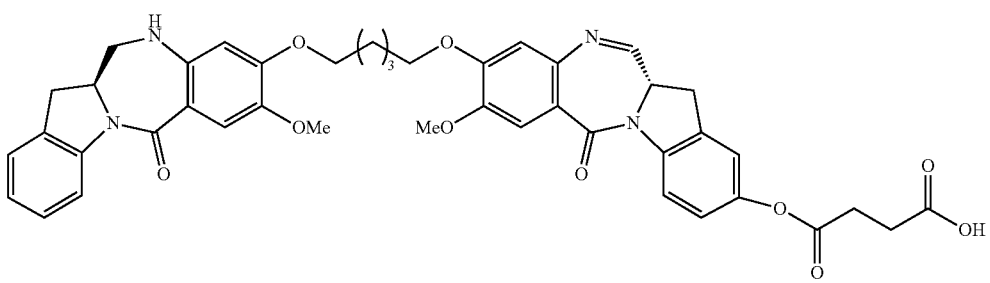
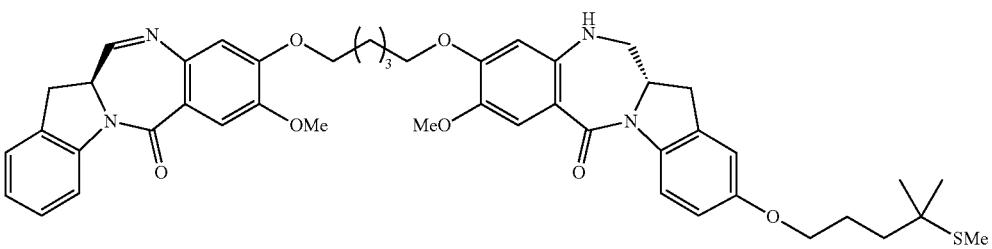
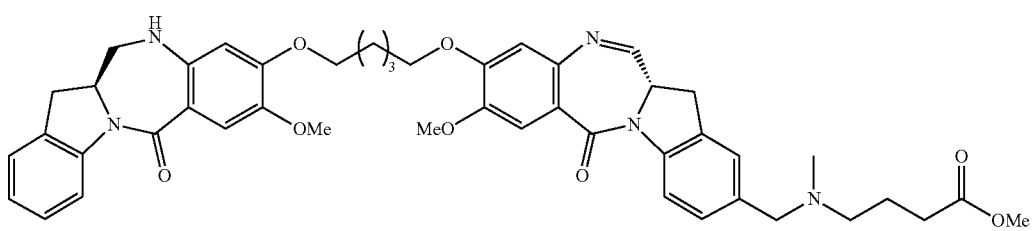
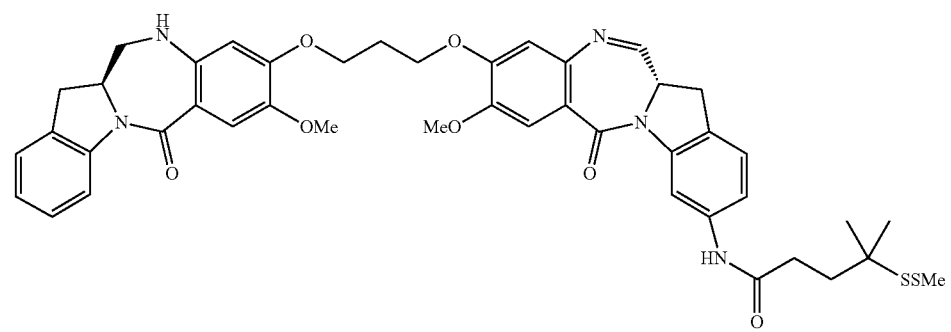

TABLE 5-continued
Structures of representative compounds in the present invention.
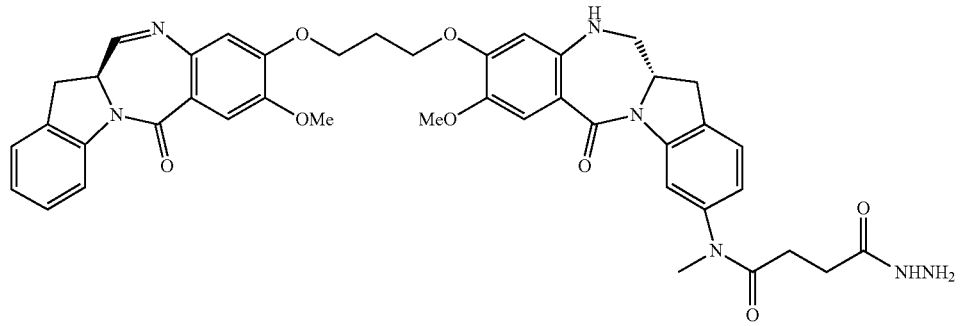 [SMILES: COc1cc2c(cc1OCCCOc1cc3c(cc1OC)C(=O)N1c4cc(N(C)C(=O)CCC(=O)NN)ccc4C[C@H]1CN3)N=C[C@@H]1Cc3ccccc3N1C2=O]
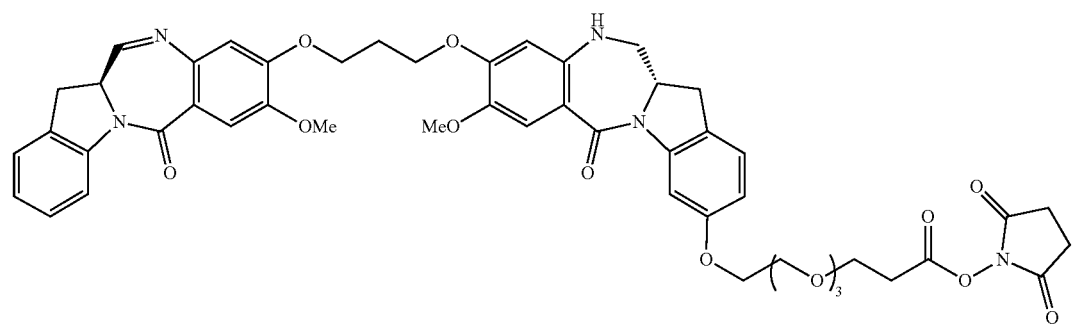
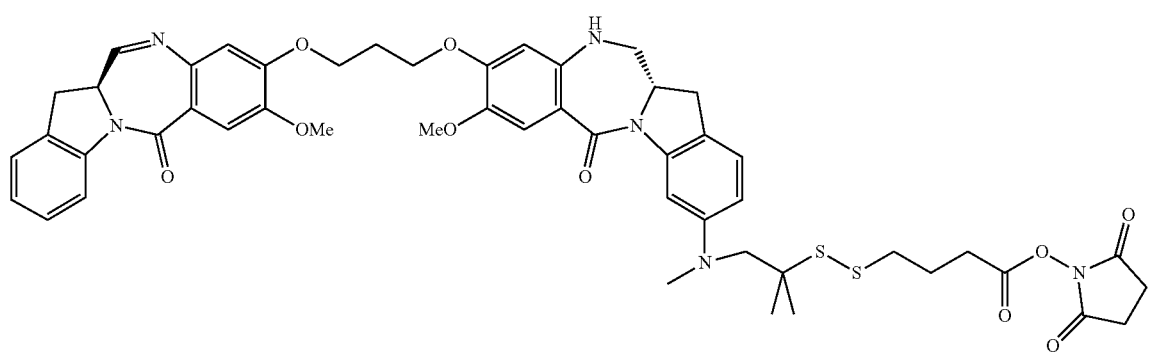 [SMILES: COc1cc2c(cc1OCCCOc1cc3c(cc1OC)C(=O)N1c4cc(N(C)CC(C)(C)SSCCCC(=O)ON5C(=O)CCC5=O)ccc4C[C@H]1CN3)N=C[C@@H]1Cc3ccccc3N1C2=O]
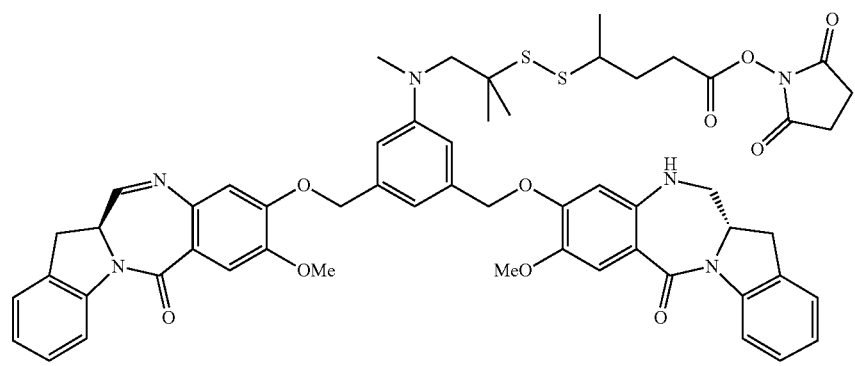 [SMILES: COc1cc2c(cc1OCc1cc(COc3cc4c(cc3OC)C(=O)N3c5ccccc5C[C@H]3CN4)cc(N(C)CC(C)(C)SSC(C)CCC(=O)ON3C(=O)CCC3=O)c1)N=C[C@@H]1Cc3ccccc3N1C2=O]

TABLE 5-continued
Structures of representative compounds in the present invention.
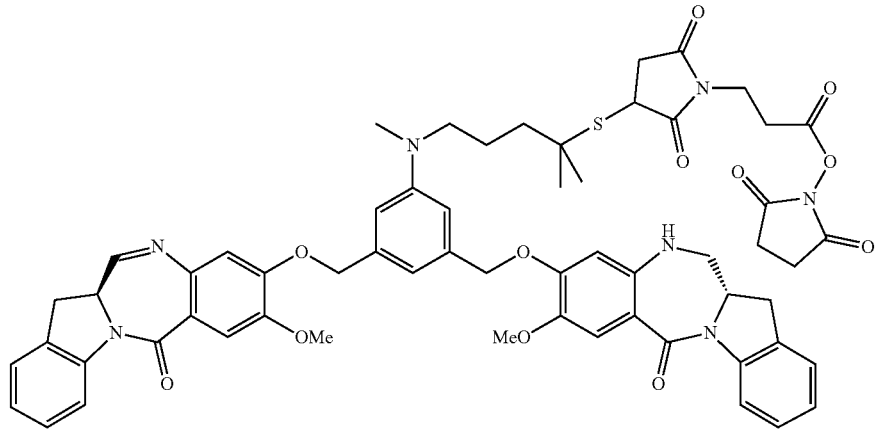 [SMILES: COc1cc2c(cc1OCc1cc(COc3cc4c(cc3OC)C(=O)N3c5ccccc5C[C@H]3CN4)cc(N(C)CCCC(C)(C)SC3CC(=O)N(CCC(=O)ON4C(=O)CCC4=O)C3=O)c1)N=C[C@@H]1Cc3ccccc3N1C2=O]
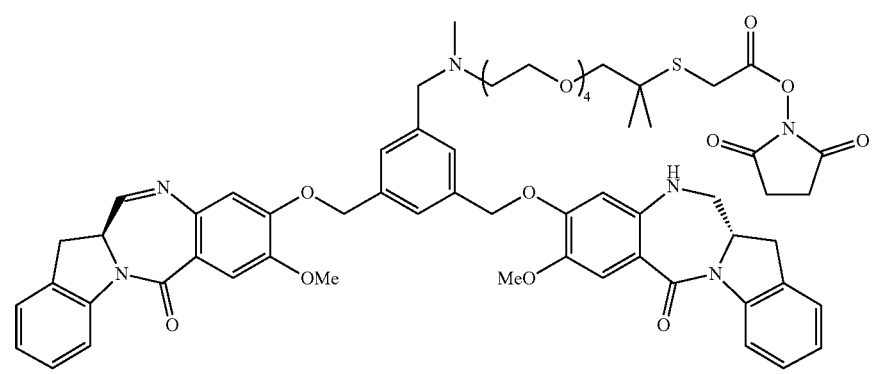
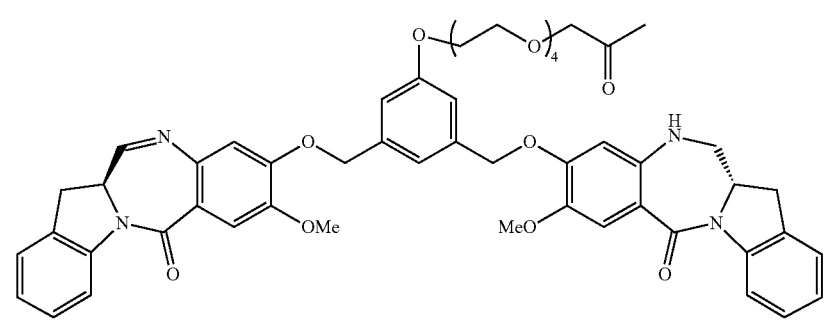
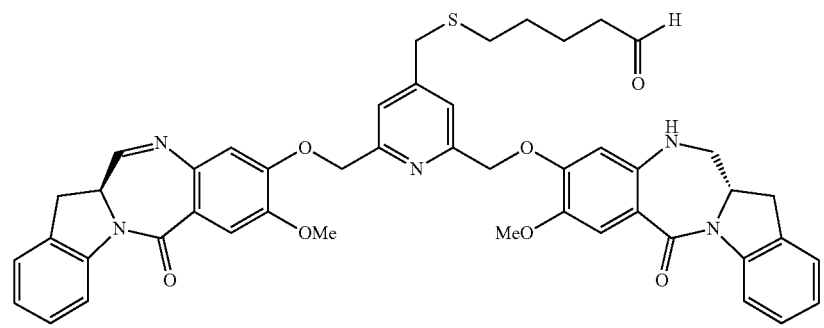 [SMILES: COc1cc2c(cc1OCc1cc(CSCCCCC=O)cc(COc3cc4c(cc3OC)C(=O)N3c5ccccc5C[C@H]3CN4)n1)N=C[C@@H]1Cc3ccccc3N1C2=O]

TABLE 5-continued
Structures of representative compounds in the present invention.
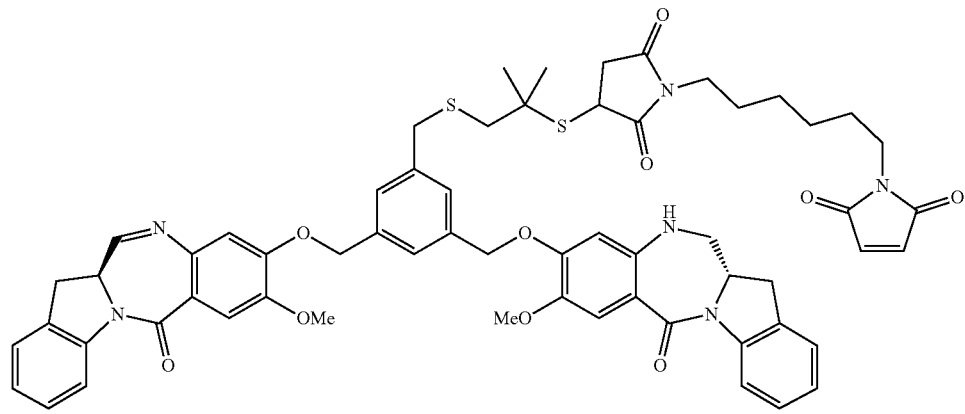 [SMILES: COc1cc2c(cc1OCc1cc(COc3cc4c(cc3OC)C(=O)N3c5ccccc5C[C@H]3CN4)cc(CSCC(C)(C)SC3CC(=O)N(CCCCCCN4C(=O)C=CC4=O)C3=O)c1)N=C[C@@H]1Cc3ccccc3N1C2=O]
TABLE 6
Structures of representative compounds in the present invention (Continued).
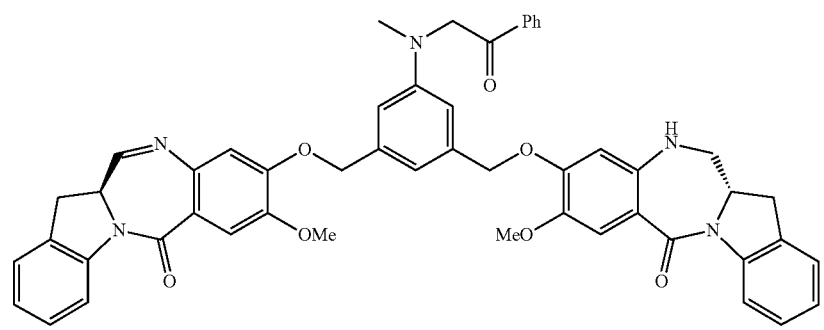 [SMILES: COc1cc2c(cc1OCc1cc(COc3cc4c(cc3OC)C(=O)N3c5ccccc5C[C@H]3CN4)cc(N(C)CC(=O)c3ccccc3)c1)N=C[C@@H]1Cc3ccccc3N1C2=O]
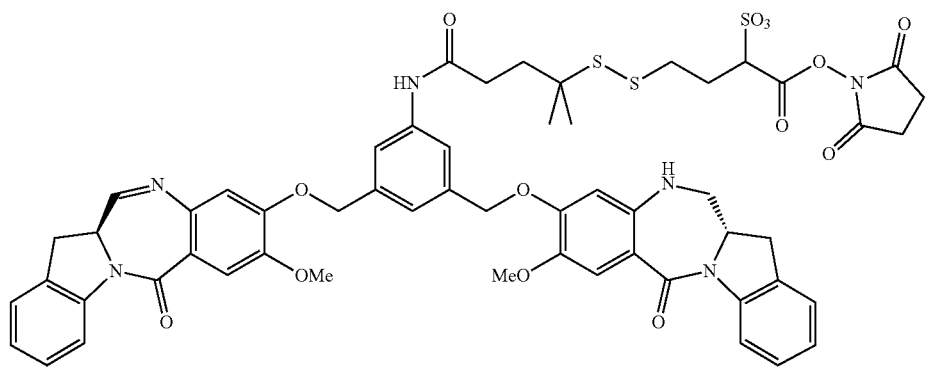

TABLE 6-continued
Structures of representative compounds in the present invention (Continued).
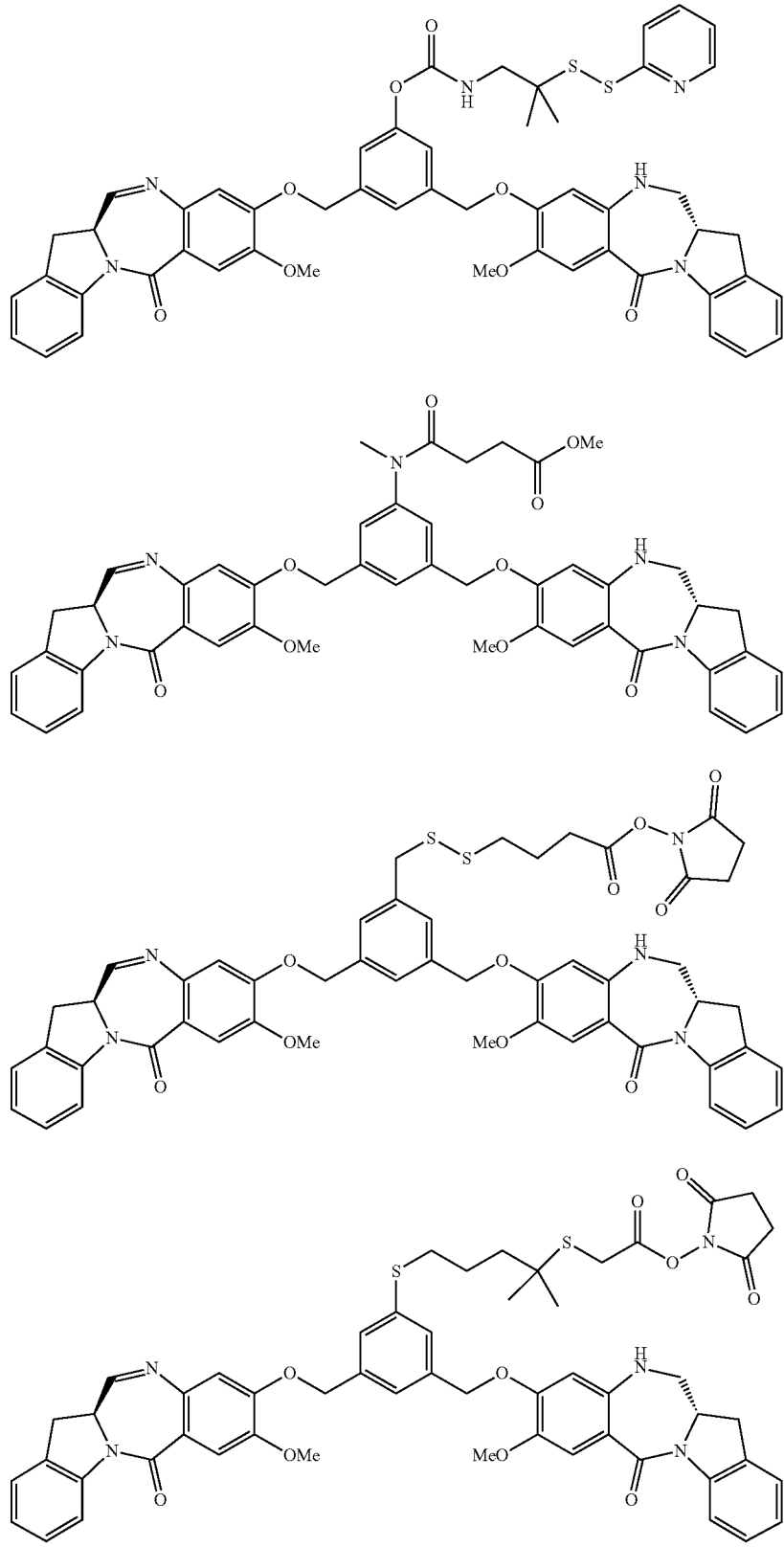

TABLE 6-continued
Structures of representative compounds in the present invention (Continued).
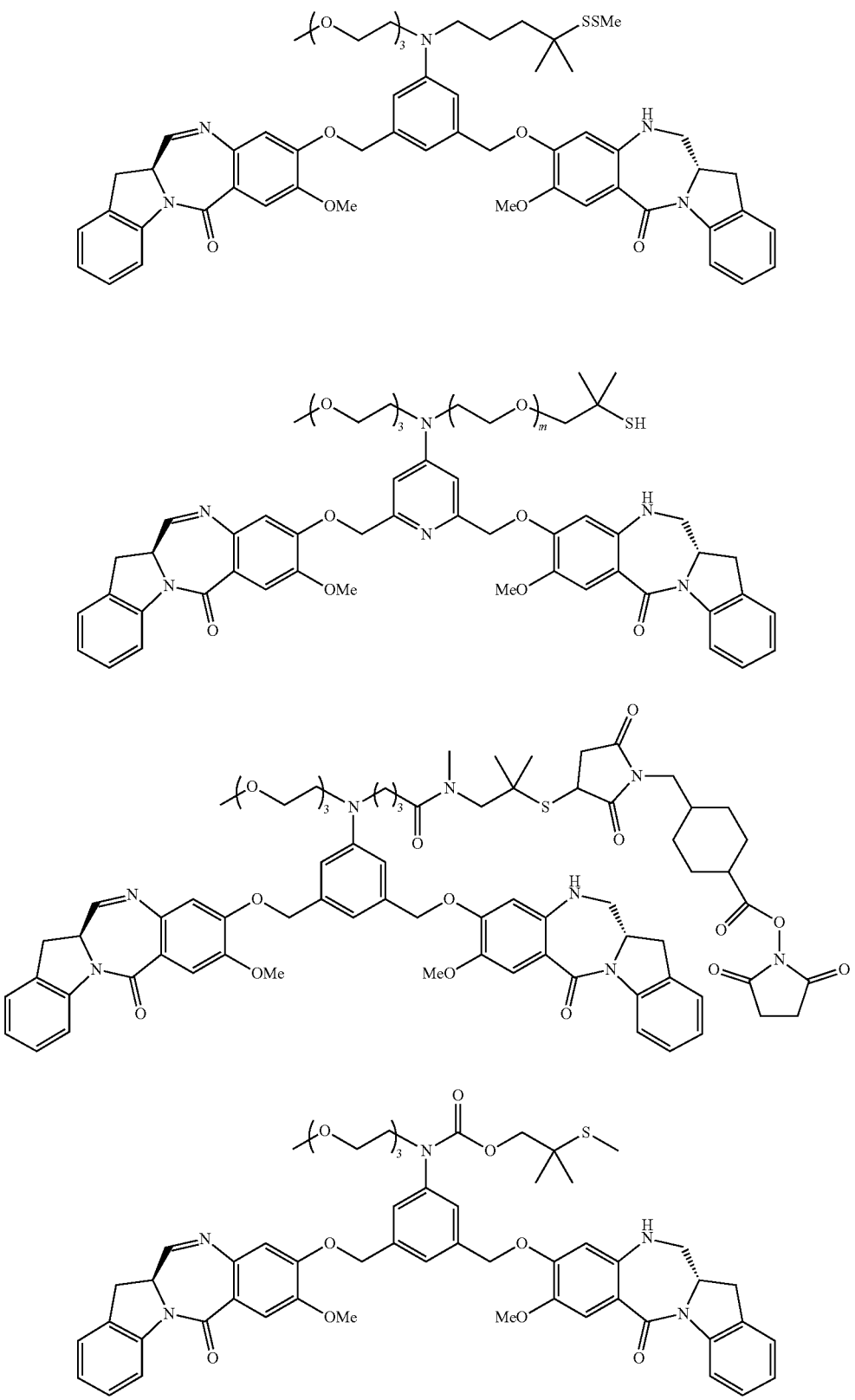

US 10,364,294 B2
113                                                              114
TABLE 6-continued
Structures of representative compounds in the present invention (Continued).
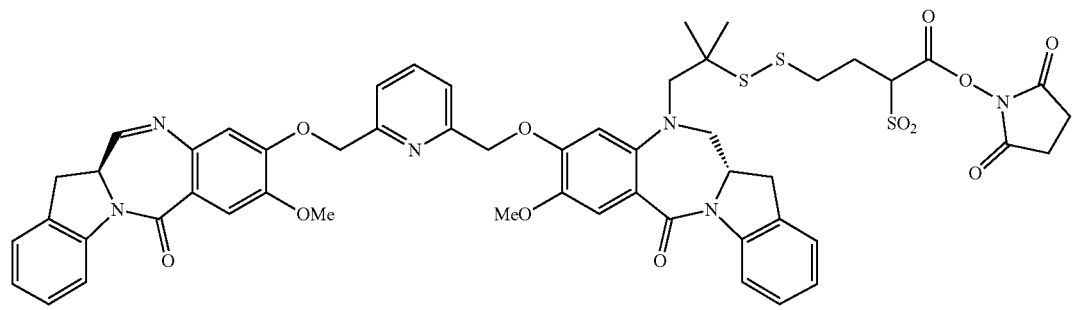
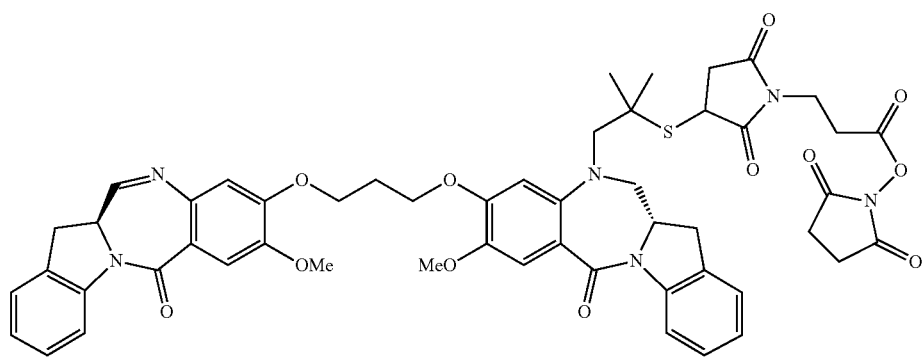 [SMILES: COc1cc2c(cc1OCCCOc1cc3c(cc1OC)C(=O)N1c4ccccc4C[C@H]1CN3CC(C)(C)SC1CC(=O)N(CCC(=O)ON3C(=O)CCC3=O)C1=O)N=C[C@@H]1Cc3ccccc3N1C2=O]
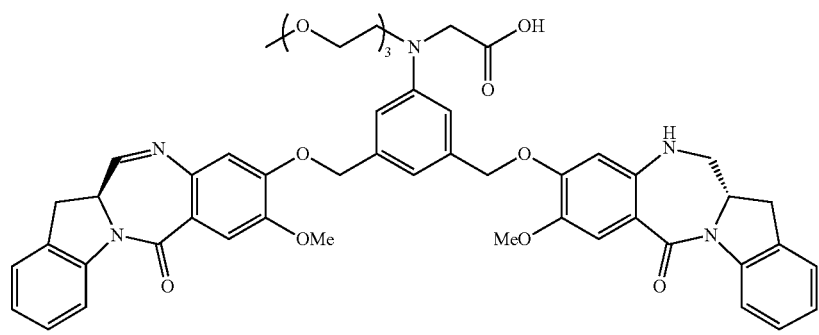
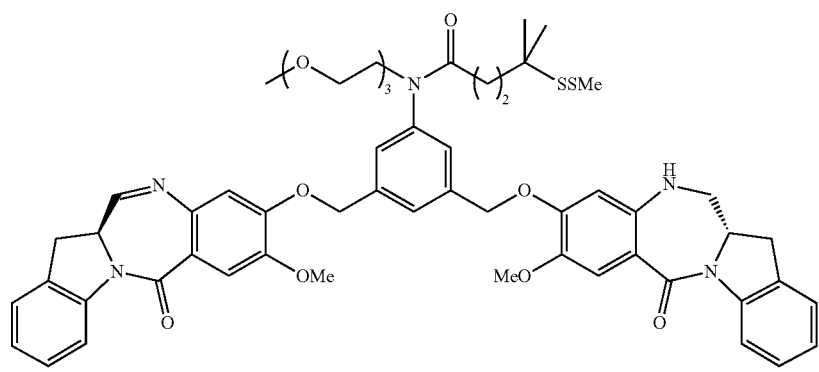

TABLE 7
Structures of representative compounds in the present invention (Continued).
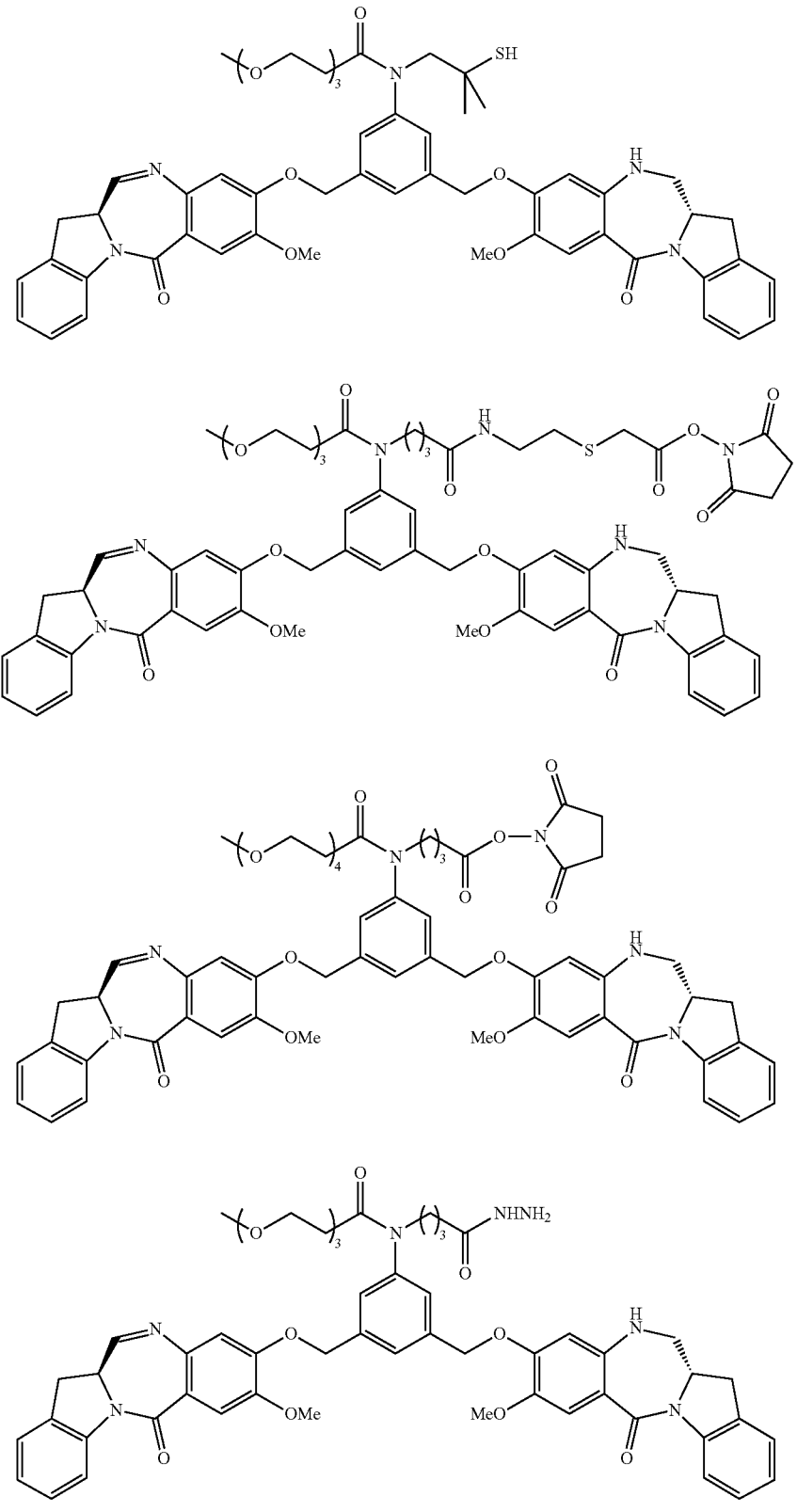

TABLE 8
Structures of representative conjugates of the present invention.
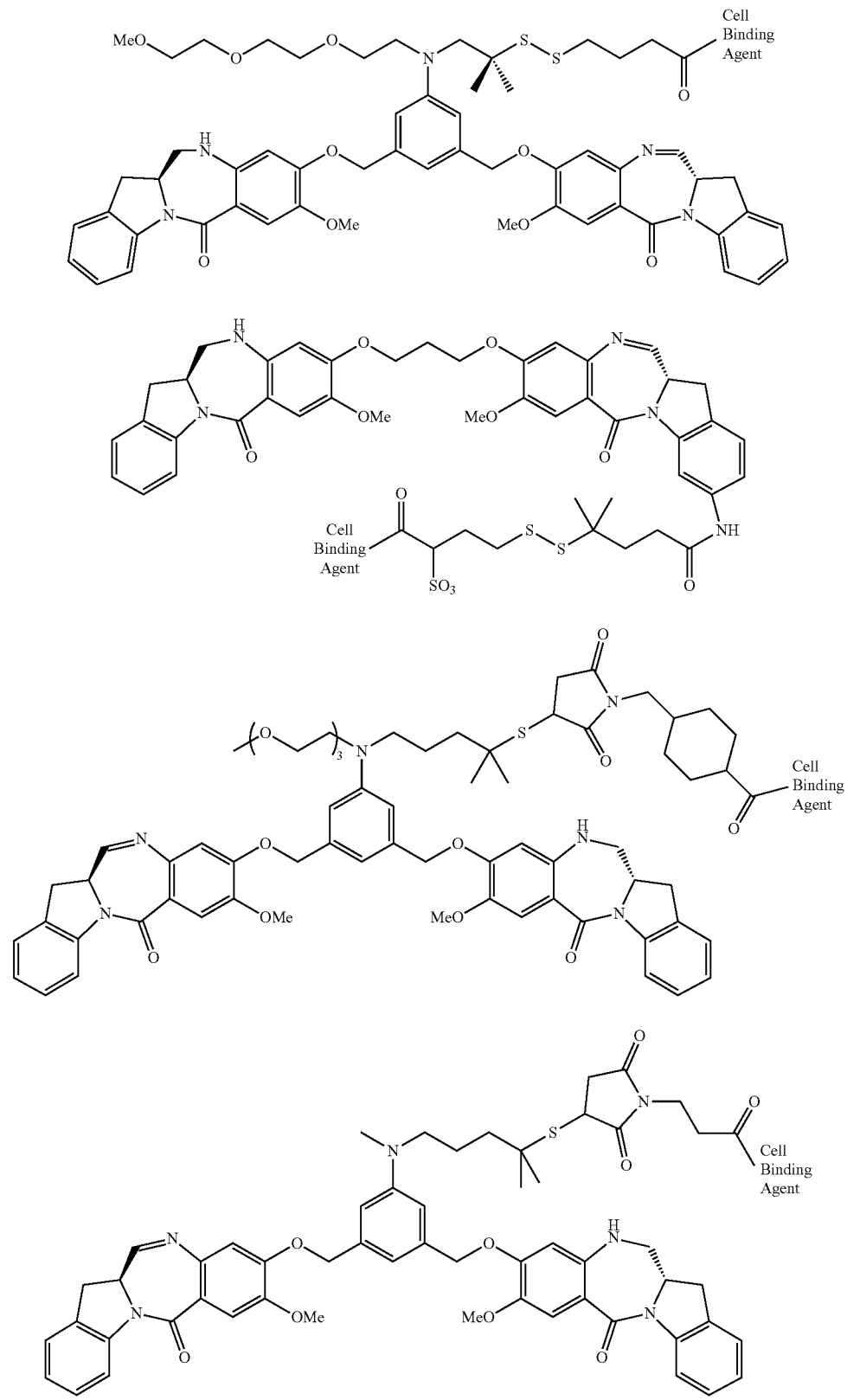

TABLE 8-continued

Structures of representative conjugates of the present invention.

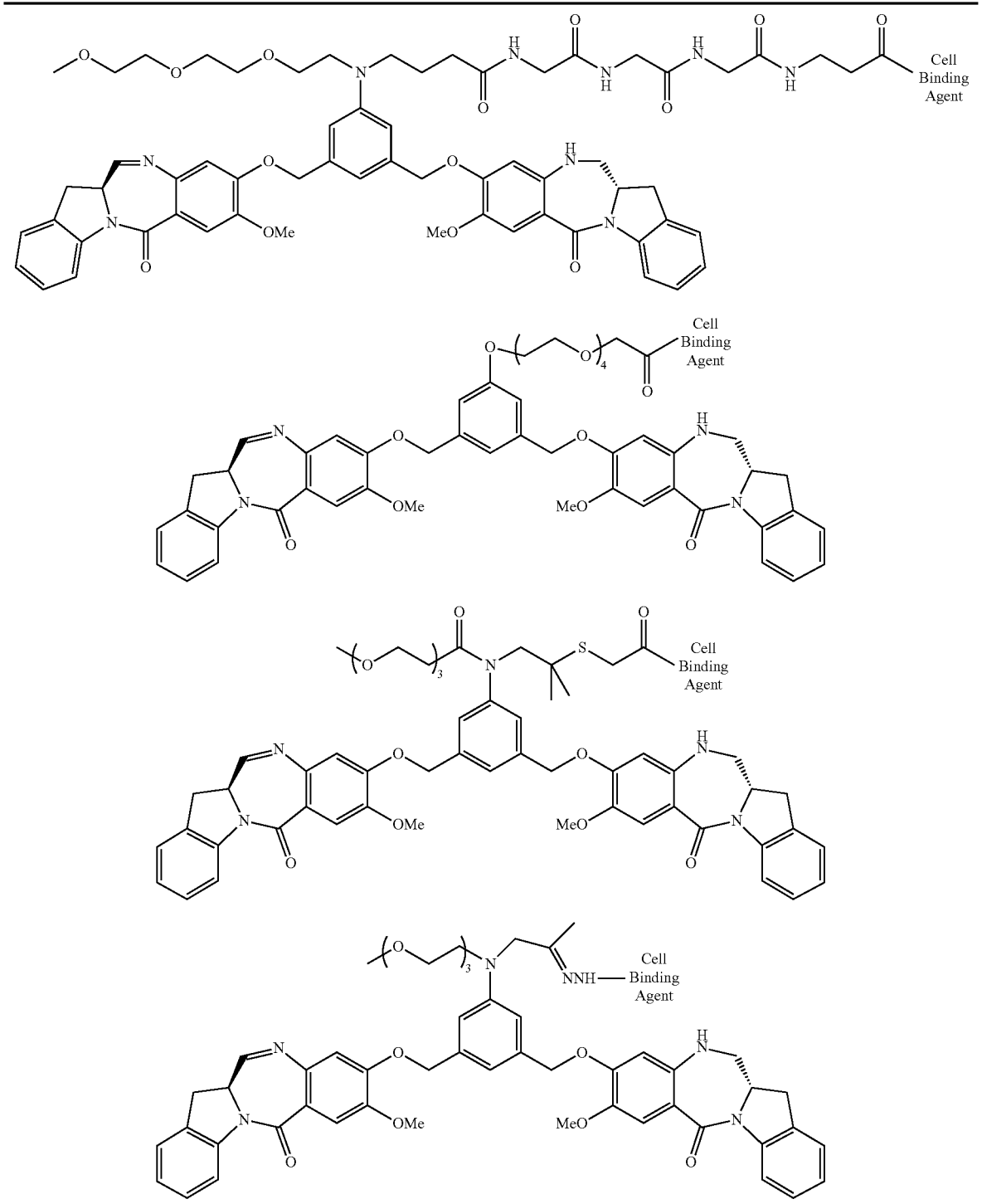

In any of the compounds or conjugates described above in Tables 1-8, the imine double bond may react with/have reacted with any of the imine-reactive reagent (such as those described herein) according to the methods of the invention to form adducts, including bisulfite adducts. Such imine-protected adducts in the compounds of Tables 1-7 may be used in further reactions according to the methods of the invention to produce conjugates of the invention. Similarly, compounds comprising imine-protected adducts may be used in the methods of the invention to produce the conjugates in Table 8.

In another embodiment, drugs optionally bearing a linking moiety (e.g., a linker group with a reactive group attached thereto) that can be used in the methods of the present invention are represented by formula (A1) or (A2):

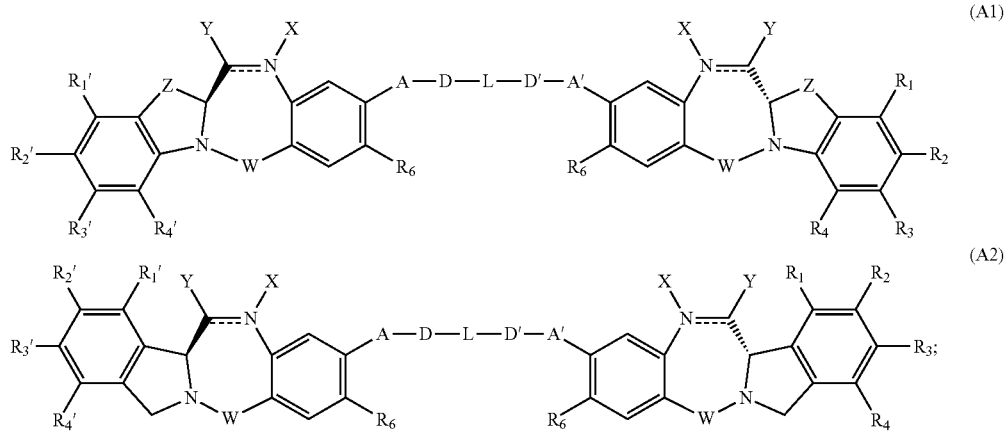

wherein:
the double line == between N and C represents a single bond or a double bond, provided that at least one of == between N and C represents a double bond, and when it is a double bond, X is absent and Y is —H, and when it is a single bond, X is —H or an amine protecting moiety that converts the compound into a prodrug; preferably, when it is a double bond, X is absent and Y is —H, and the double bond may react with the imine-reactive reagent of the invention to form an adduct (such as a bisulfite adduct) prior to the adduct is used in the methods of the invention to produce drug-CBA conjugates;

Y is selected from —H, —OR, an ester represented by —OCOR', a carbonate represented by —OCOOR', a carbamate represented by —OCONR'R", an amine or a hydroxyl amine represented by —NR'R", amide represented by —NRCOR', a peptide represented by —NRCOP, wherein P is an amino acid or a polypeptide containing between 2 to 20 amino acid units, a thioether represented by —SR', a sulfoxide represented by —SOR', a sulfone represented by —SO$_2$R', a sulfite —SO$_3$, a bisulfite —OSO$_3$, —SO$_2$M, —SO$_3$M, —OSO$_3$M, a halogen, cyano, an azido, or a thiol; wherein M is —H or a pharmaceutically acceptable cation (such as Na$^+$); or, Y is a sulfite (HSO$_3$, HSO$_2$ or a salt of HSO$_3^-$, SO$_3^{2-}$ or HSO$_2^-$ formed with a cation), metabisulfite (H$_2$S$_2$O$_5$ or a salt of S$_2$O$_5^{2-}$ formed with a cation), mono-, di-, tri-, and tetra-thiophosphate (PO$_3$SH$_3$, PO$_2$S$_2$H$_2$, POS$_3$H$_2$, PS$_4$H$_2$ or a salt of PO$_3$S$^{3-}$, PO$_2$S$_2^{3-}$, POS$_3^{3-}$ or PS$_4^{3-}$ formed with a cation), thio phosphate ester (R$^i$O)$_2$PS (OR$^i$), R$^i$S—, R$^i$SO, R$^i$SO$_2$, R$^i$SO$_3$, thiosulfate (HS$_2$O$_3$ or a salt of S$_2$O$_3^{2-}$ formed with a cation), dithionite (HS$_2$O$_4$ or a salt of S$_2$O$_4^{2-}$ formed with a cation), phosphorodithioate (P(=S)(OR$^{k'}$)(S)(OH) or a salt thereof formed with a cation), hydroxamic acid (R$^{k'}$C (=O)NOH or a salt formed with a cation), formaldehyde sulfoxylate (HOCH$_2$SO$_2^-$ or a salt of HOCH$_2$SO$_2^-$ formed with a cation, such as HOCH$_2$SO$_2^-$Na$^+$) or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl;

R, R', and R" are the same or different, and are selected from —H, substituted or unsubstituted linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000 (preferably 1-200, or 1-20), a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, aryl having from 6 to 18 carbon atoms, 3- to 18-membered heterocyclic ring having 1 to 6 heteroatoms selected from O, S, N and P, wherein the substituent is selected from halogen, —OR$_7$, —NR$_8$R$_9$, —NO$_2$, —NRCOR', —SR$_{10}$, a sulfoxide represented by —SOR', a sulfone represented by —SO$_2$R', a sulfite —SO$_3$, a bisulfite —OSO$_3$, a sulfonamide represented by —SO$_2$NRR', cyano, an azido, —COR$_{11}$, —OCOR$_{11}$ or —OCONR$_{11}$R$_{12}$;

R$_7$, R$_8$, R$_9$, R$_{10}$, R$_{11}$ and R$_{12}$ are each independently selected from —H, linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000 (preferably 1-200, or 1-20), a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, aryl having from 6 to 18 carbon atoms, 3- to 10-membered heterocyclic ring having 3- to 18-membered heterocyclic ring having 1 to 6 heteroatoms selected from O, S, N and P, and R$_{10}$ is optionally SR$_{13}$ or COR$_{13}$;

R$_{13}$ is selected from linear, branched or cyclic alkyl, alkenyl or alkynyl having from 1 to 10 carbon atoms, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, aryl having from 6 to 18 carbon atoms, 3- to 18-membered heterocyclic ring having 1 to 6 heteroatoms selected from O, S, N and P, optionally $R_{11}$ is $OR_{14}$, wherein $R_{14}$ has the same definition as R, optionally R" is —OH;

W is C=O, C=S, $CH_2$, BH, SO or $SO_2$;

$R_1$, $R_2$, $R_3$, $R_4$, $R_1'$, $R_2'$, $R_3'$, and $R_4'$ are each independently selected from —H, substituted or unsubstituted linear, branched or cyclic alkyl, alkenyl or alkynyl having from 1 to 10 carbon atoms, a polyethylene glycol unit (—$OCH_2CH_2$)$_n$, wherein n is an integer from 1 to 2000 (preferably 1-200, or 1-20), or a substituent selected from a halogen, guanidinium [—NH(C=NH)$NH_2$], —$OR_7$, —$NR_8R_9$, —$NO_2$, —NRCOR', —$SR_{10}$, a sulfoxide represented by —SOR', a sulfone represented by —$SO_2R'$, a sulfite —$SO_3$, a bisulfite —$OSO_3$, a sulfonamide represented by —$SO_2NRR'$, cyano, an azido, —$COR_{11}$, —$OCOR_{11}$ or —$OCONR_{11}R_{12}$, wherein $R_7$, $R_8$, $R_9$, $R_{10}$, $R_{11}$ and $R_{12}$ are as defined above, optionally, any one of $R_1$, $R_2$, $R_3$, $R_4$, $R_1'$, $R_2'$, $R_3'$, or $R_4'$ is the linking group with the reactive group attached thereto (if present), which may be selected from a polypyrrolo, poly-indolyl, polyimidazolyl, polypyrrollo-imidazolyl, poly-pyrrolo-indolyl or polyimidazolo-indolyl unit optionally bearing the linking group with the reactive group attached thereto;

Z is selected from —($CH_2$)$_n$—, wherein n is 1, 2 or 3, —$CR_{15}R_{16}$, —$NR_{17}$, —O— or —S—, wherein $R_{15}$, $R_{16}$ and $R_{17}$ are each independently selected from —H, linear, branched or cyclic alkyl having from 1 to 10 carbon atoms, a polyethylene glycol unit (—$OCH_2CH_2$)$_n$, wherein n is an integer from 1 to 2000 (preferably 1-200, or 1-20);

$R_6$ is —OR, —SR or —NRR', wherein R and R' have the same definition as given above, optionally $R_6$ is the linking group with the reactive group attached thereto (if present);

X' is selected from —$CH_2$, —NR, —CO, —BH, —SO or —$SO_2$ wherein R has the same definition as given above;

Y' is —O—, —$CH_2$—, —NR or —S, wherein R has the same definition as given above;

Z' is —$CH_2$ or —($CH_2$)$_n$, wherein n is 2, 3 or 4, provided that X', Y' and Z' are not all $CH_2$ at the same time;

A and A' are the same or different and are selected from —O—, —CRR'O, S, —CRR'S, —$NR_{15}$ or —CR-R'$NHR_{15}$, wherein R and R' have the same definition as given above and wherein $R_{15}$ has the same definition as R;

D and D' are the same or different, and are independently selected from linear, branched or cyclic alkyl, alkenyl or alkynyl having 1 to 10 carbon atoms, optionally substituted with any one of halogen, —$OR_7$, —$NR_8R_9$, —$NO_2$, —NRCOR', —$SR_{10}$, a sulfoxide represented by —SOR', a sulfone represented by —$SO_2R'$, a sulfite —$SO_3$, a bisulfite —$OSO_3$, a sulfonamide represented by —$SO_2NRR'$, cyano, an azido, —$COR_{11}$, —$OCOR_{11}$ or —$OCONR_{11}R_{12}$, wherein the definitions of $R_7$, $R_8$, $R_9$, $R_{10}$, $R_{11}$ and $R_{12}$ are as defined above, or a polyethylene glycol unit (—$OCH_2CH_2$)$_n$, wherein n is an integer from 1 to 2000 (preferably 1-200, or 1-20);

L is an optional phenyl group or 3- to 18-membered heterocyclic ring having 1 to 6 heteroatoms selected from O, S, N and P that is optionally substituted, wherein the substituent is the linking group with the reactive group attached thereto (if present), or is selected from linear, branched or cyclic alkyl, alkenyl or alkynyl having from 1 to 10 carbon atoms, optionally substituted with any one of halogen, —$OR_7$, —$NR_8R_9$, —$NO_2$, —NRCOR', —$SR_{10}$, a sulfoxide represented by —SOR', a sulfone represented by —$SO_2R'$, a sulfite —$SO_3$, a bisulfite —$OSO_3$, a sulfonamide represented by —$SO_2NRR'$, cyano, an azido, —$COR_{11}$, $OCOR_{11}$ or $OCONR_{11}R_{12}$, wherein $R_7$, $R_8$, $R_9$, $R_{10}$, $R_{11}$ and $R_{12}$ have the same definitions as given above, a polyethylene glycol unit (—$OCH_2CH_2$)n, wherein n is an integer from 1 to 2000 (preferably 1-200, or 1-20); optionally, L itself is the linking group with the reactive group attached thereto; or their pharmaceutically acceptable solvates, salts, hydrates or hydrated salts, their optical isomers, racemates, diastereomers, enantiomers or the polymorphic crystalline structures of these compounds; provided that the compound has no more than one linking group with the reactive group attached thereto.

In one preferred embodiment, for drugs of formula (A1) or (A2):

the double line == between N and C represents a single bond or a double bond, provided that when it is a double bond X is absent and Y is —H, and when it is a single bond, X is —H or an amine protecting group that converts the compound into a prodrug;

Y is selected from —H, —OR, NR'R", a sulfite —$SO_3M$, or a bisulfite —$OSO_3M$, wherein M is —H or a pharmaceutically acceptable cation (such as $Na^+$);

R is selected from —H, linear, branched or cyclic alkyl, alkenyl or alkynyl having from 1 to 10 carbon atoms, a polyethylene glycol unit (—$OCH_2CH_2$)$_n$, wherein n is an integer from 1 to 2000 (preferably 1-200 or 1-20), aryl having from 6 to 10 carbon atoms, heterocyclic ring having from 3 to 10 carbon atoms;

W is C=O, $CH_2$ or $SO_2$;

$R_1$, $R_2$, $R_3$, $R_4$, $R_1'$, $R_2'$, $R_3'$ and $R_4'$ are each independently selected from —H, —$NO_2$ or the linking group with a reactive group attached thereto (if present);

$R_6$ is —$OR_{18}$, wherein $R_{18}$ has the same definition as R;

Z is selected from —($CH_2$)$_n$, wherein n is 1, 2 or 3, —$CR_{15}R_{16}$, —$NR_{17}$, —O— or —S—, wherein $R_{15}$, $R_{16}$ and $R_{17}$ are each independently selected from —H, linear, branched or cyclic alkyl having from 1 to 10 carbon atoms, a polyethylene glycol unit (—$OCH_2CH_2$)$_n$, wherein n is an integer from 1 to 2000 (preferably 1-200 or 1-20);

X' is selected from —$CH_2$, or C=O;

Y' is —O—, —NR, or —S, wherein R is defined as above;

Z' is —$CH_2$— or —($CH_2$)$_2$—;

A and A' are each —O—;

D and D' are the same or different, and are independently selected from linear, branched or cyclic alkyl, alkenyl or alkynyl having 1 to 10 carbon atoms;

L is an optional phenyl group or a heterocycle ring having from 3 to 10 carbon atoms that is optionally substituted, wherein the substituent is the linking group with a reactive group attached thereto (if present), or is selected from linear, branched or cyclic alkyl, alkenyl or alkynyl having from 1 to 10 carbon atoms, optionally substituted with any one of halogen, —$OR_7$, —$NR_8R_9$, —$NO_2$, —NRCOR', —$SR_{10}$, a sulfoxide represented by —SOR', a sulfone represented by —$SO_2R'$, a sulfite —$SO_3$, a bisulfite —$OSO_3$, a sulfonamide represented by —$SO_2NRR'$, cyano, an azido, —$COR_{11}$, —$OCOR_{11}$ or —$OCONR_{11}R_{12}$, a polyethylene glycol unit (—$OCH_2CH_2$)$_n$, wherein n is an integer from 1 to 2000

(preferably 1-200 or 1-20); optionally, L itself is the linking group with a reactive group attached thereto; or their pharmaceutically acceptable solvates, salts, hydrates or hydrated salts, their optical isomers, racemates, diastereomers, enantiomers or the polymorphic crystalline structures of these compounds.

In another preferred embodiment, the drug of formula (A1) or (A2) is represented by compounds of formulae (A4) or (A5):

Z is —$CH_2$— or —NR, wherein R has the same definition as above;
A is —O— or —$NR_{15}$;
L is —$(CH_2)_{nn}$—, wherein nn is 0 or an integer between 1 and 5, or a substituted or unsubstituted alkyl or alkenyl having from 2 to 4 carbon atoms, wherein the substituent is selected from halogen, —$OR_7$, —$NR_8R_9$, —$NO_2$, —NRCOR', —$SR_{10}$, a sulfoxide represented by —SOR', a sulfone represented by —$SO_2R'$, a sulfite

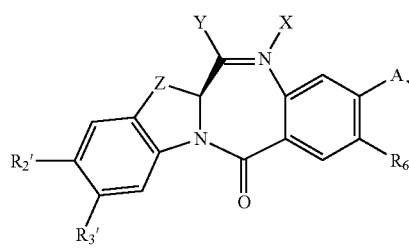
(A4)

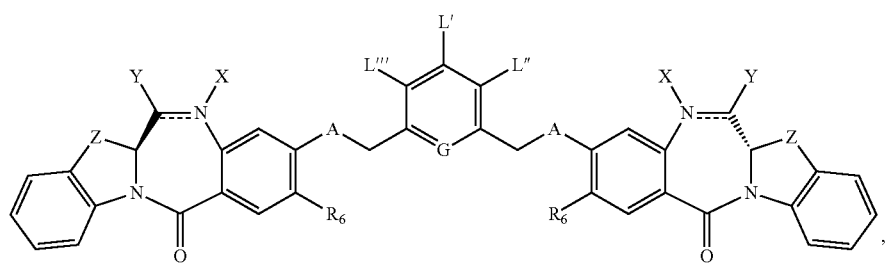
(A5)

wherein:
the double line == between N and C represents a single bond or a double bond, provided that when it is a double bond, X is absent and Y is —H, and when it is a single bond, X is —H or an amine protecting group that converts the compound into a prodrug;
Y is selected from —H, —OH, an ether represented by —OR, —NR'R", a sulfite —$SO_3M$, or a bisulfite —$OSO_3M$;
M is —H or a pharmaceutically acceptable cation (such as $Na^+$);
R, R', and R" are selected from linear, branched or cyclic alkyl, alkenyl or alkynyl having from 1 to 10 carbon atoms;
one of $R_2$, $R_3$, $R_2'$ and $R_3'$ is the linking group with a reactive group attached thereto (if present) and the others are —H, —NRCOR' or —$NO_2$;
$R_6$ is —OR, wherein R has the same definition as above;

—$SO_3$, a bisulfite —$OSO_3$, a sulfonamide represented by —$SO_2NRR'$, cyano, an azido, —$COR_{11}$, —$OCOR_{11}$, or —$OCONR_{11}R_{12}$;
$R_7$, $R_8$, $R_9$, $R_{10}$, $R_{11}$, $R_{12}$ and $R_{15}$ has the same definition as given above; optionally, L itself is the linking group with a reactive group attached thereto (if present);
one of L', L", or L''' is the linking group with a reactive group attached thereto (if present), while the others are —H; preferably L' is the linking group with a reactive group attached thereto (if present); and
G is —CH— or —N—, or their pharmaceutically acceptable solvates, salts, hydrates or hydrated salts, their optical isomers, racemates, diastereomers, enantiomers or the polymorphic crystalline structures of these compounds.

In yet another preferred embodiment, the compound of formula (A1) or (A2) is represented by compounds of formulae from formulae (A6) or (A7):

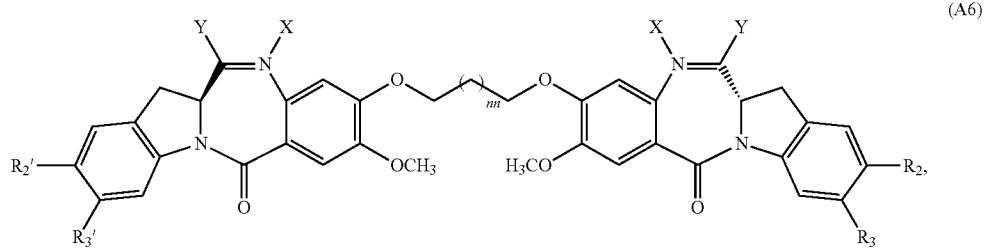
(A6)

(A7)

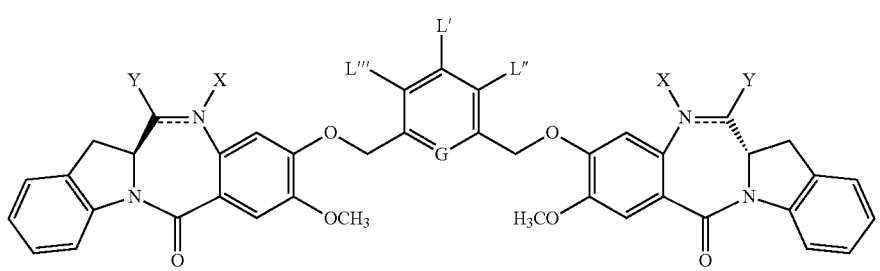

wherein:
the double line == between N and C represents a single bond or a double bond, provided that when it is a double bond, X is absent and Y is —H, and when it is a single bond, X is —H or an amine protecting group that converts the compound into a prodrug;

Y is selected from —H, —OH, an ether represented by —OR, a sulfite —SO$_3$, or a bisulfite —OSO$_3$;

R is selected from linear, branched or cyclic alkyl, alkenyl or alkynyl having from 1 to 10 carbon atoms;

nn is 0 or an integer from 1 to 5;

one of $R_2$, $R_3$, $R_2'$ and $R_3'$ is the linking group with a reactive group attached thereto (if present) and the others are —H, —NRCOR', or —NO$_2$;

one of L', L" or L'" is the linking group with a reactive group attached thereto (if present), provided that when one of L', L" or L'" is the linking group with a reactive group attached thereto, the others are —H (e.g., if L' is the linking group with a reactive group attached thereto, then L" and L'" are —H);

G is —CH— or —N—, or their pharmaceutically acceptable solvates, salts, hydrates or hydrated salts, their optical isomers, racemates, diastereomers, enantiomers or the polymorphic crystalline structures of these compounds.

In another specific embodiment, one of $R_2$, $R_3$, $R_2'$ and $R_3'$ of formula (A4) and (A6) is the linking group with a reactive group attached thereto (if present), and is represented by formula —W'—R$^x$—V—R$^y$-J, and the rest are —H; L" and L'" of formula (A5) and (A7) are —H, and L' is the linking group with a reactive group attached thereto (if present), and is represented by formula

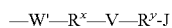

wherein:
W' is absent, —CR$^c$R$^e$—, —O—, —O—C(=O)—, —S—, —CH$_2$—S—, —O—(C=O)O—, —O—(C=O)N(R$^e$)—, —N(R$^e$)—, —N(R$^e$)—C(=O)—, —N(R$^e$)—C(=O)O—, or —C(=O)—;

R$^x$ is absent or an optionally substituted linear, branched or cyclic alkyl, alkenyl or alkynyl having 1 to 10 carbon atoms;

V is absent, —(CH$_2$—CH$_2$—O)$_n$—, —O—, —O—C(=O)—, —S—, —O—(C=O)O—, O—(C=O)N(R$^e$)—, —N(R$^e$)—, —N(R$^e$)—C(=O)—, —N(R$^e$)—C(=O)O—, —C(=O)—, an amino acid, or a peptide having 2 to 8 amino acids;

R$^y$ is absent or a linear, branched or cyclic alkyl having 1 to 10 carbon atoms;

R$^c$ is —H or a linear or branched alkyl having 1 to 4 carbon atoms;

R$^e$ is —H, a linear, branched or cyclic alkyl, alkenyl or alkynyl having 1 to 10 carbon atoms or —(CH$_2$—CH$_2$—O)$_n$—R$^c$, n is an integer from 1 to 24; and J is as described above in the fourth specific embodiment.

Preferably, R$^c$ is —H or -Me; R$^e$ is a linear or branched alkyl having 1 to 6 carbon atoms or —(CH$_2$—CH$_2$—O)$_n$—R$^c$; n is an integer from 2 to 8; and the remainder of the variables are as described above in the fourth specific embodiment.

In another preferred embodiment, V is an amino acid or a peptide having 2 to 8 amino acids. More preferably, V is valine-citrulline, gly-gly-gly or ala-leu-ala-leu.

Preferably, J is —SH, —SSR$^d$ or —COE as described above.

In another specific embodiment, one of $R_2$, $R_3$, $R_2'$ and $R_3'$ of formula (A4) and (A6) is the linking group with a reactive group attached thereto (if present), and is represented by formula —W'—R$^x$—S—Z$^s$; L" and L'" of formula (A5) and (A7) are —H, and L' is represented by —W'—R$^x$—S—Z$^s$, wherein the variables are as described in the eigth and ninth specific embodiments.

In another embodiment, the compounds of formula (A1)-(A7) (with or without pre-incubation with the imine-reactive reagent), if the linking group with a reactive group attached thereto is not already present, can further react with a bifunctional crosslinking reagent described above to form an imine-containing drug bearing the linking group with a reactive group attached thereto, which can be used in the methods of the present invention.

In certain embodiments, the imine-containing drug bearing the linking group with a reactive group attached thereto that can be used in the methods of the present invention is represented by any one of the following formulas:

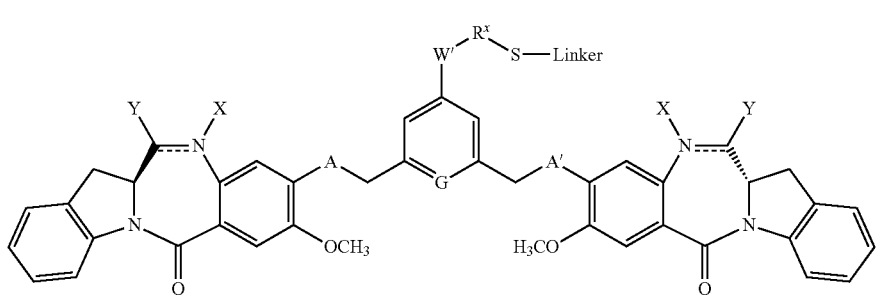

(A8)

wherein:

"Linker" is represented by formula (a1), (a2), (a3), (a4), (a5), (a6), (a7) or (a8) described above (in the ninth specific embodiment);

q is an integer from 1 to 5;

n is an integer from 2 to 6;

D is —H or —$SO_3M$;

M is —H or a pharmaceutically acceptable cation, such as $Na^+$ or $K^+$; and the remainder of the variables is as described in the eighth or ninth specific embodiments. Preferably, q is 2 and n is 4.

In a preferred embodiment, Linker is represented by formula (a1), (a4), (a5), (a9) or (a10) described above.

In certain embodiments, for compounds of formula (A8) described immediately above, the variables are as described below:

W' is —O—, —N($R^e$)—, —N($R^e$)—C(=O)—, —N(COR$^e$)—, —S— or —$CH_2$—S—;

$R^x$ is absent or selected from a linear, branched or cyclic alkyl having 1 to 6 carbon atoms;

$R^e$ is —H, a linear, branched or cyclic alkyl, alkenyl or alkynyl having 1 to 10 carbon atoms or —($CH_2$—$CH_2$—O)$_n$—$R^k$, wherein $R^k$ is a —H, a linear, branched cyclic alkyl having 1 to 6 carbon atoms, optionally bearing a primary, secondary or tertiary amino group or a 5- or 6-membered Nitrogen containing heterocycle, such as piperidine or morpholine;

n is an integer from 1 to 24; and the remainder of the variables are as described above in the embodiment immediately above.

Preferably, $R^k$ is —H or -Me and n is an integer from 2 to 8. Preferably, $R^x$ is a linear or branched alkyl having 1 to 6 carbon atoms.

In another preferred embodiment, the linker is represented by any one of the formula selected from formulas (a1), (a4), (a5), (a10) and (a11) shown above; and the remainder of the variables are as described above in the ninth specific embodiment.

In certain embodiments, for compounds of formula (A8) described in the embodiments above, the variables are as described below:

X' and Y' are both —H;

A and A' are both —O—;

$R_6$ is —OMe;

$R^x$ is a linear or branched alkyl having 1 to 6 carbon atoms; and the remainder of the variables is as described above.

Preferably, $R^x$ is —($CH_2$)$_p$—(CR$^f$R$^g$)—, wherein R$^f$ and R$^g$ are each independently selected from —H or a linear or branched alkyl having 1 to 4 carbon atoms; p is 0, 1, 2 or 3. More preferably, R$^f$ and R$^g$ are the same or different and are selected from —H and -Me; and p is 1.

In another preferred embodiment, the linker is represented by any one of the formula selected from formulas (a1), (a4), (a5), (a10) and (a11) shown above; and the remainder of the variables are as described above.

In another preferred embodiment, the drug of formula (A1), (A2) or (A3) is any one of the compounds shown in Tables 11-13 and the conjugate can be made by the method of the present invention is any one of the conjugates shown in Table 14.

TABLE 11

Structures of representative drugs that can be used in the methods of the present invention

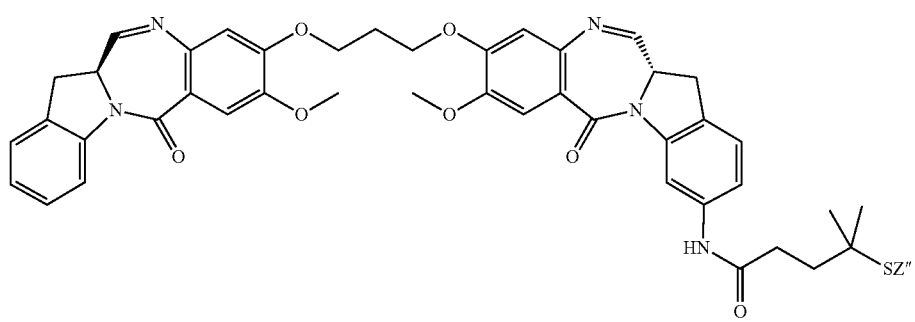

TABLE 11-continued
Structures of representative drugs that can be used in the methods of the present invention
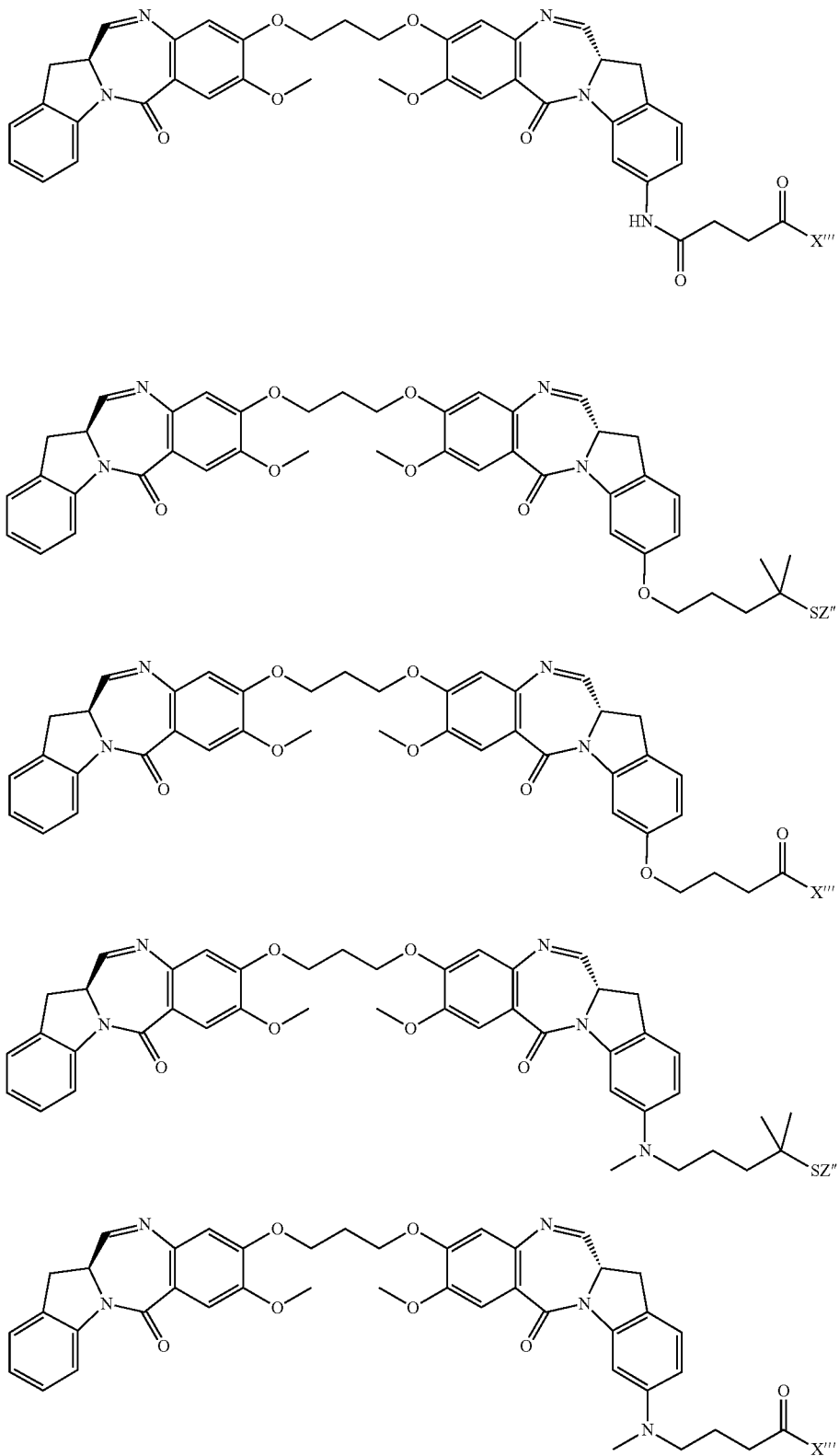

TABLE 11-continued
Structures of representative drugs that can be used in the methods of the present invention
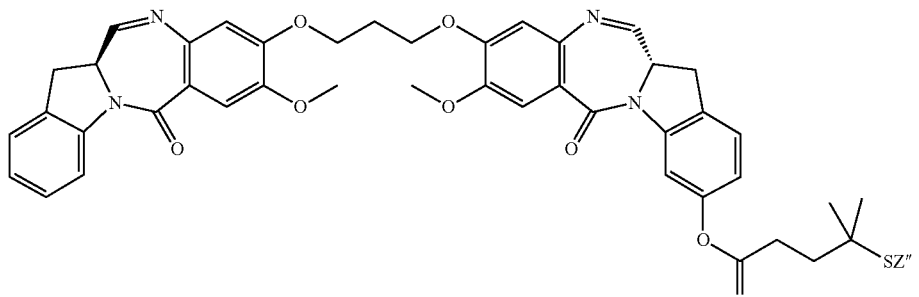
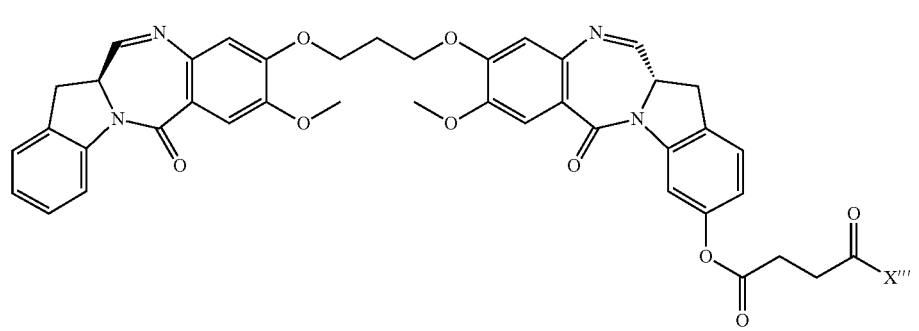
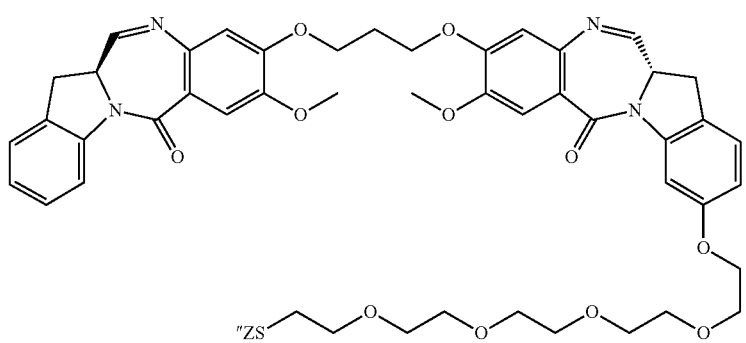
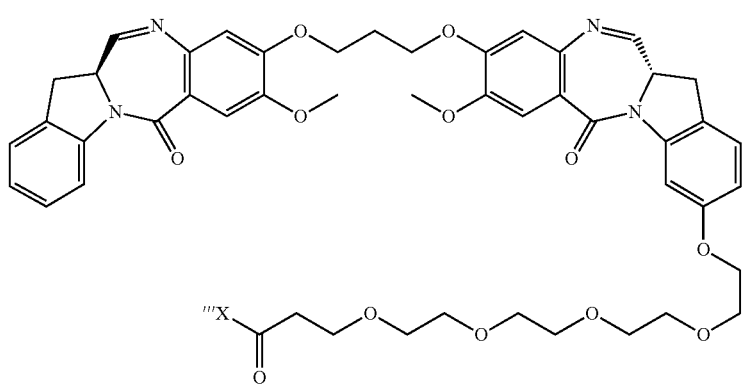

TABLE 11-continued
Structures of representative drugs that can be used in the methods of the present invention
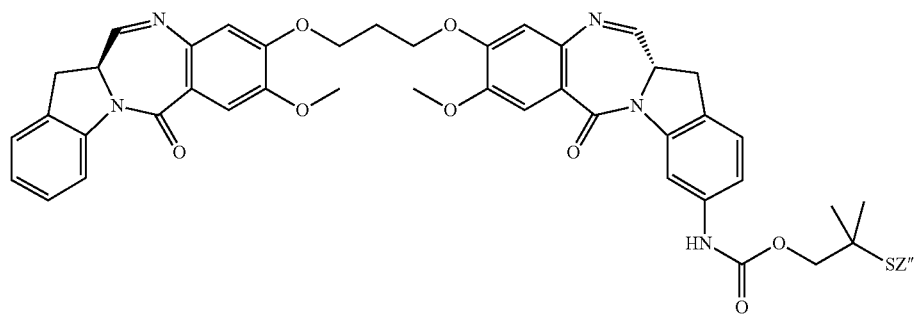
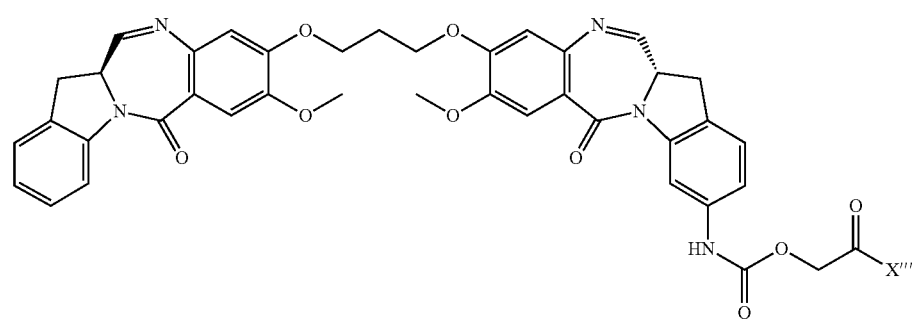
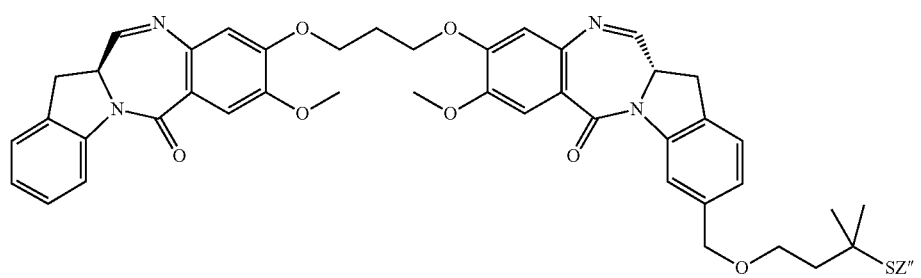
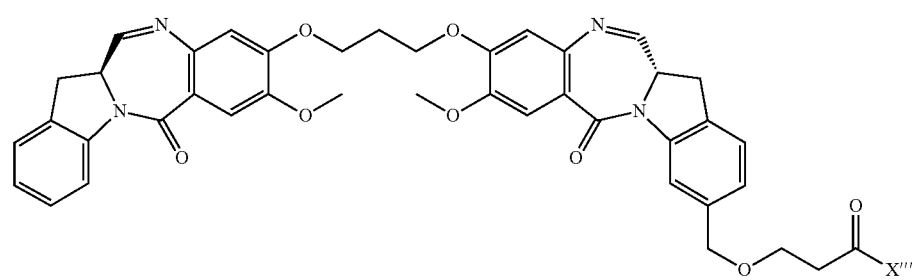
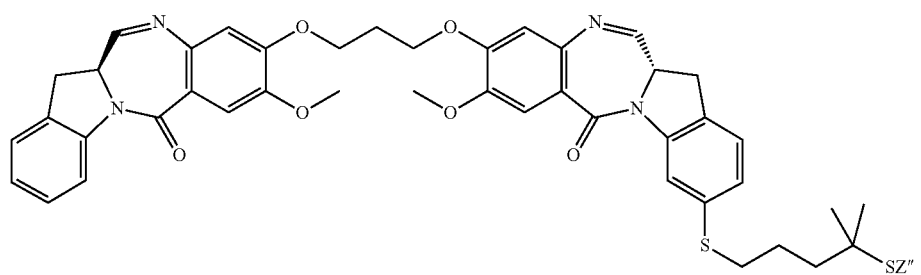

TABLE 11-continued
Structures of representative drugs that can be used in the methods of the present invention
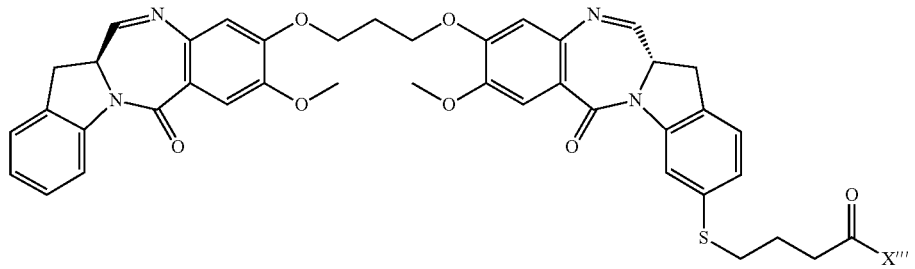
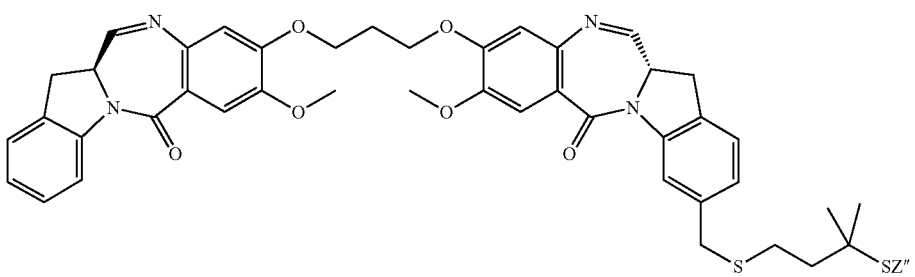
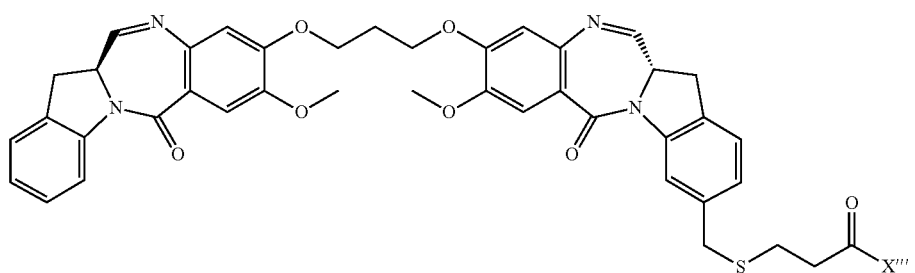
Note:
Z" = H, SMe, SPy, SPy-NO₂, Ac; X''' = NHS;
TABLE 12
Structures of representative drugs that can be used in the methods of the present invention (Continued).
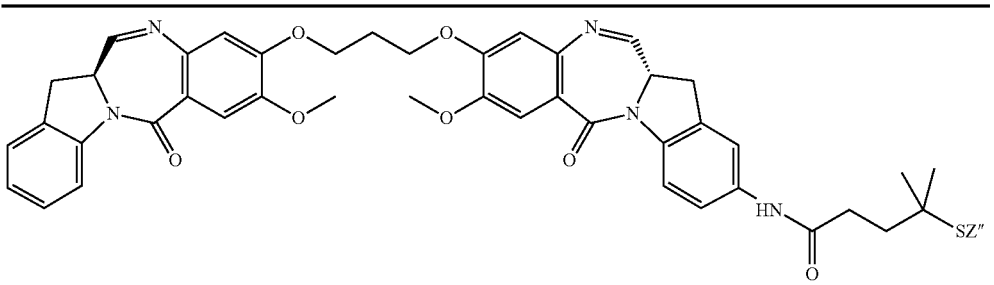

TABLE 12-continued
Structures of representative drugs that can be used in the methods of the present invention (Continued).
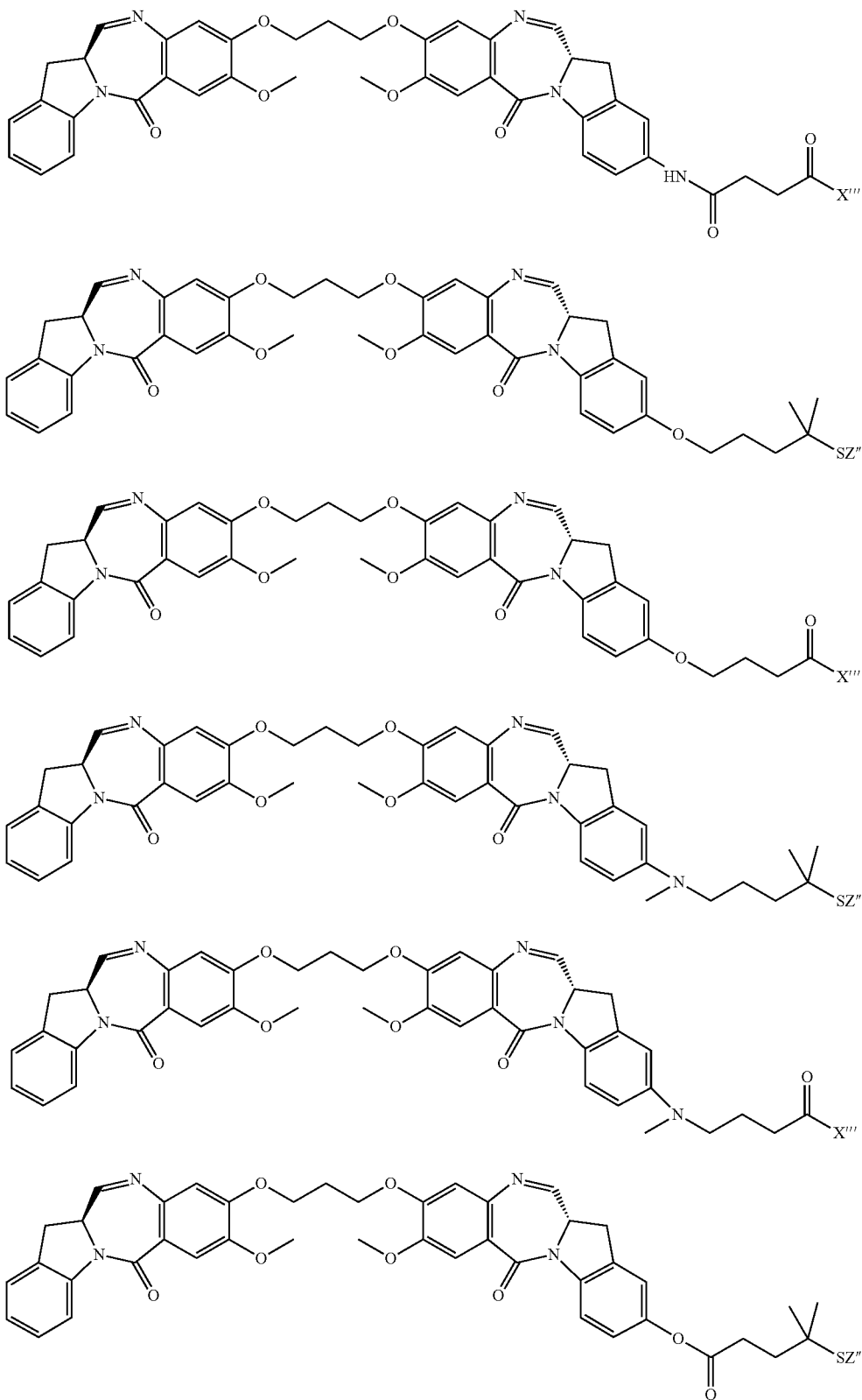

TABLE 12-continued
Structures of representative drugs that can be used in the methods of the present invention (Continued).
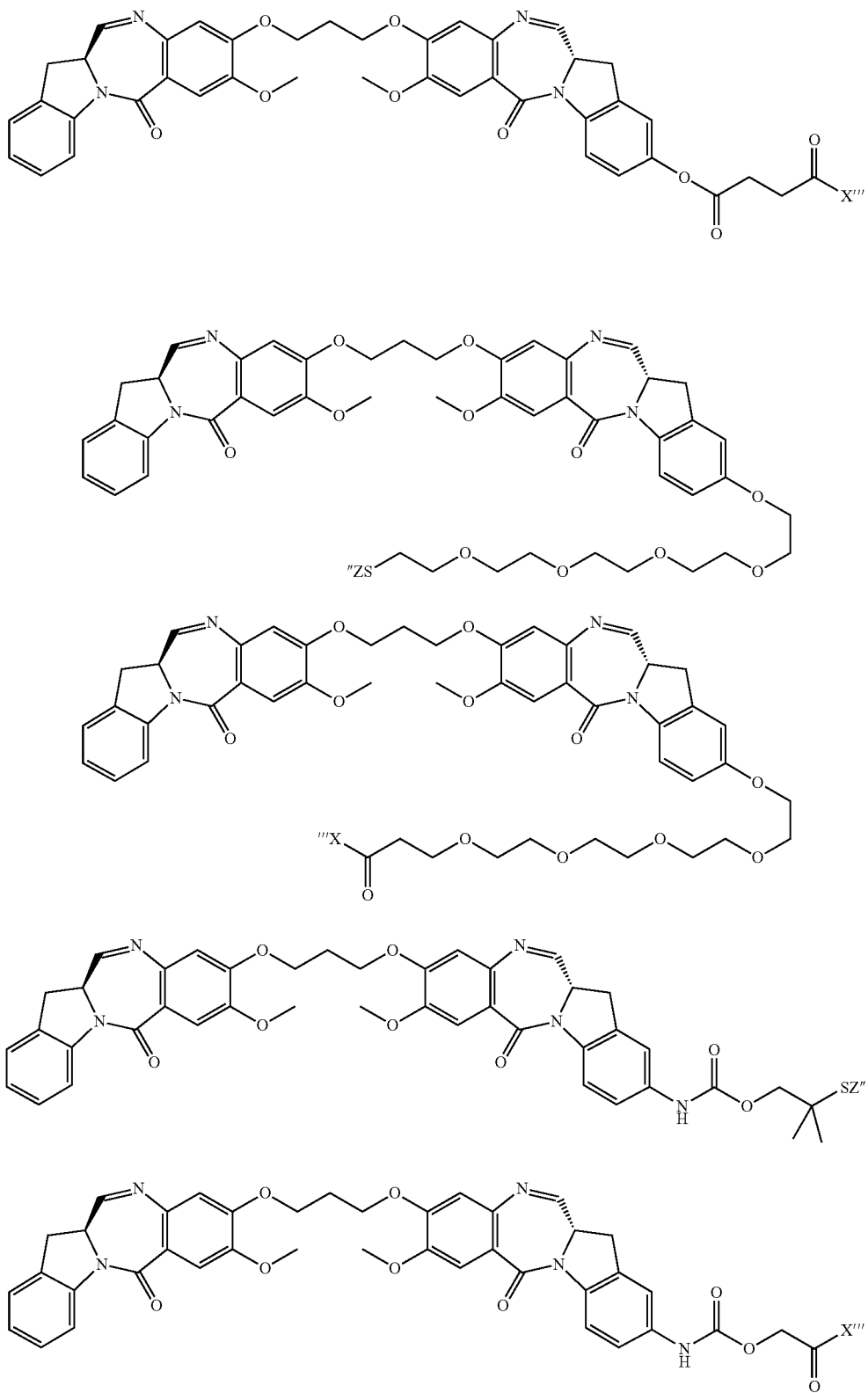

TABLE 12-continued
Structures of representative drugs that can be used in the methods of the present invention (Continued).
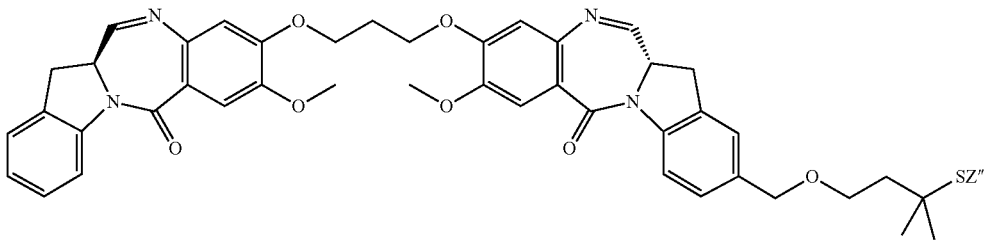
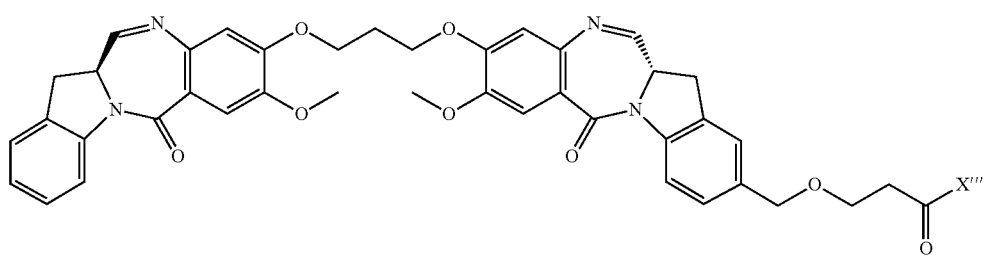
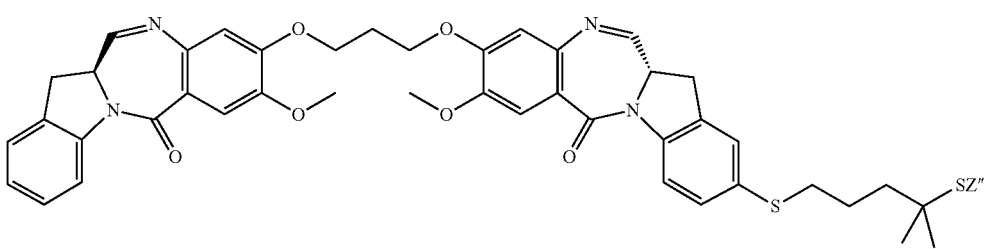
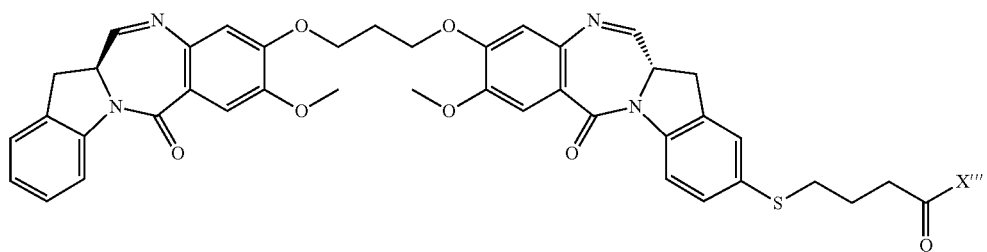
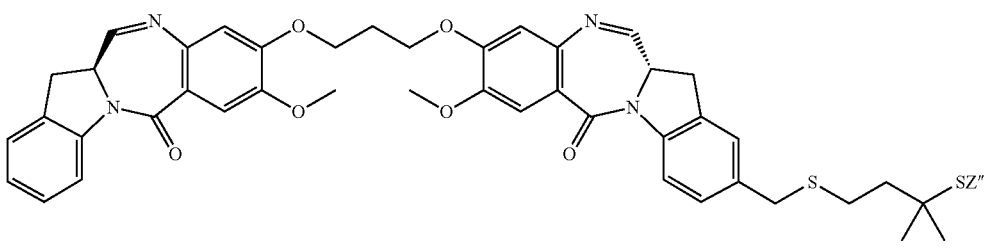
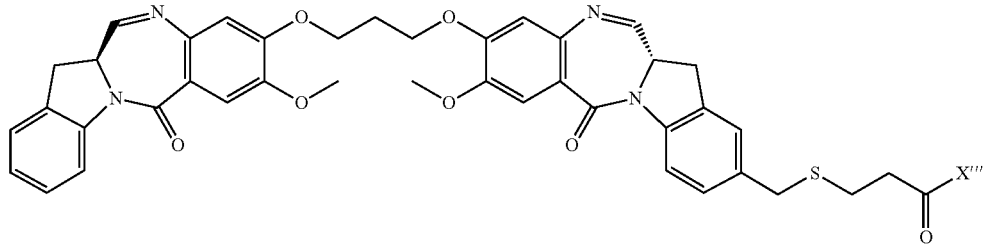
Note:
Z" = H, SMe, SPy, SPy-NO$_2$, Ac; X''' = NHS;

TABLE 13
Structures of representative drugs that can be used in the methods of the present invention (Continued).
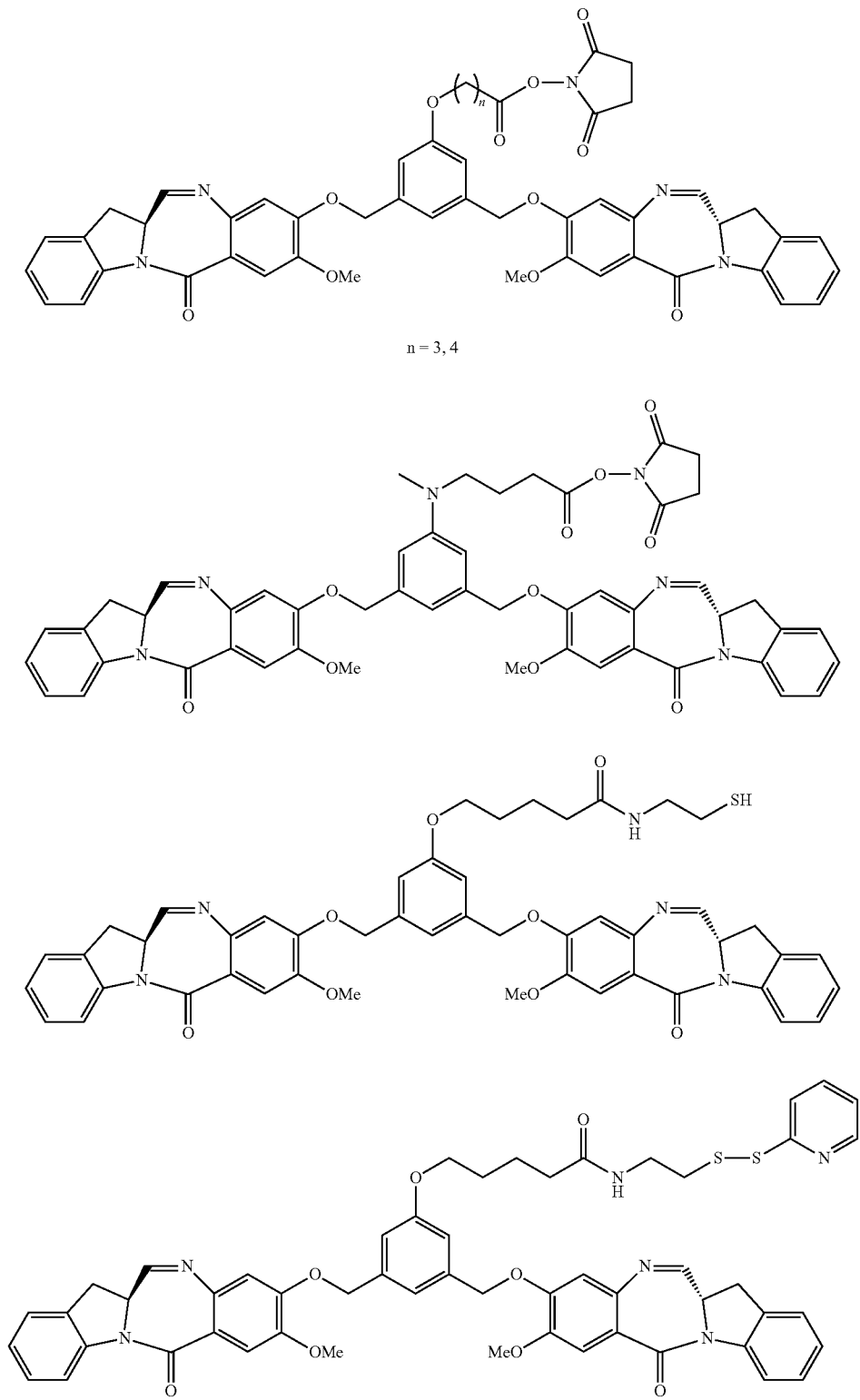

TABLE 13-continued
Structures of representative drugs that can be used in the methods of the present invention (Continued).
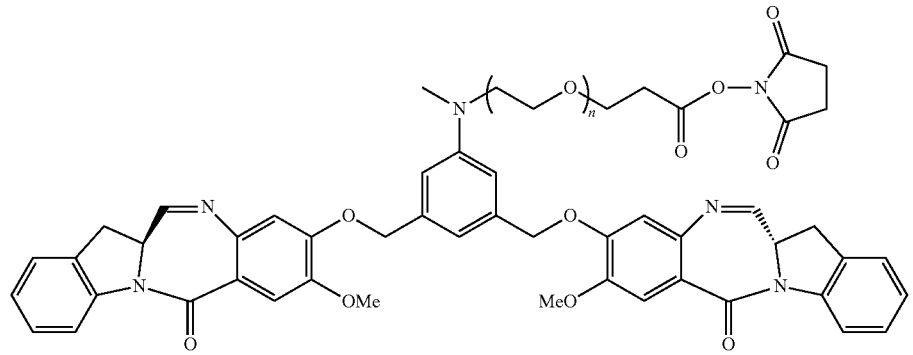
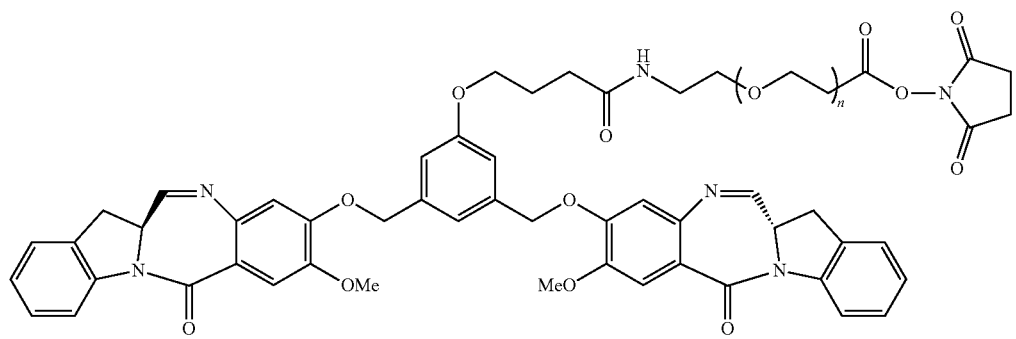
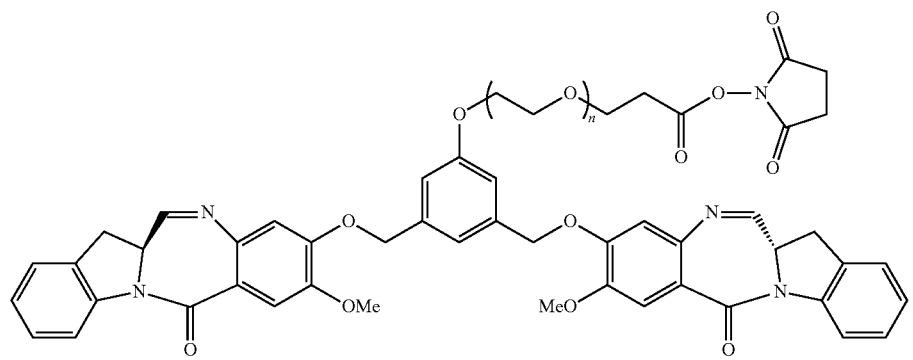
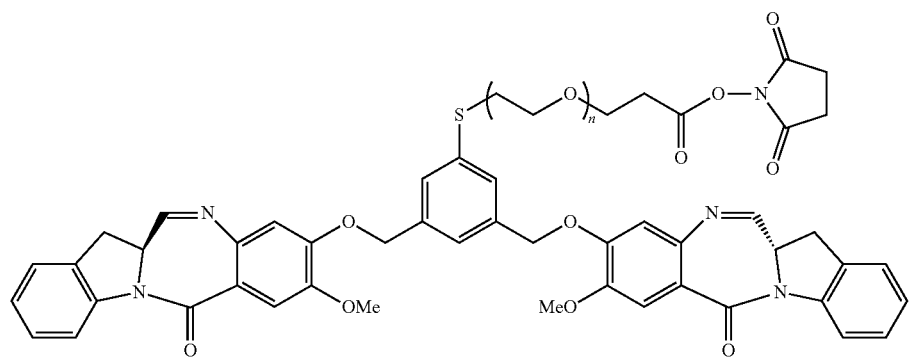

TABLE 13-continued
Structures of representative drugs that can be used in the methods of the present invention (Continued).
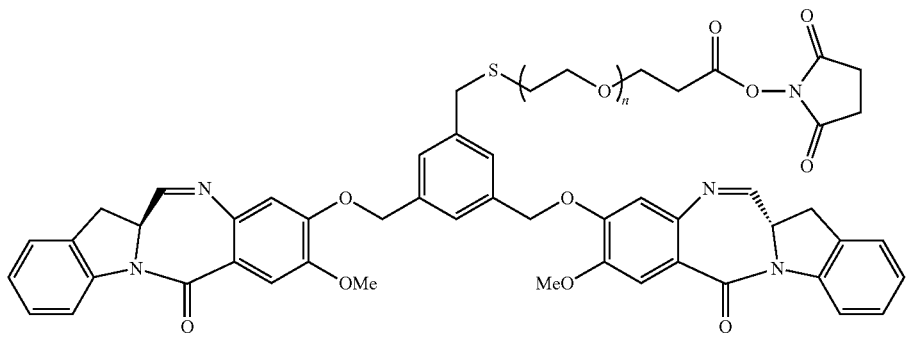
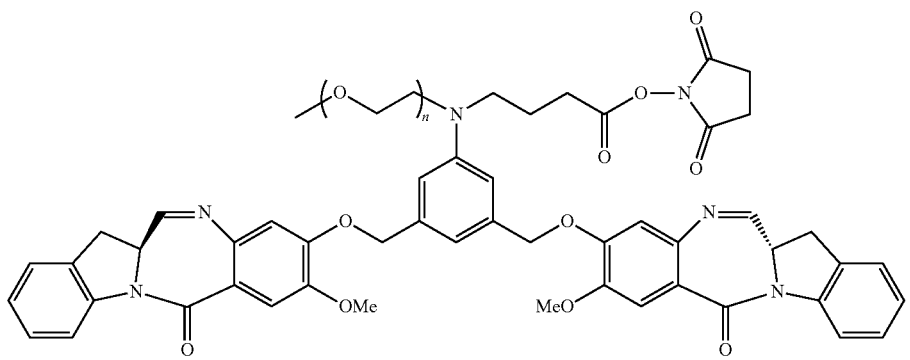
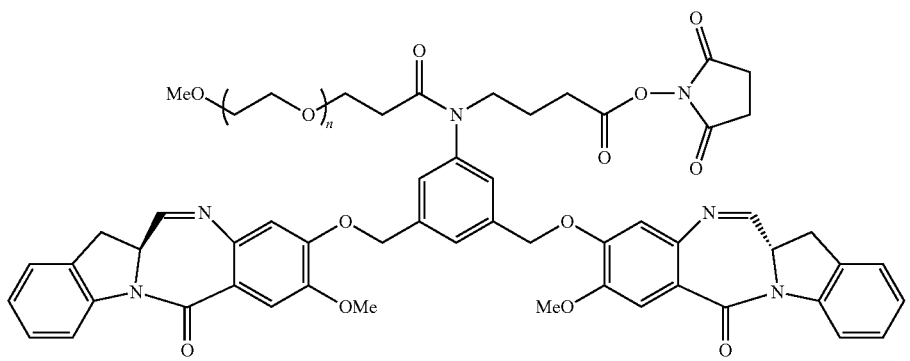
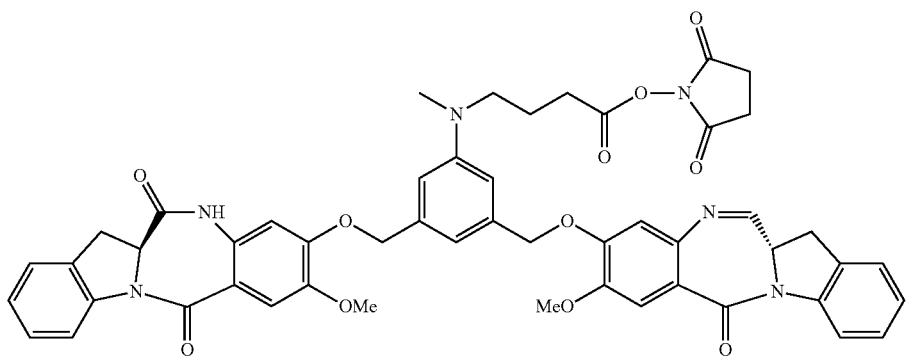 [SMILES: COc1cc2c(cc1OCc1cc(COc3cc4c(cc3OC)C(=O)N3c5ccccc5C[C@H]3C(=O)N4)cc(N(C)CCCC(=O)ON3C(=O)CCC3=O)c1)N=C[C@@H]1Cc3ccccc3N1C2=O]

TABLE 13-continued
Structures of representative drugs that can be used in the methods of the present invention (Continued).
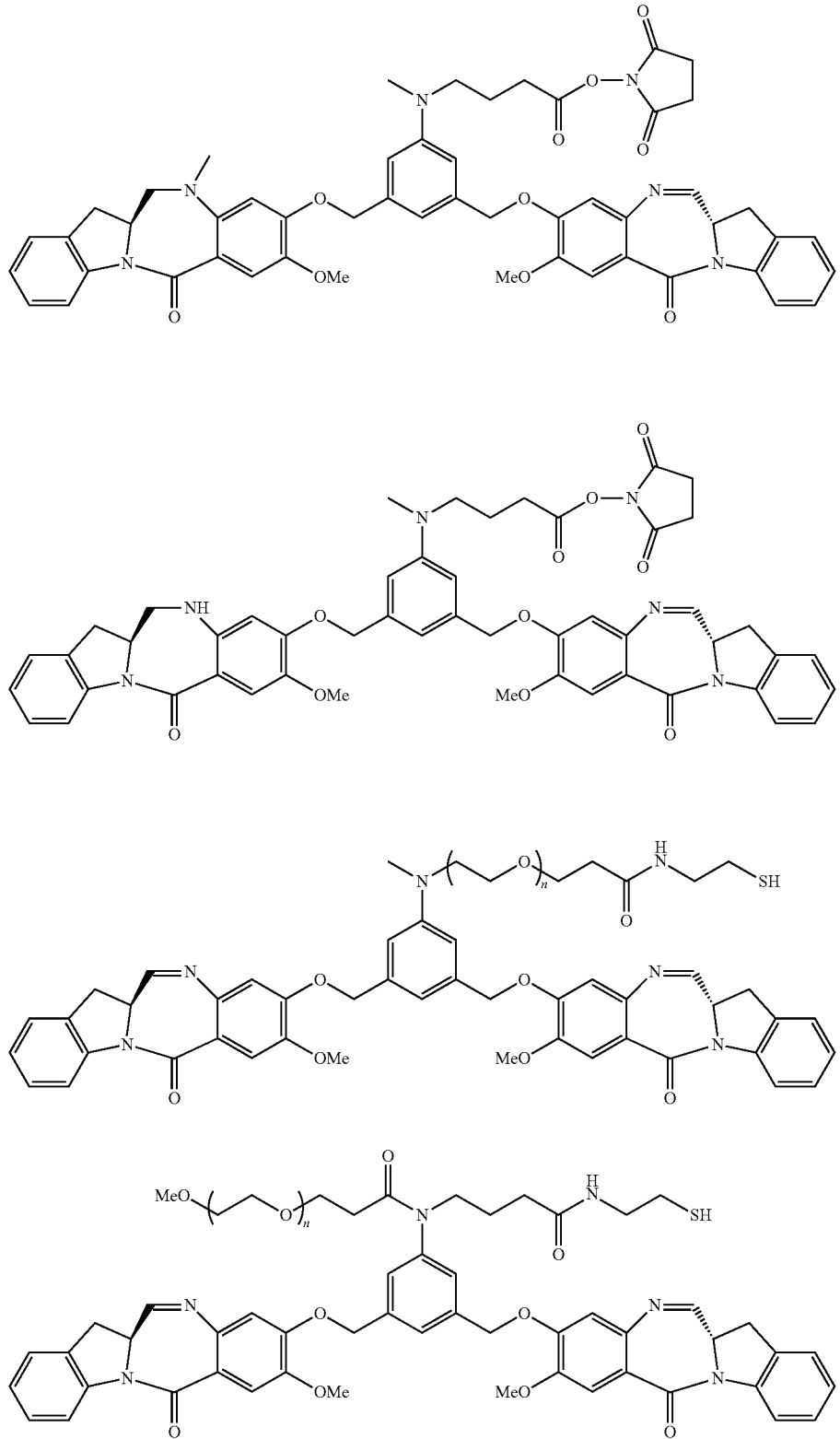

TABLE 13-continued
Structures of representative drugs that can be used in the methods of the present invention (Continued).
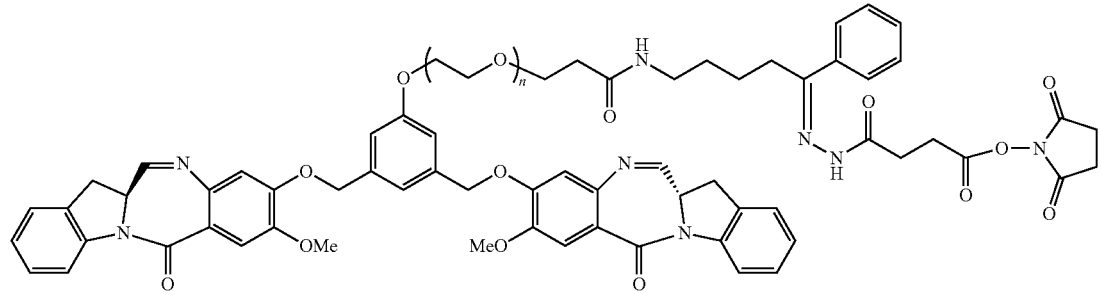
TABLE 14
Structures of representative conjugates that can be made by methods of the present invention.
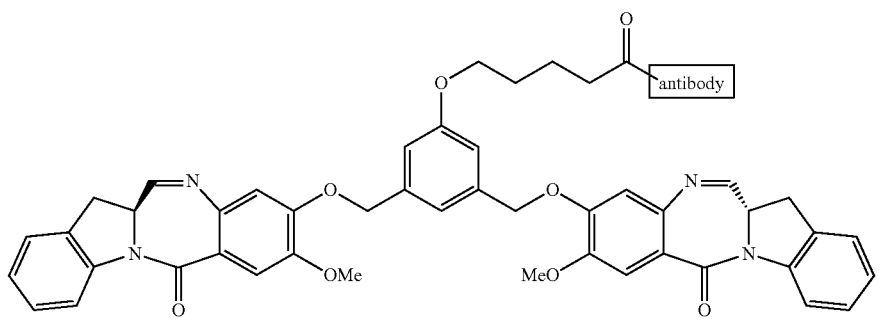
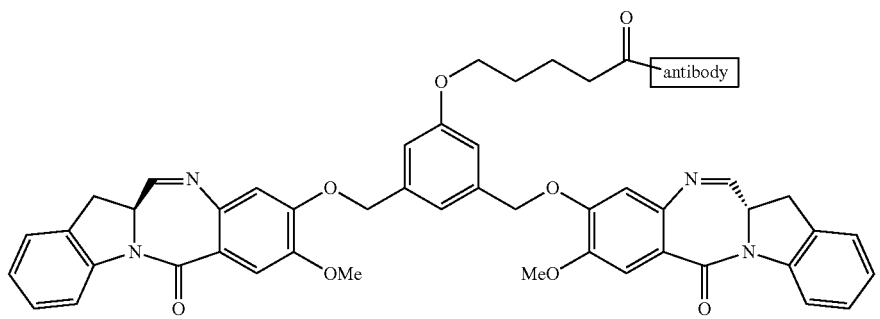
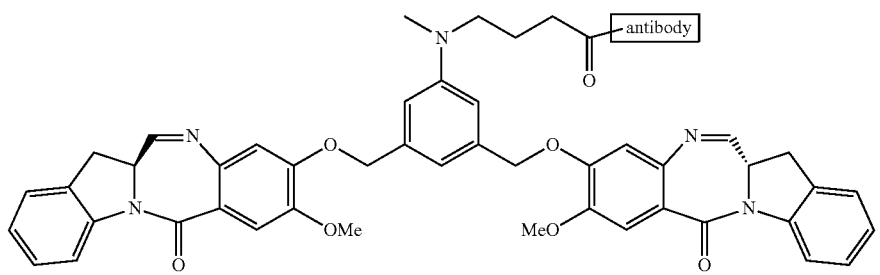

TABLE 14-continued
Structures of representative conjugates that can be made by methods of the present invention.
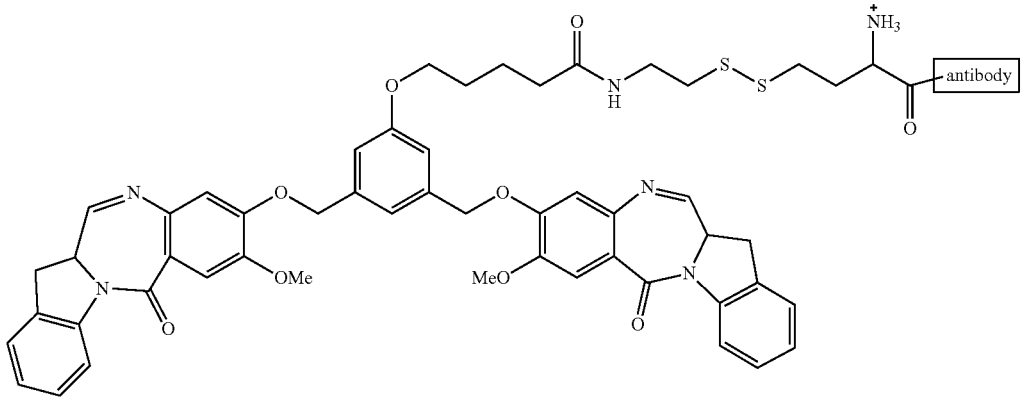
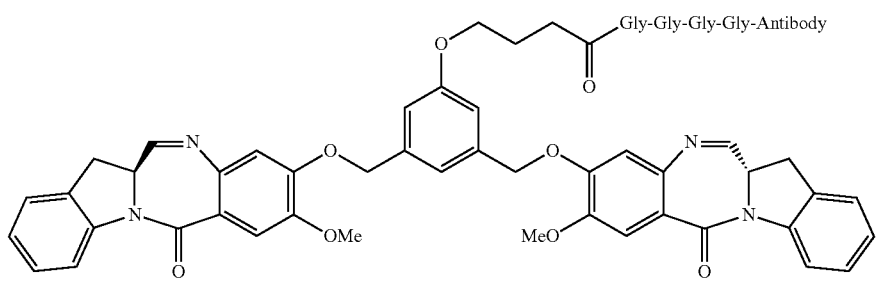
Dimer 1
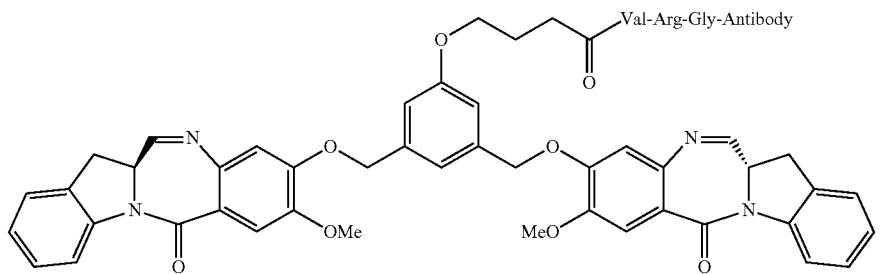
Dimer 2
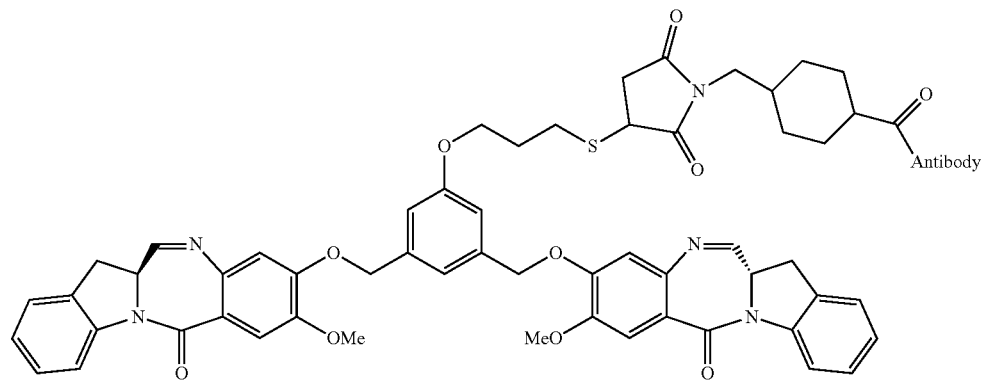
Dimer 3

TABLE 14-continued

Structures of representative conjugates that can be made by methods of the present invention.

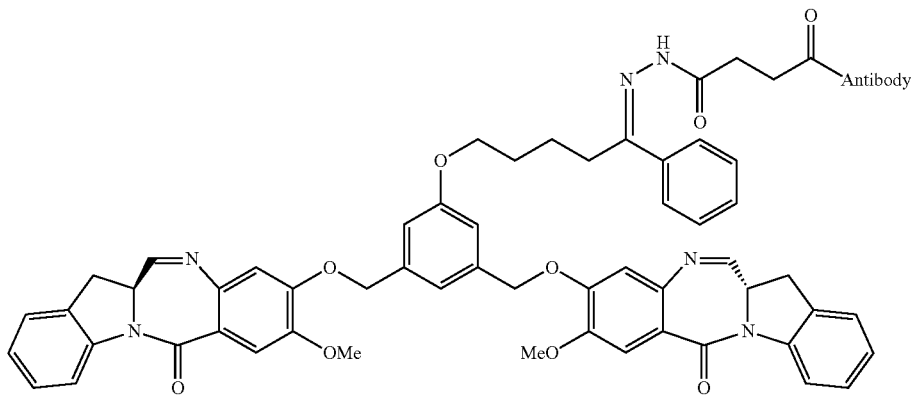

Dimer 4

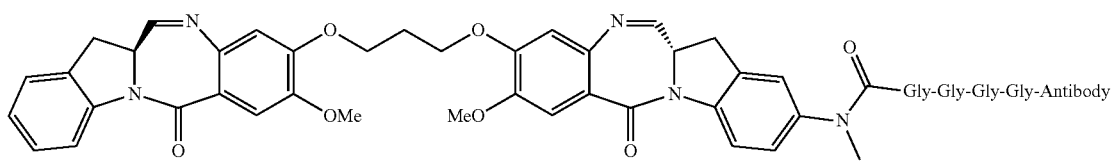

Dimer 5

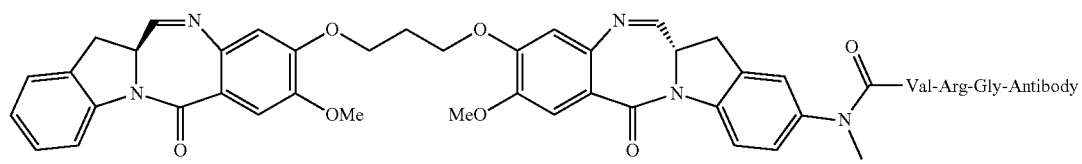

Dimer 6

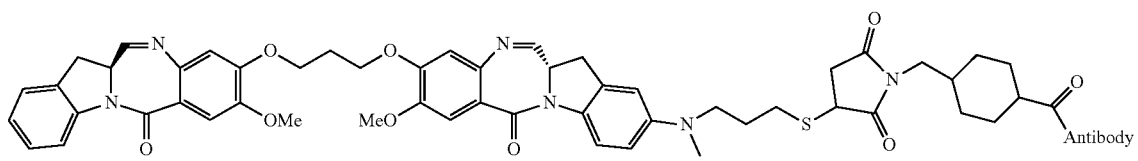

Dimer 7

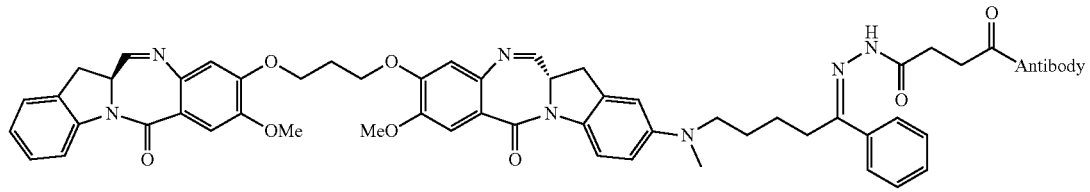

Dimer 8

Any compounds of Tables 11-13 and any conjugates of Table 14 may have at least one of its imine bonds reacted with a subject imine reactive reagent, thus forming an adduct, such as bisulfite adduct.

In one embodiment, the imine-containing drug bearing a linking moiety are those having a reactive ester group, a thiol or a thiol reactive group described above.

Alternatively, the drug described above can further react with bifunctional crosslinking agent to form a drug bearing a linking moiety. Any bifunctional crosslinking agents described can be used.

In another preferred embodiment, the drug that can be used in the present invention is any one of the compounds shown in Table 15.

TABLE 15
Representative drug compounds that can be used in the present methods.
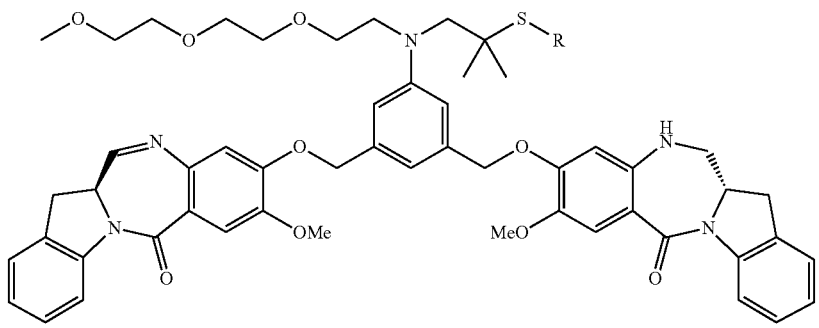
1 (R = H)
1b (R = SMe)
1c (R = S(CH$_2$)$_3$C(=O)NHS)
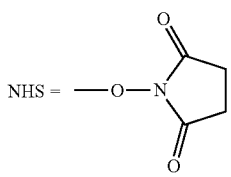
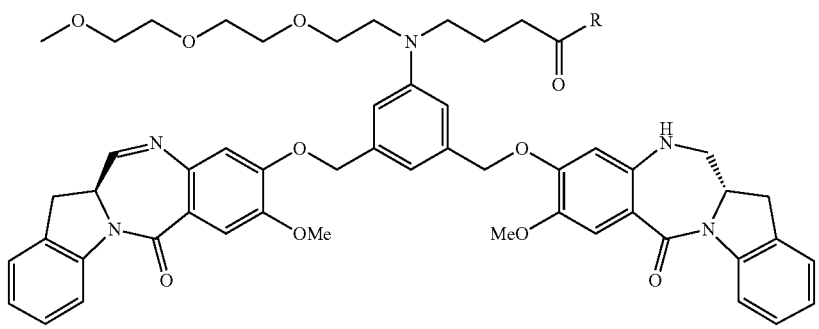
2 (R = NHS)
2b (R = OMe)
2c (R = S(CH$_2$)$_3$C(=O)NHS)
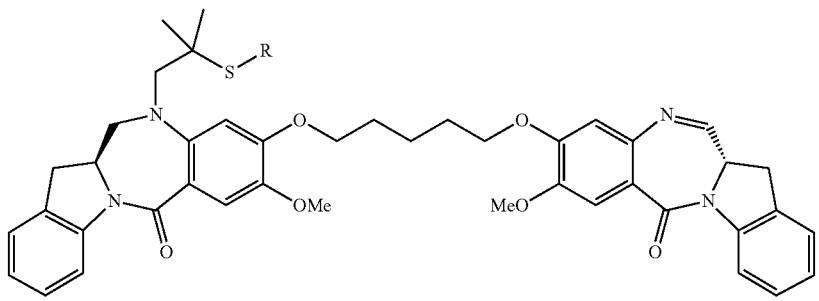
3 (R = H)
3b (R = SMe)
3c (R = S(CH$_2$)$_3$C(=O)NHS)

TABLE 15-continued
Representative drug compounds that can be used in the present methods.
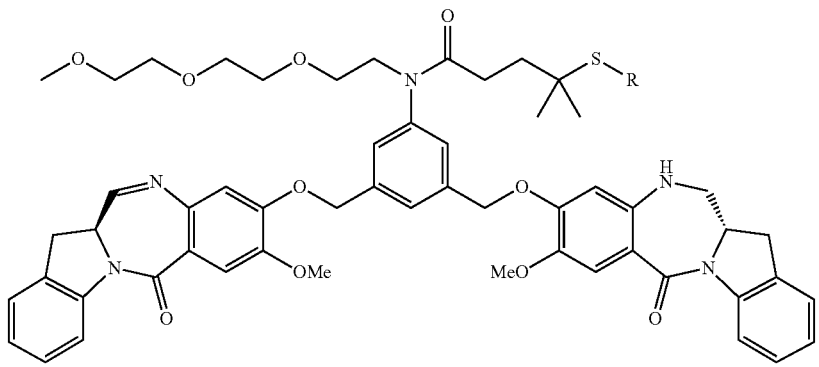
4 (R = H)
4b (R = SMe)
4c (R = S(CH₂)₃C(═O)NHS)
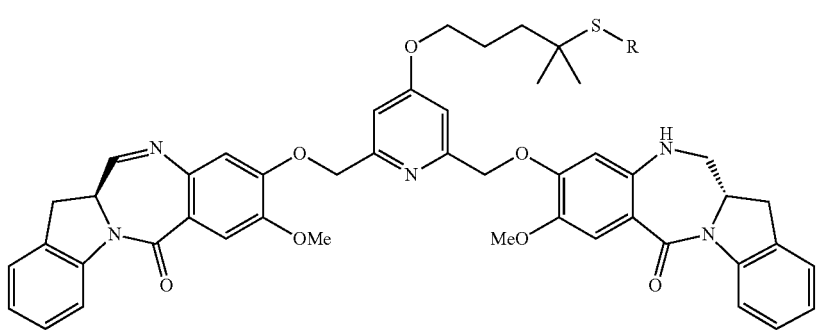
5 (R = H)
5b (R = SMe)
5c (R = S(CH₂)₃C(═O)NHS)
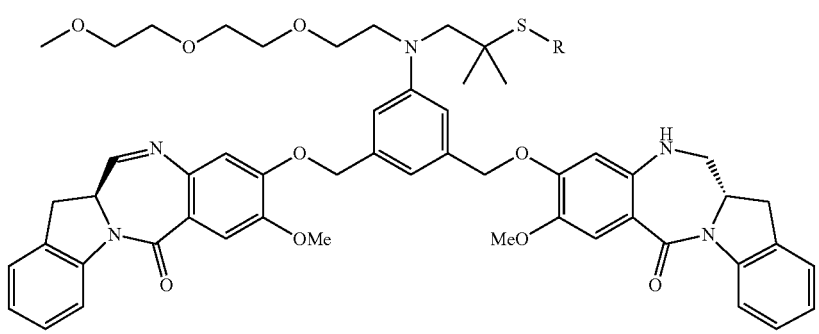
6a (R = SPy or SPyNO₂)
6b (R = mal-(CH₂)₆-mal)
6c (R = mal-(PEO)₂ₒᵣ₃-mal)
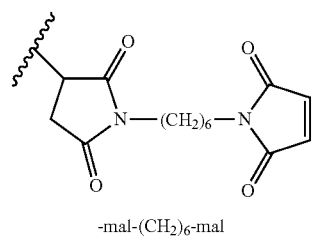
-mal-(CH₂)₆-mal TABLE 15-continued Representative drug compounds that can be used in the present methods.

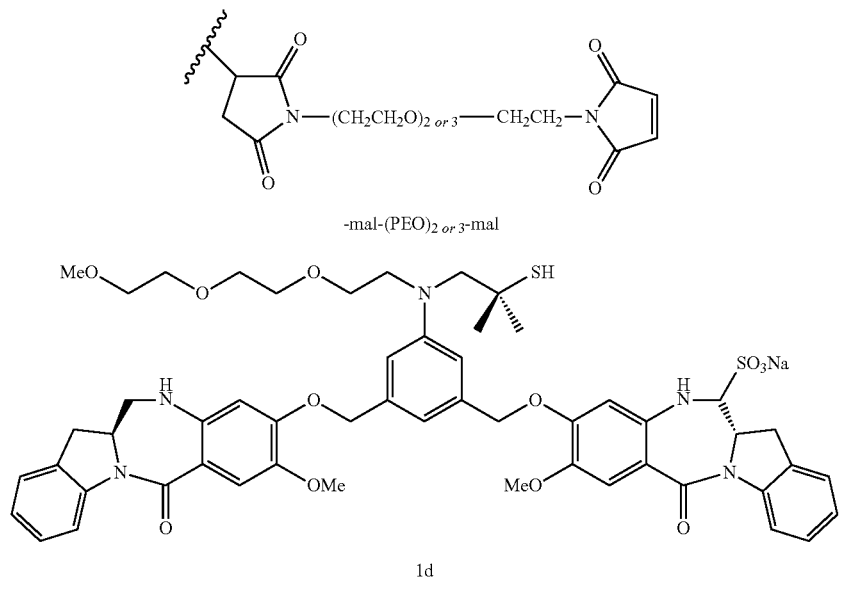

1d

Cell-Binding Agent

The effectiveness of the conjugates of the invention as therapeutic agents depends on the careful selection of an appropriate cell-binding agent. Cell-binding agents may be of any kind presently known, or that become known and includes peptides and non-peptides. Generally, these can be antibodies (especially monoclonal antibodies), lymphokines, hormones, growth factors, vitamins (such as folate etc., which may bind to a cell surface receptor therefor, e.g., a folate receptor), nutrient-transport molecules (such as transferrin), or any other cell-binding molecule or substance.

In certain embodiments, the cell-binding agents are proteins or polypetides, or compounds comprising proteins or polypetides. Preferably, the proteins or polypeptides comprise one or more Lys residues with side chain —$NH_2$ groups. Alternatively or in addition, the proteins or polypeptides comprise one or more Cys residues. The side chain —SH groups of the Cys residues may be intact, or may be in a disulfide bond that can be reduced. Preferably, reduction of the disulfide bond(s) does not significantly negatively impact the cell-binding function of the proteins or polypeptides (e.g., in the case of antibody or antigen-binding portion thereof, reduction of the disulfide bonds does not substantially increase the dissociation of light chains/heavy chains).

The Lys side chain —$NH_2$ groups and/or the Cys side chain —SH groups may be covalently linked to the linkers, which are in turn linked to the dimer compounds of the invention, thus conjugating the cell-binding agents to the dimer compounds of the invention. Each protein-based cell-binding agents may contain multiple Lys side chain —$NH_2$ groups and/or the Cys side chain —SH groups available for linking the compounds of the invention through the bifunctional crosslinkers.

More specific examples of cell-binding agents that can be used include:
polyclonal antibodies;
monoclonal antibodies;
fragments of antibodies such as Fab, Fab', and F(ab')$_2$, Fv, minibodies, diabodies, tribodies, tetrabodies (Parham, J. Immunol. 131:2895-2902 (1983); Spring et al. J. Immunol. 113:470-478 (1974); Nisonoff et al. Arch. Biochem. Biophys. 89:230-244 (1960), Kim et al., Mol. Cancer Ther., 7: 2486-2497 (2008), Carter, Nature Revs., 6: 343-357 (2006));
interferons (e.g. α, β, γ);
lymphokines such as IL-2, IL-3, IL-4, IL-6;
hormones such as insulin, TRH (thyrotropin releasing hormone), MSH (melanocyte-stimulating hormone), steroid hormones, such as androgens and estrogens;
growth factors and colony-stimulating factors such as EGF, TGF-alpha, FGF, VEGF, G-CSF, M-CSF and GM-CSF (Burgess, Immunology Today 5:155-158 (1984));
transferrin (O'Keefe et al. J. Biol. Chem. 260:932-937 (1985));
vitamins, such as folate;
Protein scaffolds based on a consensus sequence of fibronectin type III (FN3) repeats (also known as Centyrins; See U.S. Patent Publication 2010/0255056, incorporated herein by reference);
Designer Ankyrin Repeat Proteins (DARPins; U.S. Patent Application Nos. 20040132028; 20090082274; 20110118146; 20110224100, incorporated herein by reference), C. Zahnd et al. 2010, Cancer Res., 70; 1595-1605, incorporated herein by reference); and,
Fibronectin domain scaffold proteins (Adnectins: US Patent Application Nos. 20070082365; 20080139791, incorporated herein by reference).

Monoclonal antibody techniques allow for the production of extremely specific cell-binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of scFv (single chain variable region), specifically human scFv (see e.g., Griffiths et al., U.S. Pat. Nos.

5,885,793 and 5,969,108; McCafferty et al., WO 92/01047; Liming et al., WO 99/06587). In addition, resurfaced antibodies disclosed in U.S. Pat. No. 5,639,641 may also be used, as may chimeric antiobodies and humanized antibodies. Selection of the appropriate cell-binding agent is a matter of choice that depends upon the particular cell population that is to be targeted, but in general human monoclonal antibodies are preferred if an appropriate one is available.

For example, the monoclonal antibody MY9 is a murine $IgG_1$ antibody that binds specifically to the CD33 Antigen {J. D. Griffin et al 8 Leukemia Res., 521 (1984)} and can be used if the target cells express CD33 as in the disease of acute myelogenous leukemia (AML). The cell-binding agent may be any compound that can bind a cell, either in a specific or non-specific manner. Generally, these can be antibodies (especially monoclonal antibodies and antibody fragments), interferons, lymphokines, hormones, growth factors, vitamins, nutrient-transport molecules (such as transferrin), or any other cell-binding molecule or substance.

Where the cell-binding agent is an antibody, it binds to an antigen that is a polypeptide and may be a transmembrane molecule (e.g. receptor) or a ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-$\beta$; platelet-derived growth factor (PDGF); fibroblast growth factor such as aFGF and bFGF; fibroblast growth factor receptor 2 (FGFR2); epidermal growth factor (EGF); transforming growth factor (TGF) such as TGF-alpha and TGF-beta, including TGF-$\beta$1, TGF-$\beta$2, TGF-$\beta$3, TGF-$\beta$4, or TGF-$\beta$5; insulin-like growth factor-I and -II (IGF-I and IGF-II); des(1-3)-IGF-I (brain IGF-I), insulin-like growth factor binding proteins, EpCAM, GD3, FLT3, PSMA, PSCA, MUC1, MUC16, STEAP, CEA, TENB2, EphA receptors, EphB receptors, folate receptor, FOLR1, mesothelin, cripto, alpha$_v$beta$_6$, integrins, VEGF, VEGFR, EGFR, tarnsferrin receptor, IRTA1, IRTA2, IRTA3, IRTA4, IRTA5; CD proteins such as CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD134, CD137, CD138, CD152 or an antibody which binds to one or more tumor-associated antigens or cell-surface receptors disclosed in US Publication No. 20080171040 or US Publication No. 20080305044 and are incorporated in their entirety by reference; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CD11a, CD11b, CD11c, CD18, an ICAM, VLA-4 and VCAM; a tumor associated antigen such as HER2, HER3 or HER4 receptor; endoglin, c-Met, 1GF1R, PSGR, NGEP, PSMA, PSCA, LGR5, B7H4, and fragments of any of the above-listed polypeptides.

Additionally, GM-CSF, which binds to myeloid cells can be used as a cell-binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma, as can antibodies directed towards melanomas. Folic acid can be used to target the folate receptor expressed on ovarian and other tumors. Epidermal growth factor can be used to target squamous cancers such as lung and head and neck. Somatostatin can be used to target neuroblastomas and other tumor types.

Cancers of the breast and testes can be successfully targeted with estrogen (or estrogen analogues) or androgen (or androgen analogues) respectively as cell-binding agents.

In one embodiment, the cell-binding agent is humanized monoclonal antibodies. In another embodiment, the cell-binding agent is huMy9-6, or other related antibodies, which are described in U.S. Pat. Nos. 7,342,110 and 7,557,189 (incorporated herein by reference). In another embodiment, the cell-binding agent is an anti-folate receptor antibody described in U.S. Provisional Application Nos. 61/307,797, 61/346,595, 61/413,172 and U.S. application Ser. No. 13/033,723 (published as US 2012-0009181 A1). The teachings of all these applications are incorporated herein by reference in its entirety.

In certain embodiments, the cell-binding agent may be a monoclonal antibody or antigen-binding portions thereof sharing sequences critical for antigen-binding with an antibody disclosed herein, such as huMy9-6 or its related antibodies described in U.S. Pat. Nos. 7,342,110 and 7,557, 189 (incorporated herein by reference). These derivative antibodies may have substantially the same or identical (1) light chain and/or heavy chain CDR3 regions; (2) light chain and/or heavy chain CDR1, CDR2, and CDR3 regions; or (3) light chain and/or heavy chain regions, compared to an antibody described herein. Sequences within these regions may contain conservative amino acid substitutions, including substitutions within the CDR regions. Preferably, there is no more than 1, 2, 3, 4, or 5 conservative substitutions. In certain embodiments, the derivative antibodies have a light chain region and/or a heavy chain region that is at least about 90%, 95%, 99% or 100% identical to an antibody described herein. These derivative antibodies may have substantially the same binding specificity and/or affinity to the target antigen compared to an antibody described herein. Preferably, the $K_d$ and/or $k_{off}$ values of the derivative antobodies are within 10-fold (either higher or lower), 5-fold (either higher or lower), 3-fold (either higher or lower), or 2-fold (either higher or lower) of an antibody described herein.

These derivative antibodies may be fully human antobodies, or humanized antibodies, or chimeric antibodies. The derivative antibodies may be produced according to any art-recognized methods.

In one embodiment, the anti-folate receptor antibody is a humanized antibody or antigen binding fragment thereof that specifically binds a human folate receptor 1, wherein the antibody comprises: (a) a heavy chain CDR1 comprising GYFMN (SEQ ID NO: 1); a heavy chain CDR2 comprising RIHPYDGDTFYNQXaa$_1$FXaa$_2$Xaa$_3$ (SEQ ID NO: 2); and a heavy chain CDR3 comprising YDGSRAMDY (SEQ ID NO: 3); and (b) a light chain CDR1 comprising KASQS-VSFAGTSLMH (SEQ ID NO: 4); a light chain CDR2 comprising RASNLEA (SEQ ID NO: 5); and a light chain CDR3 comprising QQSREYPYT (SEQ ID NO: 6); wherein Xaa$_1$ is selected from K, Q, H, and R; Xaa$_2$ is selected from Q, H, N, and R; and Xaa$_3$ is selected from G, E, T, S, A, and V. Preferably, the heavy chain CDR2 sequence comprises RIHPYDGDTFYNQKFQG (SEQ ID NO: 7).

In another embodiment, the anti-folate receptor antibody is a humanized antibody or antigen binding fragment thereof that specifically binds the human folate receptor 1 comprising the heavy chain having the amino acid sequence of QVQLVQSGAEVVKPGASVKISCKASGYTFTGYFMN-WVKQSPGQSLEWIGRIHPY DGDTFYNQKFQG-KATLTVDKSSNTAHMELLSLTSEDFAVYYCTRYDG-SRAMDY WGQGTTVTVSSASTKGPSVFPLAPSSKST-SGGTAALGCLVKDYFPEPVTVSWNS GALTSGVHTF-PAVLQSSGLYSLSSVVTVPSSSLGTQTYICNVNH-KPSNTKVDKKV EPKSCDKTHTCPPCPAPELLGGPSV-FLFPPKPKDTLMISRTPEVTCVVVDVSHEDP EVKFNWYVDGVEVHNAKTKPREEQYNSTYRVVS VLTVLHQDWLNGKEYKCKV SNKALPAPIEK-TISKAKGQPREPQVYTLPPSRDELTKNQVSLTCLVKG-FYPSDIAV EWESNGQPENNYKTTPPVLDSDGSFFLY-SKLTVDKSRWQQGNVFSCSVMHEAL HNHYTQKSLSLSPGK (SEQ ID NO: 8).

In another embodiment, the anti-folate antibody is a humanized antibody or antigen binding fragment thereof encoded by the plasmid DNA deposited with the ATCC on Apr. 7, 2010 and having ATCC deposit nos. PTA-10772 and PTA-10773 or 10774.

In another embodiment, the anti-folate receptor antibody is a humanized antibody or antigen binding fragment thereof that specifically binds the human folate receptor 1 comprising the light chain having the amino acid sequence of DIVLTQSPLSLAVSLGQPAIISCKASQSVSFAGTSLMH-WYHQKPGQQPRLLIYRAS NLEAGVPDRFSGSGSK-TDFTLNISPVEAEDAATYYCQQSREYPYTFGGGT-KLEIK RTVAAPSVFIFPPSDEQLKSGTASVVCL-LNNFYPREAKVQWKVDNALQSGNSQE SVTEQD-SKDSTYSLSSTLTLSKADYEKHKVYACEVTHQ-GLSSPVTKSFNRGEC (SEQ ID NO: 9); or DIVLTQS-PLSLAVSLGQPAIISCKASQSVSFAGTSLMHWYHQK-PGQQPRLLIYRAS NLEAGVPDRFSGSGSKTD-FTLTISPVEAEDAATYYCQQSREYPYTFGGGTKLEIK RTVAAPSVFIFPPSDEQLKSGTASVVCLLNNFY-PREAKVQWKVDNALQSGNSQE SVTEQDSKD-STYSLSSTLTLSKADYEKHKVY-ACEVTHQGLSSPVTKSFNRGEC (SEQ ID NO: 10).

In another embodiment the anti-folate receptor antibody is a humanized antibody or antigen binding fragment thereof that specifically binds the human folate receptor 1 comprising the heavy chain having the amino acid sequence of SEQ ID NO: 8, and the light chain having the amino acid sequence of SEQ ID NO: 9 or SEQ ID NO: 10. Preferably, the antibody comprises the heavy chain having the amino acid sequence of SEQ ID NO: 8 and the light chain having the amino acid sequence of SEQ ID NO: 10 (hu FOLR1).

In another embodiment, the anti-folate receptor antibody is a humanized antibody or antigen binding fragment thereof encoded by the plasmid DNA deposited with the ATCC on Apr. 7, 2010 and having ATCC deposit nos. PTA-10772 and PTA-10773 or 10774.

In another embodiment, the anti-folate receptor antibody is a humanized antibody or antigen binding fragment thereof comprising a heavy chain variable domain at least about 90%, 95%, 99% or 100% identical to QVQLVQSGAEV-VKPGASVKISCKASGYTFTGYFMNWVKQSPGQ-SLEWIGRIHPY DGDTFYNQKFQGKATLTVDKSSN-TAHMELLSLTSEDFAVYYCTRYDGSRAMDY WGQGT-TVTVSS (SEQ ID NO: 11), and a light chain variable domain at least about 90%, 95%, 99% or 100% identical to DIVLTQSPLSLAVSLGQPAIISCKASQSVSFAGTSLMH-WYHQKPGQQPRLLIYRAS NLEAGVPDRFSGSGSK-TDFTLNISPVEAEDAATYYCQQSREYPYTFGGGT-KLEIKR (SEQ ID NO: 12); or DIVLTQSPLSLAVSLGQPAIISCKASQSVSFAGTSLMH-WYHQKPGQQPRLLIYR ASNLEAGVPDRFSGSGSK-TDFTLTISPVEAEDAATYYCQQSREYPYTFGGGT-KLEIKR (SEQ ID NO: 13).

A cell-binding agent, such as an antibody, can be modified with a heterobifunctional crosslinker bearing an amine-reactive group, such as N-hydroxysuccinimide group (NHS group), a thiol-reactive maleimido, vinylpyridine, vinyl sulfone, vinyl sulfonamide or a haloacetyl-based group, or a thiol group.

Thiol residues in antibody can be introduced by a number of methods known in the art, including: a) modification of antibody with thiol-generating reagents such as 2-iminothiolane or homocysteine thiolactone, or b) via reaction with a disulfide-containing heterobifunctional crosslinking agent such as SPP, SPDP, SPDB, sulfo-SPDB followed by reduction of the disulfide bond with DTT or TCEP to generate a free thiol, c) mutagenesis to incorporate non-native cysteine residues, such as cysteine-engineered antibodies (US2007/0092940 A1, US 2010/0003766 A1, U.S. Pat. No. 7,723,485 B2), or d) reduction of native disulfide bonds (del Rosario, R. B. et al., Cancer Res. Suppl. 1990, 50, 804s-808s).

A thiol-reactive group, such as maleimido, vinylpyridine, vinyl sulfone, vinyl sulfonamide or a haloacetyl-based group in antibody can be introduced by modifying an antibody with a heterobifunctional crosslinking agent bearing a thiol-reactive group (including but not limited to SPDB, N-succinimidyl-4-(4-nitropyridyl-2-dithio)butanoate, sulfo-SMCC, SMCC, LC-SMCC, KMUA, BMPS, GMBS, sulfo-GMBS, EMCS, sulfo-EMCS, AMAS, SVSB, SPP, NHS-(PEG)n-mal, where n=1 to 24, preferably 2, 4, 8, 12, and 24). Crosslinking agents comprising a maleimido-based moiety include N-succinimidyl 4-(maleimidomethyl)cyclohexane-carboxylate (SMCC), N-succinimidyl-4-(N-maleimidom-ethyl)-cyclohexane-1-carboxy-(6-amidocaproate), which is a "long chain" analog of SMCC (LC-SMCC), κ-maleimid-oundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), N-succinimidyl 4-(p-maleimidophenyl)-butyrate (SMPB), and N-(p-maleimidophenyl)isocyanate (PMPI). Thiol reactive compounds which contain a vinylpyridine are described (Friedman M. et. Al. *Int. J. Peptide Protein Res.*

1974, 6, 183-185; Mak A. et. Al. Anal. Biochem. 1978, 84, 432-440). Thiol reactive compounds which contain a vinyl sulfone moiety have been described (Masri M. S. J. Protein Chem., 1988, 7, 49-54; Morpurgo, M. et. Al. Bioconjugate Chem. 1996, 7, 363-368) Cross-linking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP).

The modified antibody can be purified by any suitable methods known in the art, for example, gel filtration, TFF or ion-exchange chromatography or affinity chromatography.

All references cited herein and in the examples that follow are expressly incorporated by reference in their entireties.

Cell-Binding Agent-Drug Conjugates

The present invention provides improved methods to produce cell-binding agent-drug conjugates, comprising a cell-binding agent linked to one or more cytotoxic compounds of the present invention via a variety of linkers, including, but not limited to, disulfide linkers, thioether linkers, amide bonded linkers, peptidase-labile linkers, acid-labile linkers, esterase-labile linkers.

Figure 26:
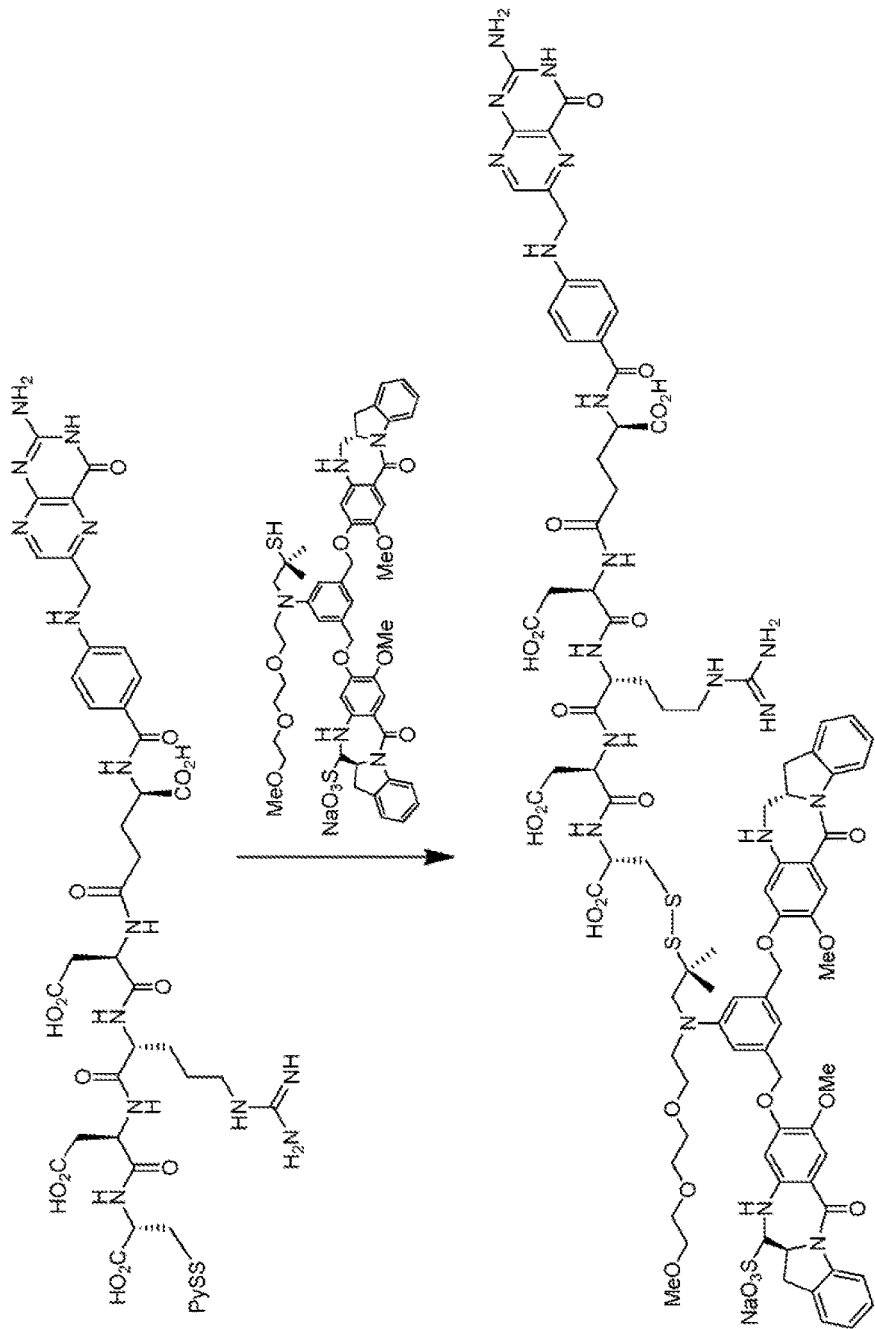
FIG. 26 shows a representative synthesis scheme for a Sulfonated folate/cytotoxic compound conjugate. Note that sodium bisulfite was added to the conjugation reaction for making the conjugate.
Figure 27:
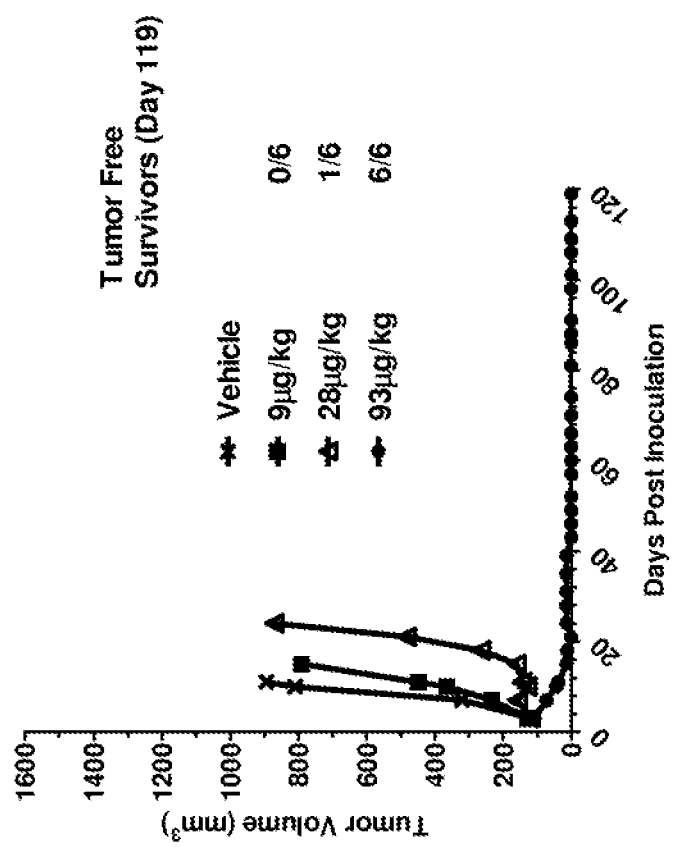
FIG. 27 shows in vivo efficacy of huMy9-6-drug 2 in MOLM-13 tumor bearing mice. Note that sodium bisulfite was added to the conjugation reaction for making the conjugate.

Representative conjugates that can be made using the methods of the invention include antibody/cytotoxic compound, antibody fragment/cytotoxic compound, epidermal growth factor (EGF)/cytotoxic compound, melanocyte stimulating hormone (MSH)/cytotoxic compound, thyroid stimulating hormone (TSH)/cytotoxic compound, somatostatin/cytotoxic compound, folate/cytotoxic compound, estrogen/cytotoxic compound, estrogen analogue/cytotoxic compound, androgen/cytotoxic compound, and androgen analogue/cytotoxic compound. A representative folate/cytotoxic compound conjugate is depicted below, with the optional —SO$_3$Na adduct on the imine bond of one of the two drug monomers. A representative synthesis scheme for this conjugate is shown in FIG. 26.

Folate/Cytotoxic Compound Conjugate

In a preferred embodiment, the present invention provides methods for producing conjugates comprising an indolinobenzodiazepine dimer compound (e.g., formulas (Ib'), (IIb'), (Iab'), (IIAb'), (IBb'), (IIBb'), (XIIIb'), (Xb'), etc.) and the cell-binding agent linked through a covalent bond. The linker can be cleaved at the site of the tumor/unwanted proliferating cells to deliver the cytotoxic agent to its target in a number of ways. The linker can be cleaved, for example, by low pH (hydrazone), reductive environment (disulfide), proteolysis (amide/peptide link), or through an enzymatic reaction (esterase/glycosidase).

In a preferred aspect, representative cytotoxic conjugates that can be produced by the methods of the invention are antibody/indolinobenzodiazepine dimer compound, antibody fragment/indolinobenzodiazepine dimer compound, epidermal growth factor (EGF)/indolinobenzodiazepine dimer compound, melanocyte stimulating hormone (MSH)/indolinobenzodiazepine dimer compound, thyroid stimulating hormone (TSH)/indolinobenzodiazepine dimer compound, somatostatin/indolinobenzodiazepine dimer compound, folate/indolinobenzodiazepine dimer compound, estrogen/indolinobenzodiazepine dimer compound, estrogen analogue/indolinobenzodiazepine dimer compound, prostate specific membrane antigen (PSMA) inhibitor/indolinobenzodiazepine dimer compound, matriptase inhibitor/indolinobenzodiazepine dimer compound, designed ankyrin repeat proteins (DARPins)/indolinobenzodiazepine dimer compound, androgen/indolinobenzodiazepine dimer compound, and androgen analogue/indolinobenzodiazepine dimer compound.

Thus in the fourteenth specific embodiment, the methods of the invention produce a conjugate comprising: a cytotoxic compound and a cell binding agent (CBA), wherein the cytotoxic compound is covalently linked to the CBA through a linking group, and wherein the cytotoxic compound and the linking group portion of the conjugate is represented by any one of the following formulas:

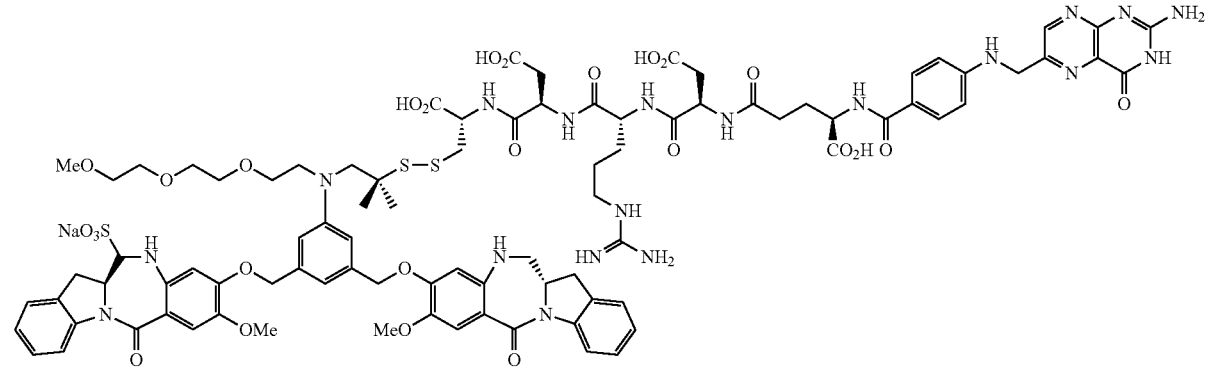

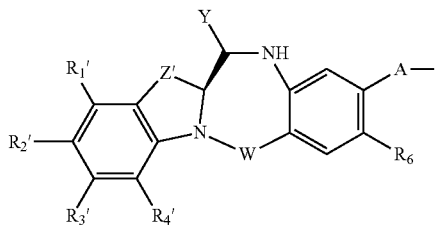
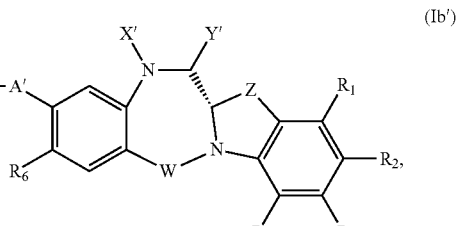

(Ib')

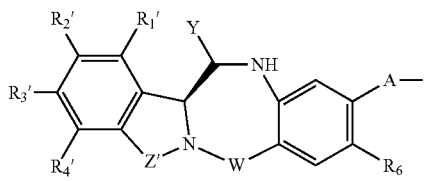
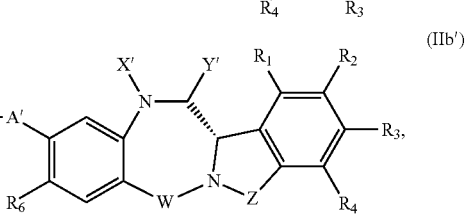

(IIb')

or a pharmaceutically acceptable salt thereof, wherein:

Y is a leaving group, and is a sulfite ($HSO_3$, $HSO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono-, di-, tri-, and tetra-thiophosphate ($PO_3SH_3$, $PO_2S_2H_2$, $POS_3H_2$, $PS_4H_2$ or a salt of $PO_3S^{3-}$, $PO_2S_2^{3-}$, $POS_3^{3-}$ or $PS_4^{3-}$ formed with a cation), thio phosphate ester ($R^iO)_2PS$ ($OR^i$), $R^iS-$, $R^iSO$, $R^iSO_2$, $R^iSO_3$, thiosulfate ($HS_2O_3$ or a salt of $S_2O_3^{2-}$ formed with a cation), dithionite ($HS_2O_4$ or a salt of $S_2O_4^{2-}$ formed with a cation), phosphorodithioate ($P(=S)(OR^{k'})(S)(OH)$ or a salt thereof formed with a cation), hydroxamic acid ($R^{k'}C(=O)NOH$ or a salt formed with a cation), formaldehyde sulfoxylate ($HOCH_2SO_2^-$ or a salt of $HOCH_2SO_2^-$ formed with a cation, such as $HOCH_2SO_2^-Na^+$) or a mixture thereof, wherein $R^i$ is a linear or branched alkyl having 1 to 10 carbon atoms and is substituted with at least one substituent selected from $-N(R^j)_2$, $-CO_2H$, $-SO_3H$, and $-PO_3H$; $R^i$ can be further optionally substituted with a substituent for an alkyl described herein; $R^j$ is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl; preferably, Y is an adduct of a bisulfite, a hydro sulfite, or a metabisulfite, or salts thereof (such as sodium salt);

X' is selected from —H, an amine-protecting group, the linking group, an optionally substituted linear, branched or cyclic alkyl, alkenyl or alkynyl having from 1 to 10 carbon atoms, a polyethylene glycol unit $-(CH_2CH_2O)_n-R^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, the linking group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

$R^c$ is —H or a substituted or unsubstituted linear or branched alkyl having 1 to 4 carbon atoms, or the linking group;

$R_1$, $R_2$, $R_3$, $R_4$, $R_1'$, $R_2'$, $R_3'$ and $R_4'$ are each independently selected from the group consisting of —H, an optionally substituted linear, branched or cyclic alkyl, alkenyl or alkynyl having from 1 to 10 carbon atoms, a polyethylene glycol unit $-(OCH_2CH_2)_n-R^c$, halogen, guanidinium [$-NH(C=NH)NH_2$], —OR, —NR'R", —NO$_2$, —NCO, —NR'COR", —SR, a sulfoxide represented by —SOR', a sulfone represented by —SO$_2$R', a sulfonate —SO$_3^-$M$^+$, a sulfate —OSO$_3^-$M$^+$, a sulfonamide represented by —SO$_2$NR'R", cyano, an azido, —COR', —OCOR', —OCONR'R" and the linking group;

M is —H or a pharmaceutically acceptable cation, such as Na$^+$;

R, for each occurrence, is independently selected from the group consisting of —H, an optionally substituted linear, branched or cyclic alkyl, alkenyl or alkynyl having from 1 to 10 carbon atoms, a polyethylene glycol unit $-(CH_2CH_2O)_n-R^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, a polyethylene glycol unit $-(CH_2CH_2O)_n-R^c$, and an optionally substituted 3-18-membered heterocyclic ring having 1 to 6 heteroatoms independently selected from O, S, N and P;

R$^c$ is —H or a substituted or unsubstituted linear or branched alkyl having 1 to 4 carbon atoms, or the linking group;

n is an integer from 1 to 24;

W is selected from C=O, C=S, CH$_2$, BH, SO and SO$_2$;

R$_6$ is —H, —R, —OR, —SR, —NR'R", —NO$_2$, halogen or the linking group;

Z and Z' are independently selected from $-(CH_2)_{n'}-$, $-(CH_2)_{n'}-CR_7R_8-(CH_2)_{na'}-$, $-(CH_2)_{n'}-NR_9-(CH_2)_{na'}-$, $-(CH_2)_{n'}-O-(CH_2)_{na'}-$ and $-(CH_2)_{n'}-S-(CH_2)_{na'}-$;

n' and na' are the same or different, and are selected from 0, 1, 2 and 3;

R$_7$ and R$_8$ are the same or different, and are each independently selected from —H, —OH, —SH, —COOH, —NHR', a polyethylene glycol unit $-(OCH_2CH_2)_n-$, an amino acid, a peptide unit bearing 2 to 6 amino acids, an optionally substituted linear, branched or cyclic alkyl having from 1 to 10 carbon atoms;

$R_9$ is independently selected from —H, an optionally substituted linear, branched or cyclic alkyl having from 1 to 10 carbon atoms, a polyethylene glycol unit —(OCH$_2$CH$_2$)$_n$—;

A and A' are the same or different, and are independently selected from —O—, oxo (—C(=O)—), —CRR'O—, —CRR'—, —S—, —CRR'S—, —N(R$_5$)— and —CRR'N(R$_5$)—, R$_5$ for each occurrence is independently —H or an optionally substituted linear or branched alkyl having 1 to 10 carbon atoms;

D and D' are the same or different, and are independently absent or selected from the group consisting of an optionally substituted linear, branched or cyclic alkyl, alkenyl or alkynyl having 1 to 10 carbon atoms, an amino acid, a peptide bearing 2 to 6 amino acids, and a polyethylene glycol unit (—OCH$_2$CH$_2$)$_n$—;

L is absent, the linking group, a polyethylene glycol unit (—OCH$_2$CH$_2$)$_n$—, an optionally substituted linear, branched or cyclic alkyl or alkenyl having 1 to 10 carbon atoms, a phenyl group, a 3- to 18-membered heterocyclic ring or a 5- to 18-membered heteroaryl ring having 1 to 6 heteroatoms independently selected from O, S, N and P, wherein the alkyl or alkenyl is optionally substituted with the linking group; phenyl or heterocyclic or heteroaryl ring can be optionally substituted, wherein the substituent can comprise the linking group.

A representative conjugate is presented below ("Ab" stands for a CBA, such as an antibody):

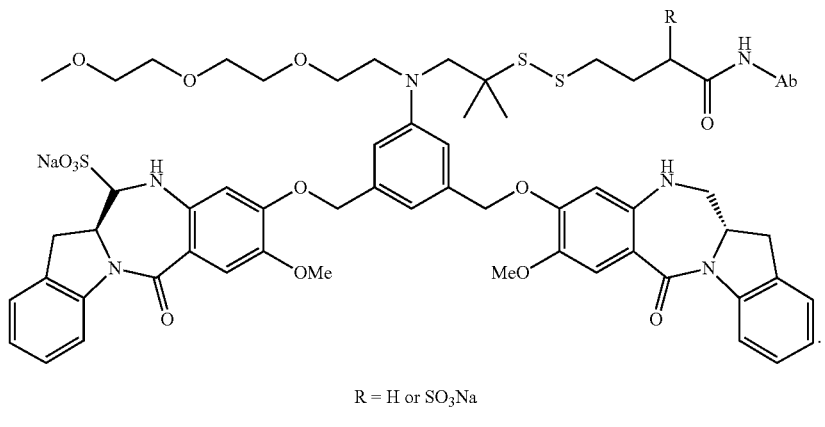

R = H or SO$_3$Na

In certain embodiments, Y is —SO$_2$M, —SO$_3$M, or —OSO$_3$M.

In certain embodiments, the conjugates that can be synthesized by the methods of the invention include the following:

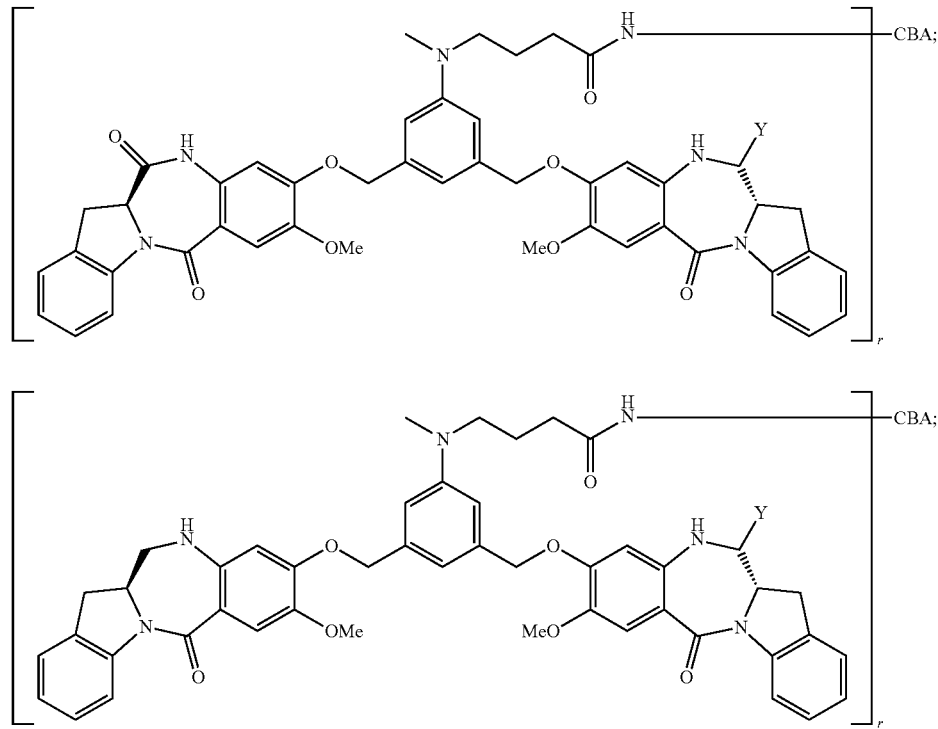

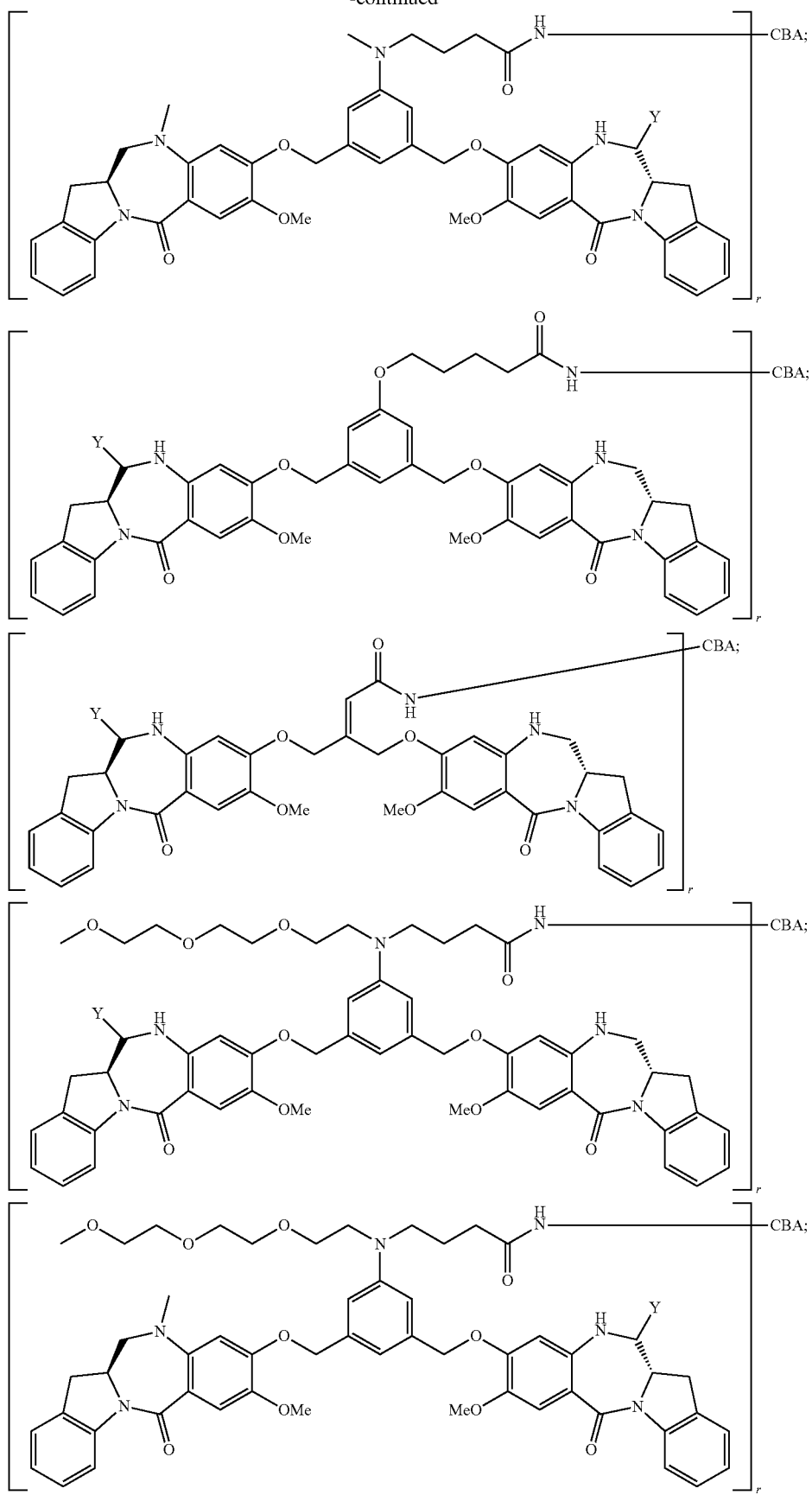

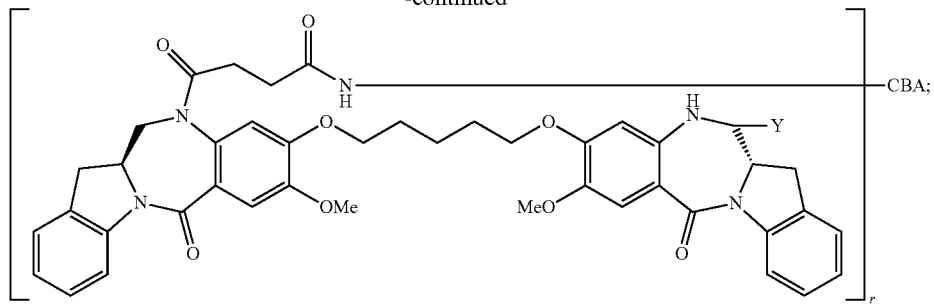

wherein:
CBA is the cell-binding agent, r is an integer from 1 to 10, Y is —H, an adduct of a bisulfite, a hydro sulfite, a metabisulfite, or salts thereof, or —SO$_3$M, and M is —H or a pharmaceutically acceptable cation.

In certain embodiments, L is absent, or is selected from an optionally substituted phenyl group and an optionally substituted pyridyl group, wherein the phenyl and the pyridyl group bears the linking group, or L is an amine group bearing the linking group (i.e., —N(linking group)-), or L is a linear, branched or cyclic alkyl or alkenyl having from 1 to 6 carbon atoms and bearing the linking group.

In the fifteenth specific embodiment, the cytotoxic compound bonded to the linking group is represented by any one of the following formulas:

an azido, —COR', —OCOR', —OCONR'R" and the linking group, provided only one of L', L", and L' is the linking group; and G is selected from —CH— or —N—. The remaining groups are as described in the fourteenth specific embodiment above.

In certain embodiments, one of L', L", or L'" is the linking group, while the others are —H. Preferably, L' is the linking group, and L" and L' are —H.

In certain embodiments, A and A' are both —O—, R$_6$ is —OMe, and G is —CH—.

In a sixteenth specific embodiment, L' is represented by the following formula:

—W'—R$^x$—V—R$^y$-J,

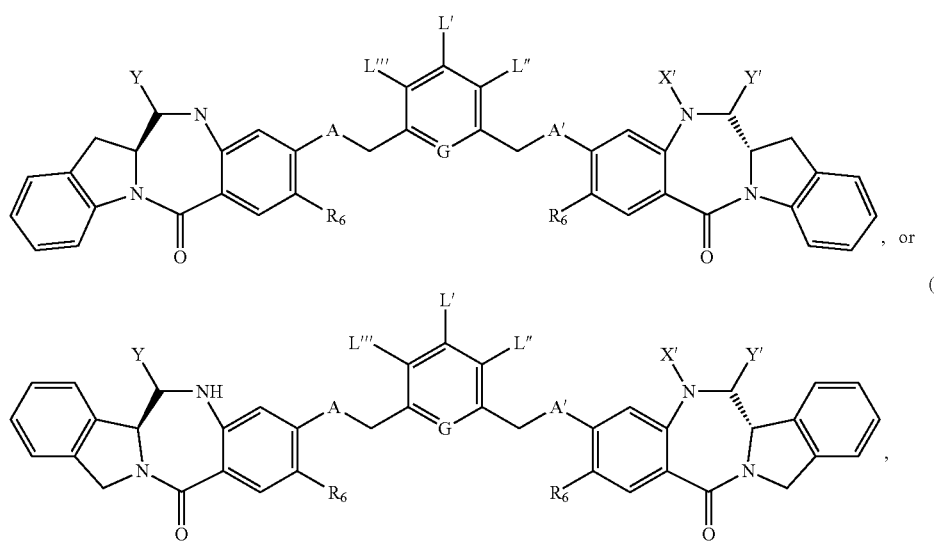

wherein:
L', L", and L' are the same or different, and are independently selected from —H, an optionally substituted linear, branched or cyclic alkyl, alkenyl or alkynyl having from 1 to 10 carbon atoms, a polyethylene glycol unit —(OCH$_2$CH$_2$)$_n$—R$^c$, halogen, guanidinium [—NH(C=NH)NH$_2$], —OR, —NR'R", —NO$_2$, —NR'COR", —SR, a sulfoxide represented by —SOR', a sulfone represented by —SO$_2$R', a sulfonate —SO$_3$M, a sulfate —OSO$_3$M, a sulfonamide represented by —SO$_2$NR'R", cyano, wherein:
W' and V are the same or different, and are each independently absent, or selected from —CR$^e$R$^{e'}$—, —O—, —O—C(=O)—, —C(=O)—O—, —S—, —SO—, —SO$_2$—, —CH$_2$—S—, —CH$_2$O—, —CH$_2$NR$^e$—, —O—(C=O)O—, —O—(C=O)N(R$^e$)—, —N(R$^e$)—, —N(R$^e$)—C(=O)—, —C(=O)—N(R$^e$)—, —N(R$^e$)—C(=O)O—, —N(C(=O)R$^e$)C(=O)—, —N(C(=O)R$^e$)—, —(O—CH$_2$—CH$_2$)$_n$—, —SS—, or —C(=O)—, or an amino acid, or a peptide having 2 to 8 amino acids;

R$^x$ and R$^y$ are the same or different, and are each independently absent or an optionally substituted linear, branched or cyclic alkyl, alkenyl, or alkynyl having 1 to 10 carbon atoms, an aryl bearing 6 to 10 carbon atoms or a 3- to 8-membered heterocyclic ring bearing 1 to 3 heteroatoms selected from O, N or S;

R$^e$ and R$^{e'}$ are the same or different, and are selected from —H, a linear, branched or cyclic alkyl, alkenyl, or alkynyl having 1 to 10 carbon atoms or —(CH$_2$—CH$_2$—O)$_n$—R$^k$, wherein R$^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5- or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms; preferably, R$^{101}$ and R$^{102}$ are each independently a linear or branched alkyl having 1 to 6 carbon atoms;

n is an integer from 1 to 24; and

J is covalently linked to the CBA, and is selected from a succinimide, a acetamido, —S—, —SS—, —CH$_2$S—, —CH(Me)S—, —C(Me)$_2$S—, —NR$^{c1}$—, —CH$_2$NR$^{c1}$—, —NR$^{c1}$N—, and —C(=O)—, wherein R$^{c1}$ is —H or a substituted or unsubstituted linear or branched alkyl having 1 to 4 carbon atoms.

In certain embodiments, J is —S—, —SS—, a succinimide, or —C(=O)—.

In certain embodiments, R$^{e'}$ is —H or -Me; R$^e$ is a linear or branched alkyl having 1 to 6 carbon atoms or —(CH$_2$—CH$_2$—O)$_n$—R$^k$; n is an integer from 2 to 8; and R$^k$ is —H, -Me or —CH$_2$CH$_2$—NMe$_2$, and the remainder of the variables are as described above in the fifteenth specific embodiment.

In certain embodiments, V is an amino acid or a peptide having 2 to 8 amino acids.

In certain embodiments, V is valine-citrulline, gly-gly-gly, or ala-leu-ala-leu.

In certain embodiments,

W' is —O—, —N(R$^e$)— or —N(R$^e$)—C(=O)—;

R$^e$ is H, a linear or branched alkyl having 1 to 4 carbon atoms, or —(CH$_2$—CH$_2$—O)$_n$—R$^k$;

R$^x$ is a linear or branched alkyl having 1 to 6 carbon atoms;

V is absent, —(O—CH$_2$—CH$_2$)$_n$—, —C(=O)—NH—, —S—, —NH—C(=O)—;

R$^y$ is absent or a linear or branched alkyl having 1 to 4 carbon atoms; and

J is —S—, —SS—, or —C(=O)—, and the remaining groups are as defined in the sixteenth specific embodiment.

In certain embodiments,

W' is —O—, —N(R$^e$)— or —N(R$^e$)—C(=O)—;

R$^e$ is —H, -Me, or —(CH$_2$—CH$_2$—O)$_n$-Me;

n is an integer from 2 to 6;

R$^x$ is linear or branched alkyl bearing 1 to 6 carbon atoms;

V and R$^y$ are absent; and

J is —C(=O)—. The remaining groups are as defined in the sixteenth specific embodiment.

In a seventeenth specific embodiment, L' in the sixteenth specific embodiment is represented by the following formula:

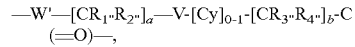
—W'—[CR$_{1''}$R$_{2''}$]$_a$—V-[Cy]$_{0-1}$-[CR$_{3''}$R$_{4''}$]$_b$-C(=O)—, wherein:

R$_{1''}$, R$_{2''}$, and R$_{3''}$ are each independently —H or a linear or branched alkyl bearing 1 to 4 carbon atoms, preferably -Me;

R$_{4''}$ is —H, a linear or branched alkyl bearing 1 to 4 carbon atoms (preferably -Me), —SO$_3$H, or —SO$_3^-$M$^+$, wherein M$^+$ is a pharmaceutically acceptable cation;

a is an integers from 0-5 (e.g., from 0 to 2, 3, 4, or 5), and b is an integer from 0-6 (e.g., from 0 to 3, 4, 5, or 6); and, Cy is an optionally substituted 5-membered heterocyclic ring bearing an N heteroatom, preferably Cy is

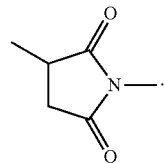

In certain embodiments, such as in the sixteenth or the seventeenth specific embodiment, W' is —N(R$^e$)—.

In certain embodiments, such as in the sixteenth or the seventeenth specific embodiment, R$^e$ is —(CH$_2$—CH$_2$—O)$_{2-6}$—R$^k$, wherein R$^k$ is a linear or branched alkyl having 1 to 6 carbon atoms.

In certain embodiments, such as in the sixteenth or the seventeenth specific embodiment, V is —S— or —SS—.

In an eighteenth specific embodiment, L' in the sixteenth or the seventeenth specific embodiment is represented by the following formula:

—NR$^e$—[CR$_{1''}$R$_{2''}$]$_a$-S—[CR$_{3''}$R$_{4''}$]$_b$-C(=O)—.

In certain embodiments, such as in the sixteenth to seventeenth specific embodiments, the conjugate is:

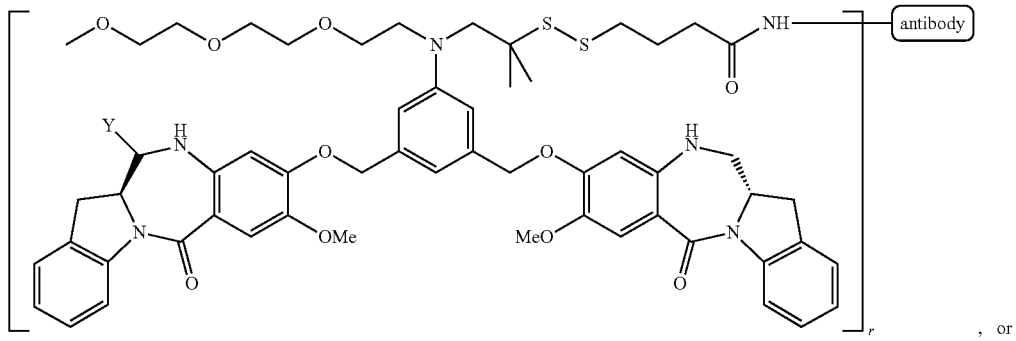

, or

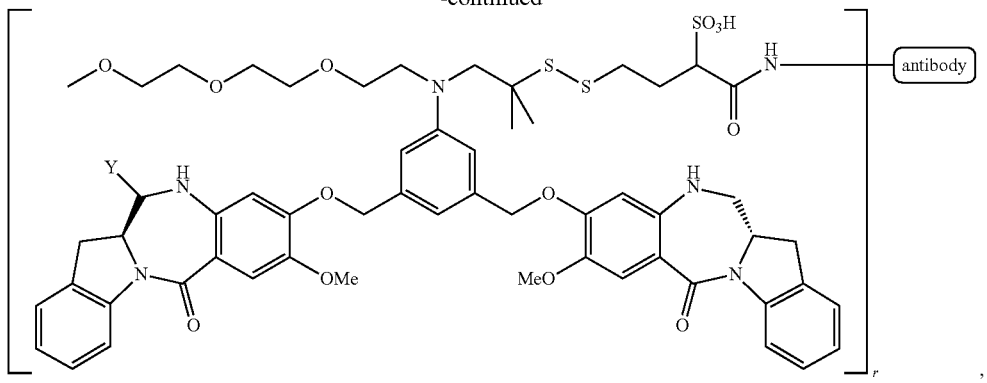

wherein r is an integer from 1 to 10, Y is —SO₃M, and M is —H or a pharmaceutically acceptable cation.

In certain embodiments, such as in the sixteenth to eighteenth specific embodiments, the antibody is huMy9-6.

In a nineteenth specific embodiment, L' in the sixteenth or the seventeenth specific embodiment is represented by the following formula:

—NR$^e$—[CR$_1$"R$_2$"]$_a$—S-Cy-[CR$_3$"R$_4$"]$_b$-C(=O)—.

In certain embodiments, such as in the sixteenth, seventeenth, and the nineteenth specific embodiments, the conjugate is:

wherein r is an integer from 1 to 10, Y is —SO₃M, and M is —H or a pharmaceutically acceptable cation.

In certain embodiments, such as in the sixteenth, seventeenth, and the nineteenth specific embodiments, the antibody is huMy9-6.

In a twentieth specific embodiment, the cytotoxic compound bonded to the linking group is represented by the following formula:

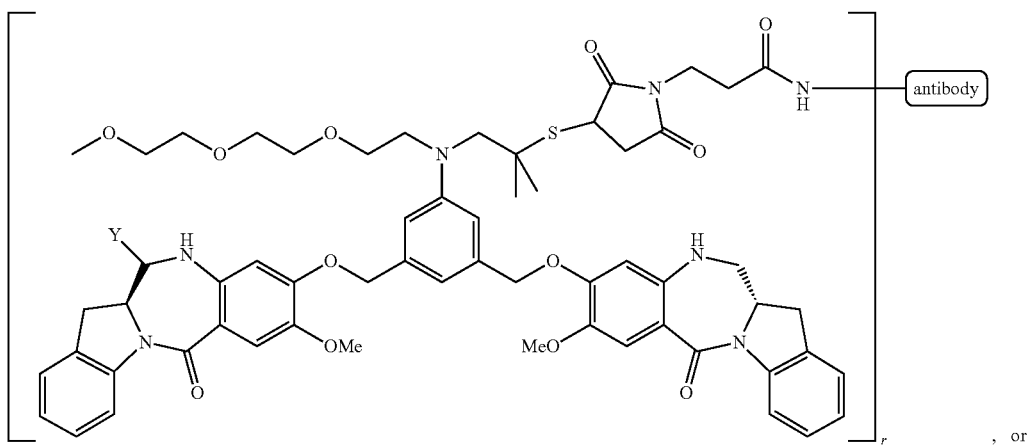

, or

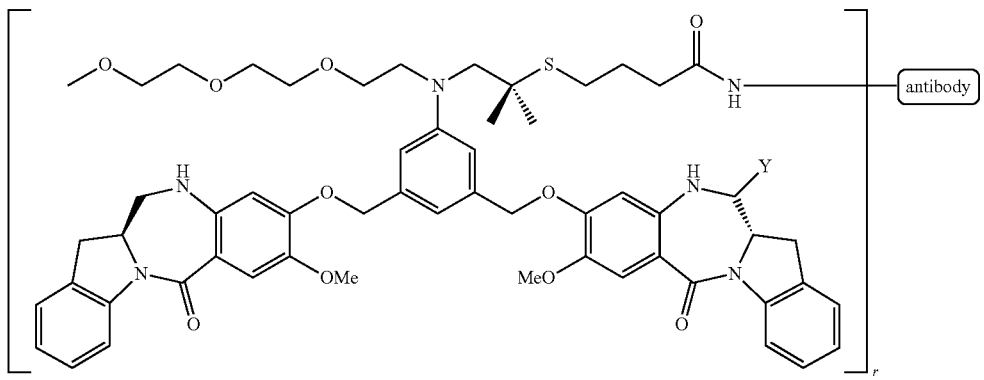

,

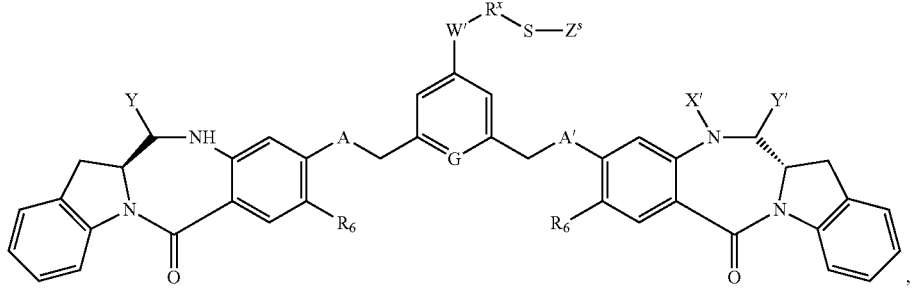

(IBb')

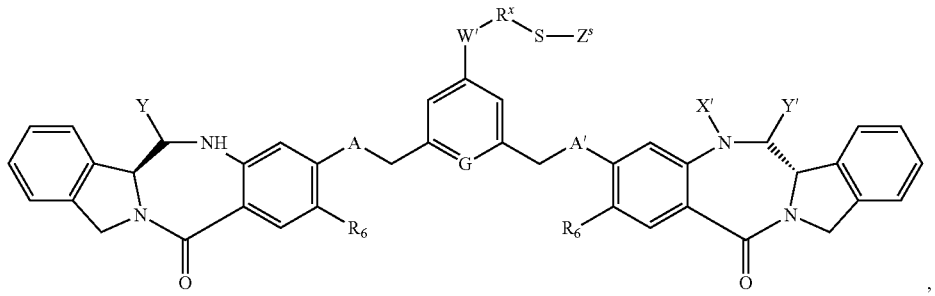

(IIBb')

wherein:
W' is absent, or selected from —O—, —N($R^e$)—, —N($R^e$)—C(=O)—, —N(C(=O)$R^e$)—, —S—, —CH$_2$—S—, or —CH$_2$N$R^e$—;

$R^x$ is absent or selected from a linear, branched or cyclic alkyl having 1 to 10 carbon atoms;

$R^e$ is —H, a linear, branched or cyclic alkyl, alkenyl or alkynyl having 1 to 10 carbon atoms or —(CH$_2$—CH$_2$—O)$_n$—$R^k$, wherein $R^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5 or 6-membered nitrogen containing heterocycle, such as piperidine or morpholine, wherein R$^{101}$ and R$^{102}$ are each independently a linear, branched, or cyclic alkyl, alkenyl or alkynyl having 1 to 10 carbon atoms;

$Z^s$ is linked to the CBA, and is either a bond, or —S$R^m$—;

$R^m$ is $R^d$ or a substituted linear or branched alkyl having 1 to 4 carbon atoms bearing a reactive ester, selected from N-hydroxysuccinimide esters, N-hydroxyphtalimide esters, N-hydroxy sulfo-succinimide esters, para-nitrophenyl esters, dinitrophenyl esters, and pentafluorophenyl esters;

$R^d$ is selected from phenyl, nitrophenyl, dinitrophenyl, carboxynitrophenyl, pyridyl or nitropyridyl; and n is an integer from 1 to 24; and the remainder of the variables are as described above in the eighth or the fifteenth specific embodiment.

In a twenty-first specific embodiment, the cytotoxic compound bonded to the linking group is represented by the following formula:

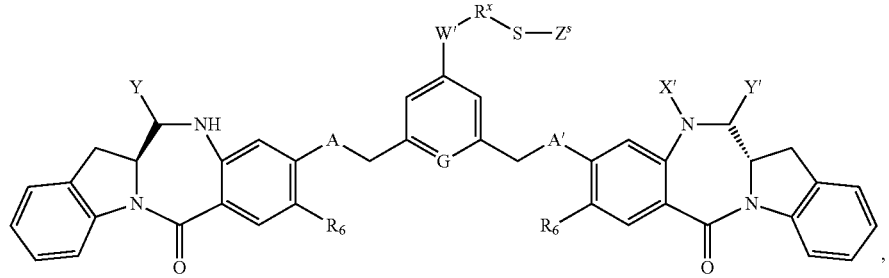

(XIIIb')

-continued

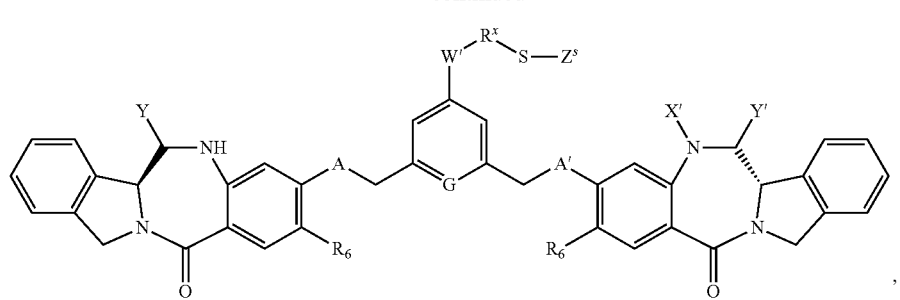

(Xb')

wherein:
W' is absent, or selected from —O—, —N($R^e$)—, —N($R^e$)—C(=O)—, —N(C(=O)$R^e$)—, —S—, —CH$_2$—S—, or —CH$_2$N$R^e$—;
$R^x$ is absent or selected from a linear, branched or cyclic alkyl having 1 to 10 carbon atoms;
$R^e$ is —H, a linear, branched or cyclic alkyl, alkenyl or alkynyl having 1 to 10 carbon atoms or —(CH$_2$—CH$_2$—O)$_n$—$R^k$, wherein $R^k$ is a —H, a linear, branched cyclic alkyl having 1 to 6 carbon atoms, optionally bearing a secondary amino (e.g., —NHR$^{101}$) or tertiary amino (—NR$^{101}$R$^{102}$) group or a 5 or 6-membered nitrogen containing heterocycle, such as piperidine or morpholine, wherein $R^{101}$ and $R^{102}$ are each independently a linear, branched, or cyclic alkyl, alkenyl or alkynyl having 1 to 10 carbon atoms;
n is an integer from 2 to 6;
$Z^s$ is linked to the CBA, and is selected from:
a bond;

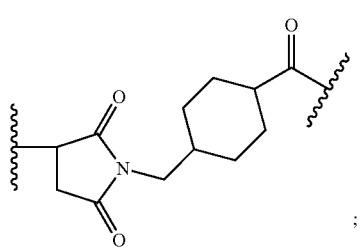 (b1)

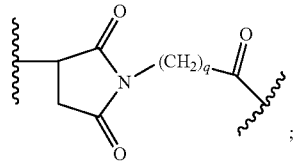 (b2)

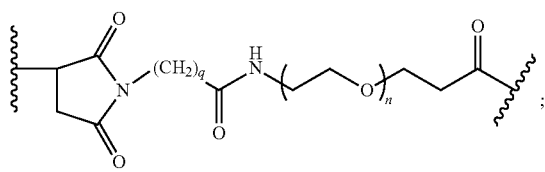 (b3)

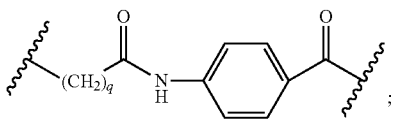 (b4)

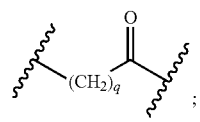 (b5)

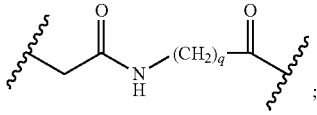 (b6)

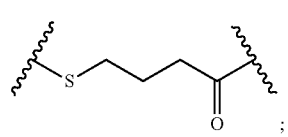 (b7)

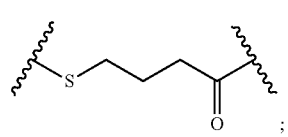 (b8)

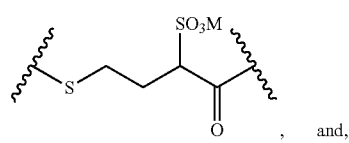 (b9)

, and,

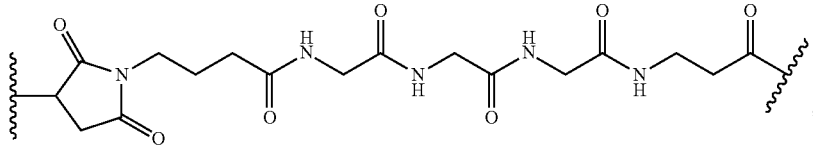

(b10)

wherein:
q is an integer from 1 to 5; and,
M is —H or a pharmaceutically acceptable cation, such as Na⁺ or K⁺.

In certain embodiments, $Z^s$ is represented by any one of the following formulas:

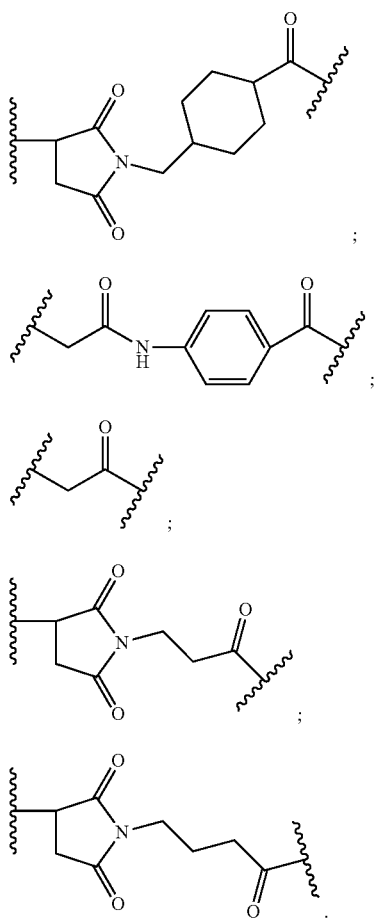

In certain embodiments, such as the 21$^{st}$ specific embodiment, W' is —N($R^e$)—.

In certain embodiments, such as the 21$^{st}$ specific embodiment, $R^e$ is —(CH$_2$—CH$_2$—O)$_n$—$R^k$, wherein $R^k$ is a —H, a linear, branched cyclic alkyl having 1 to 6 carbon atoms.

In certain embodiments, such as the 21$^{st}$ specific embodiment, $R^k$ is —H or -Me, n is 4, and q is 2.

In certain embodiments, such as the 21$^{st}$ specific embodiment, $R^x$ is a linear or branched alkyl having 1 to 6 carbon atoms.

In certain embodiments, such as the 21$^{st}$ specific embodiment, $R^x$ is —(CH$_2$)$_p$—(C$R^f R^g$)—, wherein $R^f$ and $R^g$ are each independently selected from H or a linear or branched alkyl having 1 to 4 carbon atoms; and p is 0, 1, 2 or 3.

In certain embodiments, such as the 21$^{st}$ specific embodiment, $R^f$ and $R^g$ are the same or different, and are selected from —H and -Me; and p is 1.

In a twenty-second specific embodiment, the conjugate of formula (VIIIb') and (Xb') described in the twenty-first specific embodiment, the variables are as described below:
Y is —SO$_3$M;
M is —H or a pharmaceutically acceptable cation (e.g., Na⁺);
X' and Y' are both —H;
A and A' are both —O—;
$R_6$ is —OMe; and
$R^x$ is a linear or branched alkyl having 1 to 6 carbon atoms.

In certain embodiments, such as the 14$^{th}$ to the 21$^{st}$ specific embodiment, Y is selected from —SO$_3$M, —SO$_2$M and a sulfate —OSO$_3$M. Preferably, Y is —SO$_3$M. Preferably, M is —H, Na⁺ or K⁺.

In certain embodiments, such as the 14$^{th}$ to the 22$^{nd}$ specific embodiment, W, when present, is C=O.

In certain embodiments, such as the 14$^{th}$ to the 22$^{nd}$ specific embodiment, Z and Z', when present, are —CH$_2$—.

In certain embodiments, such as the 14$^{th}$ to the 22$^{nd}$ specific embodiment, X' is selected from the group consisting of —H, —OH, an optionally substituted linear, branched or cyclic alkyl, alkenyl or alkynyl having from 1 to 10 carbon atoms, phenyl, the linking group, and an amine-protecting group. In certain embodiments, X' is —H, —OH, -Me or the linking group. Preferably, X' is —H.

In certain embodiments, such as the 14$^{th}$ to the 22$^{nd}$ specific embodiment, Y' is selected from the group consisting of —H, an oxo group, a substituted or unsubstituted linear, branched or cyclic alkyl, alkenyl or alkynyl having from 1 to 10 carbon atoms. Preferably, Y' is —H or oxo. More preferably, —H.

In certain embodiments, such as the 14$^{th}$ to the 22$^{nd}$ specific embodiment, A and A' are the same or different, and are selected from —O—, —S—, —N(R$_5$)—, and oxo (C=O). Preferably, A and A' are the same or different, and are selected from —O— and —S—. More preferably, A and A' are —O—.

In certain embodiments, such as the 14$^{th}$ to the 22$^{nd}$ specific embodiment, D and D', when present, are the same or different, and are independently selected from a polyethylene glycol unit (—OCH$_2$CH$_2$)$_n$, wherein n is an integer from 1 to 24, an amino acid, a peptide bearing 2 to 6 amino acids, or a linear, branched or cyclic alkyl, alkenyl or alkynyl having 1 to 10 carbon atoms, wherein the alkyl, alkenyl and alkynyl are optionally substituted with one or more substituents independently selected from the group consisting of halogen, —OR, —NR'COR", —SR and —COR'. Preferably, D and D' are linear or branched alkyl bearing 1 to 4 carbon atoms.

In a twenty-third specific embodiment, for compounds of formula (Ibb') or (IIBb'), described in the twentieth specific embodiment, the variables are as described below:
Y is —SO$_3$M;
M is —H or Na$^+$;
X' and Y' are both —H;
A and A' are both —O—;
R$_6$ is —OMe;
R$^x$ is a linear or branched alkyl having 1 to 6 carbon atoms.
Preferably, R$^x$ is —(CH$_2$)$_p$—(CR$^f$R$^g$)—, wherein R$^f$ and R$^g$ are each independently selected from —H or a linear or branched alkyl having 1 to 4 carbon atoms; p is 0, 1, 2 or 3. More preferably, R$^f$ and R$^g$ are the same or different, and are selected from —H and -Me; and p is 1.

In a twenty-fourth specific embodiment, the conjugate of the present invention as described in the fourteenth, fifteenth, or the twenty-first specific embodiment is represented by the following:
Y is —SO$_3$M, wherein M is —H or a pharmaceutically acceptable cation (e.g., Na$^+$);
W is C=O;
R$_1$, R$_2$, R$_1$', R$_2$', R$_4$ and R$_4$' are —H;
one of R$_3$, or R$_3$' is optionally the linking group and the other is —H;
R$_6$ is —OMe;
Z and Z' are —CH$_2$;
X' is —H;
Y' is —H; and
A and A' are —O—.

In any of the specific embodiments for the conjugate of the invention above, such as the 14$^{th}$ to the 24$^{th}$ specific embodiments, Y is selected from —SO$_3$M, —SO$_2$M and a sulfate —OSO$_3$M. Preferably, Y is —SO$_3$M.

In certain embodiments, such as the 14$^{th}$ to the 24$^{th}$ specific embodiment, M is —H, Na$^+$ or K$^+$.

In any of the specific embodiments for the conjugate of the invention above, such as the 14$^{th}$ to the 24$^{th}$ specific embodiments, W, when present, is C=O.

In any of the specific embodiments for the conjugate of the invention above, such as the 14$^{th}$ to the 24$^{th}$ specific embodiments, Z and Z', when present, are —CH$_2$—.

In any of the specific embodiments for the conjugate of the invention above, such as the 14$^{th}$ to the 24$^{th}$ specific embodiments, X' is selected from the group consisting of —H, —OH, an optionally substituted linear, branched or cyclic alkyl, alkenyl or alkynyl having from 1 to 10 carbon atoms, phenyl, the linking group, and an amine-protecting group. In certain embodiments, X' is —H, —OH, -Me or the linking group. In certain embodiments, X' is —H.

In any of the specific embodiments for the conjugate of the invention above, such as the 14$^{th}$ to the 24$^{th}$ specific embodiments, Y' is selected from the group consisting of —H, an oxo group, a substituted or unsubstituted linear, branched or cyclic alkyl, alkenyl or alkynyl having from 1 to 10 carbon atoms. In certain embodiments, Y' is —H or oxo. In certain embodiments, Y' is —H.

In any of the specific embodiments for the conjugate of the invention above, such as the 14$^{th}$ to the 24$^{th}$ specific embodiments, A and A' are the same or different, and are selected from —O—, —S—, —N(R$_5$)—, and oxo (C=O). In certain embodiments, A and A' are the same or different, and are selected from —O— and —S—. In certain embodiments, A and A' are —O—.

In any of the specific embodiments for the conjugate of the invention above, such as the 14$^{th}$ to the 24$^{th}$ specific embodiments, D and D', when present, are the same or different, and are independently selected from a polyethylene glycol unit (—OCH$_2$CH$_2$)$_n$, wherein n is an integer from 1 to 24, an amino acid, a peptide bearing 2 to 6 amino acids, or a linear, branched or cyclic alkyl, alkenyl or alkynyl having 1 to 10 carbon atoms, wherein the alkyl, alkenyl and alkynyl are optionally substituted with one or more substituents independently selected from the group consisting of halogen, —OR, —NR'COR", —SR and —COR'. In certain embodiments, D and D' are linear or branched alkyl bearing 1 to 4 carbon atoms.

In certain embodiments, the conjugate of any one of the described embodiments, such as the 14$^{th}$ to the 24$^{th}$ specific embodiments, may comprise 1-10 cytotoxic compounds, 2-9 cytotoxic compounds, 3-8 cytotoxic compounds, 4-7 cytotoxic compounds, or 5-6 cytotoxic compounds, each cytotoxic compound comprising the linking group linking the cytotoxic compound to the CBA, and each cytotoxic compound on the conjugate is the same.

In certain embodiments, the conjugate of any one of the described embodiments, such as the 14$^{th}$ to the 24$^{th}$ specific embodiments, may comprise 1-10 cytotoxic compounds, 2-9 cytotoxic compounds, 3-8 cytotoxic compounds, 4-7 cytotoxic compounds, or 5-6 cytotoxic compounds, each cytotoxic compound comprising the linking group linking the cytotoxic compound to the CBA, and each cytotoxic compound on the conjugate is the same.

In certain embodiments, the conjugate of any one of the described embodiments, such as the 14$^{th}$ to the 24$^{th}$ specific embodiments, may comprise 1-10 total cytotoxic compounds and (unmodified) imine-containing cytotoxic compounds, 2-9 total cytotoxic compounds and (unmodified) imine-containing cytotoxic compounds, 3-8 total cytotoxic compounds and (unmodified) imine-containing cytotoxic compounds, 4-7 total cytotoxic compounds and (unmodified) imine-containing cytotoxic compounds, or 5-6 total cytotoxic compounds and (unmodified) imine-containing cytotoxic compounds, each cytotoxic compounds or (unmodified) imine-containing cytotoxic compound comprising the linking group linking the cytotoxic compounds or (unmodified) imine-containing cytotoxic compound to the CBA, and each cytotoxic compounds or (unmodified) imine-containing cytotoxic compound on the conjugate is the same (except for the (bisulfite) modification).

In any of the conjugates embodiments, such as the 14$^{th}$ to the 24$^{th}$ specific embodiments, the cell-binding agent may bind to target cells selected from tumor cells, virus infected cells, microorganism infected cells, parasite infected cells, autoimmune cells, activated cells, myeloid cells, activated T-cells, B cells, or melanocytes; cells expressing the CD4, CD6, CD19, CD20, CD22, CD30, CD33, CD37, CD38, CD40, CD44, CD56, EpCAM, CanAg, CALLA, or Her-2 antigens; Her-3 antigens; or cells expressing insulin growth factor receptor, epidermal growth factor receptor, and folate receptor.

In any of the conjugates embodiments, such as the 14$^{th}$ to the 24$^{th}$ specific embodiments, the cell-binding agent may be an antibody, a single chain antibody, an antibody fragment that specifically binds to the target cell, a monoclonal antibody, a single chain monoclonal antibody, or a monoclonal antibody fragment that specifically binds the a target cell, a chimeric antibody, a chimeric antibody fragment that specifically binds to the target cell, a domain antibody, a domain antibody fragment that specifically binds to the target cell, a lymphokine, a hormone, a vitamin, a growth factor, a colony stimulating factor, or a nutrient-transport molecule.

The antibody may be a resurfaced antibody, a resurfaced single chain antibody, or a resurfaced antibody fragment.

The antibody may be a monoclonal antibody, a single chain monoclonal antibody, or a monoclonal antibody fragment thereof.

The antibody may be a humanized antibody, a humanized single chain antibody, or a humanized antibody fragment.

In any one of the specific embodiment herein, such as the $1^{st}$-$24^{th}$ specific embodiments, the imine reactive reagent is selected from the group consisting of sulfites ($H_2SO_3$, $H_2SO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono, di, tri, and tetra-thiophosphates ($PO_3SH_3$, $PO_2S_2H_3$, $POS_3H_3$, $PS_4H_3$ or a salt of $PO_3S^{3-}$, $PO_2S_2^{3-}$, $POS_3^{3-}$ or $PS_4^{3-}$ formed with a cation), thio phosphate esters (($R^iO)_2PS(OR^i$), $R^iSH$, $R^iSOH$, $R^iSO_2H$, $R^iSO_3H$), various amines (hydroxyl amine (e.g., $NH_2OH$), hydrazine (e.g., $NH_2NH_2$), $NH_2O$—$R^i$, $R^{i'}NH$—$R^i$, $NH_2$—$R^i$), $NH_2$—CO—$NH_2$, $NH_2$—C(=S)—$NH_2$, thiosulfate ($H_2S_2O_3$ or a salt of $S_2O_3^{2-}$ formed with a cation), dithionite ($H_2S_2O_4$ or a salt of $S_2O_4^{2-}$ formed with a cation), phosphorodithioate (P(=S)($OR^k$)(SH)(OH) or a salt thereof formed with a cation), hydroxamic acid ($R^kC$(=O)NHOH or a salt formed with a cation), hydrazide ($R^kCONHNH_2$), formaldehyde sulfoxylate ($HOCH_2SO_2H$ or a salt of $HOCH_2SO_2^-$ formed with a cation, such as $HOCH_2SO_2^-$Na$^+$), glycated nucleotide (such as GDP-mannose), fludarabine or a mixture thereof, wherein $R^i$ and $R^{i'}$ are each independently a linear or branched alkyl having 1 to 10 carbon atoms and are substituted with at least one substituent selected from —N($R^j)_2$, —$CO_2H$, —$SO_3H$, and —$PO_3H$; $R^i$ and $R^{i'}$ can be further optionally substituted with a substituent for an alkyl described herein; $R^j$ is a linear or branched alkyl having 1 to 6 carbon atoms; $R^k$ is a linear, branched or cyclic alkyl, alkenyl or alkynyl having 1 to 10 carbon atoms, aryl, heterocyclyl or heteroaryl.

Preferably, the imine reactive reagent is selected from sulfites, hydroxylamine, hydrazine and urea. More preferably, the imine reactive reagent is $NaHSO_3$ or $KHSO_3$.

In any one of the specific embodiment herein, such as the $1^{st}$-$24^{th}$ specific embodiments, about 0.1 to about 30 molar equivalents of the imine reactive reagent to the imine-containing cytotoxic compound is used. In certain embodiments, about 1 to about 10 molar equivalents of the imine reactive reagent to the imine-containing cytotoxic compound is used. In certain embodiments, about 3 to about 5 molar equivalents of the imine reactive reagent to the imine-containing cytotoxic compound is used.

In any one of the specific embodiment herein, such as the $1^{st}$-$24^{th}$ specific embodiments, the bifunctional crosslinking agent links the cytotoxic agent to the cell-binding agent through a thioether bond, and may have a maleimido- or haloacetyl-based moiety, wherein the bifunctional crosslinking agent having the maleimido-based moiety is selected from: N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido) hexanoate (SMPH), N-succinimidyl 4-(p-maleimidophenyl)-butyrate (SMPB), N-(p-maleimidophenyl)isocyanate (PMPI), N-succinimidyl-4-(4-nitropyridyl-2-dithio)butanoate; and, wherein the bifunctional crosslinking agent having the haloacetyl-based moiety is selected from: N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP), bis-maleimidopolyethyleneglycol (BMPEO), BM(PEO)$_2$, BM(PEO)$_3$, N-(β-maleimidopropyloxy)succinimide ester (BMPS), 5-maleimidovaleric acid NHS, HBVS, 4-(4-N-maleimidophenyl)-butyric acid hydrazide.HCl (MPBH), Succinimidyl-(4-vinylsulfonyl)benzoate (SVSB), dithiobis-maleimidoethane (DTME), 1,4-bis-maleimidobutane (BMB), 1,4-bismaleimidyl-2,3-dihydroxybutane (BMDB), bis-maleimidohexane (BMH), bis-maleimidoethane (BMOE), sulfosuccinimidyl 4-(N-maleimido-methyl)cyclohexane-1-carboxylate (sulfo-SMCC), sulfosuccinimidyl(4-iodo-acetyl)aminobenzoate (sulfo-SIAB), m-maleimidobenzoyl-N-hydroxysulfosuccinimide ester (sulfo-MBS), N-(γ-maleimidobutryloxy)sulfosuccinimde ester (sulfo-GMBS), N-(ε-maleimidocaproyloxy)sulfosuccimido ester (sulfo-EMCS), N-(κ-maleimidoundecanoyloxy)sulfosuccinimide ester (sulfo-KMUS), sulfosuccinimidyl 4-(p-maleimidophenyl)butyrate (sulfo-SMPB), CX1-1, sulfo-Mal and PEG$_n$-Mal.

In certain embodiments, the bifunctional crosslinking agent is selected from the group consisting of SMCC, Sulfo-SMCC, BMPS, GMBS, SIA, SIAB, N-succinimidyl-4-(4-nitropyridyl-2-dithio)butanoate, bis-maleimidohexane or BMPEO.

In any of the embodiments, such as the $1^{st}$-$24^{th}$ specific embodiments, the conjugate is purified by tangential flow filtration, adsorptive chromatography, adsorptive filtration, selective precipitation, non-absorptive filtration or combination thereof. Preferably, the conjugate is purified by tangential flow filtration and/or adsorptive chromatography.

In certain embodiments, such as the $1^{st}$-$24^{th}$ specific embodiments, the cell-binding agent (CBA) bearing the thiol-reactive group is:

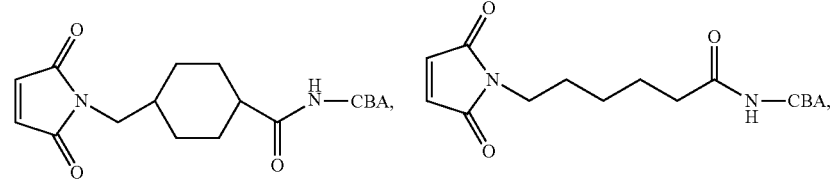

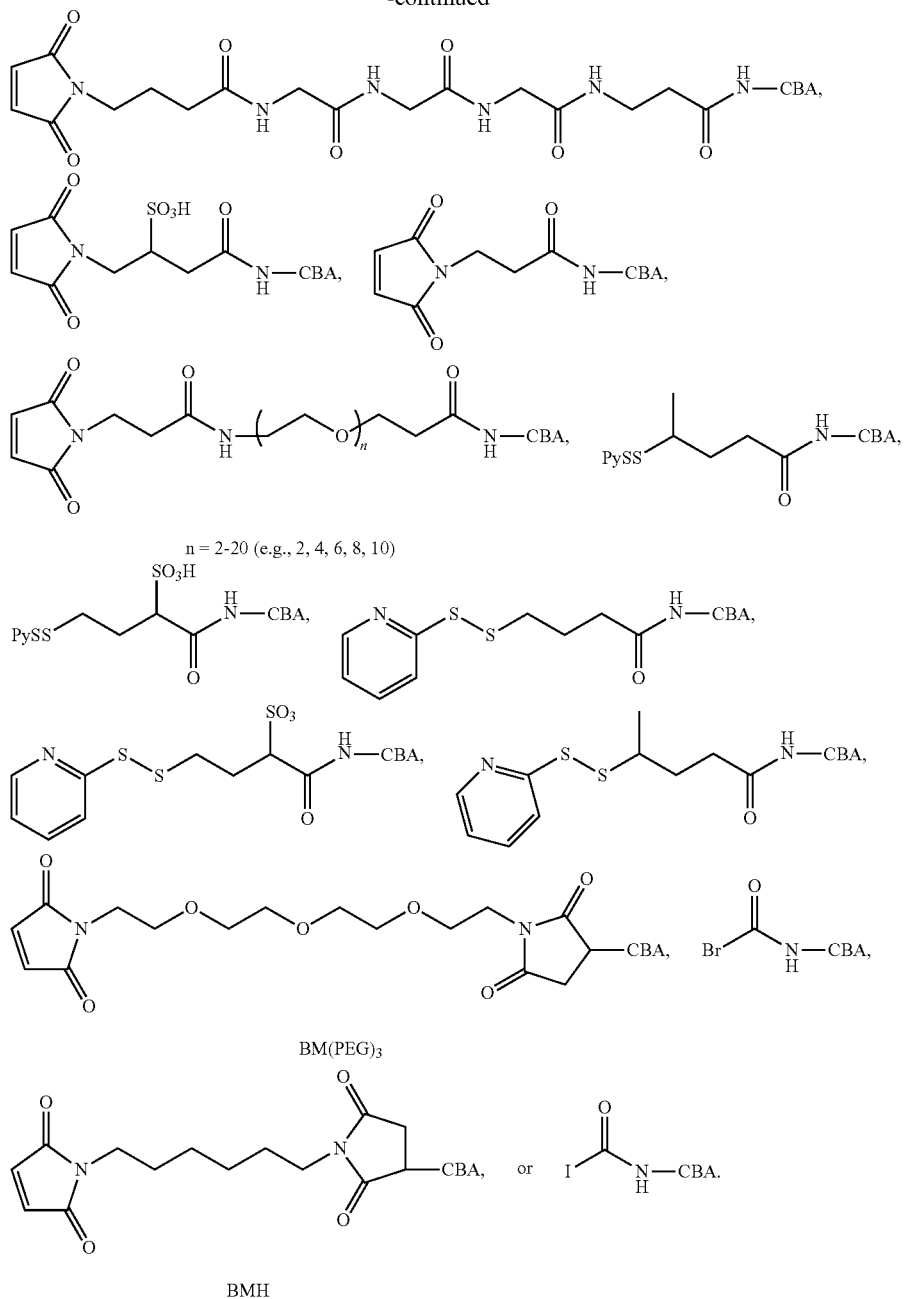
The compounds or the conjugates made by the methods of the invention specifically include:
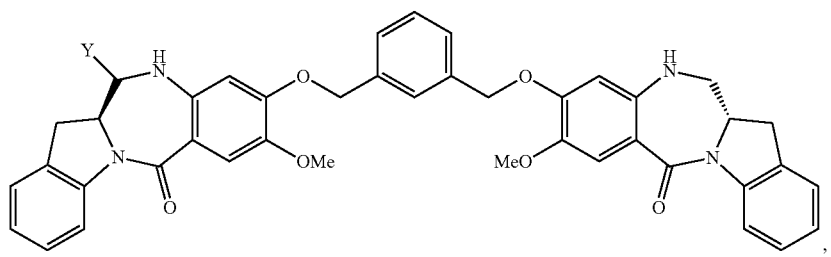

-continued
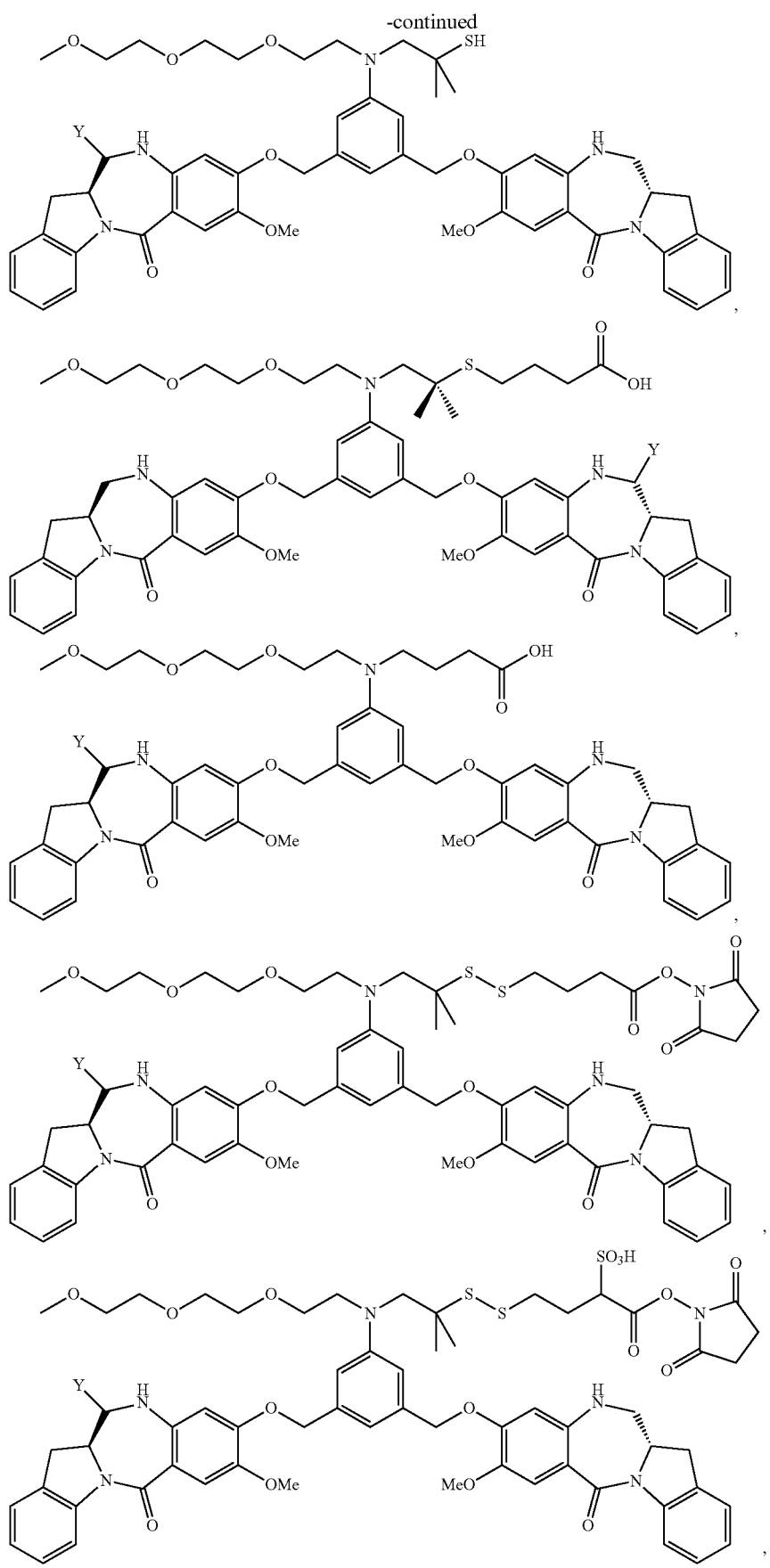

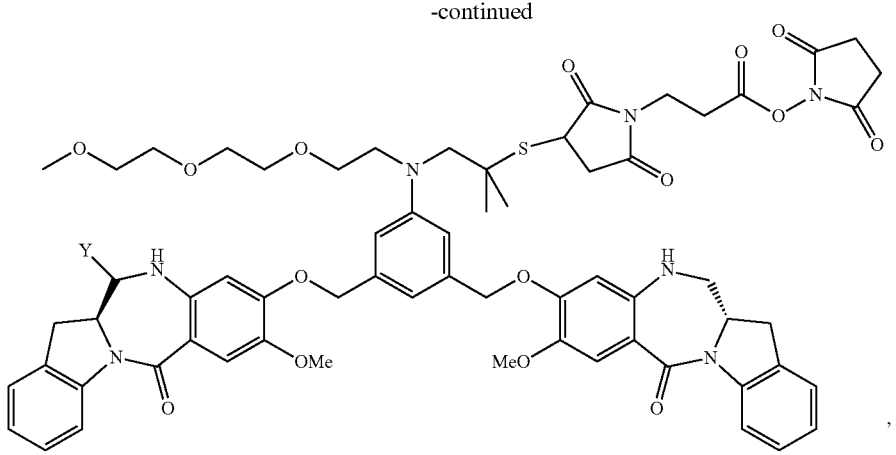
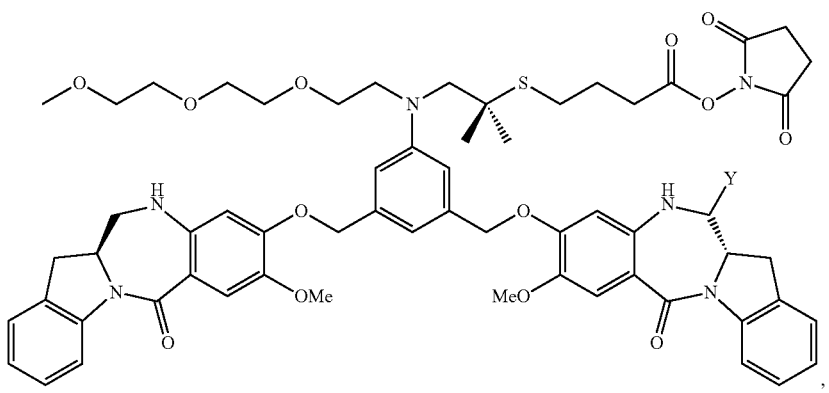
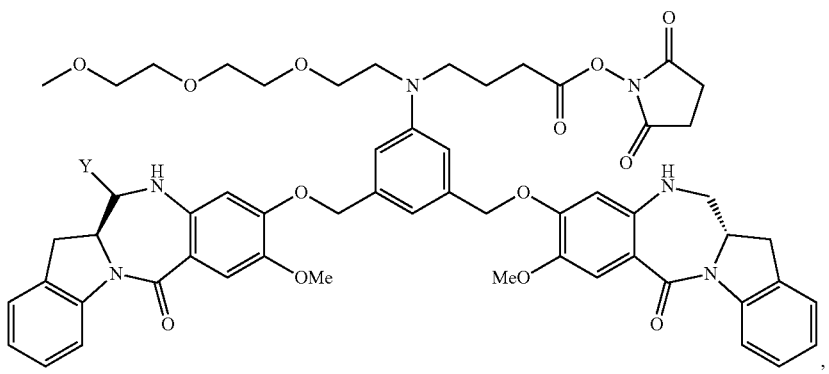
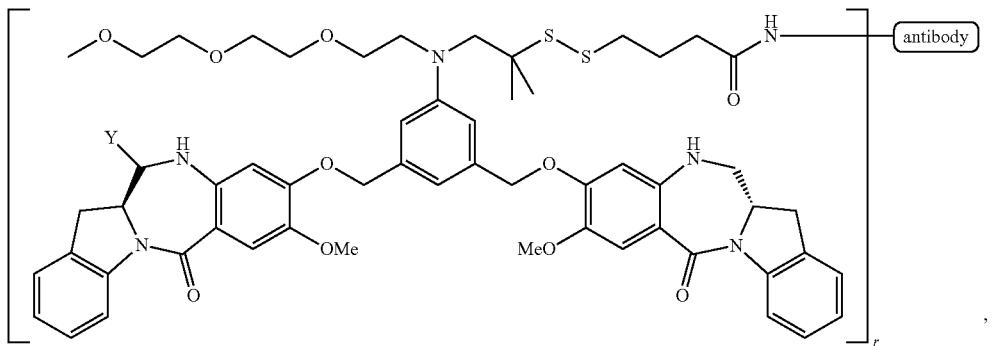

-continued
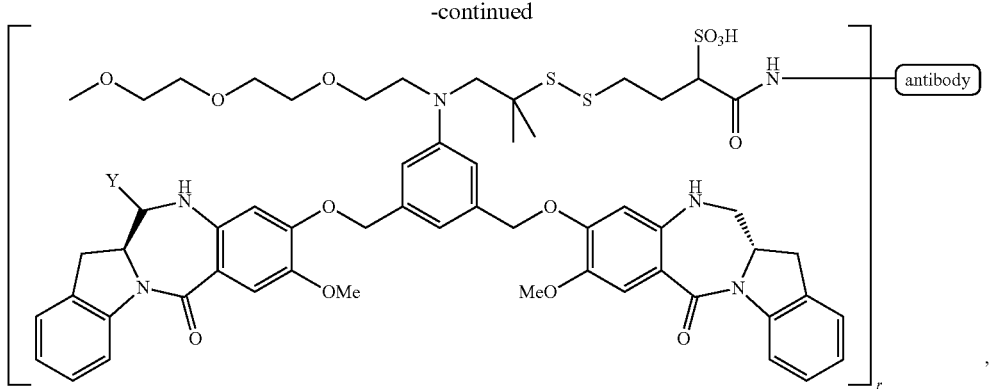
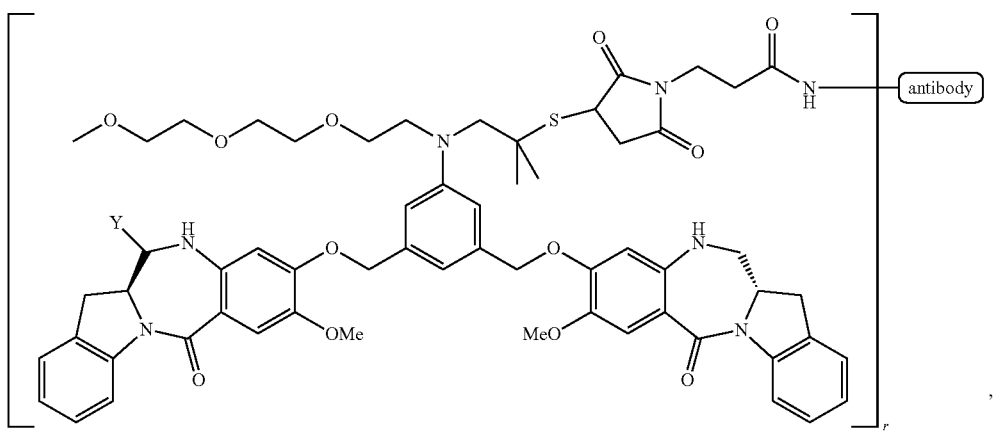
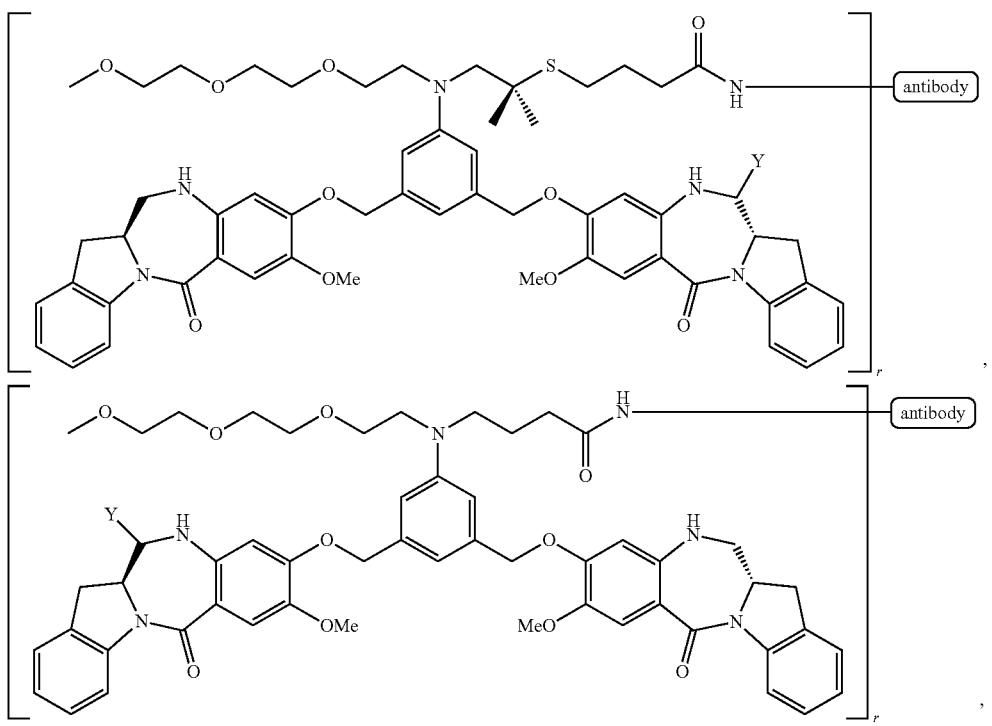
wherein r is an integer from 1 to 10, Y is —H or —SO$_3$M, and M is —H or a pharmaceutically acceptable cation.
In a 25$^{th}$ specific embodiment, the invention provides a method for preparing a conjugate of the following formula:

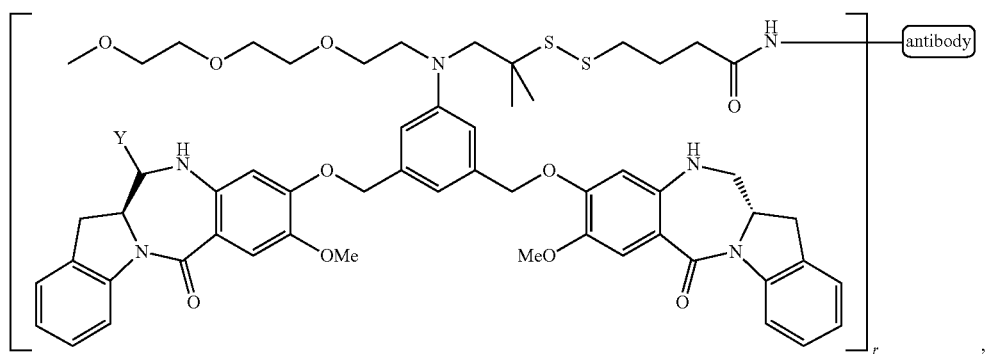
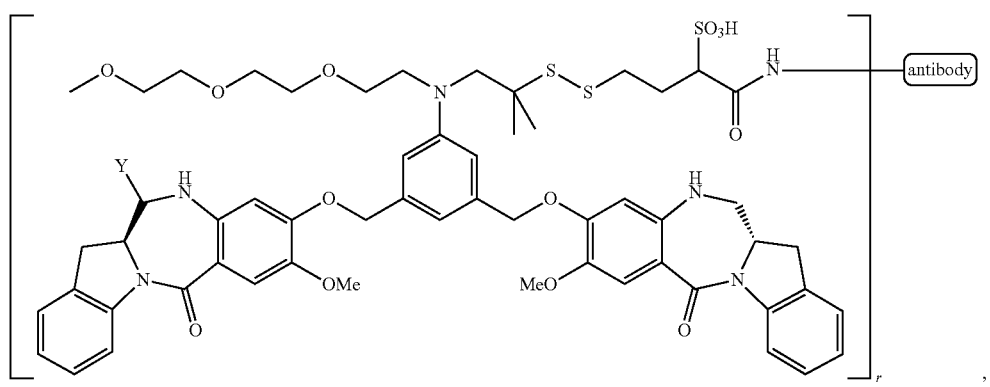
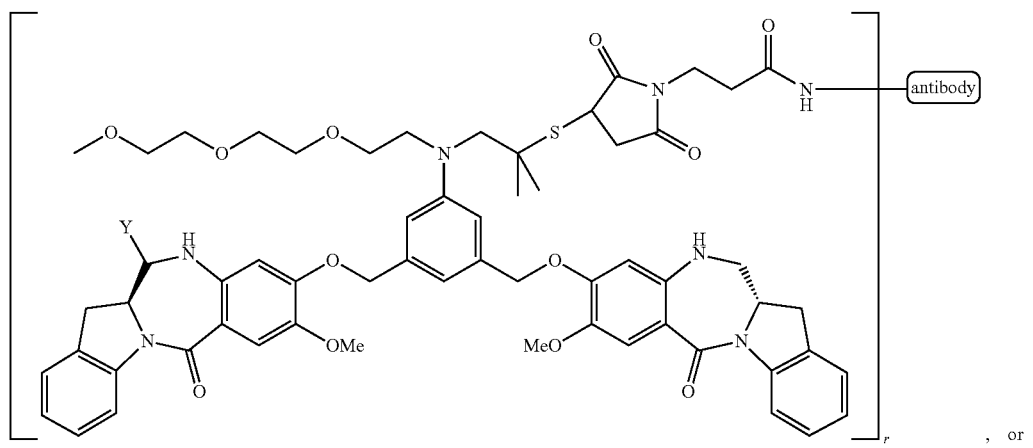
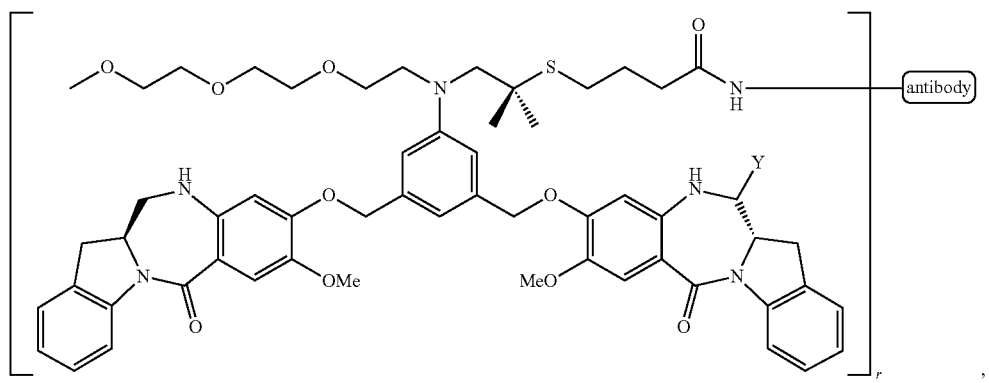

the method comprising reacting a cytotoxic compound of the following formula,

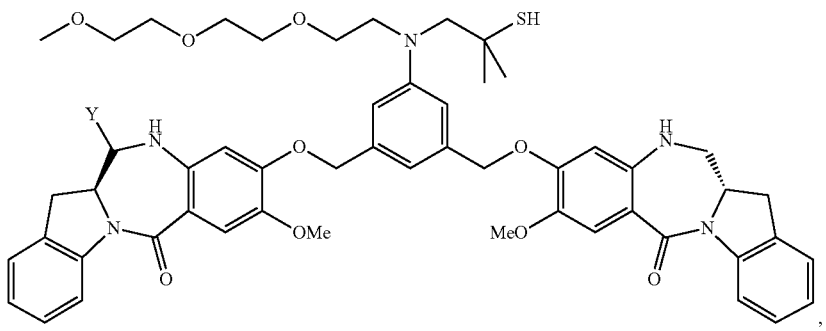

with a modified CBA of the following formula, respectively, at a pH of about 4 to about 9,

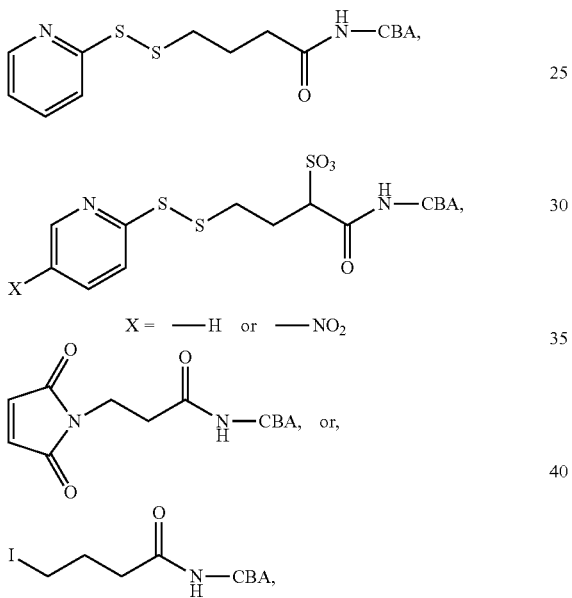

wherein:

r is an integer from 1 to 10;

Y is a leaving group, and is a sulfite ($HSO_3$, $HSO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono-, di-, tri-, and tetra-thiophosphate ($PO_3SH_3$, $PO_2S_2H_2$, $POS_3H_2$, $PS_4H_2$ or a salt of $PO_3S^{3-}$, $PO_2S_2^{3-}$, $POS_3^{3-}$ or $PS_4^{3-}$ formed with a cation), thio phosphate ester $(R^iO)_2PS$ $(OR^i)$, $R^iS-$, $R^iSO$, $R^iSO_2$, $R^iSO_3$, thiosulfate ($HS_2O_3$ or a salt of $S_2O_3^{2-}$ formed with a cation), dithionite ($HS_2O_4$ or a salt of $S_2O_4^{2-}$ formed with a cation), phosphorodithioate ($P(=S)(OR^{k'})(S)(OH)$ or a salt thereof formed with a cation), hydroxamic acid ($R^{k'}C(=O)NOH$ or a salt formed with a cation), formaldehyde sulfoxylate ($HOCH_2SO_2^-$ or a salt of $HOCH_2SO_2^-$ formed with a cation, such as $HOCH_2SO_2^-Na^+$) or a mixture thereof, wherein $R^i$ is a linear or branched alkyl having 1 to 10 carbon atoms and is substituted with at least one substituent selected from $-N(R^j)_2$, $-CO_2H$, $-SO_3H$, and $-PO_3H$; $R^i$ can be further optionally substituted with a substituent for an alkyl described herein; $R^j$ is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl; preferably Y is $-SO_3M$; and M is $-H$ or a pharmaceutically acceptable cation.

In certain embodiments, Y is $-SO_3M$; and M is $-H$ or a pharmaceutically acceptable cation.

In certain embodiments, the cytotoxic compound is produced by reacting an imine reactive reagent with an imine-containing cytotoxic compound of the following formula:

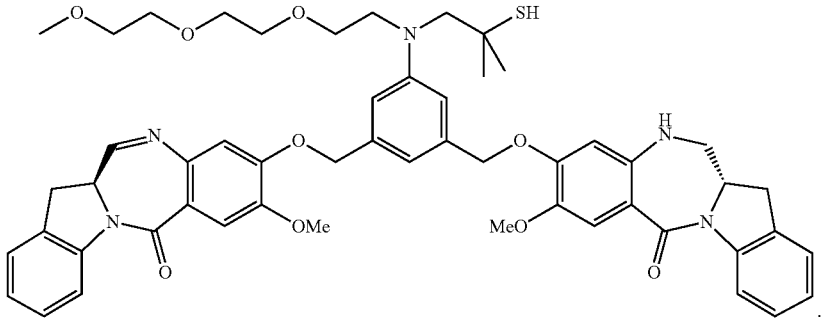 [SMILES: COCCOCCOCCN(CC(C)(C)S)c1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

In certain embodiments, the CBA is huMy9-6.

In a 26$^{th}$ specific embodiment, the invention provides a method for preparing a conjugate of the following formula:

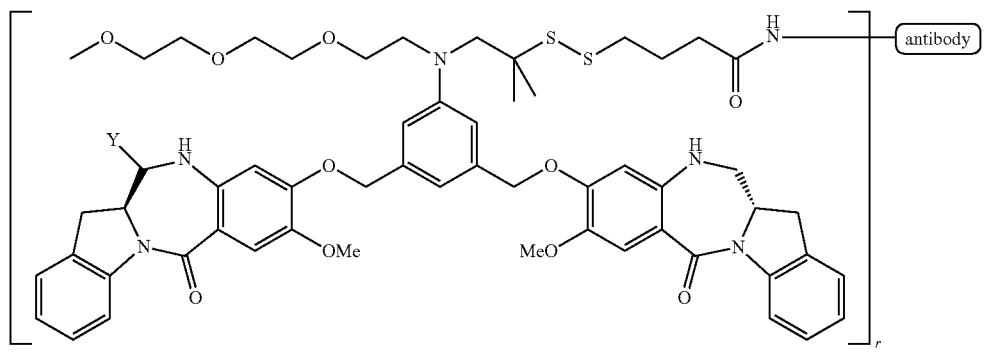
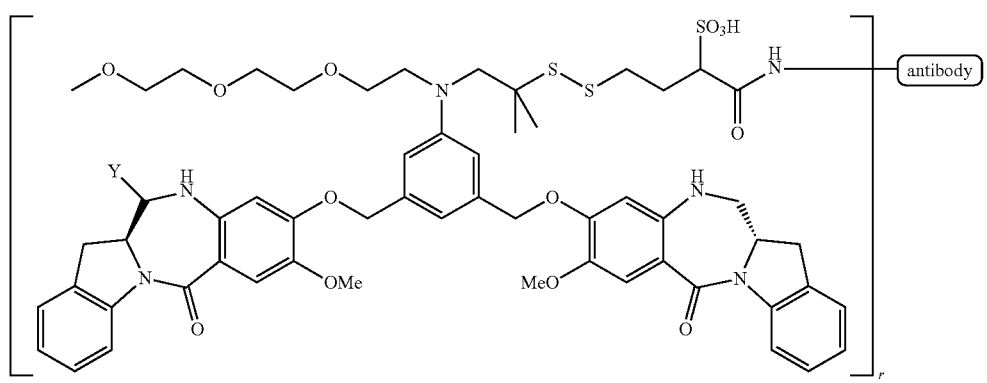
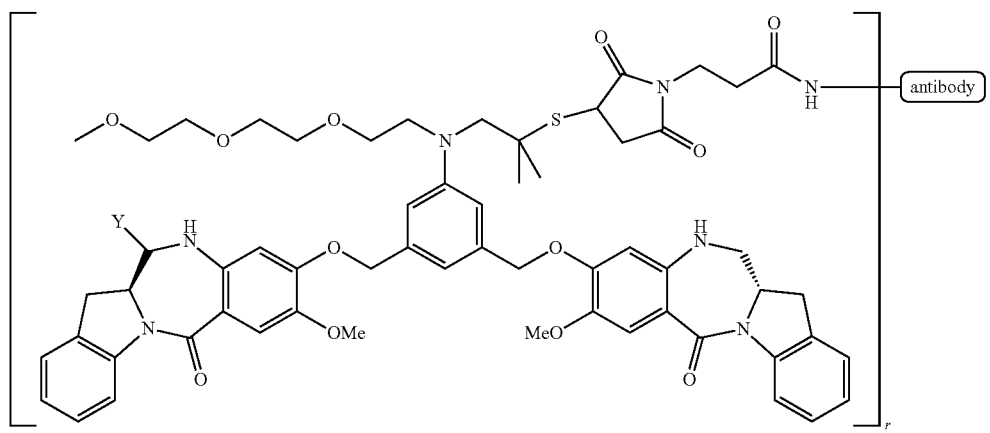
, or
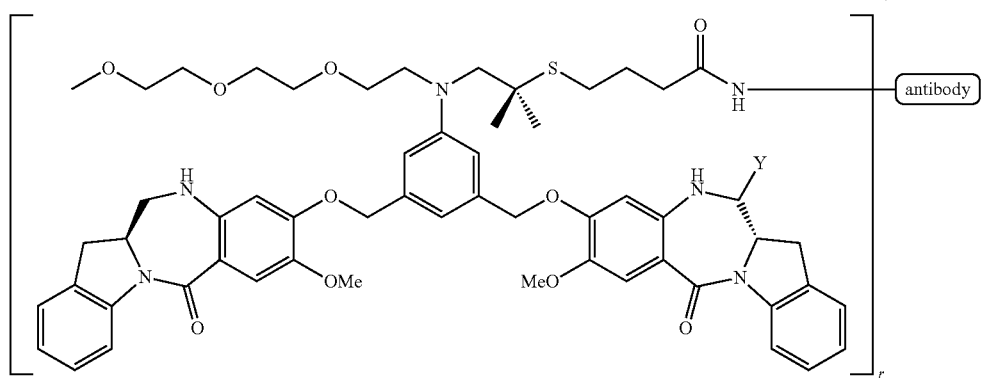
, the method comprising reacting the CBA with an imine-containing cytotoxic compound, an imine reactive reagent, and a bifunctional crosslinking agent comprising the linking group to form the conjugate, wherein:

the imine-containing cytotoxic compound is:

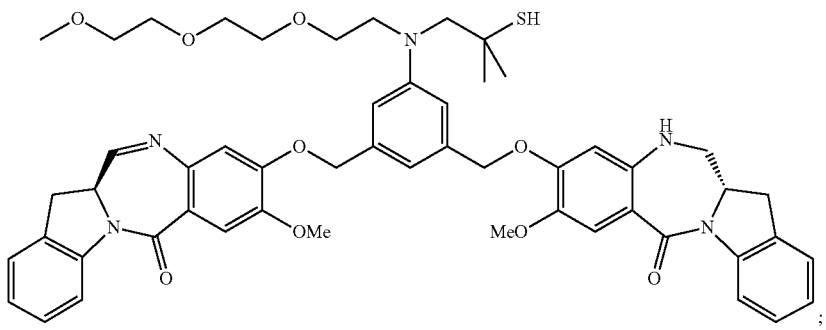 [SMILES: COCCOCCOCCN(CC(C)(C)S)c1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

the bifunctional crosslinking agent is:

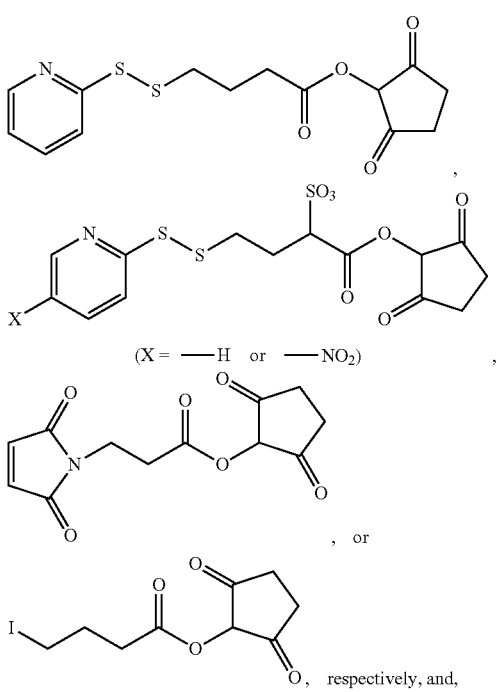

respectively, and, the imine reactive reagent is selected from: sulfites ($H_2SO_3$, $H_2SO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono, di, tri, and tetra-thiophosphates ($PO_3SH_3$, $PO_2S_2H_3$, $POS_3H_3$, $PS_4H_3$ or a salt of $PO_3S^{3-}$, $PO_2S_2^{3-}$, $POS_3^{3-}$ or $PS_4^{3-}$ formed with a cation), thio phosphate esters (($R^iO)_2PS(OR^i$), $R^iSH$, $R^iSOH$, $R^iSO_2H$, $R^iSO_3H$), various amines (hydroxyl amine (e.g., $NH_2OH$), hydrazine (e.g., $NH_2NH_2$), $NH_2O$—$R^i$, $R^{i\prime\prime}NH$—$R^i$, $NH_2$—$R^i$), $NH_2$—CO—$NH_2$, $NH_2$—C(=S)—$NH_2$, thiosulfate ($H_2S_2O_3$ or a salt of $S_2O_3^{2-}$ formed with a cation), dithionite ($H_2S_2O_4$ or a salt of $S_2O_4^{2-}$ formed with a cation), phosphorodithioate (P(=S)(OR$^k$)(SH)(OH) or a salt thereof formed with a cation), hydroxamic acid ($R^kC(=O)NHOH$ or a salt formed with a cation), hydrazide ($R^kCONHNH_2$), formaldehyde sulfoxylate ($HOCH_2SO_2H$ or a salt of $HOCH_2SO_2^-$ formed with a cation, such as $HOCH_2SO_2^-$ Na$^+$), glycated nucleotide (such as GDP-mannose), fludarabine or a mixture thereof, wherein R$^i$ and R$^{i\prime}$ are each independently a linear or branched alkyl having 1 to 10 carbon atoms and are substituted with at least one substituent selected from —N(R$^j$)$_2$, —CO$_2$H, —SO$_3$H, and —PO$_3$H; R$^i$ and R$^{i\prime}$ can be further optionally substituted with a substituent for an alkyl described herein; R$^j$ is a linear or branched alkyl having 1 to 6 carbon atoms; R$^k$ is a linear, branched or cyclic alkyl, alkenyl or alkynyl having 1 to 10 carbon atoms, aryl, heterocyclyl or heteroaryl.

In certain embodiments, Y is —SO$_3$M; and M is —H or a pharmaceutically acceptable cation.

In certain embodiments, the CBA is huMy9-6.

In Vitro Cytotoxicity of Compounds and Conjugates

The cytotoxic compounds and cell-binding agent-drug conjugates produced by the methods of the invention can be evaluated for their ability to suppress proliferation of various cancer cell lines in vitro. For example, cell lines such as the human colon carcinoma line COLO 205, the rhabdomyosarcoma cell line RH-30, and the multiple myeloma cell line MOLP-8 can be used for the assessment of cytotoxicity of these compounds and conjugates. Cells to be evaluated can be exposed to the compounds or conjugates for 1-5 days and the surviving fractions of cells measured in direct assays by known methods. IC$_{50}$ values can then be calculated from the results of the assays. Alternatively or in addition, an in vitro cell line sensitivity screen, such as the one described by the U.S. National Cancer Institute (see Voskoglou-Nomikos et al., 2003, Clinical Cancer Res. 9: 42227-4239, incorporated herein by reference) can be used as one of the guides to determine the types of cancers that may be sensitive to treatment with the compounds or conjugates produced by the methods of the invention.

Examples of in vitro potency and target specificity of antibody-cytotoxic agent conjugates produced by the methods of the present invention is shown in FIG. 17. All of the conjugates are extremely cytotoxic on the antigen positive cancer cells with an IC$_{50}$ in the low picomolar range. Antigen negative cell lines remained viable when exposed to the same conjugates. The indolinobenzodiazepine dimers showed target specific potency being 160 fold less potent when blocked with unconjugated antibody huMy9-6 (anti-CD33) (FIG. 17) and 40 less potent when blocked with unconjugated antibody FOLR1 (anti-folate receptor antibody) (result not shown). For example, the huMy9-6-SPDB-1f conjugate bearing the bisulfite adducts killed antigen positive HL60/QC cells with an $IC_{50}$ value of 10.5 pM, while the addition of an excess of unconjugated huMy9-6 antibody reduced this cytotoxic effect ($IC_{50}$=1.69 nM), demonstrating antigen specificity (FIG. 17A). In addition, the huMy9-6-SPDB-1f conjugate is also highly potent towards both the HL60/ATCC cell line with an $IC_{50}$ value of 21 pM and the NB-4 cell line with an $IC_{50}$ value of 190 pM (FIGS. 17B and 17C).

The effect of conjugation on antibody binding was measured by comparing the binding of both unconjugated huMy9-6 antibody and the huMy9-6-SPDB-1f conjugate towards the HL60/QC cell line (FIG. 18). FACS analysis revealed that there is no change in binding capability of the conjugate to naked antibody indicating that there is no compromise in binding due to conjugation of the cytotoxic agent to the antibody.

In one example, in vivo efficacy of a cell binding agent/cytotoxic agent conjugate was measured. Nude mice bearing human HL60/QC tumors were treated with huMy9-6-SPDB-1f conjugate and significant tumor regression was observed at multiple doses while untreated mice grew tumors rapidly (FIG. 19). Activity was observed at doses as low as 20 µg/kg which is at least 35-fold lower than the maximum tolerated dose.

The effect of imine saturation towards tolerability is shown in Table 9. Di-imine huFOLR1-drug1 was tested at multiple doses all of which were found to be highly toxic leaving only survivors in the lowest group tested at 50 µg/kg. In contrast the partially reduced mono-imine huFOLR1-drug2 and huFOLR1-SPDB-IGN (huFOLR1-SPDB-1f) conjugates were found to have significantly improved tolerability with the huFOLR1-SPDB-IGN (huFOLR1-SPDB-1f) conjugate showing 100% animal survival at the highest doses tested of 560 µg/kg.

EXEMPLIFICATION

Example 1

Humanized My9-6 antibody at 2 mg/ml was conjugated with 9 molar equivalents of 2-NHS ester (compound 2) for 3 hrs at 25° C. in 85% PBS, pH 7.4, containing 15% DMA (v/v) and then purified over a G25 desalting column in PBS, pH 7.4, to remove unreacted or hydrolyzed, unconjugated drug. The conjugate was dialyzed in 10 mM Histidine, 250 mM Glycine, pH 6.5 buffer, containing 1% sucrose. The conjugate drug/antibody ratio (DAR) was determined as 1.4 DAR based on UV absorbance at 280 and 320 nm and calculation using the extinction coefficients of the drug and antibody at 280 nm and 320 nm.

The conjugate was analyzed for monomer % by size exclusion chromatography (SEC) on a TSK-Gel G300SWXL column (7.8 mm×300 mm, 5 µm particle size) using an isocratic mobile phase of 400 mm sodium perchlorate, 150 mM potassium phosphate buffer, pH 7.0, at 1 ml/min. The percentage of monomer (% monomer) and aggregate were determined by monitoring the UV absorbance of all antibody species at 280 nm and measuring the area-under-the-curve (AUC) of each antibody peak. Additionally, the percentage (%) of 2 drug on both the monomer and the aggregate were determined by monitoring the UV absorbance of all antibody species at 320 nm and 280 nm and measuring the AUC of each antibody peak. The % monomer of the huMy9-6-2 conjugate containing 1.4 DAR was 91%. The % 2 on the monomer was 80%.

For free (unconjugated) drug assay, the conjugate was acetone extracted to remove protein, dried, and reconstituted in mobile phase and injected onto a VYDAC 208TP C8 reverse phase HPLC column (4.6×250 mm, 7 µm particle size) using a linear gradient of 20% acetonitrile and 80% deionized going up to 100% acetonitrile, all containing 0.025% acetic acid, at 1 ml/min over 48 min and compared to drug-methyl ester standards. The percentage of free, unconjugated drug in the conjugate was determined as <1% of conjugated drug.

The huMy9-6-2 conjugate with 1.4 drug/antibody ratio (DAR) was analyzed by mass spectrometry (MS) after deglycosylation (FIG. 1A). The MS of the conjugate showed unconjugated antibody (D0) as the largest peak, with a smaller D1 peak (antibody with 1 linked drug), and much smaller D2 and D3 peaks of 2 and 3 linked drugs per antibody. The efficiency of conjugation was low with a conjugate DAR of 1.4 after conjugation with 9-fold molar excess of 2-NHS ester over antibody.

Example 2

For the conjugation of 2-NHS ester (compound 2) using sodium bisulfite, the 2-NHS ester (compound 2) was pre-incubated with 0.9 molar equivalents of sodium bisulfite (freshly prepared $NaHSO_3$ in deionized water) in 66% DMA (dimethylacetamide) in water for 30 min at 25° C. HuMy9-6 antibody at 2 mg/ml was conjugated with 9 molar equivalents of 2-NHS ester (with added $NaHSO_3$) for 3 h at 25° C. in 85% PBS, pH 7.4, 15% DMA (v/v) and then purified over a G25 desalting column in PBS, pH 7.4 to remove unreacted or hydrolyzed drug. The conjugate was dialyzed in 10 mM histidine, 250 mM glycine, 1% sucrose, pH 6.5 buffer.

Figure 1B:
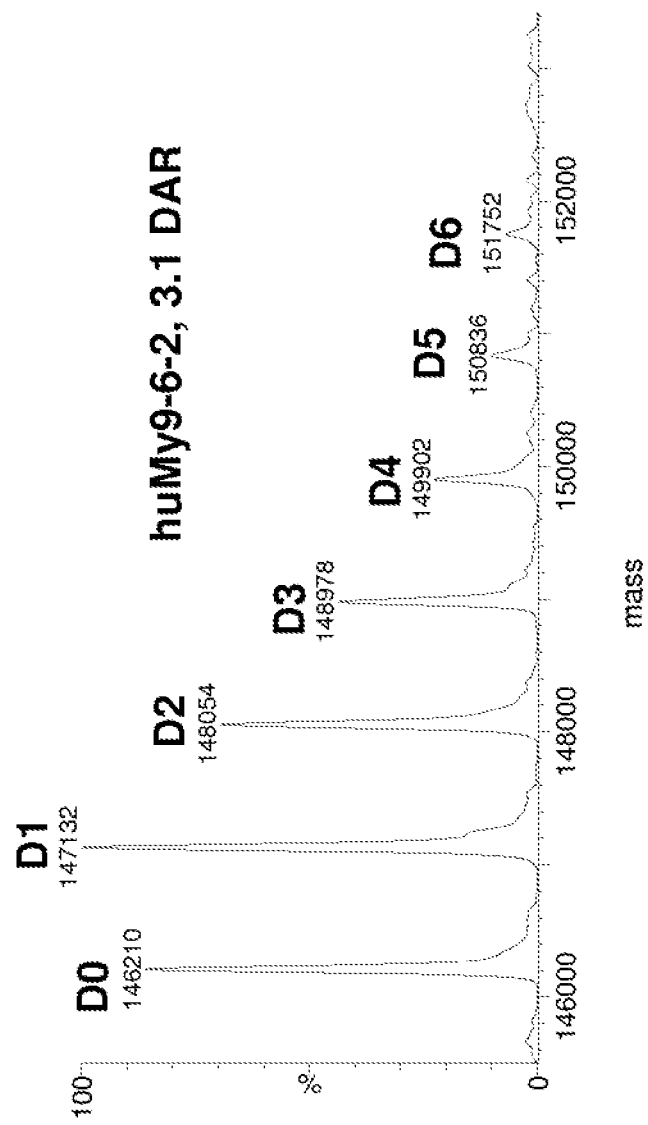

The DAR of the huMy9-6-2 conjugate prepared using sodium bisulfite was measured by UV spectrophotometry at 280 and 320 nm and calculated to be 3.1 DAR. The % monomer of the conjugate was 95% and the % 2 on the monomer was 91%. The MS of the conjugate prepared using sodium bisulfite following deglycosylation showed the largest peak of D1 with one linked drug, and also D2, D3, D4, D5, D6 peaks with 2-6 linked drugs per antibody (FIG. 1B).

The huMy9-6-2 conjugate prepared with sodium bisulfite showed a much greater drug incorporation of 3.1 DAR than the conjugate with 1.4 DAR prepared without sodium bisulfite. The MS of the 3.1 DAR conjugate prepared with sodium bisulfite showed conjugate peaks of 1-6 linked drugs with the highest D1 peak with 1 linked drug. In contrast, the MS of the 1.4 DAR conjugate prepared without sodium bisulfite showed the highest peak of unconjugated antibody (D0) and much smaller D1, D2 and D3 linked drug conjugate peaks. The drug % on the monomer for the huMy9-6-2 conjugate prepared with sodium bisulfite was 91%, which was higher than the 80% drug on the monomer for the huMy9-6-2 conjugate prepared without sodium bisulfite. The overall conjugate quality for the huMy9-6-2 conjugate prepared with sodium bisulfite, therefore, was much superior than by the traditional conjugation procedure without sodium bisulfite.

The conjugations of NHS esters of several drugs (1, 2, 3, and 4) with antibody were performed in the presence of sodium bisulfite ($NaHSO_3$) and were compared with the traditional conjugation method without $NaHSO_3$. The results are shown in Table 16. In all cases, the addition of sodium bisulfite in the conjugation showed conjugates with significantly better quality of higher DAR and higher % drug on monomer than conjugates prepared without the addition of sodium bisulfite.

TABLE 16

Comparisons of conjugations of antibody with several drug-NHS esters without or with added sodium bisulfite (NaHSO₃)

| NaHSO₃ addition | Type of drug | DAR | % monomer | % drug on monomer |
|---|---|---|---|---|
| − | 2 | 1.4 | 91 | 80 |
| + |   | 3.0 | 95 | 91 |
| − | 3 | 0.5 | 95 | 35 |
| + |   | 2.5 | 95 | 91 |
| − | 4 | 1.0 | 90 | 65 |
| + |   | 3.8 | 90 | 84 |
| − | 1 | 1.1 | 95 | 40 |
| + |   | 2.7 | 92 | 87 |

Figure 3:
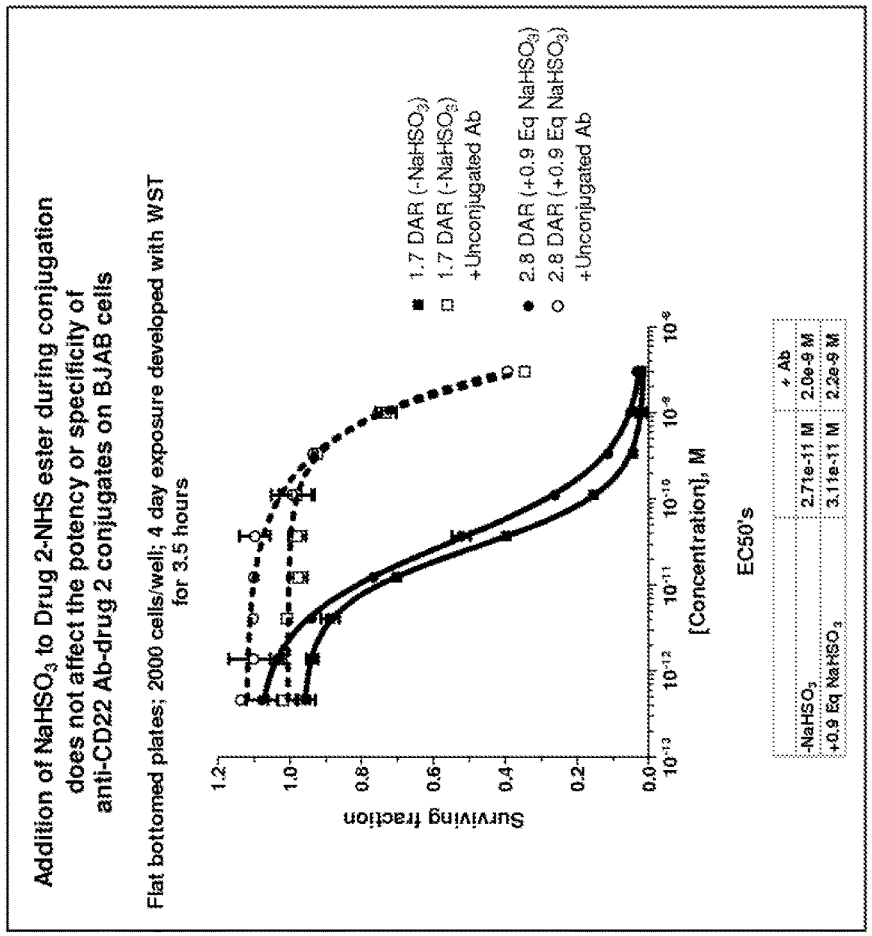
FIG. 3 shows similar in vitro cytotoxicity of anti-CD22 Ab-Drug 2 conjugates prepared without and with sodium bisulfite against CD22-antigen expressing BJAB cells.

The huMy9-6-2 conjugate prepared with sodium bisulfite showed a similar in vitro cytotoxicity to the conjugate prepared without sodium bisulfite (FIG. 2). Therefore a better quality conjugate of higher DAR and higher % drug on monomer was prepared using sodium bisulfite without any loss of cytotoxic potency. An anti-CD22 antibody-2 conjugate prepared with sodium bisulfite showed a similar in vitro cytotoxicity to the conjugate prepared without sodium bisulfite (FIG. 3).

The huMy9-6-2 conjugate prepared using sodium bisulfite was analyzed by non-reducing SDS-PAGE using a gel chip analyzer. The conjugate showed only the intact antibody band; no heavy and light chain bands were observed, showing an unexpected advantage that the added sodium bisulfite did not cause any unwanted reduction of native interchain disulfide bonds in the antibody.

2-NHS ester or SPDB-NHS esters of 3, 4, 1, and 5 were pre-incubated with 0.5 to 3 molar equivalents of sodium bisulfite (freshly prepared NaHSO3 in deionized water) in 66-98% DMA (dimethylacetamide) in water from 15 min to 4 h at 25° C. Some of these reactions were also left overnight at 4° C. and used for conjugations 20 h later.

Figure 4:
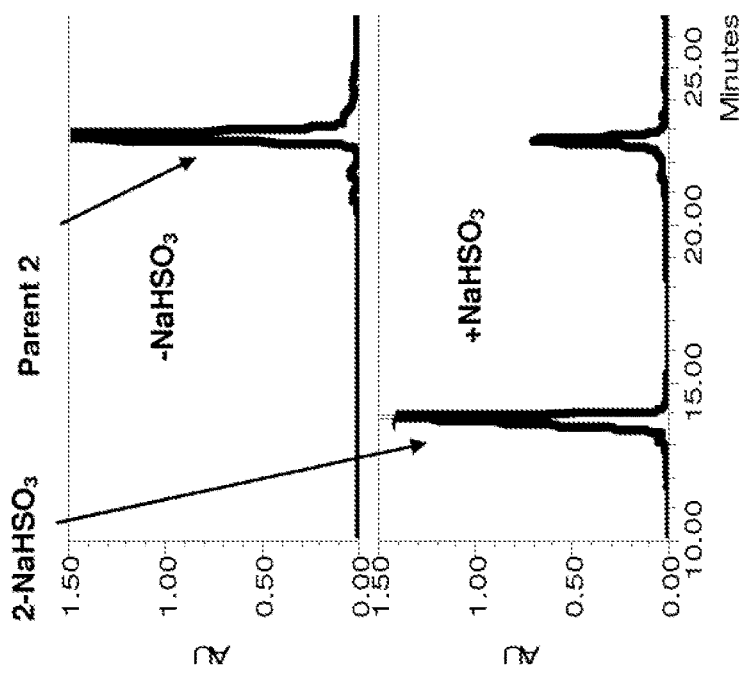
FIG. 4 shows reverse phase HPLC analysis of drug 2 and sodium bisulfite-treated drug 2.

The 2-NHS ester in DMA treated with sodium bisulfite or without added sodium bisulfite was analyzed by HPLC using a VYDAC C8 reversed phase column with a linear gradient of 20% acetonitrile and 80% deionized water going upto 100% acetonitrile, all containing 0.025% acetic acid, at 1 ml/min over 48 min. As shown in FIG. 4, parent 2-NHS ester eluted at ~23 min. After 30 min of treatment with 0.9 molar equivalents of NaHSO₃ in 66% DMA in water at 25° C., a majority of the 2-NHS was converted into the sulfonated, more polar form that eluted at ~14 min. Unexpectedly, no undesirable peak of sulfonated hydrolyzed 2 was observed. Therefore, a surprisingly favorable reaction of sodium bisulfite toward addition to the imine bond without reaction with the NHS ester was observed.

Similarly drug NHS esters are treated with imine reactive reagents other than sodium bisulfite before conjugation with antibody. An alternative conjugation approach is to treat a mixture of drug-NHS ester and antibody with sodium bisulfite or other imine reactive reagent.

Example 3

The disulfide-linked antibody-SPDB-1 conjugate was prepared using synthesized 1-SPDB-NHS ester (compound 1c). The 1-SPDB-NHS ester was pre-treated with 3 molar equivalents of sodium bisulfite (using a freshly prepared NaHSO₃ solution in water) in 96-98% DMA in water for 4-5 h at 25° C. The sodium bisulfite-treated 1-SPDB-NHS ester in DMA was analyzed using VYDAC C8 reversed phase-HPLC column using a linear gradient of 20% acetonitrile and 80% deionized water containing 0.025% acetic acid at 1 ml/min for 48 min. The reversed phase HPLC analysis showed only the desired reaction of bisulfite addition to the imine bond without the undesired reaction of bisulfite with the NHS ester.

For conjugation, a humanized antibody at 2 mg/ml was reacted with 5-7 molar equivalents of 1-SPDB-NHS ester (pre-treated with NaHSO₃) for 6 h at 25° C. in 85% PBS, pH 7.4, aqueous buffer containing 15% N,N-dimethylacetamide (DMA) and then purified over a G25 gel filtration column in PBS, pH 7.4, to remove unreacted or hydrolyzed drug. The humanized antibody-SPDB-1 conjugates were dialyzed in 10 mM Histidine, 250 mM Glycine, 1% sucrose, pH 6.5 buffer. The drug/antibody ratio (DAR) of the conjugates were measured to be 2.2-2.9 by UV absorbance measurements at 280 and 320 nm and using the extinction coefficients of the drug and antibody at 280 nm and 320 nm. The percentage of monomer in the conjugate preparation was determined by SEC (Size Exclusion Chromatography) as 90%. Based on the UV absorbance of the monomer peak in SEC it was also demonstrated that the monomer conjugate peak had linked drug molecules. The unconjugated drug % by acetone extraction and reversed-phase HPLC was shown to be less than 1%.

Figure 5A:
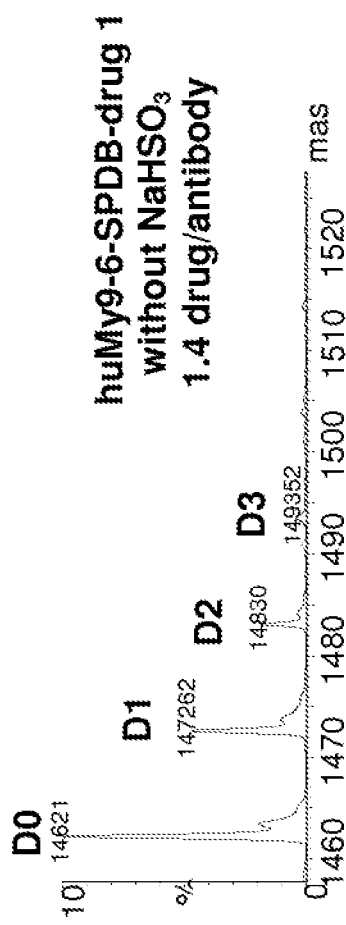
FIGS. 5A and 5B show MS analysis of deglycosylated huMy9-6-SPDB-drug 1 prepared with and without sodium bisulfite using 7 molar equivalents of 1 per antibody.
Figure 5B:
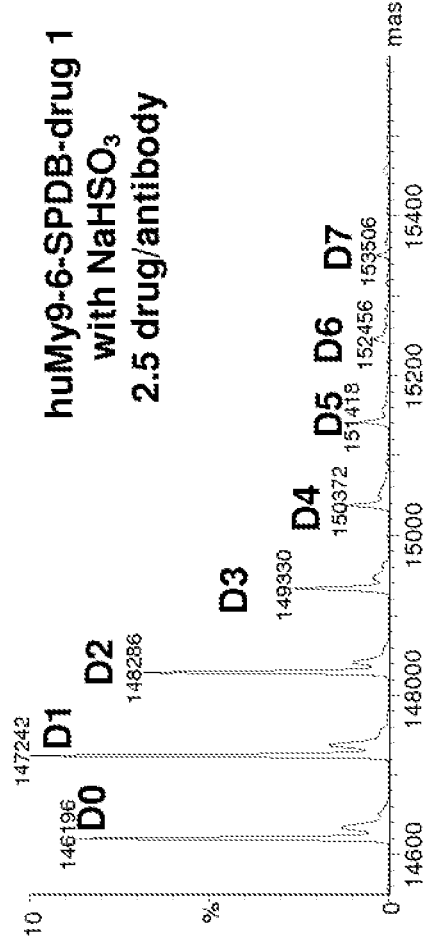

The MS of the deglycosylated antibody-SPDB-1 conjugates prepared with sodium bisulfite added before conjugation showed a much superior conjugate than that obtained without sodium bisulfite conjugation (FIG. 5). The MS of the conjugate prepared without sodium bisulfite had an average of 1.4 1/Ab and antibody species with up to three linked 1 molecules (FIG. 5A). In contrast, the MS of the conjugate prepared with sodium bisulfite showed an average of 2.5 1/Ab and antibody species with up to seven linked 1 molecules (FIG. 5B).

Figure 6:
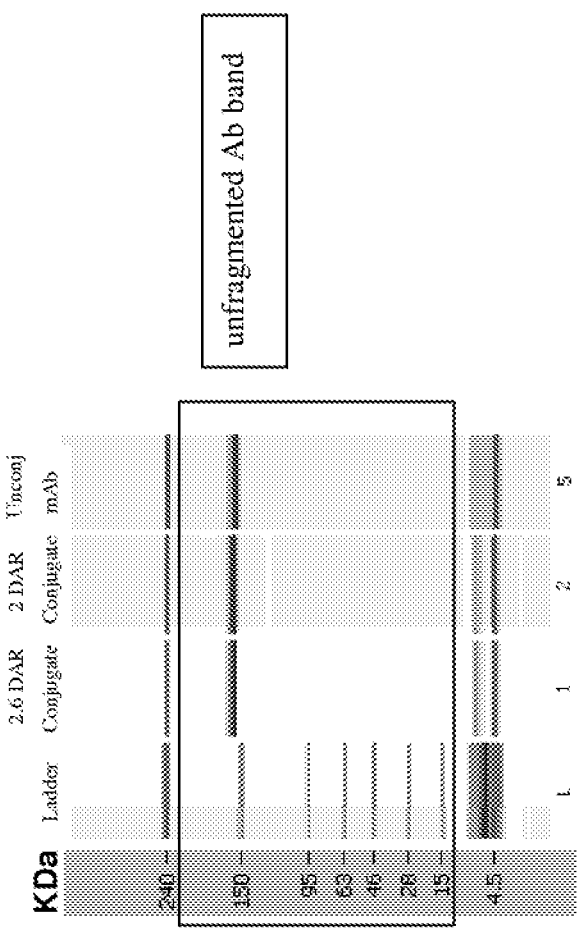
FIG. 6 shows that addition of sodium bisulfite conjugation reaction of drug 1 did not result in fragmentation of antibody (non-reducing SDS-PAGE; gel chip analysis).

The disulfide-linked antibody-SPDB-1 conjugate prepared using sodium bisulfite showed only intact antibody band by non-reducing SDS-PAGE gel chip analysis. The gel chip assay was performed using Agilent Protein 230 Protein Chip and analyzed using an Agilent 2300 Bioanalyzer. No heavy and light chain bands were observed, showing an unexpected advantage that the added sodium bisulfite did not cause any unwanted reduction of native antibody-interchain disulfide bonds (FIG. 6). The linked drug obtained in the antibody-SPDB-1 conjugate prepared using sodium bisulfite also demonstrated surprisingly that the disulfide linker in the conjugate was stable to the added sodium bisulfite.

Example 4

For conjugate preparation, 1f-SPDB-NHS ester (compound 1c, FIG. 7) was pre-incubated with 3 molar equivalents of sodium bisulfite (freshly prepared NaHSO$_3$ in deionized water) in 96% DMA (dimethylacetamide) in water for 5 h at 25° C. and then incubated overnight at 4° C. until needed for conjugation. Humanized antibody at 2-3 mg/ml was derivatized with 8 molar equivalents of 1f-SPDB-NHS ester in the absence or presence of sodium bisulfite (−/+ NaHSO$_3$) for 4 h at 25° C. in 95% 50 mM HEPES, pH 8.5, aqueous buffer containing 5% DMA (v/v) and then both were purified over G25 desalting columns into PBS, pH 7.4, to remove unreacted, hydrolyzed drug. The conjugates were dialyzed in 10 mM histidine, 250 mM glycine, 1% sucrose, pH 6.5 buffer. The conjugate DAR was measured by UV spectrophotometry at 280 and 320 nm. The monomer % and % drug on the monomer in the conjugate were determined by SEC. The unconjugated drug in the conjugate was determined by reverse phase HPLC after acetone extraction. These conjugations were performed with several humanized antibodies.

Example 5

To conjugate drug thiols with reactive disulfide linker incorporated in antibody, humanized mAb at 8 mg/ml is derivatized with 4-6 molar equivalents of SPDB hetrobifunctional linker for 1.5 h at 25° C. in 90% PBS, pH 7.5, aqueous buffer with 5% DMA (v/v) and then purified over a G25 desalting column into 35 mM citrate, 2 mM EDTA, 150 mM NaCl, pH 5.5 buffer to remove unreacted, hydrolyzed linker. The LAR (linker antibody ratio) is measured by UV absorbance at 280 and 343 nm without and with added 50 mM dithiothreitol (to measure total antibody and releasable SPy). The SPDB-modified antibody at 2 mg/ml is reacted with 2 molar equivalents of sodium bisulfite-treated drug thiol per linker for 2 to 20 h at 25° C. in 85-90% of 50 mM potassium phosphate, 50 mM NaCl, pH 7.5 buffer and then purified over a G25 desalting column in PBS, pH 7.4, to remove unreacted, hydrolyzed drug. The DAR of the antibody-SPDB-drug conjugate is measured by UV absorbance at 280 and 320 nm and the percentage of monomer and the percentage of drug on the monomer in the conjugate preparation is determined by SEC.

Example 6 Preparation of huMy9-6-sulfo-SPDB-1 (2-Step Method)

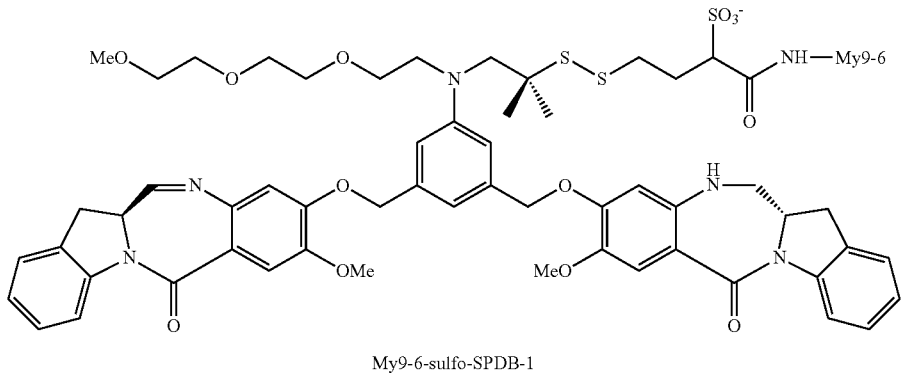

My9-6-sulfo-SPDB-1

A reaction containing 6 mg/mL huMy9-6 antibody and 9 molar equivalents sulfo-SPDB linker (20 mM stock in DMA) was incubated for 3 h at 25° C. in 50 mM EPPS buffer pH 8. Unreacted linker was removed using a NAP desalting column (Illustra Sephadex G-25 DNA Grade, GE Healthcare) and the linker to antibody ratio (LAR) was determined to be 3.7 based on antibody concentration and DTT-released thiopyridine concentration by UV-Vis ($\varepsilon_{343\ nm}$=8,080 cm$^{-1}$M$^{-1}$ for 2-thiopyridone).

Sulfo-SPDB modified huMy9-6 was diluted to 2 mg/ml in 50 mM EPPS pH 8.5, 10% v/v DMA, and reacted with 2 molar equivalents of compound 1d per linker (5 mM stock in DMA; 7.4 equivalents per antibody) for 3 h at 25° C.

Post-reaction, the conjugate was purified and buffer exchanged into 250 mM Glycine, 10 mM Histidine, 1% sucrose, 0.01% Tween-20, 50 µM sodium bisulfite at pH 6.2 using a desalting column (G-25 Sephadex, fine grade, GE Healthcare).

The purified conjugate was found to have an average of 2.9 compound 1 molecules linked per antibody (by UV-Vis using molar extinction coefficients $\varepsilon_{330\ nm}$=15,484 cm$^{-1}$M$^{-1}$ and $\varepsilon_{280\ nm}$=30,115 cm$^{-1}$M$^{-1}$ for compound 1, and $\varepsilon_{280\ nm}$=207,000 cm$^{-1}$M$^{-1}$ for My9-6 antibody), 97.8% monomer (by size exclusion chromatography), <1% unconjugated compound 1 (by acetone extraction/reverse-phase HPLC), a 60% yield based on the amount of the antibody used, and an 18% overall yield based on the amount of compound 1d used. The conjugate made using this method could be concentrated (by stirred cell or Amicon centrifugal filter device) to >3 mg/ml without conjugate precipitation.

Example 7 Preparation of huMy9-6-SPDB-1

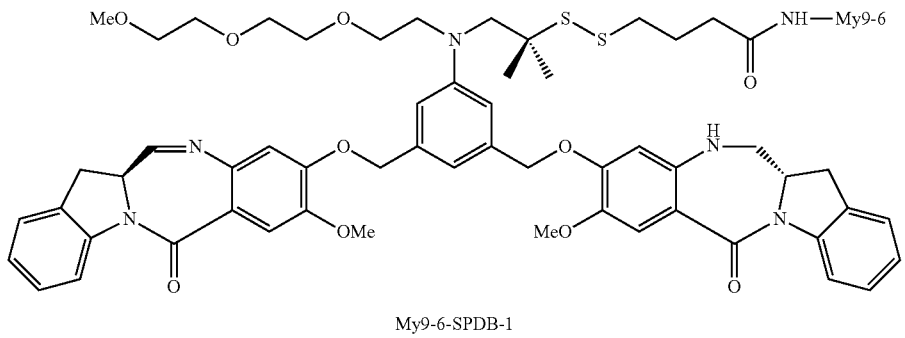

My9-6-SPDB-1

Method 1 (One-Step Reagent Method):

A reaction containing 2 mg/mL huMy9-6 antibody and 7 molar equivalents 1-SPDB-NHS (pretreated with 5-fold excess of sodium bisulfite in 90:10 DMA:water, v/v for 1 h at 25° C. and then overnight at 4° C.) in 50 mM HEPES (4-(2-hydroxyethyl)-1-piperazine ethanesulfonic acid) pH 8.5 buffer and 10% v/v DMA (N,N-Dimethylacetamide) cosolvent was allowed to incubate for 3 h at 25° C.

Post-reaction, the conjugate was purified and buffer exchanged into 250 mM Glycine, 10 mM Histidine, 1% sucrose, 0.01% Tween, 50 µM sodium bisulfite formulation buffer, using NAP desalting columns (Illustra Sephadex G-25 DNA Grade, GE Healthcare). Dialysis was performed in the same buffer for 4 hours at room temperature utilizing Slide-a-Lyzer dialysis cassettes (ThermoScientific 20,000 MWCO).

The purified conjugate was found to have an average of 4.0 compound 1 molecules linked per antibody (by UV-Vis using molar extinction coefficients $\varepsilon_{330\ nm}$=15,484 cm$^{-1}$M$^{-1}$ and $\varepsilon_{280\ nm}$=30,115 cm$^{-1}$M$^{-1}$ for compound 1, and $\varepsilon_{280\ nm}$=207,000 cm$^{-1}$M$^{-1}$ for My9-6 antibody), 92% monomer (by size exclusion chromatography, TSK3000, TOSOH Biosciences), <1% unconjugated compound 1 (by acetone extraction/reverse-phase HPLC) a 72% yield based on the amount of the antibody used, a 40% overall yield based on the amount of 1-SPDB-NHS used, and a final protein concentration of 1.0 mg/ml.

to antibody ratio (LAR) was determined to be 4.0 based on antibody concentration and DTT-released 2-thiopyridone concentration by UV-Vis ($\varepsilon_{343\ nm}$=8,080 cm$^{-1}$M$^{-1}$ for 2-thiopyridone).

SPDB modified huMy9-6 was diluted to 2 mg/ml in 50 mM EPPS pH 8.5, 10% v/v DMA and reacted with 1.75 molar equivalents of compound 1d per linker (5 mM stock in DMA; 7 equivalents per antibody) for 3 h at 25° C.

Post-reaction, the conjugate was purified and buffer exchanged into 250 mM Glycine, 10 mM Histidine, 1% sucrose, 0.01% Tween-20, 50 µM sodium bisulfite at pH 6.2 using a desalting column (Illustra Sephadex G-25 DNA Grade, GE Healthcare).

The purified conjugate was found to have an average of 3.8 compound 1 molecules linked per antibody (by UV-Vis using molar extinction coefficients $\varepsilon_{330\ nm}$=15,484 cm$^{-1}$M$^{-1}$ and $\varepsilon_{280\ nm}$=30,115 cm$^{-1}$M$^{-1}$ for compound 1, and $\varepsilon_{280\ nm}$=207,000 cm$^{-1}$M$^{-1}$ for My9-6 antibody), 91.6% monomer (by size exclusion chromatography, TSK3000, TOSOH Biosciences), <1% unconjugated compound 1 (by acetone extraction/reverse-phase HPLC), a 40% yield based on the amount of the antibody used, a 22% overall yield based on the amount of compound 1d used, and a final protein concentration of 0.5 mg/ml.

Example 8 Preparation of huMy9-6-CX1-1-1

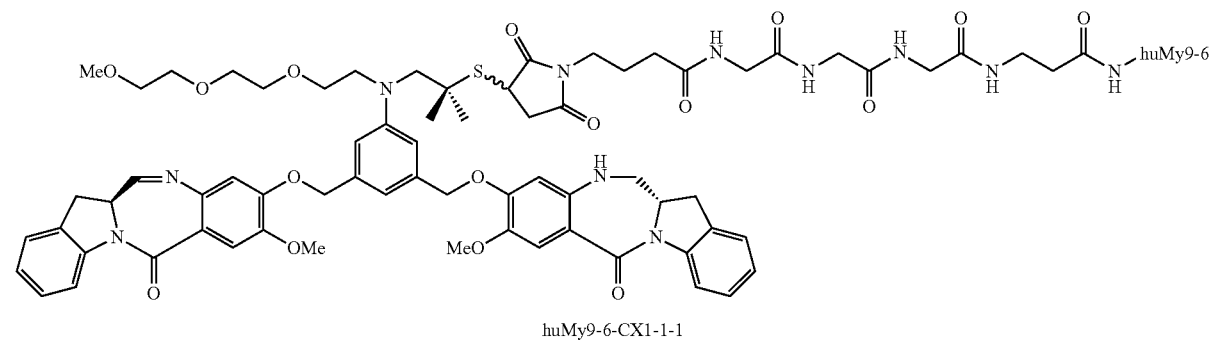

huMy9-6-CX1-1-1

Method 2 (Two-Step Method):

A reaction containing 4.8 mg/mL huMy9-6 antibody and 6 molar equivalents SPDB linker (18.5 mM stock in ethanol) was incubated for 3 h at 25° C. in PBS pH 7.4. Unreacted linker was removed using a NAP desalting column (Illustra Sephadex G-25 DNA Grade, GE Healthcare) and the linker Method 1 (In-Situ One-Step Reagent Method):

A DMA solution containing 1.9 mM compound 1d, 1 mM CX1-1 heterobifunctional linker with N-hydroxysuccinimide (NHS) and maleimide groups, and 20 mM diisopropyl ethyl amine (DIPEA) was allowed to react at ambient temperature for 8 min. Then 3 mM maleimido propionic acid (MPA) was added to quench excess compound 1d. The 1-CX1-1-NHS reaction mixture was stored frozen at −80° C., and later upon thawing was added in two portions to a buffered solution of huMy9-6 at 25° C. (2 mg/ml, 100 mM EPPS, pH 8.0, 10% v/v DMA); 4.8 molar equivalents per antibody (based on linker concentration) followed by 4.2 equivalents 30 min later. After 2 h reaction, the conjugate was purified and buffer exchanged into 250 mM Glycine, 10 mM Histidine, 1% sucrose, 0.01% Tween-20, 50 μM sodium bisulfite at pH 6.2 using a desalting column (Quick-spin protein, G-25 fine resin, Roche), dialysis, and finally 0.22 μm sterile filtration.

The purified conjugate was found to have an average of 3.3 compound 1 molecules linked per antibody (by UV-Vis using molar extinction coefficients $\varepsilon_{330\ nm}=15,484\ cm^{-1}M^{-1}$ and $\varepsilon_{280\ nm}=30,115\ cm^{-1}M^{-1}$ for compound 1, and $\varepsilon_{280\ nm}=207,000\ cm^{-1}M^{-1}$ for My9-6 antibody), 95% monomer (by size exclusion chromatography, TSK3000, TOSOH Biosciences), <1% unconjugated compound 1 (by acetone extraction/reverse-phase HPLC), a 45% yield based on the amount of the antibody used, a 17% overall yield based on the amount of compound 1d used, and a final protein concentration of 0.7 mg/ml.

Method 2 (One-Step Method):

To a buffered solution of huMy9-6 antibody (2 mg/ml, 50 mM EPPS, pH 8.5, 8% v/v DMA) was added 14 molar equivalents compound 1d (5 mM stock in DMA) followed by 7 molar equivalents of CX1-1 linker (15 mM stock solution in ethanol) and incubated for 3 h at 25° C.

Post-reaction, the conjugate was purified and buffer exchanged into 250 mM Glycine, 10 mM Histidine, 1% sucrose, 0.01% Tween-20, 50 μM sodium bisulfite at pH 6.2 using a desalting column (Illustra Sephadex G-25 DNA Grade, GE Healthcare), followed by 2× dialysis at 4° C. in Slide-a-Lyzer dialysis cassettes (ThermoScientific 20,000 MWCO).

The purified conjugate was found to have an average of 3.4 compound 1 molecules linked per antibody (by UV-Vis using molar extinction coefficients $\varepsilon_{330\ nm}=15,484\ cm^{-1}M^{-1}$ and $\varepsilon_{280\ nm}=30,115\ cm^{-1}M^{-1}$ for compound 1, and $\varepsilon_{280\ nm}=207,000\ cm^{-1}M^{-1}$ for My9-6 antibody), 90% monomer (by size exclusion chromatography, TSK3000, TOSOH Biosciences), <1% unconjugated compound 1 (by acetone extraction/reverse-phase HPLC), a 44% yield based on the amount of the antibody used, an 11% overall yield based on the amount of compound 1d used, and a final protein concentration of 1.48 mg/ml.

Example 9 MS Analysis of Deglycosylated My9-6-SPDB-1f

My9-6-SPDB-1f was made either by conjugating an NHS ester containing compound 1f directly to antibody lysines (i.e., one-step reagent method as described above), or by conjugating compound 1d to a dithiopyridine modified antibody (i.e., two-step method as described above). Mass spectrometry (MS) analysis of the deglycosylated My9-6-SPDB-1f were then carried out as above.

Figure 12:
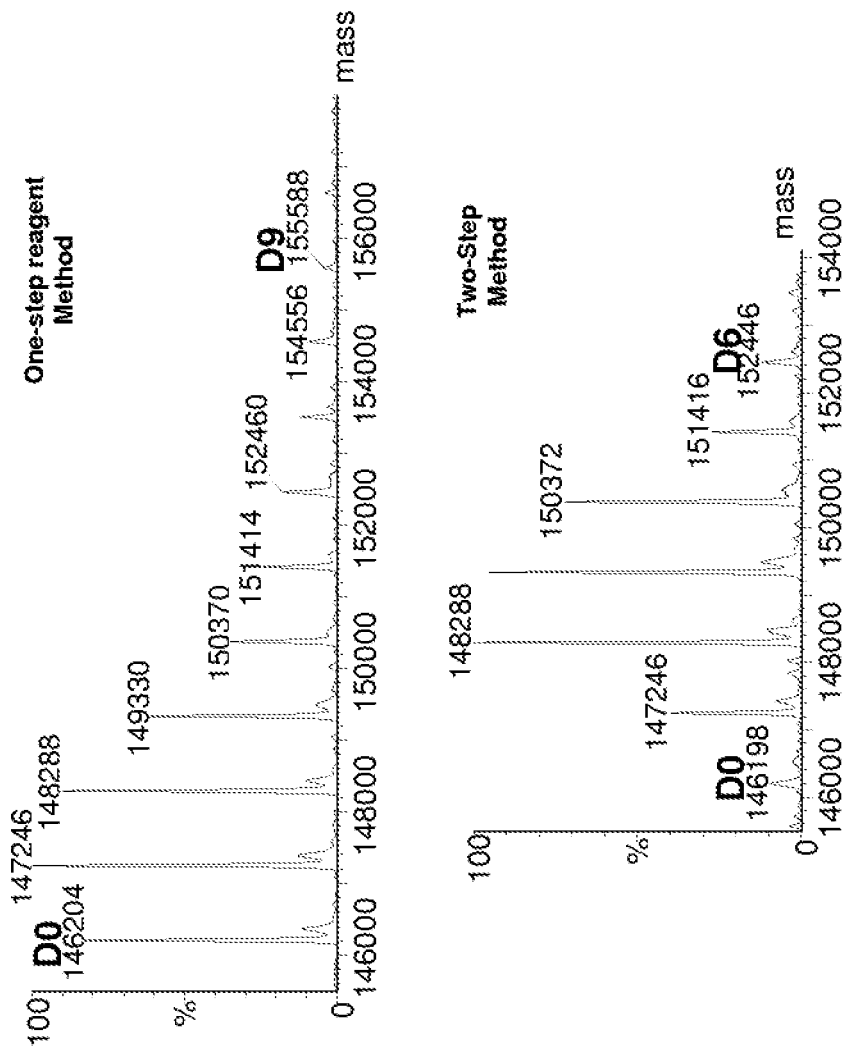
FIG. 12 shows Mass Spectrometry (MS) analysis of deglycosylated My9-6-SPDB-1 made by conjugating an NHS ester containing compound 1 (one-step reagent method) directly to antibody lysines, or conjugating compound 1d to a dithiopyridine modified antibody (two step method).

The one-step reagent method gave a conjugate with 0-9 compound 1f modifications, an asymmetric conjugated drug distribution, and a significant amount of unconjugated antibody. On the other hand, the conjugate made by the two-step method had an MS profile with 0-6 compound 1f modifications, a symmetric conjugated drug distribution, and very little unconjugated antibody. See FIG. 12. Both conjugates had a similar average compound 1f/antibody ratio of ~4 by UV-vis analysis.

Example 10 pH Effect on Two-Step Synthesis of My9-6-sulfo-SPDB-1

Figure 13:
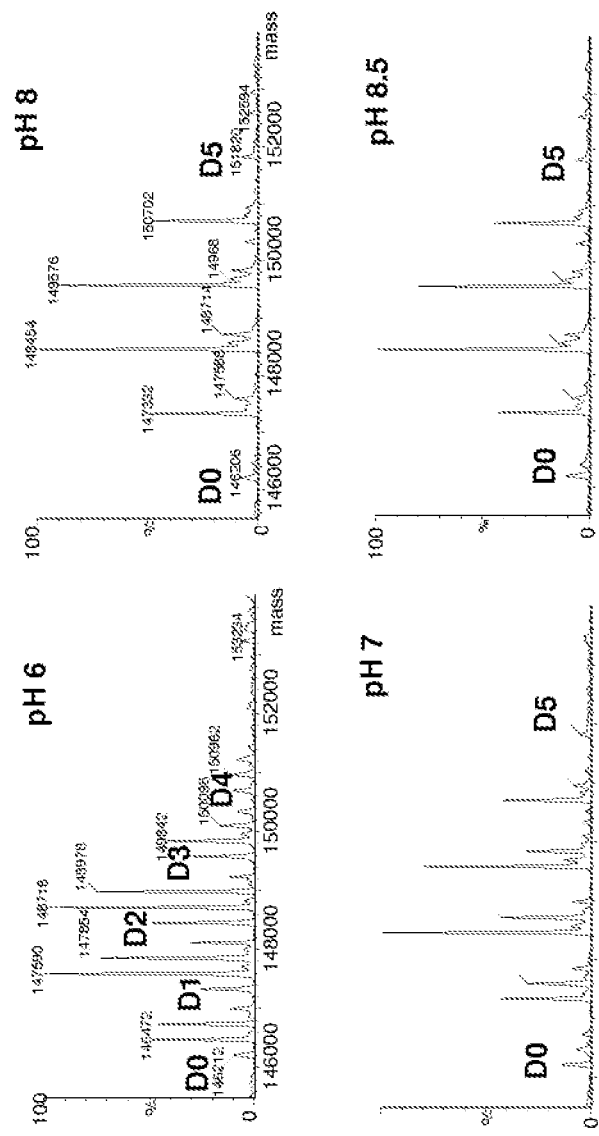
FIG. 13 shows MS data for My9-6-sulfo-SPDB-1 made using a two-step method under different pH conditions. Increased reaction time appears to be correlated with increased CD33-antigen-independent in vitro cytotoxicity measured on HL60-QC cells pretreated with 1 µM unconjugate huMy9-6. Antigen-dependent killing for all conjugates was similarly high (~4 pM $IC_{50}$). Short reaction time (1-3 h) is preferred to minimize antibody fragmentation and in vitro non-specific cell killing for My9-6-sulfo-SPDB-1.

MS data for My9-6-sulfo-SPDB-1f made using a two-step method under different pH conditions was shown in FIG. 13. Briefly, My9-6-sulfoSPDB (3.7 linker/antibody) was reacted with 3 equivalents of compound 1d per linker (or about 11.1 equivalents per antibody) for 18 h at pH 6, 7, 8, and 8.5. The MS data showed a decrease in unreacted linker (260 amu satellite peaks) with increasing reaction pH. Thus it appeared that pH affects the conjugation reaction in the synthesis of the My9-6-sulfo-SPDB-1f conjugate. Specifically, a pH of >8 is required for compound 1d to fully react with the sulfo-SPDB linker on the antibody.

Example 11 Effect of Compound/Linker Ratio on Two-Step Synthesis of chKTI-sulfo-SPDB-1

Figure 14:
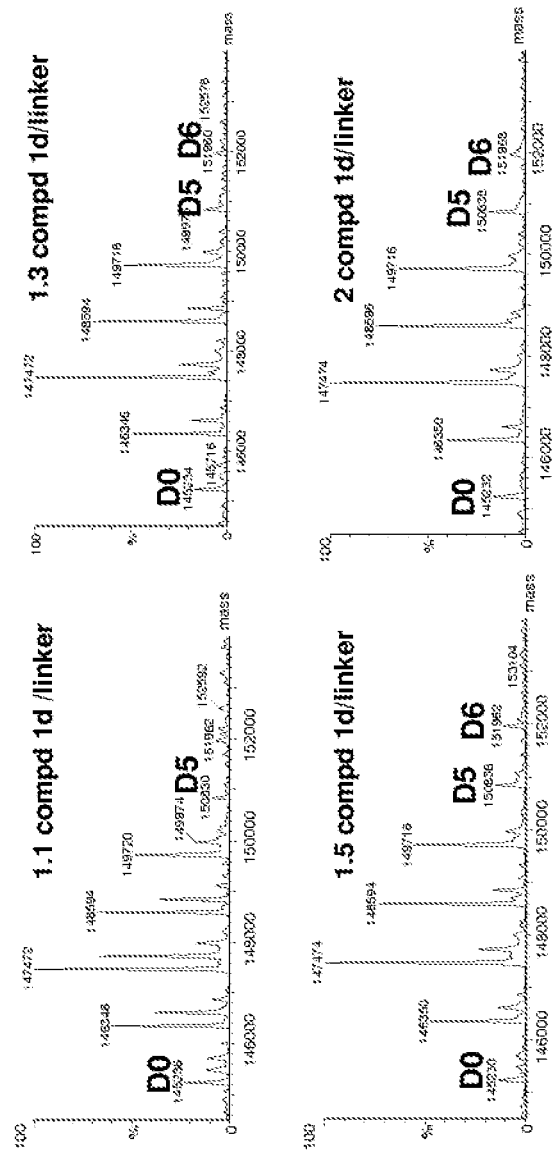
FIG. 14 shows MS data for chKTI-sulfo-SPDB-1 made using a two-step method with different compound 1d/linker ratios.

FIG. 14 shows MS data for chKTI-sulfo-SPDB-1 made using a two-step method with different compound 1d/linker ratios. chKTI-sulfoSPDB (3.7 linker/antibody) was reacted with 1.1, 1.3, 1.5 or 2 equivalents of compound 1d per linker for 3 h, at 25° C., pH 8.5. The MS showed a decrease in unreacted linker (260 amu satellite peaks) with increasing equivalents of compound 1d per linker. It appeared that under this condition, a compound 1d/linker ratio of >1.3 is required to fully react with the sulfo-SPDB linker on the antibody. Increasing the equivalents of compound 1d above 1.5 per linker led to increased antibody fragmentation (14-19%) while 1.1-1.3 compound 1d/linker did not cause significant antibody fragmentation.

Example 12 Preparation of Antibody-SPDB-Drug Conjugate

Compound 1c was pre-treated with 3 molar equivalents of sodium bisulfite (using a freshly prepared NaHSO$_3$ solution in water) in 96-98% DMA in water for 4-5 hrs at 25° C. For conjugation, the humanized antibody at 2 mg/mL was reacted with 5-7 molar equivalents of compound 1c (pre-treated with NaHSO$_3$) for 6 h at 25° C. in 85-90% PBS, pH 7.4, aqueous buffer, or 50 mM HEPES, pH 8.5, aqueous buffer, containing 10-15% N,N-dimethylacetamide (DMA) and then purified over a G25 gel filtration column in PBS, pH 7.4, to remove unreacted or hydrolyzed drug compound. The humanized antibody-SPDB-drug conjugates were dialyzed in 10 mM Histidine, 250 mM Glycine, 1% sucrose, pH 6.5 buffer. The Drug Antibody Ratio (DAR) of the conjugates were measured to be 2.2-2.9 by UV absorbance measurements at 280 and 320 nm and using the extinction coefficients of the drug and antibody at 280 nm (215,000 $M^{-1}cm^{-1}$) and 320 nm (9137 $M^{-1}cm^{-1}$). The percentage of monomer in the conjugates were determined as >90% by SEC (Size Exclusion Chromatography) using TSK-Gel G300SWXL column (7.8 mm×300 mm, 5 μm particle size). Based on the UV absorbance of the monomer peak in SEC it was also demonstrated that the monomer conjugate peaks had linked drug molecules. For free (unconjugated) drug assay, the conjugate was acetone extracted to remove protein, dried, and reconstituted in mobile phase and injected onto a VYDAC 208TP C8 reverse phase HPLC column (4.6×250 mm, 7 μm particle size) and compared to standards. The percentage of free drug compound in the conjugate was determined as <0.5% of conjugated drug compound.

Preparation of Humanized Ab-SPDB-2a Conjugate:

Humanized Ab at 8 mg/mL was derivatized with 4-6 molar equivalents of SPDB hetrobifunctional linker for 1.5 h at 25° C. in 95% PBS, PH 7.4, containing 5% DMA (v/v), and then purified over a G25 desalting column into citrate buffer (35 mM citrate buffer, pH 5.5, containing 2 mM EDTA, 150 mM NaCl) to remove unreacted linker. The LAR (Linker Antibody Ratio) were measured using UV absorbance at 280 and 343 nm without and with 50 mM dithiothreitol addition (to measure total antibody and dithiothreitol-released SPy) and were determined to be 2.7-4.1 LAR. The SPDB-modified antibody at 2 mg/mL was reacted with 2 molar equivalents of compound 2a (HCl salt) per linked SPDB for 20 h at ambient temperature in 85% citrate buffer, 15% DMA (v/v) and then purified over a G25 desalting column into PBS, pH 7.4 to remove unconjugated drug compound. The DAR of the final humanized Ab-SPDB-2a conjugate was measured by UV spectrophotometry at 280 and 350 nm and calculated to be ~1.7-2.1 DAR. The percentage of monomer and linked drug compound on the monomer in the conjugate was determined by HPLC using an SEC (size exclusion chromatography) column. See FIG. 16.

Example 13 Use of Covalent Imine Reactants to Improve Ab-Drug Conjugate Specifications (% Monomer and Drug Load)

Adduct formation was carried out with 5 molar equivalents of imine reactant over NHS-BMPS-1 in 90% DMSO/10% PBS pH 7.4 for 4 hr at 25° C. The reaction mixture was then added to huMy9-6 antibody (4 molar equivalents drug, 2 mg/ml, 10% v/v DMSO, 50 mM HEPES buffer, pH 8.5, 5 h, 25° C.). Conjugates made using sodium hydro sulfite, sodium bisulfite, or sodium metabisulfite had similar drug/Ab ratios and % monomer, while conjugates made with no additive treatment led to very low drug incorporation.

Example 14 In Vivo Tolerability Study of huFOLR-1 Conjugates

The in vivo tolerability of huFOLR-1 conjugates was investigated in female CD-1 mice. Animals were observed for seven days prior to study initiation and found to be free of disease or illness. The mice were administered a single i.v. injection of the bisulfite-bearing conjugate and the animals were monitored daily for body weight loss, morbidity or mortality. Table 9 shows that for huFOLR1-drug1, the conjugate was tolerated at only the lowest dose tested of 50 µg/kg. In contrast, both mono-imine conjugates huFOLR1-drug2 and huFOLR1-SPDB-1f were found to be better tolerated with a maximum tolerated dose of <198 µg/kg and >560 µg/kg respectively.

TABLE 9

Tolerability comparison data for (A) huFOLR1-drug1, (B) huFOLR1-drug2, and (C) huFOLR1-SPDB-1f conjugates.

| Dose (µg/kg) | % Survival |
|---|---|
| A) | |
| 50 | 100 |
| 100 | 0 |
| 200 | 0 |

TABLE 9-continued

Tolerability comparison data for (A) huFOLR1-drug1, (B) huFOLR1-drug2, and (C) huFOLR1-SPDB-1f conjugates.

| Dose (µg/kg) | % Survival |
|---|---|
| 300 | 0 |
| 400 | 0 |
| | |
| huFOLR1-drug1 MTD <100 µg/kg | |
| B) | |
| 66 | 100 |
| 132 | 100 |
| 198 | 50 |
| 264 | 25 |
| | |
| huFOLR1-drug2 MTD <198 µg/kg | |
| C) | |
| 120 | 100 |
| 160 | 100 |
| 200 | 100 |
| 320 | 100 |
| 560 | 100 |
| | |
| huFOLR1-SPDB-1f MTD >560 µg/kg | |

Example 15 Effect of Propylene Glycol in Formulation and Conjugation

This example demonstrates that the subject conjugation reactions carried out in the presence of propylene glycol as co-solvent do not show precipitation of the conjugates, and that as high as 40% (and possibly even higher) propylene glycol can be used without a decrease in the % monomer of the resulting conjugate (in the presence of 2% dimethylacetamide—data not shown).

More importantly, the presence of propylene glycol during purification leads to significant increases in yield (Table 10).

While not wishing to be bound by any particular theory, Applicants believe that one of the primary source of problems during the conjugation of the subject conjugates is the inherent hydrophobicity of the molecular components of the conjugates. This may at least partially explain the low purified yields, and sometimes aberrant mass distribution profiles observed with the subject conjugations.

It is also worth noting that the addition of isopropanol during size exclusion chromatography of the subject conjugates greatly decreases the apparent aggregate population. This observation suggests that small hydrophobic cosolvents may increase the solubility of the drug and conjugate of the invention.

Thus the subject conjugation reactions, the purification steps after the reaction, and/or the formulation of the formed conjugates are preferably carried out in the presence of small hydrophobic cosolvents, such as propylene glycol (e.g., 5, 10, 15, 20, 25, 30, 35, 40, 45%).

Antibody-sulfo-SPDB was prepared according to previously described methods by the addition of the N-hydroxysuccinimidyl (NHS) ester form of sulfo-SPDB to antibody (huMy9-6) in water containing 3% DMA, and buffered at pH 8.5 for 3 hours. The resulting intermediate (antibody-sulfo-SPDB) was purified over G25 Sephadex to remove excess linker. Antibody and linker were quantitated by UV-vis spectroscopy by measuring absorbance at 280 nm in the absence of reductant, and at 343 nm in the presence of ~50 mM DTT to measure 2-thiopyridine release from conjugated linker.

To conjugate drug, the antibody-sulfo-SPDB prepared above was reacted at 2 mg/mL antibody with a 2-fold molar excess of compound 1d in the presence of the indicated co-solvents, and with the pH maintained at 8.5 with EPPS buffer (final concentration 60 mM). Dimethylacetamide (SAFC) and propylene glycol (Alfa Aesar) were used as received with no further purification. All buffers were sterilized by passage through 0.22 micron filter (Corning) and water was purified by reverse osmosis/deionization. The reactions were incubated at 25° C. for 3 hrs and then purified using disposable G25 Sephadex columns (Nap 25, GE Healthcare) into a formulation buffer consisting of 10 mM histidine, 250 glycine, 1% sucrose, 0.01% polysorbate 20, 50 µM sodium bisulfite and buffered to pH 6.2, as well as the indicated percentage of propylene glycol (v/v).

Reaction yields and drug load were determined by absorbance spectroscopy. All samples showed >96% monomer by analytical size exclusion chromatography.

Table 10 below shows the % Yield of conjugation as a function of propylene glycol in the reaction mixture or formulation. Antibody-sulfo-SPDB-1 was prepared by reaction of compound 1d with antibody-sulfo-SPDB for 4 hours at pH 8.5 (non-aqueous components as indicated) followed by purification over G25 Sephadex.

TABLE 10

| | | Formulation | |
| --- | --- | --- | --- |
| | | All aqueous | 15% Propylene glycol |
| Reaction | 0% Propylene glycol + 10% DMA | 59 | 79 |
| | 30% Propylene glycol + 2% DMA | 53* | 83 |

*A thick white precipitate was observed atop the Sephadex column after purification Example 16 Preparation of huMy9-6-sulfo-SPDB-1d Using the Highly Reactive 4-nitroPy-sulfo-SPDB Linker A reaction containing 6 mg/mL huMy9-6 antibody and 5 molar equivalents of the highly reactive N-succinimidyl-4-(4-nitropyridyl-2-dithio)butanoate linker (20 mM stock in ethanol) was incubated for 3 h at 25° C. in 50 mM EPPS buffer at pH 8. Unreacted linker was removed using a NAP desalting column (Illustra Sephadex G-25 DNA Grade, GE Healthcare). The linker to antibody ratio (LAR) was determined to be about 2.3 based on antibody concentration and DTT-released nitropyridine-2-thione concentration by UV-Vis ($\varepsilon_{394\ nm}=14205\ cm^{-1}M^{-1}$ for 2-thio-4-nitropyridone).

Linker modified huMy9-6 was diluted to 2 mg/mL in 50 mM HEPES buffer at pH 8.5, 10% v/v DMA, and reacted with 2 molar equivalents of compound 1d per linker (5 mM stock in DMA; 4.6 equivalents per antibody) for 30 min at 25° C. Completion of disulfide exchange reaction was determined by monitoring absorbance increase at 394 nm by UV. Post-reaction, the conjugate was purified and buffer exchanged into 250 mM glycine, 10 mM histidine, 1% sucrose, 0.01% Tween-20, 50 µM sodium bisulfite at pH 6.2 using a desalting column (G-25 Sephadex, fine grade, GE Healthcare).

Figure 28:
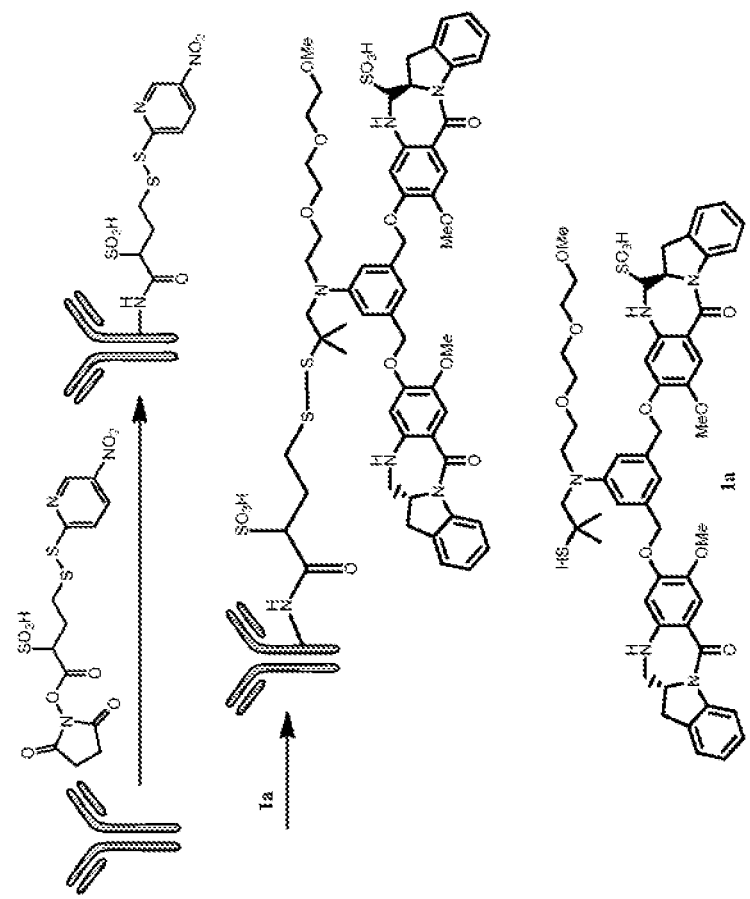
FIG. 28 shows the preparation of huMy9-6-sulfo-SPDB-1d using the highly reactive 4-nitroPy-sulfo-SPDB linker.

The purified conjugate was found to have an average of 2.1 molecules of 1d linked per antibody (by UV-Vis using molar extinction coefficients $\varepsilon_{330}=15,484\ cm^{-1}M^{-1}$ and $\varepsilon_{280\ nm}=30,115\ cm^{-1}M^{-1}$ for 1d, and $\varepsilon_{280\ nm}=207,000\ cm^{-1}M^{-1}$ for huMy9-6), 98% monomer (by size exclusion chromatography), <1% unconjugated 1d (by acetone extraction/reverse-phase HPLC), a 70% protein yield, and a 32% overall 1d yield. See FIG. 28.

The invention claimed is:

1. A method for preparing a conjugate represented by the following formula:

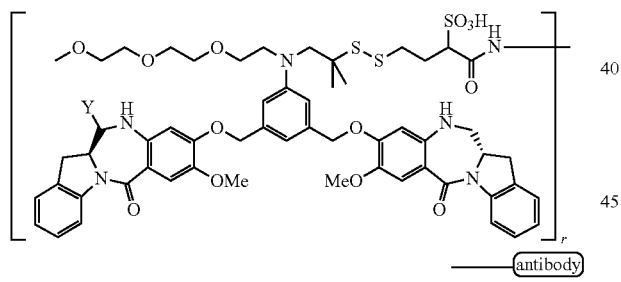

or a pharmaceutically acceptable salt thereof, the method comprising:

a) reacting a modified cytotoxic compound with a bifunctional crosslinking agent to form a second modified cytotoxic compound, wherein the modified cytotoxic compound is represented by the following formula:

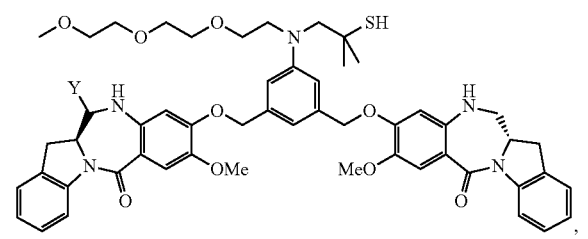

or a pharmaceutically acceptable salt thereof; the bifunctional crosslinking agent is N-succinimidyl-4-(2-pyridyldithio)2-sulfo butanoate (sulfo-SPDB); and the second modified cytotoxic compound is represented by the following formula:

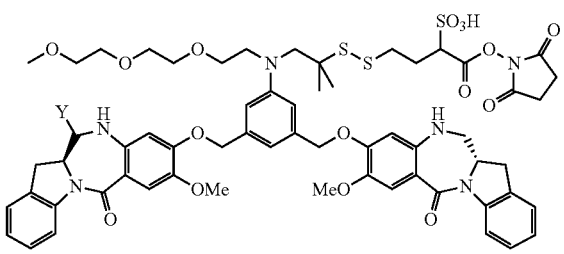

or a pharmaceutically acceptable salt thereof; and, b) reacting the second modified cytotoxic compound with the antibody at a pH of 4 to 9, to form the conjugate, wherein the second modified cytotoxic compound is not purified before reacting with the antibody in step b) and wherein the antibody is huMY9-6, r is an integer from 1 to 10, Y is —SO$_3$M, and M is H, Na$^+$ or K$^+$.

2. The method of claim 1, wherein the modified cytotoxic compound is produced by reacting an imine-containing compound represented by the following formula:

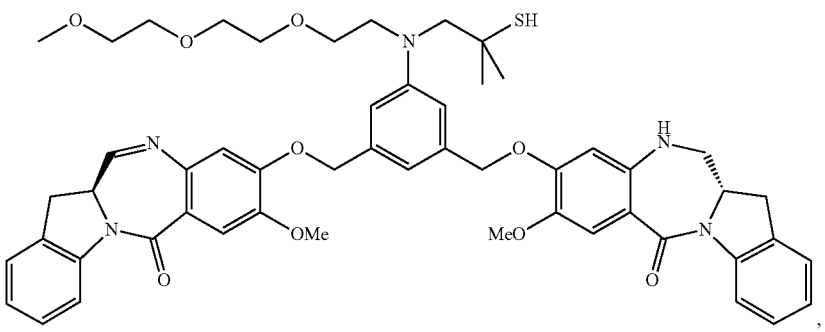 [SMILES: COCCOCCOCCN(CC(C)(C)S)c1cc(COc2cc3c(cc2OC)C(=O)N2c4ccccc4C[C@H]2C=N3)cc(COc2cc3c(cc2OC)C(=O)N2c4ccccc4C[C@H]2CN3)c1]
or a pharmaceutically acceptable salt thereof, with an imine reactive reagent, wherein the imine reactive reagent is NaHSO$_3$ or KHSO$_3$.
3. The method of claim 2, wherein the method further comprising purifying the modified cytotoxic compound prior to step a).
* * * * *

SEQUENCE LISTING

<160> NUMBER OF SEQ ID NOS: 14

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Gly Tyr Phe Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Lys, Gln, His or Arg
<220> FEATURE:
<221> NAME/KEY: MOD_RES
<222> LOCATION: (16)..(16)
<223> OTHER INFORMATION: Gln, His, Asn or Arg
<220> FEATURE:
<221> NAME/KEY: MOD_RES
<222> LOCATION: (17)..(17)
<223> OTHER INFORMATION: Gly, Glu, Thr, Ser, Ala or Val

<400> SEQUENCE: 2

Arg Ile His Pro Tyr Asp Gly Asp Thr Phe Tyr Asn Gln Xaa Phe Xaa
1               5                   10                  15

Xaa

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Asp Gly Ser Arg Ala Met Asp Tyr
1               5

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Ala Ser Gln Ser Val Ser Phe Ala Gly Thr Ser Leu Met His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ala Ser Asn Leu Glu Ala
1               5

<210> SEQ ID NO 6

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Ser Arg Glu Tyr Pro Tyr Thr
1               5

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ile His Pro Tyr Asp Gly Asp Thr Phe Tyr Asn Gln Lys Phe Gln
1               5                   10                  15

Gly

<210> SEQ ID NO 8
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
                20                  25                  30

Phe Met Asn Trp Val Lys Gln Ser Pro Gly Gln Ser Leu Glu Trp Ile
            35                  40                  45

Gly Arg Ile His Pro Tyr Asp Gly Asp Thr Phe Tyr Asn Gln Lys Phe
        50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
                100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
```

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 9
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

```
Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
    210                 215

<210> SEQ ID NO 10
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
                20                  25                  30

Gly Thr Ser Leu Met His Trp Tyr His Gln Lys Pro Gly Gln Gln Pro
            35                  40                  45

Arg Leu Leu Ile Tyr Arg Ala Ser Asn Leu Glu Ala Gly Val Pro Asp
50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
    210                 215

<210> SEQ ID NO 11
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 11

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 12
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gly Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Val Leu Thr Gln Ser Pro Leu Ser Leu Ala Val Ser Leu Gly
1               5                   10                  15

```
Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
            85                  90                  95

Glu Tyr Pro Tyr Thr Phe Gly Gly Gly Thr Lys Leu Glu Ile Lys Arg
            100                 105                 110

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Leu Ala Leu
1
```